(12) United States Patent
Mimoto et al.

(10) Patent No.: US 11,267,868 B2
(45) Date of Patent: Mar. 8, 2022

(54) FC REGION VARIANT

(71) Applicant: Chugai Seiyaku Kabushiki Kaisha, Tokyo (JP)

(72) Inventors: Futa Mimoto, Shizuoka (JP); Hitoshi Katada, Shizuoka (JP); Tomoyuki Igawa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 351 days.

(21) Appl. No.: 14/781,069

(22) PCT Filed: Apr. 2, 2014

(86) PCT No.: PCT/JP2014/059706
§ 371 (c)(1),
(2) Date: Sep. 29, 2015

(87) PCT Pub. No.: WO2014/163101
PCT Pub. Date: Oct. 9, 2014

(65) Prior Publication Data
US 2016/0039912 A1 Feb. 11, 2016

(30) Foreign Application Priority Data
Apr. 2, 2013 (JP) ............................ JP2013-077239

(51) Int. Cl.
*C07K 16/00* (2006.01)
*C12P 21/08* (2006.01)
*C07K 1/00* (2006.01)

(52) U.S. Cl.
CPC .......... *C07K 16/00* (2013.01); *C07K 2317/52* (2013.01); *C07K 2317/71* (2013.01); *C07K 2317/734* (2013.01); *C07K 2317/94* (2013.01); *C07K 2319/30* (2013.01); *Y02P 20/582* (2015.11)

(58) Field of Classification Search
None
See application file for complete search history.

(56) References Cited

U.S. PATENT DOCUMENTS

| | | | |
|---|---|---|---|
| 4,689,299 A | 8/1987 | Insel et al. | |
| 4,801,687 A | 1/1989 | Ngo | |
| 5,585,089 A | 12/1996 | Queen et al. | |
| 5,827,733 A | 10/1998 | Lee et al. | |
| 5,994,524 A | 11/1999 | Matsushima et al. | |
| 6,024,956 A | 2/2000 | Matsushima et al. | |
| 6,025,158 A | 2/2000 | Gonzalez et al. | |
| 6,074,642 A | 6/2000 | Wang et al. | |
| 6,096,506 A | 8/2000 | Lee et al. | |
| 6,165,745 A | 12/2000 | Ward et al. | |
| 6,245,894 B1 | 6/2001 | Matsushima et al. | |
| 6,458,355 B1 | 10/2002 | Hsei et al. | |
| 6,737,056 B1 | 5/2004 | Presta | |
| 6,821,505 B2 | 11/2004 | Ward | |
| 7,247,302 B1 | 7/2007 | Rosok et al. | |
| 7,261,893 B2 | 8/2007 | Geertruida et al. | |
| 7,282,568 B2 | 10/2007 | Teeling et al. | |
| 7,317,091 B2 | 1/2008 | Lazar et al. | |
| 7,320,789 B2 | 1/2008 | Aghajanian et al. | |
| 7,371,826 B2 | 5/2008 | Presta | |
| 7,632,499 B2 | 12/2009 | Davies et al. | |
| 7,632,924 B2 | 12/2009 | Cho et al. | |
| 7,662,925 B2 | 2/2010 | Lazar et al. | |
| 7,670,600 B2 | 3/2010 | Dell Acqua et al. | |
| 7,785,791 B2 | 8/2010 | Presta | |
| 7,807,159 B2 | 10/2010 | Chin et al. | |
| 7,820,800 B2 | 10/2010 | Rossi et al. | |
| 7,888,486 B2 | 2/2011 | Walsh et al. | |
| 7,951,917 B1 | 5/2011 | Arathoon et al. | |
| 7,960,512 B2 | 6/2011 | Stavenhagen et al. | |
| 8,147,829 B2 | 4/2012 | Hariharan et al. | |
| 8,188,231 B2 | 5/2012 | Lazar et al. | |
| 8,323,962 B2 | 12/2012 | Dell Acqua et al. | |
| 8,329,867 B2 | 12/2012 | Lazar et al. | |
| 8,367,805 B2 | 2/2013 | Chamberlain et al. | |
| 8,415,459 B2 | 4/2013 | La Vallie et al. | |
| 8,524,867 B2 | 9/2013 | Bernett et al. | |
| 8,551,485 B2 | 10/2013 | Bernett et al. | |
| 8,562,991 B2 | 10/2013 | Igawa et al. | |
| 8,568,726 B2 | 10/2013 | Beaumont et al. | |
| 8,592,562 B2 | 11/2013 | Kannan et al. | |
| 8,604,174 B2 | 12/2013 | Babcook et al. | |
| 8,637,641 B2 | 1/2014 | Dahiyat et al. | |
| 8,679,490 B2 | 3/2014 | Dennis et al. | |
| 8,735,545 B2 | 5/2014 | Lazar et al. | |
| 8,753,629 B2 | 6/2014 | Lazar et al. | |
| 8,802,823 B2 | 8/2014 | Lazar et al. | |
| 8,999,343 B2 | 4/2015 | Han et al. | |
| 9,029,515 B2 | 5/2015 | Pons et al. | |
| 9,051,373 B2 | 6/2015 | Lazar et al. | |
| 9,079,949 B1 | 7/2015 | Andrien et al. | |

(Continued)

FOREIGN PATENT DOCUMENTS

AU 2010/206050 8/2010
AU 2011/244851 11/2011
(Continued)

OTHER PUBLICATIONS

U.S. Appl. No. 15/210,360, filed Jul. 14, 2016, Igawa et al.
(Continued)

*Primary Examiner* — Chun W Dahle
(74) *Attorney, Agent, or Firm* — Fish & Richardson P.C.

(57) ABSTRACT

A polypeptide containing an antibody Fc region variant which has an amino acid sequence in which an amino acid alteration at position 238 according to EU numbering is combined with other specific amino acid alteration(s), was found to have decreased binding activities to all activating FcγRs, in particular FcγRIIa (R type), while maintaining its FcγRIIb-binding activity, when compared to a polypeptide containing a native IgG Fc region.

3 Claims, 19 Drawing Sheets
Specification includes a Sequence Listing.

(56) References Cited

U.S. PATENT DOCUMENTS

| | | |
|---|---|---|
| 9,107,861 B1 | 8/2015 | Andrien, Jr. et al. |
| 9,200,060 B2 | 12/2015 | Kannan et al. |
| 9,315,577 B2 | 4/2016 | Foltz et al. |
| 9,605,061 B2 | 3/2017 | Lazar et al. |
| 9,765,135 B2 | 9/2017 | Ruike |
| 9,890,218 B2 | 2/2018 | Mimoto et al. |
| 9,969,800 B2 | 5/2018 | Igawa et al. |
| 10,000,560 B2 | 6/2018 | Ruike et al. |
| 10,024,867 B2 | 7/2018 | Igawa |
| 10,253,100 B2 | 4/2019 | Igawa et al. |
| 10,472,623 B2 | 11/2019 | Igawa et al. |
| 10,519,229 B2 | 12/2019 | Igawa et al. |
| 10,618,965 B2 | 4/2020 | Igawa et al. |
| 10,738,111 B2 | 8/2020 | Ruike et al. |
| 10,766,960 B2 | 9/2020 | Igawa et al. |
| 10,919,953 B2 | 2/2021 | Katada et al. |
| 2002/0082396 A1 | 6/2002 | Matsushima et al. |
| 2003/0077283 A1 | 4/2003 | Ye |
| 2004/0001822 A1 | 1/2004 | Levanon et al. |
| 2004/0001839 A1 | 1/2004 | Levanon et al. |
| 2004/0002450 A1 | 1/2004 | Lazarovits et al. |
| 2004/0110226 A1 | 6/2004 | Lazar et al. |
| 2005/0032114 A1 | 2/2005 | Hinton et al. |
| 2005/0260213 A1 | 11/2005 | Koenig et al. |
| 2006/0134709 A1 | 6/2006 | Stavenhagen et al. |
| 2006/0141456 A1 | 6/2006 | Edwards et al. |
| 2006/0275283 A1 | 12/2006 | Van Vlijmen et al. |
| 2007/0009523 A1 | 1/2007 | Presta et al. |
| 2007/0148164 A1 | 6/2007 | Farrington et al. |
| 2007/0190056 A1 | 8/2007 | Kambadur et al. |
| 2007/0224188 A1 | 9/2007 | Allan et al. |
| 2007/0231329 A1 | 10/2007 | Lazar et al. |
| 2007/0237767 A1 | 10/2007 | Lazar et al. |
| 2007/0248602 A1 | 10/2007 | Lazar et al. |
| 2007/0253951 A1 | 11/2007 | Ng et al. |
| 2007/0269371 A1 | 11/2007 | Krummen et al. |
| 2008/0044417 A1 | 2/2008 | Johnson et al. |
| 2008/0050370 A1 | 2/2008 | Glaser et al. |
| 2008/0051563 A1 | 2/2008 | Lazar et al. |
| 2008/0089892 A1 | 4/2008 | Allan et al. |
| 2008/0138349 A1 | 6/2008 | Stavenhagen et al. |
| 2008/0181890 A1 | 7/2008 | Lazar et al. |
| 2008/0199471 A1 | 8/2008 | Bernett et al. |
| 2008/0292637 A1 | 11/2008 | Fishman |
| 2009/0035836 A1 | 2/2009 | Datta et al. |
| 2009/0041770 A1 | 2/2009 | Chamberlain et al. |
| 2009/0053240 A1 | 2/2009 | Lazar et al. |
| 2009/0076251 A1 | 3/2009 | Koenig et al. |
| 2009/0136485 A1 | 5/2009 | Seung et al. |
| 2009/0142340 A1 | 6/2009 | Lazar |
| 2009/0324589 A1 | 12/2009 | Igawa et al. |
| 2010/0098730 A1 | 4/2010 | Lowman et al. |
| 2010/0099147 A1 | 4/2010 | Hariharan et al. |
| 2010/0129365 A1 | 5/2010 | Kim et al. |
| 2010/0183621 A1 | 7/2010 | Jure-Kunkel et al. |
| 2010/0184959 A1 | 7/2010 | Guler-Gane et al. |
| 2010/0216187 A1 | 8/2010 | Lasters et al. |
| 2010/0249482 A1 | 9/2010 | Chung et al. |
| 2010/0292443 A1 | 11/2010 | Sabbadini et al. |
| 2010/0331527 A1 | 12/2010 | Davis et al. |
| 2011/0021755 A1 | 1/2011 | Lazar et al. |
| 2011/0027276 A1 | 2/2011 | Bernett et al. |
| 2011/0059093 A1 | 3/2011 | Bohrmann et al. |
| 2011/0105724 A1 | 5/2011 | Clegg et al. |
| 2011/0111406 A1 | 5/2011 | Igawa et al. |
| 2011/0135662 A1 | 6/2011 | Finney et al. |
| 2011/0223658 A1 | 9/2011 | Beliard et al. |
| 2011/0229489 A1 | 9/2011 | Pons et al. |
| 2012/0009188 A1 | 1/2012 | Behrens et al. |
| 2012/0093818 A1 | 4/2012 | Jackson et al. |
| 2012/0149876 A1 | 6/2012 | Kreudenstein et al. |
| 2012/0189639 A1 | 7/2012 | Schebye et al. |
| 2012/0237498 A1 | 9/2012 | Ahrens et al. |
| 2012/0244578 A1 | 9/2012 | Kannan et al. |
| 2012/0301488 A1 | 11/2012 | Zhang et al. |
| 2012/0303083 A1 | 11/2012 | Agnetti et al. |
| 2012/0321620 A1 | 12/2012 | Chu et al. |
| 2013/0011866 A1 | 1/2013 | Igawa et al. |
| 2013/0085074 A1 | 4/2013 | Walker et al. |
| 2013/0085265 A1 | 4/2013 | Jackson et al. |
| 2013/0131319 A1 | 5/2013 | Igawa et al. |
| 2013/0209489 A1 | 8/2013 | Han et al. |
| 2013/0247234 A1 | 9/2013 | McWhirter et al. |
| 2013/0259876 A1 | 10/2013 | Murphy et al. |
| 2013/0302399 A1 | 11/2013 | Feldhaus et al. |
| 2013/0303396 A1 | 11/2013 | Igawa et al. |
| 2013/0336963 A1 | 12/2013 | Igawa et al. |
| 2014/0044730 A1 | 2/2014 | Yancopoulos et al. |
| 2014/0082760 A1 | 3/2014 | McWhirter et al. |
| 2014/0086916 A1 | 3/2014 | Zha |
| 2014/0093496 A1* | 4/2014 | Mimoto ............... C07K 16/303 424/133.1 |
| 2014/0105889 A1 | 4/2014 | Igawa et al. |
| 2014/0112926 A1 | 4/2014 | Liu |
| 2014/0127209 A1 | 5/2014 | Grabstein et al. |
| 2014/0199294 A1 | 7/2014 | Mimoto et al. |
| 2014/0227292 A1 | 8/2014 | Flanagan et al. |
| 2014/0234340 A1 | 8/2014 | Igawa et al. |
| 2014/0255398 A1 | 9/2014 | Igawa et al. |
| 2014/0271459 A1 | 9/2014 | Dutzar et al. |
| 2014/0294833 A1 | 10/2014 | Desjarlais et al. |
| 2014/0335089 A1 | 11/2014 | Igawa et al. |
| 2014/0356371 A1 | 12/2014 | Swergold et al. |
| 2014/0363426 A1 | 12/2014 | Moore et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0079088 A1 | 3/2015 | Lowman et al. |
| 2015/0166636 A1 | 6/2015 | Igawa et al. |
| 2015/0166654 A1* | 6/2015 | Igawa ............... C07K 16/005 530/387.3 |
| 2015/0203577 A1 | 7/2015 | Igawa et al. |
| 2015/0210763 A1 | 7/2015 | Kuramochi et al. |
| 2015/0252107 A1 | 9/2015 | Stevis et al. |
| 2015/0299296 A1* | 10/2015 | Katada ............... C07K 16/00 530/387.3 |
| 2015/0299313 A1 | 10/2015 | Igawa et al. |
| 2015/0344570 A1 | 12/2015 | Igawa et al. |
| 2015/0353630 A1 | 12/2015 | Igawa et al. |
| 2016/0039912 A1* | 2/2016 | Mimoto ............... C07K 16/00 424/134.1 |
| 2016/0046693 A1 | 2/2016 | Igawa et al. |
| 2016/0053023 A1 | 2/2016 | Rosenthal et al. |
| 2016/0200807 A1 | 7/2016 | Ruike et al. |
| 2016/0229908 A1 | 8/2016 | Igawa et al. |
| 2016/0229915 A1 | 8/2016 | Igawa et al. |
| 2016/0244526 A1 | 8/2016 | Igawa et al. |
| 2016/0326237 A1 | 11/2016 | Rosenthal et al. |
| 2017/0022270 A1 | 1/2017 | Igawa et al. |
| 2017/0181987 A1 | 6/2017 | Camilla et al. |
| 2018/0155451 A1 | 6/2018 | Mimoto et al. |
| 2018/0258163 A1 | 9/2018 | Igawa et al. |
| 2019/0112393 A1 | 4/2019 | Igawa et al. |
| 2019/0185557 A1 | 6/2019 | Igawa et al. |
| 2019/0218309 A1 | 7/2019 | Igawa et al. |
| 2019/0233525 A1 | 8/2019 | Igawa et al. |
| 2019/0359704 A1 | 11/2019 | Igawa et al. |
| 2020/0199241 A1 | 6/2020 | Igawa et al. |
| 2021/0122812 A1 | 4/2021 | Igawa et al. |
| 2021/0261648 A1 | 8/2021 | Katada et al. |

FOREIGN PATENT DOCUMENTS

| | | |
|---|---|---|
| AU | 2014/250434 | 10/2015 |
| AU | 2015/227424 | 10/2015 |
| AU | 2012/222252 | 8/2016 |
| CA | 2 721 052 | 10/2009 |
| CA | 2 794 860 | 10/2011 |
| CA | 2 815 266 | 5/2012 |
| CA | 2 827 923 | 8/2012 |
| CA | 2 831 770 | 10/2012 |
| CN | 1156460 | 8/1997 |
| CN | 1291198 | 4/2001 |

(56) References Cited

FOREIGN PATENT DOCUMENTS

| | | |
|---|---|---|
| CN | 1763097 | 4/2006 |
| CN | 101001873 | 7/2007 |
| CN | 101014619 | 8/2007 |
| CN | 101098890 | 1/2008 |
| CN | 101230102 | 7/2008 |
| CN | 101277976 | 10/2008 |
| CN | 101282992 | 10/2008 |
| CN | 100455598 | 1/2009 |
| CN | 101479381 | 7/2009 |
| CN | 101511871 | 8/2009 |
| CN | 101932593 | 12/2010 |
| CN | 102056946 | 5/2011 |
| CN | 102149729 | 8/2011 |
| CN | 102325793 | 1/2012 |
| CN | 102918057 | 2/2013 |
| CN | 102993304 | 3/2013 |
| CN | 103097415 | 5/2013 |
| CN | 103221426 | 7/2013 |
| CN | 103492565 | 1/2014 |
| CN | 103827300 | 5/2014 |
| CN | 103975060 | 8/2014 |
| CN | 102633880 | 2/2015 |
| CO | 07124506 | 11/2007 |
| CO | 11080753 | 6/2011 |
| CO | 13047993 | 3/2013 |
| CO | 15075851 | 4/2015 |
| EA | 004317 | 2/2004 |
| EA | 2008/01027 | 10/2008 |
| EP | 0 770 628 | 9/2006 |
| EP | 1 787 998 | 5/2007 |
| EP | 2 006 381 | 12/2008 |
| EP | 2 189 526 | 5/2010 |
| EP | 2 196 541 | 6/2010 |
| EP | 2 202 245 | 6/2010 |
| EP | 2 206 775 A | 7/2010 |
| EP | 2 275 443 | 1/2011 |
| EP | 2 314 618 | 4/2011 |
| EP | 2 366 713 | 9/2011 |
| EP | 2 368 911 | 9/2011 |
| EP | 2 409 990 A | 1/2012 |
| EP | 2 431 393 | 3/2012 |
| EP | 2 471 813 A | 7/2012 |
| EP | 2 543 730 | 1/2013 |
| EP | 2 647 706 | 10/2013 |
| EP | 2 679 681 | 1/2014 |
| EP | 2 698 431 | 2/2014 |
| EP | 2 728 002 | 5/2014 |
| EP | 1 509 770 B | 7/2014 |
| EP | 2 762 166 | 8/2014 |
| EP | 2 762 493 A | 8/2014 |
| EP | 2 762 564 | 8/2014 |
| EP | 2 765 192 A | 8/2014 |
| EP | 2 818 183 A | 12/2014 |
| EP | 2 853 898 | 4/2015 |
| EP | 2 889 377 | 7/2015 |
| EP | 2 940 043 | 11/2015 |
| EP | 2 940 135 A | 11/2015 |
| EP | 3 156 072 A | 4/2017 |
| EP | 3 240 804 | 11/2017 |
| JP | H01-144991 | 6/1989 |
| JP | H02-501112 | 4/1990 |
| JP | H02-163085 | 6/1990 |
| JP | H07-217799 | 8/1996 |
| JP | H08-217799 | 8/1996 |
| JP | 2003-512019 | 4/2003 |
| JP | 2005-510212 | 4/2005 |
| JP | 2006-512407 | 4/2006 |
| JP | 2006-517525 | 7/2006 |
| JP | 2006-519583 | 8/2006 |
| JP | 2006-524039 | 10/2006 |
| JP | 3865418 | 1/2007 |
| JP | 2007-532139 | 11/2007 |
| JP | 2008-503720 | 2/2008 |
| JP | 2008-505174 | 2/2008 |
| JP | 2008-510466 | 4/2008 |
| JP | 2008-511292 | 4/2008 |
| JP | 2009-511067 | 3/2009 |
| JP | 2009-541352 | 11/2009 |
| JP | 2010-500020 | 1/2010 |
| JP | 2010-079667 | 3/2010 |
| JP | 2010-514460 | 5/2010 |
| JP | 2010-250830 | 11/2010 |
| JP | 2011-504096 | 2/2011 |
| JP | 2011-507963 | 3/2011 |
| JP | 2011-184418 | 9/2011 |
| JP | 2012-505833 | 3/2012 |
| JP | 2012-512641 | 6/2012 |
| JP | 4961501 | 6/2012 |
| JP | 5048866 | 10/2012 |
| JP | 2013-518606 | 5/2013 |
| JP | 2013-521772 | 6/2013 |
| JP | 2013-531486 | 8/2013 |
| JP | 2013-537425 | 10/2013 |
| JP | 2014-055145 | 3/2014 |
| JP | 2014-528906 | 10/2014 |
| JP | 2016-026190 | 2/2016 |
| JP | 2018-517674 | 7/2018 |
| JP | 6433297 | 12/2018 |
| JP | 2019-523295 | 8/2019 |
| KR | 2011/0004435 | 1/2011 |
| KR | 2011/0103431 | 9/2011 |
| KR | 2012-0035192 | 4/2012 |
| KR | 2014/0005864 | 1/2014 |
| RU | 2236222 | 9/2004 |
| RU | 2004/128259 | 8/2005 |
| RU | 2005/112742 | 1/2006 |
| RU | 2006/142852 | 6/2008 |
| RU | 2337107 | 10/2008 |
| RU | 2007/121679 | 12/2008 |
| RU | 2360925 | 7/2009 |
| RU | 2367667 | 9/2009 |
| RU | 2390527 | 5/2010 |
| RU | 2398777 | 9/2010 |
| RU | 2009/112723 | 10/2010 |
| RU | 2422460 | 6/2011 |
| RU | 2010/150931 | 6/2012 |
| SG | 183867 | 10/2012 |
| SG | 192945 | 9/2013 |
| TW | 416960 | 1/2001 |
| TW | 2010/00127 | 1/2010 |
| TW | 2011/16625 | 5/2011 |
| TW | 2012/02419 | 1/2012 |
| TW | 2016/43190 | 12/2016 |
| TW | 2017/12032 | 4/2017 |
| TW | 1605057 | 11/2017 |
| TW | 2018/08331 | 3/2018 |
| TW | 2018/08992 | 3/2018 |
| TW | 2018/19409 | 6/2018 |
| TW | 1656133 | 4/2019 |
| TW | 2020/39553 | 11/2020 |
| WO | WO 88/004692 | 6/1988 |
| WO | WO 91/13631 | 9/1991 |
| WO | WO 94/21681 | 9/1994 |
| WO | WO 95/002187 | 1/1995 |
| WO | WO 1995/14710 | 6/1995 |
| WO | WO 1995/29697 | 11/1995 |
| WO | WO 96/02576 | 2/1996 |
| WO | WO 97/34631 | 9/1997 |
| WO | WO 98/05787 | 2/1998 |
| WO | WO 99/40117 | 8/1999 |
| WO | WO 99/51642 | 10/1999 |
| WO | WO 99/58572 | 11/1999 |
| WO | WO 00/15214 | 3/2000 |
| WO | WO 00/42072 | 7/2000 |
| WO | WO 01/70968 | 9/2001 |
| WO | WO 02/09641 | 2/2002 |
| WO | WO 02/060919 | 8/2002 |
| WO | WO 03/027248 | 4/2003 |
| WO | WO 2003/057881 | 7/2003 |
| WO | WO 03/070760 | 8/2003 |
| WO | WO 03/074679 | 9/2003 |
| WO | WO 2003/105757 | 12/2003 |
| WO | WO 2004/007553 | 1/2004 |
| WO | WO 2004/024890 | 3/2004 |

(56) References Cited

FOREIGN PATENT DOCUMENTS

| | | |
|---|---|---|
| WO | WO 2004/029207 | 4/2004 |
| WO | WO 2004/035752 | 4/2004 |
| WO | WO 2004/037861 | 5/2004 |
| WO | WO 2004/058797 | 7/2004 |
| WO | WO 2004/063351 | 7/2004 |
| WO | WO 2004/092219 | 10/2004 |
| WO | WO 2004/099249 | 11/2004 |
| WO | WO 2004/108157 | 12/2004 |
| WO | WO 2005/023193 | 3/2005 |
| WO | WO 2005/037867 | 4/2005 |
| WO | WO 2005/047307 | 5/2005 |
| WO | WO 2005/047327 | 5/2005 |
| WO | WO 2005/056606 | 6/2005 |
| WO | WO 2005/056759 | 6/2005 |
| WO | WO 2005/059106 | 6/2005 |
| WO | WO 2005/066204 | 7/2005 |
| WO | WO 2005/070963 | 8/2005 |
| WO | WO 2005/077981 | 8/2005 |
| WO | WO 2005/092925 | 10/2005 |
| WO | WO 2005/094446 | 10/2005 |
| WO | WO 2005/115452 | 12/2005 |
| WO | WO 2005/123780 | 12/2005 |
| WO | WO 2006/004663 | 1/2006 |
| WO | WO 2006/015371 | 2/2006 |
| WO | WO 2006/016644 | 2/2006 |
| WO | WO 2006/019447 | 2/2006 |
| WO | WO 2006/020114 | 2/2006 |
| WO | WO 2006/023403 | 3/2006 |
| WO | WO 2006/023420 | 3/2006 |
| WO | WO 2006/031370 | 3/2006 |
| WO | WO 2006/036291 | 4/2006 |
| WO | WO 2006/047350 | 5/2006 |
| WO | WO 2006/050166 | 5/2006 |
| WO | WO 2006/053301 | 5/2006 |
| WO | WO 2006/071877 | 7/2006 |
| WO | WO 2006/076594 | 7/2006 |
| WO | WO 2006/083182 | 8/2006 |
| WO | WO 2006/083183 | 8/2006 |
| WO | WO 2006/085938 | 8/2006 |
| WO | WO 2006/085967 | 8/2006 |
| WO | WO 2006/088478 | 8/2006 |
| WO | WO 2006/088494 | 8/2006 |
| WO | WO 2006/102095 | 9/2006 |
| WO | WO 2006/105338 | 10/2006 |
| WO | WO 2006/106905 | 10/2006 |
| WO | WO 2006/113643 | 10/2006 |
| WO | WO 2006/116260 | 11/2006 |
| WO | WO 2006/116269 | 11/2006 |
| WO | WO 2006/130834 | 12/2006 |
| WO | WO 2006/133486 | 12/2006 |
| WO | WO 2007/001422 | 1/2007 |
| WO | WO 2007/008943 | 1/2007 |
| WO | WO 2007/021841 | 2/2007 |
| WO | WO 2007/022520 | 2/2007 |
| WO | WO 2007/024249 | 3/2007 |
| WO | WO 2007/024535 | 3/2007 |
| WO | WO 2007/041635 | 4/2007 |
| WO | WO 2007/044411 | 4/2007 |
| WO | WO 2007/044616 | 4/2007 |
| WO | WO 2007/047112 | 4/2007 |
| WO | WO 2007/047578 | 4/2007 |
| WO | WO 2007/084253 | 7/2007 |
| WO | WO 2007/092772 | 8/2007 |
| WO | WO 2007/114319 | 10/2007 |
| WO | WO 2007/114325 | 10/2007 |
| WO | WO 2007/150015 | 12/2007 |
| WO | WO 2007/150016 | 12/2007 |
| WO | WO 2008/002933 | 1/2008 |
| WO | WO 2008/017963 | 2/2008 |
| WO | WO 2008/022152 | 2/2008 |
| WO | WO 2008/030706 | 3/2008 |
| WO | WO 2008/031056 | 3/2008 |
| WO | WO 2008/036688 | 3/2008 |
| WO | 2008-519860 | 6/2008 |
| WO | WO 2008/091798 | 7/2008 |
| WO | WO 2008/091954 | 7/2008 |
| WO | WO 2008/092117 | 7/2008 |
| WO | WO 2008/098115 | 8/2008 |
| WO | WO 2008/121160 | 10/2008 |
| WO | WO 2008/130969 | 10/2008 |
| WO | WO 2008/143954 | 11/2008 |
| WO | WO 2008/150494 | 12/2008 |
| WO | WO 2009/000098 | 12/2008 |
| WO | WO 2009/000099 | 12/2008 |
| WO | WO 2009/008529 | 1/2009 |
| WO | WO 2009/026117 | 2/2009 |
| WO | WO 2009/032145 | 3/2009 |
| WO | WO 2009/032782 | 3/2009 |
| WO | WO 2009/041062 | 4/2009 |
| WO | WO 2009/041643 | 4/2009 |
| WO | WO 2009/053358 | 4/2009 |
| WO | WO 2009/058346 | 5/2009 |
| WO | WO 2009/058492 | 5/2009 |
| WO | WO 2009/062083 | 5/2009 |
| WO | WO 2009/086320 | 7/2009 |
| WO | WO 2009/089846 | 7/2009 |
| WO | WO 2009/095235 | 8/2009 |
| WO | WO 2009/125825 | 10/2009 |
| WO | WO 2009/131702 | 10/2009 |
| WO | WO 2009/137880 | 11/2009 |
| WO | WO 2009/139822 | 11/2009 |
| WO | WO 2009/155513 | 12/2009 |
| WO | WO 2010/015608 | 2/2010 |
| WO | WO 2010/033736 | 3/2010 |
| WO | WO 2010/035769 | 4/2010 |
| WO | WO 2010/045193 | 4/2010 |
| WO | WO 2010/058860 | 5/2010 |
| WO | WO 2010/070094 | 6/2010 |
| WO | WO 2010/077854 | 7/2010 |
| WO | WO 2010/081173 | 7/2010 |
| WO | WO 2010/085682 | 7/2010 |
| WO | WO 2010/106180 | 9/2010 |
| WO | WO 2010/106812 | 9/2010 |
| WO | WO 2010/107109 | 9/2010 |
| WO | WO 2010/107110 | 9/2010 |
| WO | WO 2010/136831 | 12/2010 |
| WO | WO 2010/151338 | 12/2010 |
| WO | WO 2010/151792 | 12/2010 |
| WO | WO 2011/008517 | 1/2011 |
| WO | WO 2011/021009 | 2/2011 |
| WO | WO 2011/043643 | 4/2011 |
| WO | WO 2011/044368 | 4/2011 |
| WO | WO 2011/091078 | 7/2011 |
| WO | WO 2011/100271 | 8/2011 |
| WO | WO 2011/107989 | 9/2011 |
| WO | WO 2011/108714 | 9/2011 |
| WO | WO 2011/111007 | 9/2011 |
| WO | WO 2011/122011 | 10/2011 |
| WO | WO 2011/150008 | 12/2011 |
| WO | WO 2011/151432 | 12/2011 |
| WO | WO 2012/016227 | 2/2012 |
| WO | WO 2012/024242 | 2/2012 |
| WO | WO 2012/033953 | 3/2012 |
| WO | WO 2012/044831 | 4/2012 |
| WO | WO 2012/058768 | 5/2012 |
| WO | WO 2012/073992 | 6/2012 |
| WO | WO 2012/093704 | 7/2012 |
| WO | WO 2012/115241 | 8/2012 |
| WO | WO 2012/125850 | 9/2012 |
| WO | WO 2012/132067 | 10/2012 |
| WO | WO 2012/133782 | 10/2012 |
| WO | WO 2012/151481 | 11/2012 |
| WO | WO 2013/002362 | 1/2013 |
| WO | WO 2013/004842 | 1/2013 |
| WO | WO 2013/012733 | 1/2013 |
| WO | WO 2013/046704 | 4/2013 |
| WO | WO 2013/046722 | 4/2013 |
| WO | WO 2013/047729 | 4/2013 |
| WO | WO 2013/047748 | 4/2013 |
| WO | WO 2013/047752 | 4/2013 |
| WO | WO 2013/063702 | 5/2013 |
| WO | WO 2013/081143 | 6/2013 |
| WO | WO 2013/125667 | 8/2013 |
| WO | WO 2013/138680 | 9/2013 |

(56) References Cited

FOREIGN PATENT DOCUMENTS

| WO | WO 2013/138681 | 9/2013 | | |
|---|---|---|---|---|
| WO | WO 2013/152001 | 10/2013 | | |
| WO | WO 2013/166099 | 11/2013 | | |
| WO | WO 2013/180200 | 12/2013 | | |
| WO | WO 2013/180201 | 12/2013 | | |
| WO | WO 2013/186719 | 12/2013 | | |
| WO | WO 2013/192240 | 12/2013 | | |
| WO | WO-2013180200 A1 * | 12/2013 | ........... | C07K 16/005 |
| WO | WO 2014/006217 | 1/2014 | | |
| WO | WO 2014/028354 | 2/2014 | | |
| WO | WO 2014/030728 | 2/2014 | | |
| WO | WO 2014/030750 | 2/2014 | | |
| WO | WO 2014/043344 | 3/2014 | | |
| WO | WO 2014/066744 | 5/2014 | | |
| WO | WO 2014/071206 | 5/2014 | | |
| WO | WO 2014/074532 | 5/2014 | | |
| WO | WO 2014/100689 | 6/2014 | | |
| WO | WO 2014/104165 | 7/2014 | | |
| WO | WO 2014/114651 | 7/2014 | | |
| WO | WO 2014/140366 | 9/2014 | | |
| WO | WO 2014/144080 | 9/2014 | | |
| WO | WO 2014/144577 | 9/2014 | | |
| WO | WO 2014/144903 | 9/2014 | | |
| WO | WO 2014/145159 | 9/2014 | | |
| WO | WO 2014/145806 | 9/2014 | | |
| WO | WO 2014/150983 | 9/2014 | | |
| WO | WO 2014/163101 | 10/2014 | | |
| WO | WO 2014/164959 | 10/2014 | | |
| WO | WO 2014/1843 84 | 11/2014 | | |
| WO | WO 2014/182676 | 11/2014 | | |
| WO | WO 2014/186599 | 11/2014 | | |
| WO | WO 2014/190441 | 12/2014 | | |
| WO | WO 2015/022658 | 2/2015 | | |
| WO | WO 2015/042250 | 3/2015 | | |
| WO | WO 2015/077491 | 5/2015 | | |
| WO | WO 2015/083764 | 6/2015 | | |
| WO | WO 2015/111008 | 7/2015 | | |
| WO | WO 2015/134894 | 9/2015 | | |
| WO | WO 2015/162590 | 10/2015 | | |
| WO | WO 2015/190538 | 12/2015 | | |
| WO | WO 2016/000813 | 1/2016 | | |
| WO | WO 2016/073853 | 5/2016 | | |
| WO | WO 2016/073879 | 5/2016 | | |
| WO | WO 2016/073906 | 5/2016 | | |
| WO | WO 2016/092439 | 6/2016 | | |
| WO | WO 2016/098356 | 6/2016 | | |
| WO | WO 2016/098357 | 6/2016 | | |
| WO | WO 2016/125495 | 8/2016 | | |
| WO | WO 2016/164358 | 10/2016 | | |
| WO | WO 2016/168613 | 10/2016 | | |
| WO | WO 2016/170176 | 10/2016 | | |
| WO | WO 2016/194992 | 12/2016 | | |
| WO | WO 2017/046994 | 3/2017 | | |
| WO | WO 2017/049011 | 3/2017 | | |
| WO | WO 2017/091719 | 6/2017 | | |
| WO | WO 2017/104783 | 6/2017 | | |
| WO | WO 2017/110981 | 6/2017 | | |
| WO | WO 2017/120523 | 7/2017 | | |
| WO | WO 2017/217525 | 12/2017 | | |
| WO | WO 2017/218592 | 12/2017 | | |
| WO | WO 2018/025982 | 2/2018 | | |
| WO | WO 2018/169993 | 9/2018 | | |
| WO | WO 2019/098212 | 5/2019 | | |
| WO | WO 2019/198807 | 10/2019 | | |
| WO | WO 2020/032230 | 2/2020 | | |

OTHER PUBLICATIONS

U.S. Appl. No. 15/210,353, filed Jul. 14, 2016, Igawa et al.
Bogdanovich et al., "Functional improvement of dystrophic muscle by myostatin blockade," *Nature*, Nov. 28, 2002;420(6914):418-21.
Fillipovich, Biochemical basis of human life, VLADOS, 2005:49-50 (with English translation).

Hoodless et al., "Mechanism and function of signaling by the TGF beta superfamily," *Curr Top Microbiol Immunol.*, 1998;228:235-72.
Kingsley et al., "The TGF-beta superfamily: new members, new receptors, and new genetic tests of function in different organisms," *Genes Dev.*, Jan. 1994;8(2): 133-46.
Lee et al., "Genetic analysis of the role of proteolysis in the activation of latent myostatin," *PLoS One*, Feb. 20, 2008;3(2):e1628.
Lee et al., "Regulation of myostatin activity and muscle growth," *Proc Natl Acad Sci U S A.*, Jul. 31, 2001;98(16):9306-11.
Matsumiya et al., "Structural comparison of fucosylated and nonfucosylated Fc fragments of human immunoglobulin G1," *J Mol Biol.*, May 4, 2007;368(3):767-79. Epub Feb. 22, 2007.
McCroskery et al., "Improved muscle healing through enhanced regeneration and reduced fibrosis in myostatin-null mice," *J Cell Sci.*, Aug. 1, 2005;118(Pt 15):3531-41.
McPherron et al., "Regulation of skeletal muscle mass in mice by a new TGF-beta superfamily member," *Nature*, May 1, 1997;387(6628): 83-90.
McPherron et al., "Double muscling in cattle due to mutations in the myostatin gene," *Proc Natl Acad Sci U S A.*, Nov. 11, 1997;94(23): 12457-61.
Szlama et al., "Latent myostatin has significant activity and this activity is controlled more efficiently by WFIKKN1 than by WFIKKN2," *FEBS J.*, Aug. 2013;280(16):3822-39. doi: 10.1111/febs.12377. Epub Jul. 5, 2013.
Wagner et al., "Loss of myostatin attenuates severity of muscular dystrophy in mdx mice," *Ann Neurol.*, Dec. 2002;52(6):832-6.
Whittemore et al., "Inhibition of myostatin in adult mice increases skeletal muscle mass and strength," *Biochem Biophys Res Commun.*, Jan. 24, 2003;300(4):965-71.
Zimmers et al., "Induction of cachexia in mice by systemically administered myostatin," *Science*, May 24, 2002;296(5572): 1486-8.
Amigorena et al., "Fc gamma RII expression in resting and activated B lymphocytes," Eur J Immunol., Aug. 1989;19(8):1379-85.
Amigorena et al., "Cytoplasmic domain heterogeneity and functions of IgG Fc receptors in B lymphocytes," Science, Jun. 26, 1992;256(5065):1808-12.
Armour et al., "Differential binding to human FcgammaRIIa and FcgammaRIIb receptors by human IgG wildtype and mutant antibodies," Mol Immunol., Dec. 2003;40(9):585-93.
Blank et al., Decreased transcription of the human FCGR2B gene mediated by the -343 G/C promoter polymorphism and association with systemic lupus erythematosus. Hum Genet., Jul. 2005;117(2-3):220-7. Epub May 14, 2005.
Boruchov et al., "Activating and inhibitory IgG Fc receptors on human DCs mediate opposing functions," J Clin Invest., Oct. 2005;115(10):2914-23. Epub Sep. 15, 2005.
Boumpas et al., "A short course of BG9588 (anti-CD40 ligand antibody) improves serologic activity and decreases hematuria in patients with proliferative lupus glomerulonephritis," Arthritis Rheum., Mar. 2003;48(3):719-27.
Bruhns et al., Specificity and affinity of human Fcgamma receptors and their polymorphic variants for human IgG subclasses, Blood, Apr. 16, 2009;113(16):3716-25. doi: 10.1182/blood-2008-09-179754. Epub Nov. 18, 2008.
Burmeister et al., "Crystal structure of the complex of rat neonatal Fc receptor with Fc," Nature, Nov. 24, 1994;372(6504):379-83.
Cartron et al., "Therapeutic activity of humanized anti-CD20 monoclonal antibody and polymorphism in IgG Fc receptor FcgammaRIIIa gene," Blood, Feb. 1, 2002;99(3):754-8.
Cemerski et al., "Suppression of mast cell degranulation through a dual-targeting tandem IgE-IgG Fc domain biologic engineered to bind with high affinity to FcγRIIb," Immunol Lett., Mar. 30, 2012;143(1):34-43, doi: 10,1016/j.imlet.2012.01.008, Epub Jan. 25, 2012.
Chen et al., "Association of a transmembrane polymorphism of Fcgamma receptor IIb (FCGR2B) with systemic lupus erythematosus in Taiwanese patients," Arthritis Rheum., Dec. 2006;54(12):3908-17.
Chu et al., "Inhibition of B cell receptor-mediated activation of primary human B cells by coengagement of CD19 and Fcgam-

(56) References Cited

OTHER PUBLICATIONS maRIIb with Fc-engineered antibodies," Mol Immunol., Sep. 2008;45(15):3926-33. doi: 10.1016/j.molimm.2008.06.027. Epub Aug. 8, 2008.
Chu et al., "Reduction of total IgE by targeted coengagement of IgE B-cell receptor and FcγRIIb with Fc-engineered antibody," J Allergy Clin Immunol., Apr. 2012; 129(4): 1102-15. doi: 10.1016/j.jaci.2011.11.029. Epub Jan. 16, 2012.
Chuntharapai et al., "Isotype-dependent inhibition of tumor growth in vivo by monoclonal antibodies to death receptor 4," J Immunol., Apr. 15, 2001;166(8):4891-8.
Clark, "IgG effector mechanisms," Chem Immunol., 1997;65:88-110.
Clark, "An alignment of IgG sequences from Human, Mouse and Rat," Part II Immunoglobulin lectures (v4), pp. 5(i)-5(ii) [retrieved on Jul. 25, 2014], Retrieved from the Internet: http://www.path.cam.ac.uk/~mrc7/lecturenotes/handout1a.pdf.
Clarkson et al., "Blockade of clearance of immune complexes by an anti-Fc gamma receptor monoclonal antibody," J Exp Med., Aug. 1, 1986;164(2):474-89.
Clynes et al., "Fc receptors are required in passive and active immunity to melanoma," Proc Natl Acad Sci USA, 95(2):652-6 (1998).
Clynes et al., "Inhibitory Fc receptors modulate in vivo cytotoxicity against tumor targets," Nat Med., 6(4):443-6 (2000).
Dall'Acqua et al., "Increasing the affinity of a human IgG1 for the neonatal Fc receptor: biological consequences," J. Immunol., 169(9):5171-80 (2002).
Dall'Acqua et al., "Properties of human IgG1s engineered for enhanced binding to the neonatal Fc receptor (FcRn)," J Biol Chem., Aug. 18, 2006;281(33):23514-24. Epub Jun. 21, 2006.
Datta-Mannan et al., "Monoclonal antibody clearance. Impact of modulating the interaction of IgG with the neonatal Fc receptor," J Biol Chem., Jan. 19, 2007;282(3): 1709-17. Epub Nov. 29, 2006.
Davis et al., "SEEDbodies: fusion proteins based on strand-exchange engineered domain (SEED) CH3 heterodimers in an Fc analogue platform for asymmetric binders or immunofusions and bispecific antibodies," Protein Eng Des Sel., Apr. 2010;23(4): 195-202. doi: 10.1093/protein/gzp094. Epub Feb. 4, 2010.
Deng et al., "Pharmacokinetics of humanized monoclonal anti-tumor necrosis factor-{alpha} antibody and its neonatal Fc receptor variants in mice and cynomolgus monkeys," Drug Metab Dispos., Apr. 2010;38(4):600-5. doi: 10.1124/dmd.109.031310. Epub Jan. 13, 2010.
Desai et al., "Fc gamma receptor IIB on dendritic cells enforces peripheral tolerance by inhibiting effector T cell responses," J Immunol., May 15, 2007;178(10):6217-26.
Dhodapkar et al., "Selective blockade of inhibitory Fcgamma receptor enables human dendritic cell maturation with IL-12p70 production and immunity to antibody-coated tumor cells," Proc Natl Acad Sci USA, Feb. 22, 2005;102(8):2910-5. Epub Feb. 9, 2005.
Duffau et al., "Platelet CD154 potentiates interferon-alpha secretion by plasmacytoid dendritic cells in systemic lupus erythematosus," Sci Transl Med., Sep. 1, 2010;2(47):47ra63. doi: 10.1126/scitranslmed.3001001.
Floto et al., "Loss of function of a lupus-associated FcgammaRIIb polymorphism through exclusion from lipid rafts," Nat Med., Oct. 2005;11(10):1056-8. Epub Sep. 18, 2005.
Fournier et al., "Activation of human peripheral IgM+ B cells is transiently inhibited by BCR-independent aggregation of Fc gammaRIIB," J Immunol., Oct. 15, 2008; 181(8):5350-9.
Ghetie et al., "Increasing the serum persistence of an IgG fragment by random mutagenesis," Nat. Biotechnol., 15(7):637-40 (1997).
Greenwood et al., "Structural motifs involved in human IgG antibody effector functions," Eur J Immunol., May 1993;23(5): 1098-104.
Gunasekaran et al., "Enhancing antibody Fc heterodimer formation through electrostatic steering effects: applications to bispecific molecules and monovalent IgG," J Biol Chem., 285(25): 19637-46 (2010).

Haakenstad et al., "The disappearance kinetics and glomerular deposition of small-latticed soluble immune complexes," Immunology, Nov. 1982;47(3):407-14.
Hamilton, "Molecular engineering: applications to the clinical laboratory," Clin Chem., Sep. 1993;39(9):1988-97.
Hanson et al., "Catalytic antibodies and their applications," Curr. Opin. Biotechnol., Dec. 2005;16(6):631-6. Epub Oct. 21, 2005.
Heyman, "Feedback regulation by IgG antibodies," Immunol Lett, Aug. 5, 2003;88(2):157-61.
Hinton et al., "An engineered human IgG1 antibody with longer serum half-life," J. Immunol., 176(1):346-56 (2006).
Horn et al., "Analysis of the binding of pro-urokinase and urokinase-plasminogen activator inhibitor-1 complex to the low density lipoprotein receptor-related protein using a Fab fragment selected from a phage-displayed Fab library," J Biol Chem., May 19, 1995;270(20): 11770-5.
Horton et al., "Potent in vitro and in vivo activity of an Fc-engineered anti-CD19 monoclonal antibody against lymphoma and leukemia," Cancer Res., Oct. 2008 1;68(19):8049-57. doi: 10.1158/0008-5472. CAN-08-2268.
Igawa et al., "Antibody recycling by engineered pH-dependent antigen binding improves the duration of antigen neutralization," Nat Biotechnol., Nov. 2010;28(1 1): 1203-7. doi: 10.1038/nbt.1691. Epub Oct. 17, 2010.
Igawa et al., "Antibody Optimization Technologies for Developing Next Generation Antibody Therapeutics," Bio Industry, 28(7): 15-21 (2011) (with English translation).
Ito et al., "The His-probe method: effects of histidine residues introduced into the complementarity-determining regions of antibodies on antigen-antibody interactions at different pH values," FEBS Lett, 309:85-88 (1992).
Janeway et al., Immunobiology, The Immune System in Health and Disease, $3^{rd}$ Edition, 1997 Garland Publishing Inc., pp. 3:1-3:11.
Jefferis et al., "Interaction sites on human IgG-Fc for Fc gamma R: current models," Immunol Lett., Jun. 3, 2002;82(1-2):57-65.
Kim et al., "Antibody Engineering for the Development of Therapeutic Antibodies," Mol. Cells, 20(1): 17-29 (2005).
Kohrt et al., "Stimulation of natural killer cells with a CD137-specific antibody enhances trastuzumab efficacy in xenotransplant models of breast cancer," J Clin Invest., Mar. 1, 2012;122(3):1066-75. doi: 10.1172/JCI61226. Epub Feb. 13, 2012.
Lazar et al., "Engineered antibody Fc variants with enhanced effector function," Proc Natl Acad Sci USA, Mar. 2006;103(11):4005-10. Epub Mar. 6, 2006.
Li et al., "CD72 down-modulates BCR-induced signal transduction and diminishes survival in primary mature B lymphocytes," J Immunol., May 1, 2006; 176(9):5321-8.
Li et al., "Inhibitory Fcγ receptor engagement drives adjuvant and anti-tumor activities of agonistic CD40 antibodies," Science, Aug. 19, 2011;333(6045): 1030-4. doi: 10.1126/science.1206954.
Li et al., "Apoptotic and antitumor activity of death receptor antibodies require inhibitory Fcγ receptor engagement," Proc Natl Acad Sci U S A., Jul. 3, 2012;109(27):10966-71. doi: 10.1073/pnas.1208698109. Epub Jun. 20, 2012.
Mackay et al., "Selective dysregulation of the FcgammaIIB receptor on memory B cells in SLE," J Exp Med., Sep. 4, 2006;203(9):2157-64. Epub Aug. 21, 2006.
Malbec et al., "Antibodies against growth factor receptors can inhibit the proliferation of transformed cells via a cis-interaction with inhibitory FcR," Immunol Lett., Mar. 30, 2012; 143(1):28-33.
Manger et al., "Fcgamma receptor IIa polymorphism in Caucasian patients with systemic lupus erythematosus: association with clinical symptoms," Arthritis Rheum., Jul. 1998;41(7): 1181-9.
Marvin et al., "Recombinant approaches to IgG-like bispecific antibodies," Acta Pharmacol Sin., Jun. 2005;26(6):649-58.
Meyer et al., "Bevacizumab immune complexes activate platelets and induce thrombosis in FCGR2A transgenic mice," J Thromb Haemost, Jan. 2009;7(l):171-81. doi: 10.1111/j.1538-7836.2008.03212.x. Epub Oct. 30, 2008.
Mi et al., "Targeting the neonatal fc receptor for antigen delivery using engineered fc fragments," J Immunol., Dec. 1, 2008;181(11):7550-61.

(56) References Cited

OTHER PUBLICATIONS

Mimoto et al., "Engineered antibody Fc variant with selectively enhanced FcγRIIb binding over both FcγRIIa(R131) and FcγRIIa(H131)," Protein Eng Des Sel., Oct. 2013;26(10):589-98. doi: 10.1093/protein/gz1022. Epub Jun. 5, 2013.

Morgan et al., "The N-terminal end of the CH2 domain of chimeric human IgG1 anti-HLA-DR is necessary for C1q, Fc gamma RI and Fc gamma RIII binding," Immunology, Oct. 1995;86(2):319-24.

Muta et al., "A 13-amino-acid motif in the cytoplasmic domain of Fc gamma RIIB modulates B-cell receptor signaling," Nature,Mar. 3, 1994;368(6466):70-3.

Nakamura et al., "Fcgamma receptor IIB-deficient mice develop Goodpasture's syndrome upon immunization with type IV collagen: a novel murine model for autoimmune glomerular basement membrane disease," J Exp Med., Mar. 6, 2000;191(5):899-906.

Nicholas et al., "Regulation of the immune response. I. Reduction in ability of specific antibody to inhibit long-lasting IgG immunological priming after removal of the Fc fragment," J Exp Med., Jun. 1, 1969;129(6):1183-201.

Nimmerjahn et al., "Fcgamma receptors as regulators of immune responses," Nat Rev Immunol., Jan. 2008;8(1):34-47.

Nimmerjahn et al., "Divergent immunoglobulin g subclass activity through selective Fc receptor binding," Science, 310(5753): 1510-2 (2005).

Olferiev et al., "The role of activating protein 1 in the transcriptional regulation of the human FCGR2B promoter mediated by the -343 G -> C polymorphism associated with systemic lupus erythematosus," J Biol Chem., Jan. 19, 2007;282(3): 1738-46. Epub Nov. 27, 2006.

Patton et al., "An acid dissociation bridging ELISA for detection of antibodies directed against therapeutic proteins in the presence of antigen," J Immunol Methods, Sep. 2005;304(1-2): 189-95.

Pavlou et al., "The therapeutic antibodies market to 2008," Eur J Pharm Biopharm., Apr. 2005;59(3):389-96.

Prickett et al., "A calcium-dependent antibody for identification and purification of recombinant proteins," Biotechniques, Jun. 1989;7(6):580-9.

Radaev et al., "The role of Fc glycosylation and the binding of peptide inhibitors," J Biol Chem., May 11, 2001 ;276(19):16478-83. Epub Jan. 31, 2001.

Radaev et al., "The structure of a human type III Fcgamma receptor in complex with Fc," J Biol Chem., May 11, 2001;276(19):16469-77. Epub Jan. 31, 2001.

Rajpal et al., A general method for greatly improving the affinity of antibodies by using combinatorial libraries, Proc. Natl. Acad. Sci. USA, Jun. 14, 2005;102(24):8466-71. Epub Jun. 6, 2005.

Rathanaswami et al., "Demonstration of an in vivo generated sub-picomolar affinity fully human monoclonal antibody to interleukin-8," Biochem. Biophys. Res. Commun., 334(4): 1004-13 (2005).

Ravetch et al., "Immune inhibitory receptors," Science, Oct. 6, 2000;290(5489):84-9.

Reichert et al., "Monoclonal antibody successes in the clinic," Nat Biotechnol., Sep. 2005;23(9): 1073-8.

Reverberi et al., "Factors affecting the antigen-antibody reaction," Blood Transfus., Nov. 2007;5(4):227-40. doi: 10.2450/2007.0047-07.

Richards et al., "Optimization of antibody binding to FcgammaRIIa enhances macrophage phagocytosis of tumor cells," Mol Cancer Ther., Aug. 2008;7(8):2517-27. doi: 10.1158/1535-7163.MCT-08-0201.

Robles-Carrillo et al., "Anti-CD40L immune complexes potently activate platelets in vitro and cause thrombosis in FCGR2A transgenic mice," J Immunol., Aug. 1, 2010; 185(3): 1577-83. doi: 10.4049/jimmunol.0903888. Epub Jun. 28, 2010.

Rudikoff et al., "Single amino acid substitution altering antigen-binding specificity," Proc Natl Acad Sci U S A., Mar. 1982;79(6): 1979-83.

Salmon et al., "Fc gamma RIIA alleles are heritable risk factors for lupus nephritis in African Americans," J Clin Invest., Mar. 1, 1996;97(5): 1348-54.

Samuelsson et al., "Anti-inflammatory activity of IVIG mediated through the inhibitory Fc receptor," Science, 291(5503):484-6 (2001).

Scappaticci et al., "Arterial thromboembolic events in patients with metastatic carcinoma treated with chemotherapy and bevacizumab," J Natl Cancer Inst., Aug. 15, 2007;99( 16): 1232-9. Epub Aug. 8, 2007.

Schulke et al., "The homodimer of prostate-specific membrane antigen is a functional target for cancer therapy," Proc Natl Acad Sci U S A., Oct. 28, 2003; 100(22): 12590-5.

Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem., Mar. 2, 2001;276(9):6591-604. Epub Nov. 28, 2000.

Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem., Jan. 31, 2003;278(5):3466-73. Epub Nov. 8, 2002.

Siberil et al., "Molecular aspects of human FcgammaR interactions with IgG: functional and therapeutic consequences," Immunol Lett, Aug. 15, 2006; 106(2): 111-8. Epub Jun. 12, 2006.

Singer et al., "Genes & Genomes," Moscow, "Mir," 1998;1:63-64.

Smith et al., "FcgammaRIIB in autoimmunity and infection: evolutionary and therapeutic implications," Nat Rev Immunol., May 2010;10(5):328-43. doi: 10.1038/nri2762.

Sondermann et al., "The 3.2-A crystal structure of the human IgG1 Fc fragment-Fc gammaRIII complex," Nature, Jul. 20, 2000;406(6793):267-73.

Su et al., Expression profile of FcgammaRIIb on leukocytes and its dysregulation in systemic lupus erythematosus, J Immunol., Mar. 1, 2007;178(5):3272-80.

Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," J Immunol., Feb. 15, 2010; 184(4): 1968-76. doi: 10.4049/jimmunol.0903296. Epub Jan. 18, 2010.

Vaccaro et al., "Engineering the Fc region of immunoglobulin G to modulate in vivo antibody levels," NatBiotechnol., Oct. 2005;23(10):1283-8. Epub Sep. 25, 2005.

Veri et al., "Monoclonal antibodies capable of discriminating the human inhibitory Fcgamma-receptor 11B (CD32B) from the activating Fcgamma-receptor IIA (CD32A): biochemical, biological and functional characterization," Immunology, 121(3):392-404 (2007).

Veri et al., "Therapeutic control of B cell activation via recruitment of Fcgamma receptor IIb (CD32B) inhibitory function with a novel bispecific antibody scaffold," Arthritis Rheum., Jul. 2010;62(7):1933-43. doi: 10.1002/art.27477.

Ward et al., "A calcium-binding monoclonal antibody that recognizes a non-calcium-binding epitope in the short consensus repeat units (SCRs) of complement C1r," Mol Immunol., Jan. 1992;29(1):83-93.

Warmerdam et al., Molecular basis for a polymorphism of human Fc gamma receptor II (CD32), J Exp Med., Jul. 1, 1990;172(1):19-25.

Wenink et al., "The inhibitory Fc gamma IIb receptor dampens TLR4-mediated immune responses and is selectively up-regulated on dendritic cells from rheumatoid arthritis patients with quiescent disease," J Immunol., Oct. 1, 2009;183(7):4509-20. doi: 10.4049/jimmunol.0900153. Epub Sep. 4, 2009.

Wernersson et al., "IgG-mediated enhancement of antibody responses is low in Fc receptor gamma chain-deficient mice and increased in Fc gamma RII-deficient mice," J Immunol., Jul. 15, 1999;163(2):618-22.

Wilson et al., "An Fcγ receptor-dependent mechanism drives antibody-mediated target-receptor signaling in cancer cells," Cancer Cell, Jan. 18, 2011;19(1):101-13. doi: 10.1016/j.ccr.2010.11.012.

Wu et al., "Development of motavizumab, an ultra-potent antibody for the prevention of respiratory syncytial virus infection in the upper and lower respiratory tract," J. Mol. Biol., May 4, 2007;368(3):652-65. Epub Feb. 20, 2007.

(56) References Cited

OTHER PUBLICATIONS

Xu et al., "Fc gamma Rs modulate cytotoxicity of anti-Fas antibodies: implications for agonistic antibody-based therapeutics," J Immunol., Jul. 15, 2003;171(2):562-8.

Yarmush et al., "Immunoadsorption: strategies for antigen elution and production of reusable adsorbents," Biotechnol Prog., May-Jun. 1992;8(3): 168-78.

Yeung et al., "Engineering human IgG1 affinity to human neonatal Fc receptor: impact of affinity improvement on pharmacokinetics in primates," J. Immunol., Jun. 15, 2009;182(12):7663-71. doi: 10.4049/jimmunol.0804182.

Yuasa et al., "Deletion of fegamma receptor IIB renders H-2(b) mice susceptible to collagen-induced arthritis," J Exp Med., Jan. 4, 1999;189(1): 187-94.

Zalevsky et al., "The impact of Fc engineering on an anti-CD19 antibody: increased Fcgamma receptor affinity enhances B-cell clearing in nonhuman primates," Blood, 113(16):3735-43 (2009). Epub Dec. 24, 2008.

Zalevsky et al., "Enhanced antibody half-life improves in vivo activity," Nat Biotechnol., Feb. 2010;28(2): 157-9, doi: 10.1038/nbt.1601 Epub Jan. 17, 2010.

Zhang et al., "Effective therapy for a murine model of human anaplastic large-cell lymphoma with the anti-CD30 monoclonal antibody, HeFi-l,does not require activating Fc receptors," Blood, Jul. 15, 2006;108(2):705-10. Epub Mar. 21, 2006.

Zhang et al., "Immune complex/Ig negatively regulate TLR4-triggered inflammatory response in macrophages through Fc gamma RIIb-dependent PGE2 production," J Immunol., Jan. 1, 2009;182(1):554-62.

International Search Report and Written Opinion for App. Ser. No. PCT/JP2012/054624, dated Apr. 3, 2013, 7 pages.

International Preliminary Report on Patentability for App. Ser. No. PCT/JP2012/054624, dated Aug. 27, 2013, 7 pages.

International Search Report for App. Ser. No. PCT/JP2012/075092, dated Dec. 25, 2012, 4 pages.

International Preliminary Report on Patentability for App. Ser. No. PCT/JP2012/075092, dated Apr. 1, 2014, 10 pages.

International Search Report for App. Ser. No. PCT/JP2013/054461, dated May 7, 2013, 7 pages.

International Preliminary Report on Patentability for App. Ser. No. PCT/JP2013/054461, dated Aug. 26, 2014, 6 pages.

International Search Report for App. Ser. No. PCT/JP2013/072507, dated Oct. 29, 2013, 4 pages.

International Preliminary Report on Patentability for App. Ser. No. PCT/JP2013/072507, dated Feb. 24, 2015, 6 pages.

International Preliminary Report on Patentability for App. Ser. No. PCT/JP2012/066665, dated Jan. 16, 2014, 10 pages.

International Search Report and Written Opinion for App. Ser. No. PCT/JP2012/066665, dated Sep. 25, 2012, 10 pages.

International Search Report for App. Ser. No. PCT/JP2013/084809, dated Apr. 1, 2014, 4 pages.

International Preliminary Report on Patentability for App. Ser. No. PCT/JP2013/084809, dated Jun. 30, 2015, 7 pages.

International Search Report for App. Ser. No. PCT/JP2014/059706, dated Jul. 15, 2014, 4 pages.

International Preliminary Report on Patentability for App. Ser. No. PCT/JP2014/059706, dated Oct. 6, 2015, 10 pages.

Vidarsson et al., "IgG subclasses and allotypes: from structure to effector functions," Front Immunol. Oct. 20, 2014;5:520. doi:10.3389/ fimmu.2014.00520. eCollection 2014.

Bruhns, "Properties of mouse and human IgG receptors and their contribution to disease models," Blood, Jun. 14, 2012;119(24):5640-9, doi: 10.1182/blood-2012-01-380121. Epub Apr. 25, 2012.

Hjelm et al., "Antibody-mediated regulation of the immune response," Scand J Immunol., Sep. 2006;64(3): 177-84.

Idusogie et al., "Mapping of the C1q binding site on rituxan, a chimeric antibody with a human IgG1 Fc," J Immunol., Apr. 15, 2000;164(8):4178-84.

Bjellqvist et al., "The focusing positions of polypeptides in immobilized pH gradients can be predicted from their amino acid sequences," Electrophoresis. Oct. 1993;14(10):1023-31.

Ramos et al., "Evaluation of CA-125 and soluble CD-23 in patients with pelvic endometriosis: a case-control study," Rev. Assoc. Med. Bras. (1992). Jan.-Feb. 2012;58(1):26-32).

Araujo et al., "Increased rheumatoid factor interference observed during immunogenicity assessment of an Fc-engineered therapeutic antibody," J Phaim Biomed Anal., Jul. 15, 2011;55(5):1041-9. doi: 10.1016/j.jpba.2011.03.008. Epub Mar. 11, 2011.

Borrok et al., J Biol Chem. Feb. 13, 2015;290(7):4282~90. doi: 10.1074/jbc. M114. 603712. Epub Dec. 23, 2014.

Iwabe et al., "Pathogenetic significance of increased levels of interleukin-a in the peritoneal fluid of patients with endometriosis," Fertil Steril. May 1998:69(5):924-30.

Maurer et al., "Antigenicity of polypeptides (poly alpha amino acids): calcium-dependent and independent antibodies," J Immunol., Sep. 1970;105(3):567-73.

Mazda et al., "Regulation of Muscle Homeostasis and Metabolism by the TGF-β Superfamily Cytokine, Myostatin/growth Differentiation Factor 8 (GDF8)," Journal of Kyoto prefectural university of medicine, 2013; 122(3): 133-41.

Meulenbroek et al., "Properties of human IgG subclasses," Chapter 2.3 of Human IgG Subclasses: Useful Diagnostic Markers for Immunocompetence, published online by Sanquin, Amsterdam, The Netherlands. Retrieved from the Internet on Mar. 23 and 24, 2017: <http://ednieuw.home.xs4all.nl/IgGsubclasses/subkl23.htm>, 8 pages.

Wang et al., "Monoclonal Antibodies with Identical Fc Sequences Can Bind to FcRn Differentially with Pharmacokinetic Consequences," Drug Metabolism and Disposition, Sep. 2011; 39(9):1469-77.

Warncke et al., "Different adaptations of IgG effector function in human and nonhuman primates and implications for therapeutic antibody treatment," J Immunol. May 1, 2012 :188(9):4405-11. doi: 10.4049/jimmunol. 1200090. Epub Mar. 28, 2012.

Xolair (omalizumab) Prescribing Information, https://www.gene.com/download/pdf/xolair_prescribing.pdf, Jul. 2016, 27 pages.

International Search Report for App. Ser. No. PCT/JP2016/003616, dated Nov. 25, 2016, 4 pages.

Biasini et al., "Tmmunopurification of pathological prion protein aggregates," PLoS One, Nov. 12, 2009;4(11):e7816. doi: 10.1371/journal.pone.0007816.

Pakula et al., "Genetic Analysis of Protein Stability and Function," Annu. Rev. Genet., 1989;23:289-310.

Kamei et al., "Quantitative methods for developing Fc mutants with extended half dives," Biotechnol Bioeng., Dec. 20, 2005;92(6):748-60.

U.S. Appl. No. 15/495,026, filed Apr. 24, 2017, Igawa et al.

Roopenian et al., "FcRn: the neonatal Fc receptor comes of age," Nat Rev Immunol., 7(9):715-25 (2007), 8 pages. Epub Aug. 17, 2007.

Brown et al., "Tolerance to Single, but Not Multiple, Amino Acid Replacements in Antibody VHCDR2," J Immunol. May 1, 1996; 156(9):3285-91.

Cooper et al., "Variable domain-identical antibodies exhibit IgG subclass-related differences in affinity and kinetic constants as determined by surface plasmon resonance," Mol Immunol. Jun. 1994; 31(8): 577-84.

Vajdos et al., "Comprehensive Functional Maps of the Antigen binding Site of an Anti-ErbB2 Antibody Obtained with Shotgun Scanning Mutagenesis," J Mol Biol. Jul. 5, 2002; 320(2):415-28.

USPTO Non-Final Office Action in U.S. Appl. No. 14/974,488, dated Aug. 16, 2017, 18 pages.

USPTO Final Office Action in U.S. Appl. No. 15/210,360, dated Jul. 25, 2017, 23 pages.

Beringhelli et al., "pH and ionic strength dependence of protein (un)folding and ligand binding to bovine beta-lactoglobulins A and B," Biochemistry, Dec. 24, 2002;41(51): 15415-22.

Epstein, "Non-randomness of amino-acid changes in the evolution of homologous proteins," Nature, Jul. 22, 1967;215(5099):355-9.

Idusogie et al., "Engineered antibodies with increased activity to recruit complement," J Immunol., Feb. 15, 2001;166(4):2571-5.

(56) References Cited

OTHER PUBLICATIONS

Information Meeting on Antibody Engineering Technologies, Copyright © Chugai Pharmaceutical Co., Ltd., Dec. 18, 2012.
Liu et al., "Asymmetrical Fc engineering greatly enhances antibody-dependent cellular cytotoxicity (ADCC) effector function and stability of the modified antibodies," *J Biol Chem.*, Feb. 7, 2014;289(6):3571-90, doi: 10.1074/jbc.M113.513366. Epub Dec. 5, 2013.
Luttrell et al., "Reaction coupling of chelation and antigen binding in the calcium ion-dependent antibody binding of cyclic AMP," *J Biol Chem.*, Nov. 15, 1991;266(32):21626-30.
Mimoto et al., "Novel asymmetrically engineered antibody Fc variant with superior FcγR binding affinity and specificity compared with afucosylated Fc variant," *MAbs.*, Mar.-Apr. 2013;5(2):229-36. doi: 10,4161/mabs.23452, Epub Feb. 13, 2013.
Moore et al., "Engineered Fc variant antibodies with enhanced ability to recruit complement and mediate effector functions," MAbs., Mar.-Apr. 2010;2(2): 181-9.
Okabe, "Proprietary Innovative Antibody Engineering Technologies in Chugai Pharmaceutical," Information meeting on Antibody Engineering Technologies, Dec. 18, 2012, 78 pages.
U.S. Appl. No. 15/860,163, filed Jan. 2, 2018, Mimoto et al.
U.S. Appl. No. 15/963,449, filed Apr. 26, 2018, Ruike et al.
U.S. Appl. No. 15/963,455, filed Apr. 26, 2018, Ruike et al.
U.S. Appl. No. 15/977,757, filed May 11, 2018, Igawa et al.
U.S. Appl. No. 61/313,102, filed Mar. 11, 2010, Pons.
Alley et al., "Antibody-drug conjugates: targeted drug delivery for cancer," Curr Opin Chem Biol., 14(4):529-37 (2010), 8 pages, doi: 10.1016/j.cbpa.2010.06.170. Epub Jul. 17, 2010.
Alignment of constant region sequences from WO 2009/125825 (document submitted in EP opposition and posted by EPO on Feb. 2, 2018); 1 page.
Alignment of the amino acid sequences of the Fc regions of antibodies exemplified in EP 2275443 (document submitted in EP opposition and posted by EPO on Feb. 2, 2018); 1 page.
Alignment of variable heavy and light chain amino acid sequences from WO 2009/125825 (document submitted in EP opposition and posted by EPO on Feb. 2, 2018); 2 pages.
Akbarzadeh-Sharbaf et al., "In silico design, construction and cloning of Trastuzumab humanized monoclonal antibody: A possible biosimilar for Herceptin," Adv Biomed Res 2012 :1: 21. doi: 10. 4103/ 2277-9175, 98122, Epub Jul. 6, 2012.
Atherton et al., "Acid-base balance: maintenance of plasma pH," Anaesthesia & Intensive Care Medicine. 2009:10(11 ):557-61 (abstract).
Baeuerle et al., "BiTE: Teaching antibodies to engage T-cells for cancer therapy," Curr Opin Mol Ther., Feb. 2009;11(1):22-30.
Breitbart et al., "Highly Specific Detection of Myostatin Prodomain by an Immunoradiometric Sandwich Assay in Serum of Healthy Individuals and Patients," PLoS One. Nov. 15, 2013;8(11):e80454, doi: 10.1371/journal.pone.0080454. eCollection 2013.
Claims as granted for EP 2275443 (document submitted in EP opposition); 6 pages.
Datta-Mannan et al., "Humanized IgG1 Variants with Differential Binding Properties to the Neonatal Fc Receptor: Relationship to Pharmacokinetics in Mice and Primates," Drug Metab Dispos. Jan. 2007 :35 (1) :86-94, Epub Oct. 18, 2006.
Davda et al., "Properties of a general PK/PD model of antibody-ligand interactions for therapeutic antibodies that bind to soluble endogenous targets," Mabs. 2(5):576-88 (2010), 13 pages, doi: 10.4161/mabs.2.5.12833, Epub Sep. 1, 2010.
Davydov, "Omalizumab (Xolair) for Treatment of Asthma," Am Fam Physician. Jan. 15, 2005;71(2):341-2.
De Bono et al., "ING-1, a monoclonal antibody targeting Ep-CAM in patients with advanced adenocarcinomas," Clin Cancer Res., Nov. 15, 2004;10(22):7555-65.
De Felice et al., "Formation of amyloid aggregates from human lysozyme and its disease-associated variants using hydrostatic pressure," FASEB J., Jul. 2004, 18(10): 1099-101. (dol:10.1096/fj.03-1072fje; PMID 15155566).
Declaration of Nimish Gera, Ph.D., CV and Exhibits, Sep. 1, 2016 (submitted in the matter of EP 2275443, Opposition thereto by Alexion Pharmaceuticals, Inc.); 24 pages.
De Groot et al., "Reducing risk, improving outcomes: bioengineering less immunogenic protein therapeutics," Clin Immunol., May 2009;131(2):189-201. doi: 10.1016/j.clim.2009.01.009. Epub Mar. 6, 2009.
Desjarlais et al., "Optimizing engagement of the immune system by anti-tumor antibodies: an engineer's perspective," Drug Discovery Today, 12(21-22):898-910 (2007), 13 pages. Epub Oct. 22, 2007.
Dufner et al., "Harnessing phage and ribosome display for antibody optimization," Trends Biotechnol., Nov. 2006;24(11):523-9, Epub Sep. 26, 2006.
"EMA product information: Annexes to file of the tocilizumab preparation RoActemra (WC500054890)", published by EMA on Jan. 8, 2010.
Experimental data characterizing the binding of rituximab to its antigen CD20 and to human FcRn (document submitted in EP opposition and posted by EPO on Feb. 5, 2018); 6 pages.
Expert Declaration by Dr. Madhusudan Natarajan, submitted in EP opposition regarding EP 2552955 and posted by EPO on Feb. 5, 2018; 4 pages.
Fillipovic, Biochemical basis of human life, VLADOS, 2005:38-43 (with English translation).
Gurbaxani et al., "Analysis of a family of antibodies with different half-lives in mice fails to find a correlation between affinity for FcRn and serum half-life," Mol Immunol Mar. 2006:43(9):1462-73, Epub Sep. 1, 2005.
"Goebl et al., ""Neonatal Fc Receptor Mediates Internalization of Fe Transfected Human Endothelial Cells,"" Molecular Biology of the Cell, Dec. 2008 : 19 (12) :5490-5505 ".
Haringman et al., "A randomized controlled trial with an anti-CCL2 (anti-monocyte chemotactic protein 1) monoclonal antibody in patients with rheumatoid arthritis," Arthritis Rheum., Aug. 2006;54(8):2387-92.
Hebert, "The clearance of immune complexes from the circulation of man and other primates," Am J. Dis., Mar. 1991;17(3):352-61.
Hinton et al., "Engineered human IgG antibodies with longer serum half-lives in primates," J Biol Chem., Feb. 20, 2004;279(8):6213-6, Epub Dec. 29, 2003.
Igawa et al., "Reduced elimination of IgG antibodies by engineering the variable region," Protein Eng Des Sel., May 2010;23(5):385-92. Epub Feb. 15, 2010.
Ishii et al., "FcRn, a critical regulator of antibody pharmacokinetics," Folia Pharmacol Jpn., Jun. 2010; 136(5):280-4 (with English translation).
"Irani et al., ""Molecular properties of human IgG subclasses and their implications for designing therapeutic monoclonal antibodies against infectious diseases,"" Mol Immunol, Oct. 2015 :67 (2 Pt A): 171-82. doi: 10. 1016/j. molimm. 2015. 03. 255. Epub Apr. 18, 2015".
Juszczak et al., "Ipilimumab: a novel immunomodulating therapy causing autoimmune hypophysitis: a case report and review," Eur J Endocrinol 167(1): 1-5 (2012), 5 pages, doi: 10.1530/EJE-12-0167. Epub Apr. 10, 2012.
Kabat et al., "Sequences of proteins of immunological interest", U.S. Department of Health and Human Services, National Institutes of Health, NIH Publication No. 91-3242, 5th ed., 1991, vol. 1, pp. 679-687.
Kim et al., "Production of a Polyclonal Anti-Myostatin Antibody and the Effects of In Ovo Administration of the Antibody on Posthatch Broiler Growth and Muscle Mass," Poult Sci. Jun. 2007; 86(6): 1196-205.
King et al., Applications and Engineering of Monoclonal Antibodies. 1998:68-71.
Lewis et al., "Differential responses of human tumor cell lines to anti-p185HER2 monoclonal antibodies," Cancer Immunol Immunother., Sep. 1993;37(4):255-63.
Liang et al., "Immunity against a therapeutic xenoprotein/Fc construct delivered by gene transfer is reduced through binding to the inhibitory receptor FcγRIIb," J Gene Med., Sep. 2011; 13(9):470-7.
Lutterbuese et al., "T cell-engaging BiTE antibodies specific for EGFR potently eliminate KRAS- and BRAF-mutated colorectal

(56) References Cited

OTHER PUBLICATIONS cancer cells," Proc Natl Acad Sci U.S.A., 107(28): 12605-10 (2010), 6 pages, doi: 10.1073/pnas.1000976107, Epub Jun. 28, 2010.

Martin et al., "Reviews Preclinical Safety and Immune-Modulating Effects of Therapeutic Monoclonal Antibodies to Interleukin-6 and Tumor Necrosis Factor-alpha in Cynomolgus Macaques," J. Immunotoxicol., 1(3):131-9 (2004), 9 pages. Doi: 10,1080/15476910490894904.

Matsunaga et al., "A pH-dependent conformational transition of Abeta peptide and physicochemical properties of the conformers in the glial cell," Biochem J., Feb. 1, 2002;361(Pt3):547-56.

Maxfield et al., "Endocytic Recycling," Nat Rev Mol Cell Biol. Feb. 2004;5(2): 121-32.

Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res. Jun. 15, 2001;61(12):4744-9.

Montero-Julian et al., "Pharmacokinetic study of anti-interleukin-6 (IL-6) therapy with monoclonal antibodies: enhancement of IL-6 clearance by cocktails of anti-IL-6 antibodies," Blood, Feb. 15, 1995; 85(4):917-24.

Nam et al., "Current evidence for the management of rheumatoid arthritis with biological disease-modifying antirheumatic drugs: a systematic literature review informing the EULAR recommendations for the management of RA," Ann Rheum Dis., 69(6):976-86 (2010). doi: 10.1136/ard.2009.126573. Epub May 6, 2010.

Niebecker et al., "Safety of therapeutic monoclonal antibodies," CurrDrug Saf., Oct. 2010;5(4):275-86.

Nishimoto et al., "Mechanisms and pathologic significances in increase in serum interleukin-6 (IL-6) and soluble IL-6 receptor after administration of an anti-IL-6 receptor antibody, tocilizumab, inpatients with rheumatoid arthritis and Castleman disease" Blood.,112(10):3959-64 (2008), 8 pages, doi: 10.1182/blood-2008-05-155846. Epub Sep. 10, 2008.

O'Donovan et al., "EGFR and HER-2 Antagonists in Breast Cancer," Anticancer Res. May-Jun. 2007 :27 (3 A): 1285-94.

Experimental information regarding off-rate of Xolair Fab for binding to human IgE at pH7.4 and pH5,5 (document submitted in EP opposition and posted by EPO on Feb. 2, 2018); 3 pages.

Official Action dated Oct. 13, 2016, issued for EP Application No. 11714860.1 and submitted as evidence during EP opposition; 3 pages.

Papista et al., "Dysfunctions of the IgA system: a common link between intestinal and renal diseases," Cell Mol Immunol, Mar. 2011;8(2): 126-34, doi: 10.1038/cmi.2010.69. Epub Jan. 31, 2011.

Petkova et al., "Enhanced half-life of genetically engineered human IgG1 antibodies in a humanized FcRn mouse model: potential application in humorally mediated autoimmune disease," Int Immunol,, 18(12): 1759-69 (2006), 11 pages. Epub Oct. 31, 2006.

Presta, "Molecular engineering and design of therapeutic antibodies," Curr Opin Immunol. Aug. 2008 :20 (4):460-70, doi: 10.1016/j.coi.2008. 06.012.

Presta at el., "Humanization of an Anti-Vascular Endothelial Growth Factor Monoclonal Antibody for the Therapy of Solid Tumors and Other Disorders," Cancer Res. Oct. 15, 1997 :57 (20) :4593-9.

Product labelling information for Rituxan (Rituximab), dated Nov. 1997.

Qiao et al., "Dependence of antibody-mediated presentation of antigen on FcRn," Proc Natl Acad Sci U S A., Jul. 8, 2008;105(27):9337-42, Epub Jul. 1, 2008.

Raghavan et al., "Analysis of the pH Dependence of the Neonatal Fc Receptor/immunoglobulin G Interaction Using Antibody and Receptor Variants," Biochemistiy, Nov. 14, 1995;34(45): 14649-57.

Riechelmann et al., "Phase I trial with the CD44v6-targeting immunoconjugate bivatuzumab mertansine in head and neck squamous cell carcinoma," Oral Oncol., Sep. 2008;44(9):823-9. doi: 10.1016/j.oraloncology.2007.10.009. Epub Jan. 18, 2008.

Rudge et al., "VEGF Trap complex formation measures production rates of VEGF, providing a biomarker for predicting efficacious angiogenic blockade," 104(47): 18363-70 (2007), 8 pages. Epub Nov. 13, 2007.

Russo et al., "The CXCL8/IL-8 chemokine family and its receptors in inflammatory diseases," Expert Rev Clin Immunol., May 2014;10(5):593-619. doi: 10.1586/1744666X.2014.894886. Epub Mar. 29, 2014.

Satoh et al., "Non-fucosylated therapeutic antibodies as next-generation therapeutic antibodies," Expert Opin Biol Ther., Nov. 2006;6(11): 1161-73.

Schuster et al., "Signaling of human ciliary neurotrophic factor (CNTF) revisited. The interleukin-6 receptor can serve as an alpha-receptor for CTNF," J Biol Chem., Mar. 14, 2003;278(11):9528-35.

Seda et al., "B-cell receptor signaling and its crosstalk with other pathways in normal and malignant cells," Eur J Haematol. Mar. 2015;94(3): 193-205. doi: 10.1111/ejh.12427. Epub Sep. 13, 2014.

Sims et al., "HMGB1 and RAGE in inflammation and cancer," Annu Rev Immunol., 28:367-88 (2010), 24 pages.

Strohl, "Optimization of Fc-mediated effector functions of monoclonal antibodies," Curr Opin Biotechnol. Dec. 2009;20(6):685-91.

Supplementary data provided by opponent for EP Application No. 11714860.1 (document submitted in EP opposition and posted by EPO on Feb. 20, 2018); 3 pages.

Takeuchi et al., "The Japanese experience with biologic therapies for rheumatoid arthritis," Nat Rev Rheumatol., 6(11):644-52 (2010), doi: 10.1038/nrrheum.2010.154. Epub Sep. 28, 2010.

Tanabe et al., "Characterization of the Monoclonal Antibodies Against Human Protein C Specific for Calcium Ion-induced Conformers," Japanese Journal of Thrombosis and Hemostasis, 1992;3(1):29-35.

Tanzi et al., "Twenty years of the Alzheimer's disease amyloid hypothesis: a genetic perspective," Cell, Feb. 2005, 120(4):545-55. (doi:10.1016/j.cell.2005.02.008;PMID 15734686).

Trinh et al., "Ipilimumab in the treatment of melanoma," Expert Opin Biol Ther., Jun. 2012;12(6):773-82, doi: 10.1517/14712598. 2012.675325. Epub Apr. 14, 2012.

Vaccaro et al., "Divergent activities of an engineered antibody in murine and human systems have implications for therapeutic antibodies," Proc Natl Acad Sci US A. Dec. 5, 2006; 103(49): 18709-14, Epub Nov. 20, 2006.

Waelbroeck et al., "The pH Dependence of Insulin Binding," J Biol Chem. Jul. 25, 1982 :257 (14) :8284-91.

Wang et al., "HMG-1 as a late mediator of endotoxin lethality in mice," Science, 285(5425):248-51 (1999).

Ward et al., "Evidence to support the cellular mechanism involved in semm IgG homeostasis in humans," Int Immuno I. Feb. 2003 : 15(2): 187-95.

Weiner et al., "Monoclonal antibodies: versatile platforms for cancer immunotherapy," Nat Rev Immunol,, 10(5):317-27 (2010), 26 pages, doi: 10.1038/nri2744.

Welch et al., "Adalimumab (Humira) for the Treatment of Rheumatoid Arthritis" Am Fam Physician, Dec. 15, 2008 :78 (12) :1406-1408.

Wu et al., "Humanization of a murine monoclonal antibody by simultaneous optimization of framework and CDR residues," J Mol Biol., Nov. 19, 1999;294(1): 151-62.

Wu et al., "Structure-based engineering of a monoclonal antibody for improved solubility," Protein Eng Des Sel., Aug. 2010;23(8):643-51. doi:10.1093/protein/gzq037. Epub Jun. 11, 2010.

Xiao et al., "Pharmacokinetics of anti-hepcidin monoclonal antibody Ab 12B9m and hepcidin in cynomolgus monkeys" AAPS J. 12(4):646-57 (2010), 12 pages, doi: 10.1208/s12248-010-9222-0. Epub Aug. 25, 2010.

Yang et al., "Dataset of the binding kinetic rate constants of anti-PCSK9 antibodies obtained using the Biacore TIOO, Protean XPR36, Octet RED384, and IBIS MX96 biosensor platforms," Data Brief. Jul. 27, 2016 :8:1173-83. doi: 10. 1016/J. dib. 2016.07.044. eCol lection Sep. 2016.

Yang et al., "Maximizing in vivo target clearance by design of pH-dependent target binding antibodies with altered affinity to FcRn," MAbs. Oct. 2017 :9(7): 1105-1117. doi: 10. 1080/19420862. 2017. 1359455. Epub Aug. 8, 2017.

(56) References Cited

OTHER PUBLICATIONS

Yarilin, Fundamentals of Immunology. M: Medicina, 1999, p. 169-72, 354-8 (with English translation).
Yeung et al., "A Therapeutic Anti-VEGF Antibody with Increased Potency Independent of Pharmacokinetic Half-life," Cancer Res. Apr. 15, 2010;70(8):3269-77. doi: 10.1158/0008-5472.CAN-09-4580 Eoub Mar. 30, 2010.
Ying et al., "Large Yellow Croaker MSTN-1 Prodomain Prokaryotic Expression, Polyclonal Antibody Preparation and Antibody Function Identification," Chinese Journal of Cell Biology. Oct. 2014;36(10): 1344-1349 (in Japanese, with English abstract).
Zheng et al., "Translational pharmacokinetics and pharmacodynamics of an FcRn-variant anti-CD4 monoclonal antibody from preclinical model to phase I study." Clin Pharmacol Ther., 89(2):283-90 (2011), doi: 10,1038/clpt.2010.311. Epub Dec. 29, 2010.
USPTO Final Office Action in U.S. Appl. No. 14/001,218, dated Jan. 29, 2018, 11 pages.
USPTO Restriction Requirement in U.S. Appl. No. 14/423,269, dated May 4, 2017, 5 pages.
USPTO Non-Final Office Action in U.S. Appl. No. 14/423,269, dated Nov. 28, 2017, 58 pages.
USPTO Restriction Requirement in U.S. Appl. No. 14/654,895, dated Sep. 21, 2017, 7 pages.
USPTO Non-final Office Action in U.S. Appl. No. 14/654,895, dated Feb. 7, 2018, 39 pages.
USPTO Non-final Office Action in U.S. Appl. No. 15/024,063, dated Feb. 7, 2018, 91 pages.
Holash et al., "VEGF-Trap: a VEGF blocker with potent antitumor effects," Proc Natl Acad Sci U S A., Aug. 20, 2002;99(17): 11393-8. Epub Aug. 12, 2002.
U.S. Appl. No. 15/963,449, Ruike et al., filed Apr. 26, 2018.
U.S. Appl. No. 14/001,218, Mimoto et al., filed Aug. 23, 2013.
U.S. Appl. No. 14/007,947, Igawa et al., filed Sep. 26, 2013.
U.S. Appl. No. 14/347,034, Igawa et al., filed Mar. 25, 2014.
U.S. Appl. No. 15/230,904, Igawa et al., filed Aug. 8, 2016.
U.S. Appl. No. 14/347,321, Igawa et al., filed Mar. 26, 2014.
U.S. Appl. No. 14/347,187, Igawa et al., filed Mar. 25, 2014.
U.S. Appl. No. 14/361,013, Igawa et al., filed May 28, 2014.
U.S. Appl. No. 15/952,945, filed Apr. 13, 2018, Igawa et al.
U.S. Appl. No. 16/028,140, filed Jul. 5, 2018, Igawa et al.
U.S. Appl. No. 16/065,192, filed Jun. 22, 2018, Ruike et al.
U.S. Appl. No. 16/108,897, filed Aug. 22, 2018, Igawa et al.
U.S. Appl. No. 16/264,735, filed Feb. 1, 2019, Igawa et al.
U.S. Appl. No. 16/323,142, filed Feb. 4, 2019, Kakiuchi et al.
[Anonymous] "Rabbit Antibody to Human pro-Myo statin (amino acids 79-92)," Meridian Life Science Inc., Nov. 13, 2015 (Nov. 13, 2015), XP055478289, Retrieved from the Internet: URL:https://meridianlifescience.com/biospecs/K24340R.pdf [retrieved on May 24, 2018].
[Anonymous] "Blog entry," Jun. 1, 2014 (Jun. 1, 2014), Retrieved from the Internet: URL:https://www.thundersplace.org/male-supplements/the-chemical-pe-thread-7.html92 [retrieved on May 23, 2018].
[Anonymous] "polyclonal human pro-Myo statin (aa 79-92) antibody," Immun Diagnostik Antibodies Catalogue, Jun. 30, 2016 (Jun. 30, 2016), Retrieved from the Internet: URL:https://www.immundiagnostik.com/fileadmin/pdf/AK3004.pdf [retrieved on May 24, 2018].
[Anonymous] "Mouse GDF-8/Myostatin Propeptide Antibody," R&D Catalogue AF 1539, Feb. 6, 2018 (Feb. 6, 2018), XP055478493, Retrieved from the Internet: URL:https://resources..rndsystems.com/pdfs/datasheets/afl539.pdf [retrieved on May 25, 2018].
Antibodies from www.bioinf.org.uk: Dr. Andrew C.R. Martin's Group, downloaded Jul. 11, 2018, 9 pages.
Bayry et al., "Immuno affinity purification of foot and mouth disease virus type specific antibodies using recombinant protein adsorbed to polystyrene wells," J Virol Methods, Aug. 1999, 81(1-2):21-30.
Becker et al., "Prevention of postoperative abdominal adhesions by a sodium hyaluronate-based bioresorbable membrane: a prospective, randomized, double-blind multicenter study," J Am Coll Surg, Oct. 1996, 183(4): 297-306.
Bulun, "Endometriosis," New Eng J Med, Jan. 2009, 360(3):268-279.
Chaparro-Riggers et al., "Increasing serum half-life and extending cholesterol lowering in vivo by engineering antibody with pH-sensitive binding to PCSK9," J Biol Chem, Mar. 30, 2012, 287(14): 11090-11097, doi: 10.1074/jbc.M111.319764, Epub Jan. 31, 2012.
Devanaboyina et al., "The effect of pH dependence of antibody-antigen interactions on subcellular trafficking dynamics," MAbs, Nov. 1, 2013, 5(6):851-859.
Donnez et al., "Current thinking on the pathogenesis of endometriosis," Gynecol Obstet Invest, Dec. 2002, 54(Suppl 1): 52-58; post presentation discussion 59-62.
Ejima et al., "Effective elution of antibodies by arginine and arginine derivatives in affinity column chromatography," Analytical Biochem, Oct. 15, 2005, 345(2):250-257.
GE Healthcare, Biacore Sensor Surface Handbook BR-1005-71 Edition AB, 2005, pp. 1-100.
Giudice et al., "Endometriosis," Lancet, Nov. 2004, 364(9447): 1789-1799.
Guo, "Recurrence of endometriosis and its control," Hum Reprod Update, Jul.-Aug. 2009 (Epub Mar. 2009), 15(4): 441-461.
Han et al., "Targeting the myostatin signaling pathway to treat muscle wasting diseases," Curr Opin Support Palliat Care, Dec. 2011, 5(4):334-341. doi:10.1097/SPC.0b013e32834bddf9.
Harvey et al., Lippincott's Illustrated Reviews: Immunology Second Edition; Chapter 2 "Antigens and Receptors," pp. 11-23 and Chapter 11 "Lymphocyte Effector Functions," pp. 141-157, 2008.
Hill et al., "The myostatin propeptide and the follistatin-related gene are inhibitory binding proteins of myostatin in normal serum," J Biol Chem, Oct. 25, 2002, 277(43):40735-40741. Epub Aug. 22, 2002.
Hirose, Nihon Yakurigaku Zasshi, May 2006, 127(5):362-367 (with English translation).
Igawa et al., "Engineering the variable region of therapeutic IgG antibodies," MAbs, May-Jun. 2011, 3(3):243-252, Epub May 1, 2011.
Jaeger, Clinical Immunology and Allergology, Second Edition, M.: Medicina, 1990, 2:484-5 (with English translation).
Kamata et al., "Comparison of pH and ionic strength dependence of interactions between monoclonal antibodies and bovine B-lactoglobulin," Biosci Biotechnol Biochem, Jan. 1996, 60(1):25-29.
Kim et al., "Production of a monoclonal anti-myostatin antibody and the effects of in ovo administration of the antibody on posthatch broiler growth and muscle mass," Poult Sci, Jun. 2006, 85(6):1062-1071.
King et al., Applications and Engineering of Monoclonal Antibodies, Taylor & Francis, ISBN 0-203-21169-3, pp. 1-236 (Year 2005).
MacCallum et al., "Antibody-antigen interactions: contact analysis and binding site topography," J Mol Biol, Oct. 11, 1996, 262:732-745.
Maxwell et al., "Crystal structure of the human leukocyte Fc receptor, FcγRIIa," Nat Struct Biol, May 1999, 6(5)437-442.
Mellman, "The importance of being acid: the role of acidification in intracellular membrane traffic," J Exp Biol, Nov. 1992, 172:39-45.
OriGene Technologies, Inc., AP02123SU-N, Polyclonal Antibody to Myostatin (79-92)—Serum, Mar. 19, 2013, https://ml.acris-antibodies.com/pdf/AP02123SU-N.pdf.
Popov et al., "The stoichiometry and affinity of the interaction of murine Fc fragments with the MHC class I-related receptor, FcRn," Mol Immunol, Apr. 1996, 33(6):521-530.
Roitt et al., Immunology, M., Mir, 2000, pp. 97-113 (including what are believed to be corresponding pages from an English language edition of Immunology).
Roitt et al., Immunology, M., Mir, 2000, pp. 373-374 (with English translation).

(56) References Cited

OTHER PUBLICATIONS

Rojas et al., "Formation, distribution, and elimination of infliximab and anti-infliximab immune complexes in cynomolgus monkeys," J Pharmacol Exp Ther, May 2005, 313(2):578-585. Epub Jan. 12, 2005.
Schroter et al., "A generic approach to engineer antibody pH-switches using combinatorial histidine scanning libraries and yeast display," MAbs, 2015, 7(1): 138-151. doi: 10.4161/19420862.2014.985993.
Sondermann et al., "Crystal structure of the soluble form of the human Fcγ-receptor IIb: a new member of the immunoglobulin superfamily at 1.7 A resolution," EMBO J, Mar. 1, 1999, 18(5):1095-1103.
Sondermann et al., "Molecular basis for immune complex recognition: a comparison of Fc-receptor structures," J Mol Biol, Jun. 8, 2001, 309(3):737-749.
Stepanov, Molecular biology. Structure and Functions of Proteins, M.: Nauka, 2005, pp. 61-62 (with English translation).
Vercellini et al., "Postoperative oral contraceptive exposure and risk of endometrioma recurrence," Am J Obstet Gynecol, May 2008 (Epub Feb. 2008), 198(5): 504,e1-5.
Yada et al., Lippincott's Illustrated Reviews: Immunology, Second Edition, Nov. 30, 2013, Chapter 2, pp. 11-23 and Chapter 11, pp. 149-165 (in Japanese, with English equivalent).
Yarilin, Fundamentals of Immunology, M.: Medicina, 1999, pp. 175 and 182 (with English translation).
Yarilin, Fundamentals of Immunology, M: Medicina, 1999, pp. 172-174 (with English translation).
USPTO Final Office Action in U.S. Appl. No. 14/423,269, dated Aug. 15, 2018, 25 pages.
USPTO Non-final Office Action in U.S. Appl. No. 15/952,945, dated Sep. 20, 2018, 32 pages.
USPTO Non-Final Office Action in U.S. Appl. No. 13/595,139, dated Nov. 14, 2012, 10 pages.
Fish & Richardson P.C., Amendment in Reply to Office Action dated Nov. 14, 2012 in U.S. Appl. No. 13/595,139, filed May 14, 2013, 19 pages.
USPTO Non-Final Office Action in U.S. Appl. No. 13/595,139, dated Mar. 13, 2015, 12 pages.
Fish & Richardson P.C., Amendment & Reply to Office Action dated Mar. 13, 2015 in U.S. Appl. No. 13/595,139, filed Jun. 11, 2015, 19 pages.
USPTO Non-Final Office Action in U.S. Appl. No. 13/595,139, dated Aug. 3, 2015, 13 pages.
Fish & Richardson P.C., Reply to Office Action dated Aug. 3, 2015 in U.S. Appl. No. 13/595,139, filed Dec. 2, 2015, 28 pages.
USPTO Final Office Action in U.S. Appl. No. 13/595,139, dated Feb. 12, 2016, 12 pages.
Fish & Richardson P.C., Reply to Office Action dated Feb. 12, 2016 in U.S. Appl. No. 13/595,139, filed Jul. 11, 2016, 4 pages.
USPTO Non-Final Office Action in U.S. Appl. No. 13/595,139, dated Nov. 23, 2016, 11 pages.
USPTO Final Office Action in U.S. Appl. No. 13/595,139, dated May 30, 2017, 23 pages.
USPTO Final Office Action in U.S. Appl. No. 13/595,139, dated Aug. 1, 2013, 8 pages.
USPTO Non-Final Office Action in U.S. Appl. No. 13/595,139, dated Sep. 26, 2018, 32 pages.
U.S. Appl. No. 15/963,449, filed Ruike et al., filed Apr. 26, 2018.
U.S. Appl. No. 15/976,288, Igawa et al., filed May 10, 2018.
U.S. Appl. No. 14/007,947, Igawa et al., filed Dec. 30, 2013.
U.S. Appl. No. 14/654,895, Igawa et al., filed Jun. 23, 2015.
Bonvin et al., "De novo isolation of antibodies with pH-dependent binding properties," mAbs, Mar./Apr. 2015, 7(2): 294-302.
Cunningham et al., "The Covalent Structure of a Human γG-Immunoglobulin. VII. Amino Acid Sequence of Heavy-Chain Cyanogen Bromide Fragments H-H4," Biochemistry, Aug. 4, 1970, 9(16):3161-70.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-18.
Examination Report No. 1 for AU 2013306700 (IP Australia), dated Jun. 7, 2018, 3 pages.
Fan et al., "Self-Association of Human PCSK9 Correlates with Its LDLR-Degrading Activity," Biochemistry, Feb. 12, 2008, 47(6):1631-9. doi: 10.1021/bi7016359. Epub Jan. 16, 2008.
Gheti et al., "Multiple Roles for the Major Histocompatibility Complex Class I-Related Receptor FcRn," Annu Rev Immunol, Apr. 2000, 18:739-66.
Goel et al., "Plasticity within the Antigen-Combining Site May Manifest as Molecular Mimicry in the Humoral Immune Response," J Immunol, Dec. 15, 2004, 173(12):7358-67.
Hu et al., "Combinatorial libraries against libraries for selecting neoepitope activation-specific antibodies," Proc Natl Acad Sci USA, Apr. 2010, 107(14):6252-57.
Kurki et al., "Desmin antibodies in acute infectious myopericarditis," APMIS, Jun. 1989, 97(6):527-32.
Lloyd et al., "Modelling the human immune response: performance of a $10^{11}$ human antibody repertoire against a broad panel of therapeutically relevant antigens," Protein Eng Des Sel, Mar. 2009, 22(3): 159-68, doi: 10.1093/protein/gzn058. Epub Oct. 29, 2008.
Male et al., Chapter 3 "Antibodies," Immunology, 7th edition, 2006, pp. 77-78.
Medesan et al., "Comparative studies of rat IgG to further delineate the Fc:FcRn interaction site," Eur J Immunol, Jul. 1998, 28(7):2092-100.
Murtaugh et al., "A Combinatorial Histidine Scanning Library Approach to Engineer Highly pH-Dependent Protein Switches," Protein Sci, Sep. 2011, 20(9): 1619-31. doi: 10.1002/pro.696. Epub Aug. 3, 2011.
Perng et al., "Desmin Aggregate Formation by R120G αB-Crystallin Is Caused by Altered Filament Interactions and Is Dependent upon Network Status in Cells," Mol Biol Cell, May 2004, 15(5):2335-46.
Roitt et al., "Fc Receptors are Expressed by Granulocytes, Mononuclear Cells, and Mast Cells," Immunology, 7th Edition, 2000, pp. 111-112 (including what are believed to be corresponding pages from an English language edition of Immunology).
Sazinsky et al., "Aglycosylated immunoglobulin Gi variants productively engage activating Fc receptors," Proc Natl Acad Sci USA, Dec. 23, 2008, 105(51):20167-72. doi: 10.1073/pnas.0809257105, Epub Dec. 12, 2008.
Travis et al., "Isolation of Albumin from Whole Human Plasma and Fractionation of Albumin-Depleted Plasma," Biochem J, Aug. 1, 1976, 157(2):301-6.
Weiss et al., "Rapid mapping of protein functional epitopes by combinatorial alanine scanning," Proc Natl Acad Sci USA, Aug. 1, 2000, 97(16):8950-4.
Yarilin, Fundamentals of Immunology, M.: Medicina, 1999, pp. 181-184 (with English translation).
USPTO Restriction Requirement in U.S. Appl. No. 14/379,825, dated Dec. 22, 2016, 8 pages.
USPTO Non-Final Office Action in U.S. Appl. No. 14/379,825, dated Jul. 20, 2017, 18 pages.
USPTO Final Office Action in U.S. Appl. No. 14/379,825, dated Apr. 2, 2018, 20 pages.
USPTO Non-Final Office Action in U.S. Appl. No. 14/379,825, dated Nov. 1, 2018, 27 pages.
USPTO Final Office Action in U.S. Appl. No. 14/379,825, dated Jun. 14, 2019, 30 pages.
USPTO Restriction Requirement in U.S. Appl. No. 14/404,051, dated Apr. 4, 2016, 13 pages.
USPTO Non-Final Office Action in U.S. Appl. No. 14/404,051, dated Dec. 6, 2016, 22 pages.
USPTO Final Office Action in U.S. Appl. No. 14/404,051, dated Oct. 18, 2017, 15 pages.
USPTO Advisory Action Before the Filing of an Appeal Brief and Notice of Non-Compliant Amendment (37 CFR 1.121) in U.S. Appl. No. 14/404,051, dated Jun. 28, 2018, 4 pages.
USPTO Advisory Action Before the Filing of an Appeal Brief in U.S. Appl. No. 14/404,051, dated Aug. 30, 2018, 3 pages.

(56) References Cited

OTHER PUBLICATIONS

USPTO Non-Final Office Action in U.S. Appl. No. 14/404,051, dated Oct. 11, 2019, 30 pages.
USPTO Non-Final Office Action in U.S. Appl. No. 14/423,269, dated Oct. 2, 2019, 24 pages.
USPTO Advisory Action in U.S. Appl. No. 14/402,574, dated Feb. 16, 2017, 3 pages.
USPTO Final Office Action in U.S. Appl. No. 14/402,574, dated Oct. 31, 2016, 16 pages.
USPTO Non-Final Office Action in U.S. Appl. No. 14/402,574, dated May 6, 2016, 31 pages.
USPTO Restriction Requirement in U.S. Appl. No. 14/402,574, dated Feb. 11, 2016, 10 pages.
USPTO Final Office Action in U.S. Appl. No. 14/402,574, dated Jul. 16, 2018, 10 pages.
USPTO Non-Final Office Action in U.S. Appl. No. 14/402,574, dated Jan. 16, 2018, 24 pages.
USPTO Non-Final Office Action in U.S. Appl. No. 14/422,207, dated Feb. 7, 2017, 17 pages.
USPTO Non-Final Office Action in U.S. Appl. No. 14/422,207, dated Feb. 11, 2016, 11 pages.
USPTO Restriction Requirement in U.S. Appl. No. 14/422,207, dated Nov. 20, 2015, 6 pages.
USPTO Final Office Action in U.S. Appl. No. 14/422,207, dated Nov. 16, 2017, 30 pages.
USPTO Non-Final Office Action in U.S. Appl. No. 14/422,207, dated Jun. 18, 2019, 43 pages.
U.S. Appl. No. 14/404,051, Igawa et al., filed Nov. 26, 2014.
U.S. Appl. No. 14/423,269, Katada et al., filed Feb. 23, 2015.
U.S. Appl. No. 16/697,310, filed Nov. 27, 2019, Igawa et al.
U.S. Appl. No. 16/806,027, filed Mar. 2, 2020, Igawa et al.
U.S. Appl. No. 16/763,134, filed May 11, 2020, Feng et al.
U.S. Appl. No. 16/889,066, filed Jun. 1, 2020, Ruike et al.
Annotated amino acid sequence of the variable heavy (VH) and variable light (VL) domains of the monoclonal antibodies bevacizumab/Avastin, adalimumab/Humira, omalizumab/Xolair, and rituximab/Mabthera, 10 pages (submitted to the EPO with the written submission to attend oral proceedings on Sep. 6, 2019 by Opponent 1 in EP 11714860.1).
Arici, "Local Cytokines in Endometrial Tissue: The Role of Interleukin-8 in the Pathogenesis of Endometriosis," Ann NY Acad Sci, Mar. 2002, 955:101-109, discussion 118, pp. 396-406.
Ascierto et al., "Clinical Experiences With Anti-CD137 and Anti-PD1 Therapeutic Antibodies," Semin Oncol, Oct. 2010, 37(5):508-516, doi: 10.1053/j.seminoncol.2010.09.008.
Buckler, Section 2.4 "Library Selection," Antibody Drug Discovery, edited by Clive R. Wood, Imperial College Press, 2012, vol. 4—Molecular Medicine and Medicinal Chemistry, pp. 49-57.
Chen et al., "Enhancement and destruction of antibody function by somatic mutation: unequal occurrence is controlled by V gene combinatorial associations," EMBO J, Jun. 15, 1995, 14(12):2784-2794.
Colman, "Effects of amino acid sequence changes on antibody-antigen interactions," Res Immunol, Jan. 1994, 145(1):33-36.
Decision of the Opposition Division dated Dec. 19, 2019 in EP 2 552 955, 18 pages (document submitted by Patentee (Chugai Seiyaku Kabushiki Kaisha) in the grounds of appeal on Apr. 28, 2020 in EP2 552 955).
Diamond et al., "Somatic mutation of the T15 heavy chain gives rise to an antibody with autoantibody specificity," Proc Natl Acad Sci USA, Sep. 1984, 81(18):5841-5844.
Dubrot et al., "Treatment with anti-CD137 mAbs causes intense accumulations of liver T cells without selective antitumor immunotherapeutic effects in this organ," Cancer Immunol Immunother, Aug. 2010, 59(8):1223-1233, doi: 10,1007/s00262-010-0846-9, Epub Mar. 25, 2010.
English translation of JP 2010-266121 (priority document for EP 2 647 706), 132 pages (submitted to European Patent Office on May 25, 2020, by Applicant during the examination procedure for EP 3 517 550).

English translation of JP 2011-217886 (priority document for EP 2 647 706), 365 pages (submitted to European Patent Office on May 25, 2020, by Applicant during the examination procedure for EP 3 517 550).
Evidence for the publication date of Zalevsky et al., Nat Biotechnol, Feb. 2010, 28(2): 157-159, 1 page (submitted to the EPO with the written submission to attend oral proceedings on Sep. 6, 2019 by Opponent 1 in EP 11714860.1).
Expert Declaration of Joachim Boucneau, dated Sep. 6, 2019, 13 pages (submitted to the EPO with the written submission to attend oral proceedings on Sep. 6, 2019 by Opponent 1 in EP 11714860.1).
Finlay et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J Mol Biol, May 8, 2009, 388(3):541-558.
Gonzalez et al., "BMP-1/Tolloid-like Metalloproteases Process Endorepellin, the Angiostatic C-terminal Fragment of Perlecan," J Biol Chem, Feb. 2, 20055, 280(8):7080-7087. Epub Dec. 9, 2004.
Hamid et al., "Anti-programmed death-1 and anti-programmed death-ligand 1 antibodies in cancer therapy," Expert Opin Biol Ther, Jun. 2013, 13(6):847-861. doi: 10.1517/14712598.2013.770836. Epub Feb. 19, 2013.
Hanahan et al., "Hallmarks of Cancer: The Next Generation," Cell, Mar. 4, 2011, 144(5):646-674, doi: 10.1016/j.cell.2011.02.013.
Hasemann et al., "Mutational Analysis of Arsonate Binding by a $CRI_{A+}$ Antibody—$V_H$ and $V_L$ Junctional Diversity are Essential for Binding Activity," J Biol Chem, Apr. 25, 1991, 266(12):7626-7632.
Hoogenboom, "Selecting and screening recombinant antibody libraries," Nat Biotechnol, Sep. 2005, 23(9):1105-1116.
Houot et al., "Therapeutic effect of CD137 immunomodulation in lymphoma and its enhancement by $T_{reg}$ depletion," Blood, Oct. 15, 2009, 114(16):3431-3438. doi: 10.1182/blood-2009-05-223958. Epub Jul. 29, 2009.
Igawa et al., "Engineered Monoclonal Antibody with Novel Antigen-Sweeping Activity In Vivo," PLoS One, May 7, 2013, 8(5):e63236, 10 pages, doi: 10.1371/journal.pone.0063236, Print 2013.
Igawa et al., "pH-dependent antigen-binding antibodies as a novel therapeutic modality," Biochim Biophys Acta, Nov. 2014, 1844(11): 1943-1950. doi: 10.1016/j.bbapap.2014.08.003. Epub Aug. 12, 2014.
Igawa et al., "Sweeping antibody as a novel therapeutic antibody modality capable of eliminating soluble antigens from circulation," Immunol Rev, Mar. 2016, 270(1):132-151.
Ito et al., "Molecular Designs of Antibodies and Peptides by Phage Display," Seibutsubutsuri, 2008, 48(5):294-298 (with English translation).
Kanyavuz et al., "Breaking the law: unconventional strategies for antibody diversification," Nat Rev Immunol, Jun. 2019, 19(6):355-368. doi: 10.1038/s41577-019-0126-7.
King, "Preparation, structure and function of monoclonal antibodies," Applications and Engineering of Monoclonal Antibodies, CRC Press, 1998, pp. 2, 13-14.
Kipriyanov et al., "Review—Generation of Recombinant Antibodies," Mol Biotechnol, Sep. 1999, 12(2): 173-201.
Li et al., "Antitumor activities of agonistic anti-TNFR antibodies require differential FcγRIIB coengagement in vivo," Proc Natl Acad Sci USA, Nov. 26, 2013, 110(48): 19501-19506. doi: 10.1073/pnas. 1319502110, Epub Nov. 11, 2013.
Mariuzza et al., "The Structural Basis of Antigen-Antibody Recognition," Annu Rev Biophys Biophys Chem, Jun. 1987, 16:139-159.
Misawa et al., "Rapid and High-Sensitivity Cell-Based Assays of Protein—Protein Interactions Using Split Click Beetle Luciferase Complementation: An Approach to the Study of G-Protein-Coupled Receptors," Anal Chem, Mar. 15, 2010, 82(6):2552-2560, doi:10. 1021/ac100104q.
Muramatsu, "Latent myostatin specific elimination by sweeping antibody® is a novel therapeutic approach to improve muscle strength," Abstracts/Neuromuscular Disorders, 2019, 29(Supplement 1):S86.
Ohno et al., "Antigen-binding specificities of antibodies are primarily determined by seven residues of $V_H$," Proc Natl Acad Sci USA, May 1985, 82(9):2945-2949.

(56) References Cited

OTHER PUBLICATIONS

Pace et al., "How to measure and predict the molar absorption coefficient of a protein," Protein Sci, Nov. 1995, 4(11):2411-2423.
Patentee submission dated Jul. 16, 2015 (Response to Search Report filed on Jul. 16, 2015), 30 pages (document submitted by the Opponent on May 6, 2020 in Opposition of EP 2 679 681).
Pirruccello-Straub, "Blocking extracellular activation of myostatin as a strategy for treating muscle wasting," Scientific Reports, Feb. 2, 2018, 8:2292, 15 pages.
Prieto et al., "CTLA-4 Blockade with Ipilimumab: Long-term Follow-up of 177 Patients with Metastatic Melanoma," Clin Cancer Res, Apr. 1, 2012, 18(7):2039-2047. doi: 10.1158/1078-0432,CCR-11-1823, Epub Jan. 23, 2012.
Proprietor's (Chugai Seiyaku Kabushiki Kaisha) Submission dated Sep. 19, 2016 in EP11714860.1, 3 pages (submitted to the EPO with the written submission to attend oral proceedings on Sep. 6, 2019 by Opponent 1 EP 11714860,1).
Proprietor's (Chugai Seiyaku Kabushiki Kaisha) Submission dated Sep. 5, 2016 in EP11714860.1, 6 pages (submitted to the EPO with the written submission to attend oral proceedings on Sep. 6, 2019 by Opponent 1 inEP 11714860,1).
Proprietor's (Chugai Seiyaku Kabushiki Kaisha) Submission dated Feb. 20, 2017 in EP 2 275 443, 35 pages (submitted to the EPO with the written submission to attend oral proceedings on Sep. 6, 2019 by Opponent 5 in EP 11714860.1).
Rich et al., "A global study using affinity-based biosensors," Anal Biochem, Mar. 15, 2009, 386(2):194-216, doi: 10.1016/j.ab.2008.11.021. Epub Nov. 27, 2008.
Roitt et al., "Overview: Antibody—a flexible adaptor," Immunology, M., Mir, 2000, p. 9 (with English translation).
Safdari et al., "Antibody humanization methods—a review and update," Biotechnol Genet Eng Rev, 2013,29:175-186.
Schabowsky et al., "A Novel Form of 4-1BBL Has Better Immunomodulatory Activity than an Agonistic Anti-4-1BB Ab without Ab Associated Severe Toxicity," Vaccine, Dec. 11, 2009, 28(2):512-522, doi: 1016/j.vaccine.2009.09.127. Epub Oct. 29, 2009.
Schlothauer et al., "Novel human IgG1 and IgG4 Fc-engineered antibodies with completely abolished immune effector functions," Protein Eng Des Sel, Oct. 2016, 29(10):457-466. doi: 10.1093/protein/gzw040. Epub Aug. 29, 2016.
Sigma product information for ACES buffer, 1 page (submitted to the EPO with the written submission to attend oral proceedings on Sep. 6, 2019 by Opponent 1 in EP 11714860.1).
Summers et al., "Fine-tuning of dendritic cell biology by the TNF superfamily," Nat Rev Immunol, Apr. 10, 2012, 12(5):339-351. doi: 10.1038/nri3193.
Table summarizing alleged lack of novelty over WO 2009/086320A, Jul. 9, 2009, 4 pages (submitted to the EPO with the written submission to attend oral proceedings on Sep. 6, 2019 by Opponent 1 in EP 11714860.1).
Tarantul, "Antibodies," Explanatory Biotechnological Dictionary—Russian-English, Moscow, Languages of Slavic Cultures, 2009, p. 72 (with English translation).
Vinay et al., "4-1BB signaling beyond T cells," Cell Mol Immunol, Jul. 2011, 8(4):281-284. doi: 10.1038/cmi.2010.82. Epub Jan. 10, 2011.
Wolfman et al., "Activation of latent myostatin by the BMP-1/tolloid family of metalloproteinases," Proc Natl Acad Sci USA, Dec. 2., 2003, 100(26): 15842-15846. Epub Dec. 11, 2003.
Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.
USPTO Final Office Action in U.S. Appl. No. 14/404,051, dated Jul. 14, 2020, 31 pages.
USPTO Notice of Allowance and Examiner-Initiated Interview Summary in U.S. Appl. No. 14/423,269, dated Jun. 5, 2020, 10 pages.
USPTO Final Office Action in U.S. Appl. No. 14/422,207, dated Mar. 27, 2020, 16 pages.
USPTO Final Office Action in U.S. Appl. No. 15/952,945, dated Jun. 3, 2019, 18 pages.
U.S. Appl. No. 14/347,034, Igawa et al., filed Mar. 25, 2014 (abandoned).
U.S. Appl. No. 17/028,210, filed Sep. 22, 2020, Katada et al.
U.S. Appl. No. 17/046,395, filed Oct. 9, 2020, Fukuzawa et al.
U.S. Appl. No. 17/144,342, filed Jan. 8, 2021, Igawa et al.
Abe et al., "Effect of $\beta_2$-microglobulin adsorption column on dialysis-related amyloidosis," Kidney Int, Oct. 2003, 64(4): 1522-1528, doi: 10.1046/j.1523-1755.2003.00235.x.
"Alexa FluorR 488 anti-β-Amyloid, 1-16 Antibody 6E10," Catalog 803013, Biolegend, Sep. 10, 2018, 3 pages, <https://www.biolegend.com/en-US/global-elements/pdf-popup/alexa-fluor-488-antibeta-amyloid--1-16-antibody-10833?filename=Alexa%20Fluorreg%20488%20anti-beta-Amyloid%201-16%20Antibody.pdf&pdfgen=true>.
Alignment sequences 1047 and 30, Jan. 26, 2021, 1 page (document cited in the office action dated Feb. 2, 2021 for EP 15869566.8).
Alignment sequences 472 and 24, Jan. 26, 2021, 1 page (document cited in the office action dated Feb. 2, 2021 for EP 15869566.8).
"Anti-Glial Fibrillary Acidic Protein (GFAP) Mouse mAb (G-A-5)," IF03L, Millipore Sigma, Aug. 27, 2007, 3 pages, <https://www.emdmillipore.com/US/en/product/Anti-Glial-Fibrillary-Acidic-Protein-GFAP-Mouse-mAb-G-A-5,EMD_BIOIF03L#anchor_PDS>.
"Anti-Huntingtin antibody [EPR5526] abl09115," Abeam, 11 pages, printed from the internet Apr. 13, 2020, <https://www.abcam.com/huntingtin-antibody-epr5526-abl09115.pdP>.
Arlaud et al., "A Study on the Structure and Interactions of the Cl Sub-Components C1r and C1s in the Fluid Phase," Biochim Biophys Acta, Nov. 6, 1980, 616(1): 105-115.
Arnoux et al., "Metformin reverses early cortical network dysfunction and behavior changes in Huntington's disease," Elife, Sep. 4, 2018, 7, pii: e38744, 32 pages, doi: 10,7554/eLife.38744.
Bork, "Powers and Pitfalls in Sequence Analysis: The 70% Hurdler," Genome Res, Apr. 2000, 10(4):398-400.
Bowie et al., "Deciphering the Message in Protein Sequences: Tolerance to Amino Acid Substitutions," Science, Mar. 16, 1990, 247(4948):1306-1310.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J Cell Biol, Nov. 1990, 111(5 Pt 1):2129-2138.
Dagbay et al., "Structural basis of specific inhibition of extracellular activation of pro- or latent myostatin by the monoclonal antibody SRK-015," J Biol Chem, Apr. 17, 2020, 295(16):5404-5418.
Declaration of Muramatsu Hiroyasu, signed Oct. 21, 2020, 5 pages (document cited in the office action dated Feb. 2, 2021 for EP 15869566.8).
Di Stefano et al., "Role of Interleukin-8 in the Pathogenesis and Treatment of COPD," Chest, Sep. 2004, 126(3):676-678, doi: 10,1378/chest.126.3.676.
Flores et al., "Dominant Expression of the Inhibitory FcγRIIB Prevents Antigen Presentation by Murine Plasmacytoid Dendritic Cells," J Immunol, Dec. 1, 2009, 183(11):7129-39. doi: 10.4049/jimmunol.0901169.
Gary et al., Chapter 8 "Making Antibodies in Bacteria," Making and Using Antibodies: A Practical Handbook, CRC Press, Taylor & Francis Group, 2006, pp. 157-177.
"GD-IgAl (KM55) anti-human rat monoclonal antibody," Catalog No. 10777, IBL America, 6 pages, printed from the internet Apr. 13, 2020, <https://www.iblamerica.com/gd-igal-km55-antihuman-rat-igg-moab/>.
Jones et al., "Mutations in GFAP Disrupt the Distribution and Function of Organelles in Human Astrocytes," Cell Rep, Oct. 23, 2018, 25(4):947-958,e4, doi: 10.1016/j.celrep.2018.09.083.
Kabat et al., "Sequences of Proteins of Immunological Interest," 1991, National Institute of Health Publication No. 91-3242, pp. 103, 310.
Kedia et al., "Desmin forms toxic, seeding-competent amyloid aggregates that persist in muscle fibers," Proc Natl Acad Sci USA, Aug. 20, 2019, 116(34): 16835-16840. doi: 10.1073/pnas.1908263116. Epub Aug. 1, 2019.

(56) References Cited

OTHER PUBLICATIONS

Kim et al., "Affinity Maturation of Monoclonal Antibodies by Multi-Site-Directed Mutagenesis," Methods Mol Biol, 2014, 1131:407-20. doi: 10.1007/978-1-62703-992-5 24.
Kontermann et al., Chapter 4 "Mouse Immune Libraries for the Generation of ScFv Fragments Directed Against Human Cell Surface Antigens," 1:47-62 and Chapter 27 "Engineering of the Fc Region for Improved PK (FcRn Interaction)," Antibody Engineering, 2010, 1:415-427.
Lazar et al., "Transforming Growth Factor a: Mutation of Aspartic Acid 47 and Leucine 48 Results in Different Biological Activities," Mol Cell Biol, Mar. 1988, 8(3): 1247-1252.
Liberti et al., "Antigenicity of polypeptides (poly-alpha-amino acids). Physicochemical studies of a calcium-dependent antigen-antibody reaction," Biochemistry, Apr. 27, 1971, 10(9): 1632-1639.
Matsumoto et al., "Functional analysis of activated C1s, a subcomponent of the first component of human complement, by monoclonal antibodies," J Immunol, Nov. 1, 1986, 137(9):2907-2912.
Mendez-Fernandez et al., "The inhibitory FcγRIIb modulates the inflammatory response and influences atherosclerosis in male apoE$^{-/-}$ mice," Atherosclerosis, Jan. 2011, 214(1):73-80. doi: 10.1016/j.atherosclerosis.2010.10.018.
"Monoclonal Mouse Anti-Human Desmin (Concentrate) Clone D33," Code No. M0760, Agilent Dako, 3 pages, printed from the internet Apr. 13, 2020 <https://www.agilent.com/en/product/immunohistochemistry/antibodies controls/primaryantibodies/desmin-(concentrate)-76523>.
Mortensen et al., "Structure and activation of C1, the complex initiating the classical pathway of the complement cascade," Proc Natl Acad Sci USA, Jan. 31, 2017, 114(5):986-991. doi: 10.1073/pnas.1616998114, Epub Jan. 19, 2017.
Nagaoka et al., "Single amino acid substitution in the mouse IgG1 Fc region induces drastic enhancement of the affinity to protein A," Protein Eng, Apr. 2003, 16(4):243-245. doi: 10.1093/proeng/gzg037.
Petillot et al., "Analysis of the N-linked oligosaccharides of human C1s using electrospray ionisation mass spectrometry," FEBS Lett, Jan. 30, 1995, 358(3):323-328.
Poosarla et al., "Computational de novo Design of Antibodies binding to a Peptide with High Affinity," Biotechnol Bioeng, Jun. 2017, 114(6):1331-1342.
Rivas et al., "Calcium-Linked Self-Association of Human Complement C1s," Biochemistry, Dec. 1, 1992, 31(47):11707-11712.
Rossi et al., "Classical Complement Pathway Components C1r and C1s: Purification from Human Serum and in Recombinant Form and Functional Characterization," Methods Mol Biol, 2014, 1100:43-60. doi: 10.1007/978-1-62703-724-2_4.
Schuster et al., "The human interleukin-6 (IL-6) receptor exists as a preformed dimer in the plasma membrane," FEBS Lett, Mar. 13, 2003, 538(1-3): 113-116.
Shi et al., "TNT003, an inhibitor of the serine protease C1s, prevents complement activation induced by cold agglutinins," Blood, Jun. 26, 2014, 123(26):4015-4022. doi: 10.1182/blood-2014-02-556027. Epub Apr. 2, 2014.
Sikkink et al., "Biochemical and aggregation analysis of Bence Jones proteins from different light chain diseases," Amyloid, Mar. 2008, 15(1):29-39.
Singer et al., Chapter 3 "The Logic and Machinery of Gene Expression," Genes & Genomes, Moscow, Mir, 1998, pp. 115-188 (with what are believed to be the corresponding pages from an English version of Genes & Genomes).
Stavenhagen et al., "Enhancing the potency of therapeutic monoclonal antibodies via Fc optimization," Adv Enzyme Regul, 2008, 48:152-164.
Suzuki et al., "IgA nephropathy and IgA vasculitis with nephritis have a shared feature involving galactose-deficient IgA1-oriented pathogenesis," Kidney Int, Mar. 2018, 93(3):700-705. doi: 10.1016/j.kint.2017.10.019. Epub Jan. 10, 2018.
Tackenberg et al., "Impaired inhibitory Fcγ receptor IIB expression on B cells in chronic inflammatory demyelinating polyneuropathy," Proc Natl Acad Sci USA, Mar. 24, 2009, 106(12):4788-4792, doi: 10.1073/pnas.0807319106.
Torres et al., "The immunoglobulin constant region contributes to affinity and specificity," Trend Immunol, Feb. 2008, 29(2):91-97.
Wang et al., "Molecular Basis of Assembly and Activation of Complement Component C1 in Complex with Immunoglobulin G1 and Antigen," Mol Cell, Jul. 7, 2016, 63(1): 135-45. doi: 10.1016/j.molcel.2016.05.016. Epub Jun. 16, 2016.
Warmerdam et al., "The human low affinity immunoglobulin G Fc receptor IIC gene is a result of an unequal crossover event," J Biol Chem, Apr. 5, 1993, 268(10):7346-7349.
USPTO Non-Final Office Action in U.S. Appl. No. 14/379,825, dated Nov. 4, 2020, 31 pages.
USPTO Applicant-Initiated Interview Summary in U.S. Appl. No. 14/422,207, dated Oct. 21, 2020, 3 pages.
USPTO Advisory Action for U.S. Appl. No. 14/422,207, dated Jan. 1, 2021, 4 pages.
USPTO Applicant-Initiated Interview Summary in U.S. Appl. No. 14/422,207, dated Apr. 16, 2021, 2 pages.
U.S. Appl. No. 16/323,142, Kakiuchi et al., filed Feb. 4, 2019.
U.S. Appl. No. 17/333,256, Kakiuchi ey al., filed May 28, 2021.
U.S. Pat. No. 10,738,111, Ruike et al., issued Aug. 11, 2020.
U.S. Appl. No. 15/963,455, Ruike et al., filed Apr. 26, 2018.
U.S. Pat. No. 10,519,229, Igawa et al., issued Dec. 31, 2019.
U.S. Appl. No. 14/001,218, Mimoto et al., filed Dec. 2, 2013.
U.S. Pat. No. 10,618,965, Igawa et al., issued Apr. 14, 2020.
U.S. Appl. No. 16/806,027, Igawa et al., filed Mar. 2, 2020.
U.S. Pat. No. 9,890,218, Mimoto et al., issued Feb. 13, 2018.
U.S. Appl. No. 15/860,163, Mimoto et al., filed Jan. 2, 2018.
U.S. Appl. No. 14/347,034, Igawa et al., filed March 25, 2014 (abandoned)
U.S. Appl. No. 15/230,904, Igawa et al., filed Aug. 8, 2016 (abandoned).
U.S. Appl. No. 16/028,140, Igawa et al., filed Jul. 5, 2018.
U.S. Appl. No. 14/347,321, Igawa et al., filed Mar. 26, 2014 (abandoned).
U.S. Appl. No. 15/977,757, Igawa et al., filed May 11, 2018.
U.S. Pat. No. 10,253,100, Igawa et al., issued Apr. 9, 2019.
U.S. Appl. No. 16/264,735, Igawa et al., filed Feb. 1, 2019.
U.S. Appl. No. 14/361,013, Igawa et al., filed May 28, 2014 (abandoned).
U.S. Appl. No. 16/108,897, Igawa et al., filed Aug. 22, 2018.
U.S. Appl. No. 14/379,825, Igawa et al., filed Aug. 20, 2014.
U.S. Appl. No. 14/404,051, Igawa et al., filed Nov. 26, 2014 (abandoned).
U.S. Appl. No. 17/144,342, Igawa et al., filed Jan. 8, 2021.
U.S. Pat. No. 10,919,953, Katada et al., issued Feb. 16, 2021.
U.S. Appl. No. 17/028,210, Katada et al., filed Sep. 22, 2020.
U.S. Pat. No. 10,766,960, Igawa et al., issued Sep. 8, 2020.
U.S. Pat. No. 10,000,560, Ruike et al., issued Jun. 19, 2018.
U.S. Pat. No. 9,969,800, Igawa et al., issued May 15, 2018.
U.S. Appl. No. 15/210,353, Igawa et al., filed Jul. 14, 2016.
U.S. Appl. No. 15/210,360, Igawa et al., filed Jul. 14, 2016.
U.S. Appl. No. 13/637,415, Igawa et al., filed Feb. 4, 2013.
U.S. Appl. No. 15/050,145, Igawa et al., filed Feb. 22, 2016.
U.S. Appl. No. 15/495,026, Igawa et al., filed Apr. 24, 2017.
U.S. Appl. No. 16/065,192, Ruike et al., filed Jun. 22, 2018.
U.S. Appl. No. 16/889,066, Ruike et al., filed Jun. 1, 2020.
U.S. Appl. No. 16/697,310, Igawa etal., filed Nov. 27, 2019
U.S. Appl. No. 16/763,134, Feng et al., filed May 11, 2020.
U.S. Appl. No. 17/046,395, Fukuzawa et al., filed Oct. 9, 2020.
U.S. Appl. No. 17/266,024, Igawa et al., filed Feb. 4, 2021.
U.S. Appl. No. 17/494,199, Igawa et al., filed Oct. 5, 2021.
U.S. Appl. No. 17/602,196, Wakabayashi et al., filed Oct. 7, 2021.
U.S. Appl. No. 17/610,204, Koga, filed Nov. 10, 2021.
U.S. Appl. No. 17/333,256, Kakiuchi et al., filed May 28, 2021.
Abdiche et al., "Antibodies Targeting Closely Adjacent or Minimally Overlapping Epitopes Can Displace One Another," PLoS One, Jan. 6, 2017, 12(1):e0169535, doi: 10,1371/joumal.pone. 0169535.

(56) References Cited

OTHER PUBLICATIONS

Almitairi et al., "Structure of the C1r—C1s interaction of the C1 complex of complement activation," Proc Natl Acad Sci USA, Jan. 2, 20183, 115(4):768-773, doi:10.1073/pnas.1718709115.
Annex 1 accompanying Response to Statement of Grounds of Appeal of Opponent 2 (Alexion Pharmaceuticals, Inc.), 29 pages, dated Sep. 16, 2020, in opposition proceedings of EP 2 552 955.
Application as filed for EP 2 698 431, 375 pages (document cited during opposition proceedings of EP 2 698 431 on Jun. 23, 2021).
Arduin et al., "Highly reduced binding to high and low affinity mouse Fc gamma receptors by L234A/L235A and N297A Fc mutations engineered into mouse IgG2a," Mol Immunol, Feb. 2015, 63(2):456-463.
Bally et al., "Identification of the C1q-binding Sites of Human C1r and C1s—A Refined Three-Dimensional Model of the C1 Complex of Complement," J Biol Chem, Jul. 1, 20097, 284(29): 19340-19348, doi: 10.1074/jbc.M109.004473.
Datta-Mannan et al., "FcRn Affinity-Pharmacokinetic Relationship of Five Human IgG4 Antibodies Engineered for Improved In Vitro FcRn Binding Properties in Cynomolgus Monkeys," DrugMetab Dispos, Aug. 2012, 40(8)4545-1555.
Decision of the Opposition Division in FP 2 275 443, dated Apr. 26, 2018, 29 pages (submitted on Sep. 3, 2021 with the response to office action in EP 3 702 368 A).
Ellison et al., "Linkage and sequence homology of two human immunoglobulin gamma heavy chain constant region genes," Proc Natl Acad Sci USA, Mar. 1982, 79(6): 1984-1988.
English translation of PCT/JP2011/072550, 283 pages, corresponding to WO 2012/132067, cited in IDS filed on Jan. 5, 2016. The translation was submitted in the opposition proceedings of EP 2 698 431 on Jun. 23, 2021.
English translation of PCT/JP2012/054624, 110 pages, corresponding to WO 2012/115241, cited in IDS filed on Nov. 14, 2016. The translation was submitted in the opposition proceedings of EP 2 698 431 on Jun. 23, 2021.
EUTM register extract—Biacore, 4 pages (document downloaded on Aug. 26, 2020, submitted in Opposition of EP 2 552 955, and posted by EPO on Sep. 15, 2020).
Gal et al., "Early complement proteases: C1r, C1s and MASPs. A structural insight into activation and functions," Mol Immunol, 2009 Sept, 46(14):2745-2752, doi:10.1016/j.molimm.2009.04.026.
Gershoni et al., "Epitope Mapping—The First Step in Developing Epitope-Based Vaccines," BioDrugs, 2007, 21(3): 145-156.
Guidance on the use of International Nonproprietary Names (INNs) for Pharmaceutical Substances, World Health Organisation, 2017, 54 pages (document submitted in opposition proceedings of EP 2 552 955 and posted by EPO on Sep. 16, 2020).
Han et al., "Monoclonal antibodies: interspecies scaling with minimal preclinical information," Ther Deliv, Mar. 2011, 2(3):359-368.
Huck et al., "Sequence of a human immunoglobulin gamma 3 heavy chain constant region gene: comparison with the other human C gamma genes," Nucleic Acids Res, Feb. 2, 19865, 14(4): 1779-1789.
Jakubke et al., "Physicochemical properties," Amino Acids, Peptides and Proteins, Moscow, Mir, 1985, pp. 356-363 (with English translation).
Jung et al., "Aglycosylated IgG variants expressed in bacteria that selectively bind FcKRI potentiate tumor cell killing by monocyte-dendritic cells," Proc Natl Acad Sci USA, Jan. 12, 2010, 107(2):604-609.

Lacroix et al., "Assembly and Enzymatic Properties of the Catalytic Domain of Human Complement Protease C1r," J Biol Chem, Sep. 28, 2001, 276(39):36233-36240. doi: 10.1074/jbc.M105688200.
Lescar et al., "Crystal Structure of a Cross-reaction Complex between Fab F9.13.7 and Guinea Fowl Lysozyme," J Biol Chem, Jul. 28, 1995, 270(30): 18067-18076.
NCBI database: GenBank Accession No. AAC82527.1, Jun. 10, 2016, "immunoglobulin gamma-1 heavy chain constant region, partial [*Homo sapiens*]" (https ://www.ncbi.nlm.nih.gov/protein/AAC82527.1).
NCBI database: GenBank Accession No. AAB59393.1, Aug. 1, 2016, "immunoglobulin gamma-2 heavy chain, partial [*Homo sapiens*]," (https://www.ncbi.nlm.nih.gov/protein/AAB59393.l).
NCBI database: GenBank Accession No. AAB59394.1, Aug. 1, 2016, "immunoglobulin gamma-4 heavy chain, partial [*Homo sapiens*]," (https://www.ncbi.nlm.nih.gov/protein/AAB59394.l).
NCBI database: GenBank Accession No. CAA27268.1, Jul. 25, 2016, "C gamma 3, partial [*Homo sapiens*]," (https://www.ncbi.nlm.nih.gov/protein/CAA27268.1).
Notice of Opposition by Opponent 1 (Ablynx N.V.), dated Feb. 2, 2018, submitted in opposition proceedings of EP 2 552 955, 50 pages.
Statement of Facts and Arguments in Support of Opposition by Opponent 2 (Alexion Pharmaceuticals, Inc.), dated Feb. 2, 2018, submitted in opposition proceedings of EP 2 552 955, 39 pages.
Opposition Statement of Opponent 5 (Shire Human Genetic Therapies, Inc.), dated Feb. 5, 2018, submitted in opposition proceedings of EP 2 552 955, 70 pages.
PCT/JP2011/001888, filed Mar. 30, 2011, 203 pages, corresponding to WO 2011/122011, cited in IDS filed on Jan. 5, 2016 (document cited in opposition proceedings of EP 2 698 431 on Jun. 23, 2021).
Presta et al., "Engineering therapeutic antibodies for improved function," Biochem Soc Trans, Aug. 2002, 30(4):487-490.
Rossi et al., "Baculovirus-mediated Expression of Truncated Modular Fragments from the Catalytic Region of Human Complement Serine Protease C1s," J Biol Chem, Jan. 9, 1998, 273(2): 1232-1239. doi:10.1074/jbc.273,2.1232.
Salfeld et al., "Isotype selection in antibody engineering," Nat Biotechnol, Dec. 25, 2007:1369-1372.
Response by Opponent 1 (Ablynx N.V.), dated Sep. 6, 2019, submitted in opposition proceedings of EP 2 552 955, 57 pages.
Final Written Submissions of Opponent 2 (Alexion Pharmaceuticals, Inc.), dated Sep. 6, 2019, submitted in opposition proceedings of EP 2 552 955, 26 pages.
Reply from Opponent 5 (Shire Human Genetic Therapies, Inc.), dated Sep. 6, 2019, submitted in opposition proceedings of EP 2 552 955, 15 pages.
Takahashi et al., "Structure of human immunoglobulin gamma genes: implications for evolution of a gene family," Cell, Jun. 1982, 29(2):671-679.
Tseng et al., "Probing the Structure of C1 with an Anti-C1s Monoclonal Antibody: The Possible Existence of Two Forms of C1 in Solution," Mol Immunol, 1997, 34(8-9):671-679. doi:10.1016/s0161-5890(97)00039-4.
Wines et al., "The IgG Fc Contains Distinct Fc Receptor (FcR) Binding Sites: The Leukocyte Receptors FcKRI and FcRKIIa Bind to a Region in the Fc Distinct from That Recognized by Neonatal FcR and Protein A," J Immunol, May 1, 20005, 164(10):5313-5318.
USPTO Final Office Action in U.S. App. U.S. Appl. No. 14/379,825, dated Jun. 16, 2021, 43 pages.

\* cited by examiner

SEQUENCE LISTING

```
<160> NUMBER OF SEQ ID NOS: 52

<210> SEQ ID NO 1
<211> LENGTH: 447
<212> TYPE: PRT
<213> ORGANISM: Artificial
<220> FEATURE:
<223> OTHER INFORMATION: an artificially synthesized peptide sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
```

```
                    260                 265                 270
Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
                435                 440                 445

<210> SEQ ID NO 2
<211> LENGTH: 447
<212> TYPE: PRT
<213> ORGANISM: Artificial
<220> FEATURE:
<223> OTHER INFORMATION: an artificially synthesized peptide sequence

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
        435                 440                 445

<210> SEQ ID NO 3
<211> LENGTH: 447
<212> TYPE: PRT
<213> ORGANISM: Artificial
<220> FEATURE:
<223> OTHER INFORMATION: an artificially synthesized peptide sequence

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
```

```
                    100                 105                 110
Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 4
<211> LENGTH: 447
<212> TYPE: PRT
<213> ORGANISM: Artificial
<220> FEATURE:
<223> OTHER INFORMATION: an artificially synthesized peptide sequence

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
```

-continued

```
                20                  25                  30
His Ala Trp Ser Trp Val Arg Gln Pro Gly Glu Gly Leu Glu Trp
            35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
        420                 425                 430
Ala Leu His Asn His Tyr Thr Gln Glu Ser Leu Ser Leu Ser Pro
        435                 440                 445
```

<210> SEQ ID NO 5
<211> LENGTH: 447
<212> TYPE: PRT
<213> ORGANISM: Artificial
<220> FEATURE:
<223> OTHER INFORMATION: an artificially synthesized peptide sequence

<400> SEQUENCE: 5

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Asp Leu Leu Gly Asp Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Glu Glu Asp
            260                 265                 270

Gly Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 6
<211> LENGTH: 214
<212> TYPE: PRT
<213> ORGANISM: Artificial
<220> FEATURE:
<223> OTHER INFORMATION: an artificially synthesized peptide sequence

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 7
<211> LENGTH: 218
<212> TYPE: PRT
<213> ORGANISM: Artificial
<220> FEATURE:
<223> OTHER INFORMATION: an artificially synthesized peptide sequence

<400> SEQUENCE: 7

Asp Ile Gln Leu Thr Gln Ser Pro Ser Ser Leu Ser Ala Ser Val Gly
```

```
1               5                   10                  15
Asp Arg Val Thr Ile Thr Cys Arg Ala Ser Gln Ser Val Asp Tyr Asp
                20                  25                  30

Gly Asp Ser Tyr Met Asn Trp Tyr Gln Gln Lys Pro Gly Lys Ala Pro
                35                  40                  45

Lys Leu Leu Ile Tyr Ala Ala Ser Tyr Leu Glu Ser Gly Val Pro Ser
            50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 8
<211> LENGTH: 446
<212> TYPE: PRT
<213> ORGANISM: Artificial
<220> FEATURE:
<223> OTHER INFORMATION: an artificially synthesized peptide sequence

<400> SEQUENCE: 8

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
                20                  25                  30

Tyr Met Tyr Trp Val Lys Gln Ala Pro Gly Gln Gly Leu Glu Trp Ile
                35                  40                  45

Gly Glu Ile Asn Pro Ser Asn Gly Asp Thr Asn Phe Asn Glu Lys Phe
            50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
```

```
                145                 150                 155                 160
Ser Gly Ala Leu Thr Ser Gly Val His Thr Phe Pro Ala Val Leu Gln
                165                 170                 175

Ser Ser Gly Leu Tyr Ser Leu Ser Ser Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro
                435                 440                 445

<210> SEQ ID NO 9
<211> LENGTH: 218
<212> TYPE: PRT
<213> ORGANISM: Artificial
<220> FEATURE:
<223> OTHER INFORMATION: an artificially synthesized peptide sequence

<400> SEQUENCE: 9

Asp Ile Val Leu Thr Gln Ser Pro Ala Thr Leu Ser Val Ser Pro Gly
1               5                   10                  15

Glu Arg Ala Thr Ile Ser Cys Arg Ala Ser Gln Arg Val Ser Ser Ser
                20                  25                  30

Thr Tyr Ser Tyr Met His Trp Tyr Gln Gln Lys Pro Gly Gln Pro Pro
                35                  40                  45

Lys Leu Leu Ile Lys Tyr Ala Ser Asn Leu Glu Ser Gly Val Pro Ala
                50                  55                  60

Arg Phe Ser Gly Ser Gly Ser Gly Thr Asp Phe Thr Leu Thr Ile Ser
```

```
                65                  70                  75                  80
Ser Val Glu Pro Glu Asp Phe Ala Thr Tyr Tyr Cys Gln His Ser Trp
                    85                  90                  95

Glu Ile Pro Pro Thr Phe Gly Gly Gly Thr Lys Leu Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
            130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 10
<211> LENGTH: 443
<212> TYPE: PRT
<213> ORGANISM: Artificial
<220> FEATURE:
<223> OTHER INFORMATION: an artificially synthesized peptide sequence

<400> SEQUENCE: 10

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
                20                  25                  30

Met Ser Trp Val Arg Gln Ala Pro Gly Lys Gly Leu Glu Trp Ile Gly
            35                  40                  45

Val Ile Asn Ser Ala Gly Asn Thr Tyr Tyr Ala Ser Trp Ala Lys Gly
50                  55                  60

Arg Phe Thr Val Ser Lys Thr Ser Thr Thr Val Asp Leu Asn Leu Thr
65                  70                  75                  80

Ser Leu Thr Thr Glu Asp Thr Ala Thr Tyr Phe Cys Ala Arg Tyr Val
                85                  90                  95

Phe Ser Ser Gly Ser His Asp Ile Trp Gly Pro Gly Thr Leu Val Thr
                100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
            130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
                180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
```

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
        245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440

<210> SEQ ID NO 11
<211> LENGTH: 217
<212> TYPE: PRT
<213> ORGANISM: Artificial
<220> FEATURE:
<223> OTHER INFORMATION: an artificially synthesized peptide sequence

<400> SEQUENCE: 11

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Gly Ser Trp
            20                  25                  30

Leu Ala Trp Tyr Gln Gln Lys Pro Gly Gln Pro Pro Lys Glu Leu Ile
        35                  40                  45

Tyr Gly Thr Ser Thr Leu Glu Ser Gly Val Pro Ser Arg Phe Ile Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Gly Tyr Ser Glu Asp Asn
                85                  90                  95

Ile Asp Asn Ala Phe Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro

```
                    130                 135                 140
Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 12
<211> LENGTH: 32
<212> TYPE: PRT
<213> ORGANISM: Homo sapiens

<400> SEQUENCE: 12

Val Asp Asp Ala Pro Gly Asn Ser Gln Gln Ala Thr Pro Lys Asp Asn
1               5                   10                  15

Glu Ile Ser Thr Phe His Asn Leu Gly Asn Val His Ser Pro Leu Lys
                20                  25                  30

<210> SEQ ID NO 13
<211> LENGTH: 543
<212> TYPE: PRT
<213> ORGANISM: Artificial
<220> FEATURE:
<223> OTHER INFORMATION: an artificially synthesized peptide sequence

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Gln Ser Pro Ser Val Phe Pro Leu Thr Arg
        115                 120                 125

Cys Cys Lys Asn Ile Pro Ser Asn Ala Thr Ser Val Thr Leu Gly Cys
    130                 135                 140

Leu Ala Thr Gly Tyr Phe Pro Glu Pro Val Met Val Thr Trp Asp Thr
145                 150                 155                 160

Gly Ser Leu Asn Gly Thr Thr Met Thr Leu Pro Ala Thr Thr Leu Thr
                165                 170                 175

Leu Ser Gly His Tyr Ala Thr Ile Ser Leu Leu Thr Val Ser Gly Ala
            180                 185                 190

Trp Ala Lys Gln Met Phe Thr Cys Arg Val Ala His Thr Pro Ser Ser
        195                 200                 205
```

Thr Asp Trp Val Asp Asn Lys Thr Phe Ser Val Cys Ser Arg Asp Phe
    210                 215                 220

Thr Pro Pro Thr Val Lys Ile Leu Gln Ser Ser Cys Asp Gly Gly Gly
225                 230                 235                 240

His Phe Pro Pro Thr Ile Gln Leu Leu Cys Leu Val Ser Gly Tyr Thr
                245                 250                 255

Pro Gly Thr Ile Asn Ile Thr Trp Leu Glu Asp Gly Gln Val Met Asp
            260                 265                 270

Val Asp Leu Ser Thr Ala Ser Thr Thr Gln Glu Gly Glu Leu Ala Ser
        275                 280                 285

Thr Gln Ser Glu Leu Thr Leu Ser Gln Lys His Trp Leu Ser Asp Arg
290                 295                 300

Thr Tyr Thr Cys Gln Val Thr Tyr Gln Gly His Thr Phe Glu Asp Ser
305                 310                 315                 320

Thr Lys Lys Cys Ala Asp Ser Asn Pro Arg Gly Val Ser Ala Tyr Leu
                325                 330                 335

Ser Arg Pro Ser Pro Phe Asp Leu Phe Ile Arg Lys Ser Pro Thr Ile
            340                 345                 350

Thr Cys Leu Val Val Asp Leu Ala Pro Ser Lys Gly Thr Val Asn Leu
        355                 360                 365

Thr Trp Ser Arg Ala Ser Gly Lys Pro Val Asn His Ser Thr Arg Lys
370                 375                 380

Glu Glu Lys Gln Arg Asn Gly Thr Leu Thr Val Thr Ser Thr Leu Pro
385                 390                 395                 400

Val Gly Thr Arg Asp Trp Ile Glu Gly Glu Thr Tyr Gln Cys Arg Val
                405                 410                 415

Thr His Pro His Leu Pro Arg Ala Leu Met Arg Ser Thr Thr Lys Thr
            420                 425                 430

Ser Gly Pro Arg Ala Ala Pro Glu Val Tyr Ala Phe Ala Thr Pro Glu
        435                 440                 445

Trp Pro Gly Ser Arg Asp Lys Arg Thr Leu Ala Cys Leu Ile Gln Asn
450                 455                 460

Phe Met Pro Glu Asp Ile Ser Val Gln Trp Leu His Asn Glu Val Gln
465                 470                 475                 480

Leu Pro Asp Ala Arg His Ser Thr Thr Gln Pro Arg Lys Thr Lys Gly
                485                 490                 495

Ser Gly Phe Phe Val Phe Ser Arg Leu Glu Val Thr Arg Ala Glu Trp
            500                 505                 510

Glu Gln Lys Asp Glu Phe Ile Cys Arg Ala Val His Glu Ala Ala Ser
        515                 520                 525

Pro Ser Gln Thr Val Gln Arg Ala Val Ser Val Asn Pro Gly Lys
    530                 535                 540

<210> SEQ ID NO 14
<211> LENGTH: 219
<212> TYPE: PRT
<213> ORGANISM: Artificial
<220> FEATURE:
<223> OTHER INFORMATION: an artificially synthesized peptide sequence

<400> SEQUENCE: 14

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

```
Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Asn
                 85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
210                 215

<210> SEQ ID NO 15
<211> LENGTH: 543
<212> TYPE: PRT
<213> ORGANISM: Artificial
<220> FEATURE:
<223> OTHER INFORMATION: an artificially synthesized peptide sequence

<400> SEQUENCE: 15

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
 50                  55                  60

Lys Gly Arg Val Thr Leu Thr Ala Asp Lys Ser Thr Ser Thr Ala Tyr
 65                  70                  75                  80

Met Glu Leu Ser Ser Leu Thr Ser Glu Asp Thr Ala Val Tyr Tyr Cys
                 85                  90                  95

Thr Arg Phe Tyr Ser Tyr Thr Tyr Trp Gly Gln Gly Thr Leu Val Thr
            100                 105                 110

Val Ser Ser Ala Ser Thr Gln Ser Pro Ser Val Phe Pro Leu Thr Arg
        115                 120                 125

Cys Cys Lys Asn Ile Pro Ser Asp Ala Thr Ser Val Thr Leu Gly Cys
130                 135                 140

Leu Ala Thr Gly Tyr Phe Pro Glu Pro Val Met Val Thr Trp Asp Thr
145                 150                 155                 160

Gly Ser Leu Asp Gly Thr Thr Met Thr Leu Pro Ala Thr Thr Leu Thr
                165                 170                 175
```

```
Leu Ser Gly His Tyr Ala Thr Ile Ser Leu Thr Val Ser Gly Ala
            180                 185                 190

Trp Ala Lys Gln Met Phe Thr Cys Arg Val Ala His Thr Pro Ser Ser
        195                 200                 205

Thr Asp Trp Val Asp Asp Lys Thr Phe Ser Val Cys Ser Arg Asp Phe
210                 215                 220

Thr Pro Pro Thr Val Lys Ile Leu Gln Ser Ser Cys Asp Gly Gly Gly
225                 230                 235                 240

His Phe Pro Pro Thr Ile Gln Leu Leu Cys Leu Val Ser Gly Tyr Thr
                245                 250                 255

Pro Gly Thr Ile Asp Ile Thr Trp Leu Glu Asp Gly Gln Val Met Asp
            260                 265                 270

Val Asp Leu Ser Thr Ala Ser Thr Thr Gln Glu Gly Glu Leu Ala Ser
        275                 280                 285

Thr Gln Ser Glu Leu Thr Leu Ser Gln Lys His Trp Leu Ser Asp Arg
    290                 295                 300

Thr Tyr Thr Cys Gln Val Thr Tyr Gln Gly His Thr Phe Glu Asp Ser
305                 310                 315                 320

Thr Lys Lys Cys Ala Asp Ser Asn Pro Arg Gly Val Ser Ala Tyr Leu
                325                 330                 335

Ser Arg Pro Ser Pro Phe Asp Leu Phe Ile Arg Lys Ser Pro Thr Ile
            340                 345                 350

Thr Cys Leu Val Val Asp Leu Ala Pro Ser Lys Gly Thr Val Asp Leu
        355                 360                 365

Thr Trp Ser Arg Ala Ser Gly Lys Pro Val Asp His Ser Thr Arg Lys
    370                 375                 380

Glu Glu Lys Gln Arg Asn Gly Thr Leu Thr Val Thr Ser Thr Leu Pro
385                 390                 395                 400

Val Gly Thr Arg Asp Trp Ile Glu Gly Glu Thr Tyr Gln Cys Arg Val
                405                 410                 415

Thr His Pro His Leu Pro Arg Ala Leu Met Arg Ser Thr Thr Lys Thr
            420                 425                 430

Ser Gly Pro Arg Ala Ala Pro Glu Val Tyr Ala Phe Ala Thr Pro Glu
        435                 440                 445

Trp Pro Gly Ser Arg Asp Lys Arg Thr Leu Ala Cys Leu Ile Gln Asn
    450                 455                 460

Phe Met Pro Glu Asp Ile Ser Val Gln Trp Leu His Asn Glu Val Gln
465                 470                 475                 480

Leu Pro Asp Ala Arg His Ser Thr Thr Gln Pro Arg Lys Thr Lys Gly
                485                 490                 495

Ser Gly Phe Phe Val Phe Ser Arg Leu Glu Val Thr Arg Ala Glu Trp
            500                 505                 510

Glu Gln Lys Asp Glu Phe Ile Cys Arg Ala Val His Glu Ala Ala Ser
        515                 520                 525

Pro Ser Gln Thr Val Gln Arg Ala Val Ser Val Asn Pro Gly Lys
    530                 535                 540

<210> SEQ ID NO 16
<211> LENGTH: 545
<212> TYPE: PRT
<213> ORGANISM: Homo sapiens

<400> SEQUENCE: 16

Gln Pro Pro Pro Pro Pro Pro Asp Ala Thr Cys His Gln Val Arg Ser
```

-continued

```
1               5                   10                  15
Phe Phe Gln Arg Leu Gln Pro Gly Leu Lys Trp Val Pro Glu Thr Pro
                20                  25                  30
Val Pro Gly Ser Asp Leu Gln Val Cys Leu Pro Lys Gly Pro Thr Cys
                35                  40                  45
Cys Ser Arg Lys Met Glu Glu Lys Tyr Gln Leu Thr Ala Arg Leu Asn
                50                  55                  60
Met Glu Gln Leu Leu Gln Ser Ala Ser Met Glu Leu Lys Phe Leu Ile
65                      70                  75                  80
Ile Gln Asn Ala Ala Val Phe Gln Glu Ala Phe Glu Ile Val Val Arg
                    85                  90                  95
His Ala Lys Asn Tyr Thr Asn Ala Met Phe Lys Asn Asn Tyr Pro Ser
                    100                 105                 110
Leu Thr Pro Gln Ala Phe Glu Phe Val Gly Phe Phe Thr Asp Val
                115                 120                 125
Ser Leu Tyr Ile Leu Gly Ser Asp Ile Asn Val Asp Asp Met Val Asn
    130                 135                 140
Glu Leu Phe Asp Ser Leu Phe Pro Val Ile Tyr Thr Gln Leu Met Asn
145                 150                 155                 160
Pro Gly Leu Pro Asp Ser Ala Leu Asp Ile Asn Glu Cys Leu Arg Gly
                165                 170                 175
Ala Arg Arg Asp Leu Lys Val Phe Gly Asn Phe Pro Lys Leu Ile Met
                180                 185                 190
Thr Gln Val Ser Lys Ser Leu Gln Val Thr Arg Ile Phe Leu Gln Ala
                195                 200                 205
Leu Asn Leu Gly Ile Glu Val Ile Asn Thr Thr Asp His Leu Lys Phe
    210                 215                 220
Ser Lys Asp Cys Gly Arg Met Leu Thr Arg Met Trp Tyr Cys Ser Tyr
225                 230                 235                 240
Cys Gln Gly Leu Met Met Val Lys Pro Cys Gly Gly Tyr Cys Asn Val
                245                 250                 255
Val Met Gln Gly Cys Met Ala Gly Val Val Glu Ile Asp Lys Tyr Trp
                260                 265                 270
Arg Glu Tyr Ile Leu Ser Leu Glu Glu Leu Val Asn Gly Met Tyr Arg
            275                 280                 285
Ile Tyr Asp Met Glu Asn Val Leu Leu Gly Leu Phe Ser Thr Ile His
    290                 295                 300
Asp Ser Ile Gln Tyr Val Gln Lys Asn Ala Gly Lys Leu Thr Thr Thr
305                 310                 315                 320
Ile Gly Lys Leu Cys Ala His Ser Gln Gln Arg Gln Tyr Arg Ser Ala
                325                 330                 335
Tyr Tyr Pro Glu Asp Leu Phe Ile Asp Lys Lys Val Leu Lys Val Ala
                340                 345                 350
His Val Glu His Glu Glu Thr Leu Ser Arg Arg Arg Glu Leu Ile
                355                 360                 365
Gln Lys Leu Lys Ser Phe Ile Ser Phe Tyr Ser Ala Leu Pro Gly Tyr
    370                 375                 380
Ile Cys Ser His Ser Pro Val Ala Glu Asn Asp Thr Leu Cys Trp Asn
385                 390                 395                 400
Gly Gln Glu Leu Val Glu Arg Tyr Ser Gln Lys Ala Ala Arg Asn Gly
                405                 410                 415
Met Lys Asn Gln Phe Asn Leu His Glu Leu Lys Met Lys Gly Pro Glu
                420                 425                 430
```

```
Pro Val Ser Gln Ile Ile Asp Lys Leu Lys His Ile Asn Gln Leu
        435                 440                 445

Leu Arg Thr Met Ser Met Pro Lys Gly Arg Val Leu Asp Lys Asn Leu
    450                 455                 460

Asp Glu Glu Gly Phe Glu Ala Gly Asp Cys Gly Asp Asp Glu Asp Glu
465                 470                 475                 480

Cys Ile Gly Gly Ala Gly Asp Gly Met Ile Lys Val Lys Asn Gln Leu
                485                 490                 495

Arg Phe Leu Ala Glu Leu Ala Tyr Asp Leu Asp Val Asp Asp Ala Pro
            500                 505                 510

Gly Asn Ser Gln Gln Ala Thr Pro Lys Asp Asn Glu Ile Ser Thr Phe
            515                 520                 525

His Asn Leu Gly Asn Val His Ser Pro Leu Lys His His His His His
        530                 535                 540

His
545

<210> SEQ ID NO 17
<211> LENGTH: 119
<212> TYPE: PRT
<213> ORGANISM: Artificial
<220> FEATURE:
<223> OTHER INFORMATION: an artificially synthesized peptide sequence

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115

<210> SEQ ID NO 18
<211> LENGTH: 449
<212> TYPE: PRT
<213> ORGANISM: Artificial
<220> FEATURE:
<223> OTHER INFORMATION: an artificially synthesized peptide sequence

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
```

```
            50                  55                  60
Lys Gly Arg Ile Thr Ile Ser Arg Asp Asp Ser Lys Asn Thr Phe Tyr
 65                  70                  75                  80

Leu Gln Met Asn Ser Leu Arg Ala Glu Asp Thr Ala Val Tyr Tyr Cys
                 85                  90                  95

Ala Arg Gly Ser His Tyr Phe Gly His Trp His Phe Ala Val Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro

<210> SEQ ID NO 19
<211> LENGTH: 464
```

```
<212> TYPE: PRT
<213> ORGANISM: Artificial
<220> FEATURE:
<223> OTHER INFORMATION: an artificially synthesized peptide sequence

<400> SEQUENCE: 19

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Pro Thr Ser Pro Lys Val Phe
        115                 120                 125

Pro Leu Ser Leu Cys Ser Thr Gln Pro Asp Gly Asn Val Val Ile Ala
130                 135                 140

Cys Leu Val Gln Gly Phe Phe Pro Gln Glu Pro Leu Ser Val Thr Trp
145                 150                 155                 160

Ser Glu Ser Gly Gln Gly Val Thr Ala Arg Asn Phe Pro Pro Ser Gln
            165                 170                 175

Asp Ala Ser Gly Asp Leu Tyr Thr Thr Ser Ser Gln Leu Thr Leu Pro
        180                 185                 190

Ala Thr Gln Cys Leu Ala Gly Lys Ser Val Thr Cys His Val Lys His
    195                 200                 205

Tyr Thr Asn Pro Ser Gln Asp Val Thr Val Pro Cys Pro Val Pro Ser
210                 215                 220

Thr Pro Pro Thr Pro Ser Pro Ser Thr Pro Pro Thr Pro Ser Pro Ser
225                 230                 235                 240

Cys Cys His Pro Arg Leu Ser Leu His Arg Pro Ala Leu Glu Asp Leu
            245                 250                 255

Leu Leu Gly Ser Glu Ala Asn Leu Thr Cys Thr Leu Thr Gly Leu Arg
        260                 265                 270

Asp Ala Ser Gly Val Thr Phe Thr Trp Thr Pro Ser Ser Gly Lys Ser
    275                 280                 285

Ala Val Gln Gly Pro Pro Glu Arg Asp Leu Cys Gly Cys Tyr Ser Val
290                 295                 300

Ser Ser Val Leu Pro Gly Cys Ala Glu Pro Trp Asn His Gly Lys Thr
305                 310                 315                 320

Phe Thr Cys Thr Ala Ala Tyr Pro Glu Ser Lys Thr Pro Leu Thr Ala
            325                 330                 335

Thr Leu Ser Lys Ser Gly Asn Thr Phe Arg Pro Glu Val His Leu Leu
        340                 345                 350

Pro Pro Pro Ser Glu Glu Leu Ala Leu Asn Glu Leu Val Thr Leu Thr
    355                 360                 365

Cys Leu Ala Arg Gly Phe Ser Pro Lys Asp Val Leu Val Arg Trp Leu
370                 375                 380
```

```
Gln Gly Ser Gln Glu Leu Pro Arg Glu Lys Tyr Leu Thr Trp Ala Ser
385                 390                 395                 400

Arg Gln Glu Pro Ser Gln Gly Thr Thr Thr Phe Ala Val Thr Ser Ile
            405                 410                 415

Leu Arg Val Ala Ala Glu Asp Trp Lys Lys Gly Asp Thr Phe Ser Cys
            420                 425                 430

Met Val Gly His Glu Ala Leu Pro Leu Ala Phe Thr Gln Lys Thr Ile
        435                 440                 445

Asp Arg Leu Ala Gly Lys Glu Gln Lys Leu Ile Ser Glu Glu Asp Leu
    450                 455                 460
```

<210> SEQ ID NO 20
<211> LENGTH: 214
<212> TYPE: PRT
<213> ORGANISM: Artificial
<220> FEATURE:
<223> OTHER INFORMATION: an artificially synthesized peptide sequence

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 450
<212> TYPE: PRT
<213> ORGANISM: Artificial
<220> FEATURE:
<223> OTHER INFORMATION: an artificially synthesized peptide sequence

<400> SEQUENCE: 21

```
Glu Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ala Pro Gly Asn Trp Gly Ser Pro Tyr Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430
```

```
Met His Glu Ala Leu His Asn His Tyr Thr Gln Lys Ser Leu Ser Leu
            435                 440                 445

Ser Pro
    450

<210> SEQ ID NO 22
<211> LENGTH: 214
<212> TYPE: PRT
<213> ORGANISM: Artificial
<220> FEATURE:
<223> OTHER INFORMATION: an artificially synthesized peptide sequence

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 451
<212> TYPE: PRT
<213> ORGANISM: Artificial
<220> FEATURE:
<223> OTHER INFORMATION: an artificially synthesized peptide sequence

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
450

<210> SEQ ID NO 24
<211> LENGTH: 214
```

```
<212> TYPE: PRT
<213> ORGANISM: Artificial
<220> FEATURE:
<223> OTHER INFORMATION: an artificially synthesized peptide sequence

<400> SEQUENCE: 24
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 25
<211> LENGTH: 443
<212> TYPE: PRT
<213> ORGANISM: Artificial
<220> FEATURE:
<223> OTHER INFORMATION: an artificially synthesized peptide sequence

<400> SEQUENCE: 25
```

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

```
Thr Leu Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 26
<211> LENGTH: 214
<212> TYPE: PRT
<213> ORGANISM: Artificial
<220> FEATURE:
<223> OTHER INFORMATION: an artificially synthesized peptide sequence

<400> SEQUENCE: 26

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30
```

```
Leu Asn Trp Tyr Gln Gln Lys Pro Gly Lys Ala Pro Glu Leu Leu Ile
            35                  40                  45

Tyr Tyr Gly Ser His Leu Leu Ser Gly Val Pro Ser Arg Phe Ser Gly
        50                  55                  60

Ser Gly Ser Gly Thr Asp Phe Thr Phe Thr Ile Ser Ser Leu Glu Ala
 65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Ala Asp Ala Ala
            100                 105                 110

Pro Thr Val Ser Ile Phe Pro Pro Ser Glu Gln Leu Thr Ser Gly
            115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
            210

<210> SEQ ID NO 27
<211> LENGTH: 214
<212> TYPE: PRT
<213> ORGANISM: Artificial
<220> FEATURE:
<223> OTHER INFORMATION: an artificially synthesized peptide sequence

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 447
<212> TYPE: PRT
<213> ORGANISM: Artificial
<220> FEATURE:
<223> OTHER INFORMATION: an artificially synthesized peptide sequence

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

Tyr Lys Cys Lys Val Ser Asn Lys Ala Tyr Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 29
<211> LENGTH: 214
<212> TYPE: PRT
<213> ORGANISM: Artificial
<220> FEATURE:
<223> OTHER INFORMATION: an artificially synthesized peptide sequence

<400> SEQUENCE: 29

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
            35                  40                  45

Tyr Tyr Gly Ser His Leu Leu Ser Gly Val Pro Ser Arg Phe Ser Gly
            50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
            85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 30

```
<211> LENGTH: 447
<212> TYPE: PRT
<213> ORGANISM: Artificial
<220> FEATURE:
<223> OTHER INFORMATION: an artificially synthesized peptide sequence

<400> SEQUENCE: 30

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380
```

Ser Asn Gly Gln Pro Glu Asn Tyr Lys Thr Thr Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 31
<211> LENGTH: 330
<212> TYPE: PRT
<213> ORGANISM: Artificial
<220> FEATURE:
<223> OTHER INFORMATION: an artificially synthesized peptide sequence

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 32
<211> LENGTH: 326
<212> TYPE: PRT
<213> ORGANISM: Artificial
<220> FEATURE:
<223> OTHER INFORMATION: an artificially synthesized peptide sequence

<400> SEQUENCE: 32

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 33
<211> LENGTH: 377
<212> TYPE: PRT
<213> ORGANISM: Artificial
<220> FEATURE:
<223> OTHER INFORMATION: an artificially synthesized peptide sequence

<400> SEQUENCE: 33

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365
```

```
Lys Ser Leu Ser Leu Ser Pro Gly Lys
        370             375
```

<210> SEQ ID NO 34
<211> LENGTH: 327
<212> TYPE: PRT
<213> ORGANISM: Artificial
<220> FEATURE:
<223> OTHER INFORMATION: an artificially synthesized peptide sequence

<400> SEQUENCE: 34

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65              70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 35

```
<211> LENGTH: 1125
<212> TYPE: DNA
<213> ORGANISM: Homo sapiens

<400> SEQUENCE: 35
atgtggttct tgacaactct gctcctttgg gttccagttg atgggcaagt ggacaccaca      60
aaggcagtga tcactttgca gcctccatgg gtcagcgtgt tccaagagga aaccgtaacc     120
ttgcactgtg aggtgctcca tctgcctggg agcagctcta cacagtggtt tctcaatggc     180
acagccactc agacctcgac ccccagctac agaatcacct ctgccagtgt caatgacagt     240
ggtgaataca ggtgccagag aggtctctca gggcgaagtg acccatacag ctgaaaatc     300 cacagaggct ggctactact gcaggtctcc agcagagtct tcacggaagg agaacctctg     360
gccttgaggt gtcatgcgtg gaaggataag ctggtgtaca atgtgcttta ctatcgaaat     420
ggcaaagcct ttaagttttt ccactggaat tctaacctca ccattctgaa aaccaacata     480
agtcacaatg gcacctacca ttgctcaggc atgggaaagc atcgctacac atcagcagga     540
atatctgtca ctgtgaaaga gctatttcca gctccagtgc tgaatgcatc tgtgacatcc     600
ccactcctgg aggggaatct ggtcaccctg agctgtgaaa caaagttgct cttgcagagg     660
cctggtttgc agctttactt ctccttctac atgggcagca agaccctgcg aggcaggaac     720
acatcctctg aataccaaat actaactgct agaagagaag actctgggtt atactggtgc     780
gaggctgcca cagaggatgg aaatgtcctt aagcgcagcc tgagttgga gcttcaagtg     840 cttggcctcc agttaccaac tcctgtctgg tttcatgtcc ttttctatct ggcagtggga     900
ataatgtttt tagtgaacac tgttctctgg gtgacaatac gtaaagaact gaaaagaaag     960
aaaaagtggg atttagaaat ctctttggat tctggtcatg agaagaaggt aatttccagc    1020
cttcaagaag acagacattt agaagaagag ctgaaatgtc aggaacaaaa agaagaacag    1080
ctgcaggaag gggtgcaccg gaaggagccc caggggggcca cgtag                    1125

<210> SEQ ID NO 36
<211> LENGTH: 374
<212> TYPE: PRT
<213> ORGANISM: Homo sapiens

<400> SEQUENCE: 36

Met Trp Phe Leu Thr Thr Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140
```

```
Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
            165                 170                 175

Thr Ser Ala Gly Ile Ser Val Thr Val Lys Glu Leu Phe Pro Ala Pro
        180                 185                 190

Val Leu Asn Ala Ser Val Thr Ser Pro Leu Leu Glu Gly Asn Leu Val
    195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
            245                 250                 255

Leu Tyr Trp Cys Glu Ala Ala Thr Glu Asp Gly Asn Val Leu Lys Arg
        260                 265                 270

Ser Pro Glu Leu Glu Leu Gln Val Leu Gly Leu Gln Leu Pro Thr Pro
    275                 280                 285

Val Trp Phe His Val Leu Phe Tyr Leu Ala Val Gly Ile Met Phe Leu
290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
            325                 330                 335

Val Ile Ser Ser Leu Gln Glu Asp Arg His Leu Glu Glu Glu Leu Lys
        340                 345                 350

Cys Gln Glu Gln Lys Glu Glu Gln Leu Gln Glu Gly Val His Arg Lys
    355                 360                 365

Glu Pro Gln Gly Ala Thr
370

<210> SEQ ID NO 37
<211> LENGTH: 951
<212> TYPE: DNA
<213> ORGANISM: Homo sapiens

<400> SEQUENCE: 37
atgactatgg agacccaaat gtctcagaat gtatgtccca gaaacctgtg gctgcttcaa    60
ccattgacag ttttgctgct gctggcttct gcagacagtc aagctgctcc cccaaaggct   120
gtgctgaaac ttgagccccc gtggatcaac gtgctccagg aggactctgt gactctgaca   180
tgccaggggg ctcgcagccc tgagagcgac tccattcagt ggttccacaa tgggaatctc   240
attcccaccc acacgcagcc cagctacagg ttcaaggcca caacaatga cagcggggag   300 tacacgtgcc agactggcca gaccagcctc agcgaccctg tgcatctgac tgtgctttcc   360
gaatggctgg tgctccagac ccctcacctg gagttccagg aggagaaaac catcatgctg   420
aggtgccaca gctggaagga caagcctctg gtcaaggtca cattcttcca gaatggaaaa   480
tcccagaaat ctcccatttt ggatcccacc ttctccatcc acaagcaaac cacagtcac   540 agtggtgatt accactgcac aggaaacata ggctacacgc tgttctcatc aagcctgtg   600 accatcactg tccaagtgcc agcatgggc agctcttcac caatgggggt cattgtggct   660
gtggtcattg cgactgctgt agcagccatt gttgctgctg tagtggcctt gatctactgc   720
aggaaaaagc ggatttcagc caattccact gatcctgtga aggctgccca atttgagcca   780
```

```
cctggacgtc aaatgattgc catcagaaag agacaacttg aagaaaccaa caatgactat    840
gaaacagctg acggcggcta catgactctg aacccagggg cacctactga cgatgataaa    900
aacatctacc tgactcttcc tcccaacgac catgtcaaca gtaataacta a             951
```

<210> SEQ ID NO 38
<211> LENGTH: 316
<212> TYPE: PRT
<213> ORGANISM: Homo sapiens

<400> SEQUENCE: 38

Met Thr Met Glu Thr Gln Met Ser Gln Asn Val Cys Pro Arg Asn Leu
1               5                   10                  15

Trp Leu Leu Gln Pro Leu Thr Val Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 39
<211> LENGTH: 876
<212> TYPE: DNA
<213> ORGANISM: Homo sapiens

<400> SEQUENCE: 39

```
atgggaatcc tgtcattctt acctgtcctt gccactgaga gtgactgggc tgactgcaag    60
tcccccagc cttggggtca tatgcttctg tggacagctg tgctattcct ggctcctgtt   120
gctgggacac ctgcagctcc cccaaaggct gtgctgaaac tcgagcccca gtggatcaac   180
gtgctccagg aggactctgt gactctgaca tgccggggga ctcacagccc tgagagcgac   240
tccattcagt ggttccacaa tgggaatctc attccaccc acacgcagcc agctacagg    300
ttcaaggcca caacaatga cagcggggag tacacgtgcc agactggcca gaccagcctc   360
agcgaccctg tgcatctgac tgtgctttct gagtggctgg tgctccagac ccctcacctg   420
gagttccagg agggagaaac catcgtgctg aggtgccaca gctggaagga caagcctctg   480
gtcaaggtca cattcttcca gaatggaaaa tccaagaaat tttcccgttc ggatcccaac   540
ttctccatcc cacaagcaaa ccacagtcac agtggtgatt accactgcac aggaaacata   600
ggctacacgc tgtactcatc caagcctgtg accatcactg tccaagctcc cagctcttca   660
ccgatgggga tcattgtggc tgtggtcact gggattgctg tagcggccat tgttgctgct   720
gtagtggcct tgatctactg caggaaaaag cggatttcag ccaatcccac taatcctgat   780
gaggctgaca agttggggc tgagaacaca atcacctatt cacttctcat gcacccggat   840
gctctggaag agcctgatga ccagaaccgt atttag                               876
```

<210> SEQ ID NO 40
<211> LENGTH: 291
<212> TYPE: PRT
<213> ORGANISM: Homo sapiens

<400> SEQUENCE: 40

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205
```

```
Pro Val Thr Ile Thr Val Gln Ala Pro Ser Ser Pro Met Gly Ile
    210                 215                 220

Ile Val Ala Val Val Thr Gly Ile Ala Val Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290

<210> SEQ ID NO 41
<211> LENGTH: 765
<212> TYPE: DNA
<213> ORGANISM: Homo sapiens

<400> SEQUENCE: 41
atgtggcagc tgctcctccc aactgctctg ctacttctag tttcagctgg catgcggact      60
gaagatctcc caaaggctgt ggtgttcctg agcctcaat ggtacagggt gctcgagaag     120
gacagtgtga ctctgaagtg ccaggagcc tactcccctg aggacaattc acacagtgg     180 tttcacaatg agagcctcat ctcaagccag gcctcgagct acttcattga cgctgccaca     240
gttgacgaca gtggagagta caggtgccag acaaacctct ccaccctcag tgacccggtg     300
cagctagaag tccatatcgg ctggctgttg ctccaggccc ctcggtgggt gttcaaggag     360
gaagacccta ttcacctgag gtgtcacagc tggaagaaca ctgctctgca taaggtcaca     420
tatttacaga atggcaaagg caggaagtat tttcatcata attctgactt ctacattcca     480
aaagccacac tcaaagacag cggctcctac ttctgcaggg ggcttgttgg gagtaaaaat     540
gtgtcttcag agactgtgaa catcaccatc actcaaggtt tgtcagtgtc aaccatctca     600
tcattctttc cacctgggta ccaagtctct ttctgcttgg tgatggtact cctttttgca     660
gtggacacag gactatattt ctctgtgaag acaaacattc gaagctcaac aagagactgg     720
aaggaccata aatttaaatg gagaaaggac cctcaagaca atga                      765

<210> SEQ ID NO 42
<211> LENGTH: 254
<212> TYPE: PRT
<213> ORGANISM: Homo sapiens

<400> SEQUENCE: 42

Met Trp Gln Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95
```

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 43
<211> LENGTH: 702
<212> TYPE: DNA
<213> ORGANISM: Homo sapiens

<400> SEQUENCE: 43

```
atgtggcagc tgctcctccc aactgctctg ctacttctag tttcagctgg catgcggact      60
gaagatctcc caaaggctgt ggtgttcctg agccctcaat ggtacagcgt gcttgagaag     120
gacagtgtga ctctgaagtg ccagggagcc tactcccctg aggacaattc cacacagtgg    180
tttcacaatg agagcctcat ctcaagccag gcctcgagct acttcattga cgctgccaca    240
gtcaacgaca gtggagagta caggtgccag acaaacctct ccaccctcag tgacccggtg    300
cagctagaag tccatatcgg ctggctgttg ctccaggccc ctcggtgggt gttcaaggag    360
gaagacccta ttcacctgag gtgtcacagc tggaagaaca ctgctctgca taaggtcaca    420
tatttacaga atggcaaaga caggaagtat tttcatcata attctgactt ccacattcca    480
aaagccacac tcaaagatag cggctcctac ttctgcaggg ggcttgttgg gagtaaaaat    540
gtgtcttcag agactgtgaa catcaccatc actcaaggtt tggcagtgtc aaccatctca    600
tcattctctc cacctgggta ccaagtctct ttctgcttgg tgatggtact ccttttttgca    660
gtggacacag gactatattt ctctgtgaag acaaacattt ga                       702
```

<210> SEQ ID NO 44
<211> LENGTH: 233
<212> TYPE: PRT
<213> ORGANISM: Homo sapiens

<400> SEQUENCE: 44

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

```
Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

<210> SEQ ID NO 45
<211> LENGTH: 107
<212> TYPE: PRT
<213> ORGANISM: Artificial
<220> FEATURE:
<223> OTHER INFORMATION: an artificially synthesized peptide sequence

<400> SEQUENCE: 45

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
        50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys
            100                 105

<210> SEQ ID NO 46
<211> LENGTH: 107
<212> TYPE: PRT
<213> ORGANISM: Artificial
<220> FEATURE:
<223> OTHER INFORMATION: an artificially synthesized peptide sequence

<400> SEQUENCE: 46

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 47
<211> LENGTH: 112
<212> TYPE: PRT
<213> ORGANISM: Artificial
<220> FEATURE:
<223> OTHER INFORMATION: an artificially synthesized peptide sequence

<400> SEQUENCE: 47

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asp Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Arg Asn Pro Leu Thr Phe Gly Gly Gly Thr Lys Val Glu Ile Gln
            100                 105                 110

<210> SEQ ID NO 48
<211> LENGTH: 107
<212> TYPE: PRT
<213> ORGANISM: Artificial
<220> FEATURE:
<223> OTHER INFORMATION: an artificially synthesized peptide sequence

<400> SEQUENCE: 48

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys

<210> SEQ ID NO 49
<211> LENGTH: 112
<212> TYPE: PRT
<213> ORGANISM: Artificial
<220> FEATURE:
<223> OTHER INFORMATION: an artificially synthesized peptide sequence

<400> SEQUENCE: 49

Asp Ile Val Met Thr Gln Ser Pro Glu Ser Leu Val Leu Ser Leu Gly
1               5                   10                  15

Gly Thr Ala Thr Ile Asn Cys Arg Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Thr Leu Leu Phe Ser Trp Ala Ser Ile Arg Asp Ser Gly Val
    50                  55                  60

Pro Asp Arg Phe Ser Ala Ser Gly Ser Gly Thr Glu Phe Thr Leu Thr
65                  70                  75                  80

Ile Ser Asp Leu Gln Ala Glu Asp Ala Ala Val Tyr Tyr Cys Gln Gln
                85                  90                  95

Tyr Tyr Arg Ala Pro Ser Phe Gly Gln Gly Thr Lys Leu Gln Ile Lys
            100                 105                 110

<210> SEQ ID NO 50
<211> LENGTH: 121
<212> TYPE: PRT
<213> ORGANISM: Artificial
<220> FEATURE:
<223> OTHER INFORMATION: an artificially synthesized peptide sequence

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser
        115                 120

<210> SEQ ID NO 51
<211> LENGTH: 126
<212> TYPE: PRT
<213> ORGANISM: Artificial
<220> FEATURE:
<223> OTHER INFORMATION: an artificially synthesized peptide sequence

<400> SEQUENCE: 51

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
            85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser
            115                 120                 125

<210> SEQ ID NO 52
<211> LENGTH: 444
<212> TYPE: PRT
<213> ORGANISM: Artificial
<220> FEATURE:
<223> OTHER INFORMATION: an artificially synthesized peptide sequence

<400> SEQUENCE: 52

Gln Val Gln Leu Gln Glu Ser Gly Pro Gly Leu Val Lys Pro Ser Glu
 1               5                  10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
 130                 135                 140

Gly Cys Leu Val Lys Asp Tyr Phe Pro Glu Pro Val Thr Val Ser Trp
 145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
 210                 215                 220

Cys Pro Pro Cys Pro Ala Pro Glu Phe Leu Gly Gly Pro Ser Val Phe
 225                 230                 235                 240

Leu Phe Pro Pro Lys Pro Lys Asp Thr Leu Met Ile Ser Arg Thr Pro
            245                 250                 255
```

```
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu
            435                 440
```

FC REGION VARIANT

CROSS-REFERENCE TO RELATED APPLICATIONS

This application is the National Stage of International Application Serial No. PCT/JP2014/059706, filed on Apr. 2, 2014, which claims the benefit of Japanese Application Serial No. 2013-077239, filed on Apr. 2, 2013.

TECHNICAL FIELD

The present invention relates to Fc region variants in which amino acid alterations have been introduced into an antibody Fc region to reduce binding activities to all activating FcγRs, in particular FcγRIIa (R type), while maintaining a binding activity to FcγRIIb, compared to a polypeptide containing a naturally-occurring human IgG Fc region; polypeptides comprising the Fc region variants; and pharmaceutical compositions comprising the polypeptides.

BACKGROUND ART

Antibodies are drawing attention as pharmaceuticals as they are highly stable in plasma and have few side effects. A number of IgG-type antibody pharmaceuticals are now available on the market and many antibody pharmaceuticals are currently under development (Non-patent Documents 1 and 2). Meanwhile, various technologies applicable to second-generation antibody pharmaceuticals have been reported, including those that enhance effector function, antigen-binding ability, pharmacokinetics and stability, and those that reduce the risk of immunogenicity (Non-patent Document 3). In general, the requisite dose of an antibody pharmaceutical is very high. This in turn has led to problems such as high production cost as well as difficulty in producing subcutaneous formulations. In theory, the dose of an antibody pharmaceutical may be reduced by improving antibody pharmacokinetics or improving the affinity between antibodies and antigens.

Literature has reported methods for improving antibody pharmacokinetics using artificial substitution of amino acids in constant regions (Non-patent Documents 4 and 5). Similarly, affinity maturation has been reported as a technology for enhancing antigen-binding ability or antigen-neutralizing activity (Non-patent Document 6). This technology enables enhancement of antigen-binding activity by introduction of amino acid mutations into the CDR of a variable region or such. The enhancement of antigen-binding ability enables improvement of in vitro biological activity or reduction of dosage, and further enables improvement of in vivo efficacy (Non-patent Document 7).

The antigen-neutralizing capacity of a single antibody molecule depends on its affinity. By increasing the affinity, an antigen can be neutralized by a smaller amount of an antibody. Various methods can be used to enhance antibody affinity (Non-patent Document 6). Furthermore, if affinity could be made infinite by covalently binding an antibody to an antigen, a single antibody molecule could neutralize one antigen molecule (a divalent antibody can neutralize two antigen molecules). However, in the methods to date, for a single antibody molecule, binding to one antigen molecule (two antigens if bivalent) is the limit. On the other hand, it has been recently reported that the use of antigen-binding molecules that bind to antigens in a pH-dependent manner allows a single antigen-binding molecule to bind to multiple antigen molecules (Patent Document 1 and Non-patent Document 8). Under the neutral condition in plasma, pH-dependent antigen-binding molecules bind strongly to antigens, and release the antigens under the acidic conditions in endosomes. Furthermore, the antigen-binding molecules can bind to antigen again when they are recycled into the plasma by FcRn after releasing the antigens; therefore, a single pH-dependent antigen-binding molecule can repeatedly bind to multiple antigens.

Furthermore, it has been reported that since pH-dependent antigen-binding molecules altered to enhance FcRn binding under a neutral condition (pH 7.4) have an effect of being able to bind repeatedly to antigens and an effect of eliminating antigens from plasma, administration of such antigen-binding molecules enables antigen elimination from plasma (Patent Document 2). A pH-dependent antigen-binding molecule comprising an ordinary IgG antibody Fc region showed almost no binding to FcRn under neutral conditions. Therefore, uptake of complexes formed between the antigen-binding molecule and antigen into cells may be mainly through non-specific uptake. According to this report, pH-dependent antigen-binding molecules that have been altered to enhance FcRn binding under a neutral condition (pH 7.4) can further accelerate the antigen elimination than the pH-dependent antigen-binding molecule comprising an ordinary IgG antibody Fc region (Patent Document 2).

Since plasma retention of antigens is very short compared to antibodies having an FcRn-mediated recycling mechanism, binding of an antigen in plasma to the antibodies having a recycling mechanism (wherein the binding is not pH-dependent) usually prolongs its retention period in plasma and increases the plasma antigen concentration. For example, in the case of plasma antigens with multiple types of physiological functions, even if one type of physiological activity is blocked by antibody binding, symptoms caused by other physiological functions may be exacerbated by the plasma concentration of the antigens due to antibody binding. Since there are cases where eliminating plasma antigens is favorable from such viewpoint, methods similar to those described above for applying alterations to the Fc region to enhance FcRn-binding with the objective of accelerating antigen elimination have been reported, but so far there has been no report on other methods for accelerating antigen elimination.

In addition, side effects of several therapeutic antibodies originating from interaction between IgG and FcγR have been reported. For example, it is known that a group of patients who were administered with bevacizumab, an anti-VEGF antibody, have an increased rate of developing thromboembolism (Non-patent Document 9). Furthermore, thromboembolism has been similarly observed in clinical development tests of an antibody against the CD40 ligand, and the clinical trial was discontinued (Non-patent Document 10). FcγRIIa, an activating Fcγ receptor, is expressed on platelet cells (Non-patent Document 11), and later studies using animal models and such have suggested that both of the administered antibodies cause platelets to aggregate by binding to FcγRIIa on the platelets, and form blood clots as a result (Non-patent Documents 12 and 13). It has been reported that in patients with systemic lupus erythematosus, which is an autoimmune disease, platelets are activated via an FcγRIIa-dependent mechanism and that platelet activation correlates with the severity of symptoms (Non-patent Document 14).

Furthermore, it has been reported from studies using animal models that multivalent antigen-antibody immune complexes induce anaphylaxis via activating FcγRs (Non-patent Document 15).

In addition, there are reports that incorporation of multivalent antigen-antibody immune complexes via activating FcγRs causes an increase in antibody titer production against the antigen (Non-patent Documents 16 and 17). This result suggests the possibility that antibodies against a therapeutic antibody itself may be more easily produced when it is a therapeutic antibody that recognizes multivalent antigens. If antibodies against a therapeutic antibody are produced, blood kinetics of the therapeutic antibody becomes worse or neutralizing antibodies may weaken the effects of the therapeutics.

This way, an antibody binds to a multivalent antigen to form an immune complex, and interaction of the complex with activating FcγRs may induce various side effects, and this will reduce the value of the antibody as pharmaceuticals.

PRIOR ART DOCUMENTS

Patent Documents

[Patent Document 1] WO2009/125825
[Patent Document 2] WO2011/122011

Non-Patent Documents

[Non-patent Document 1] Monoclonal antibody successes in the clinic, Janice M Reichert, Clark J Rosensweig, Laura B Faden & Matthew C Dewitz, Nat. Biotechnol. (2005) 23, 1073-1078
[Non-patent Document 2] Pavlou A K, Belsey M J., The therapeutic antibodies market to 2008, Eur. J. Pharm. Biopharm. (2005) 59 (3), 389-396
[Non-patent Document 3] Kim S J, Park Y, Hong H J., Antibody engineering for the development of therapeutic antibodies, Mol. Cells. (2005) 20 (1), 17-29
[Non-patent Document 4] Hinton P R, Xiong J M, Johlfs M G, Tang M T, Keller S, Tsurushita N, J. Immunol. (2006) 176 (1), 346-356
[Non-patent Document 5] Ghetie V, Popov S, Borvak J, Radu C, Matesoi D, Medesan C, Ober R J, Ward E S., Nat. Biotechnol. (1997) 15 (7), 637-640
[Non-patent Document 6] Rajpal A, Beyaz N, Haber L, Cappuccilli G, Yee H, Bhatt R R, Takeuchi T, Lerner R A, Crea R., Proc. Natl. Acad. Sci. USA. (2005) 102 (24), 8466-8471
[Non-patent Document 7] Wu H, Pfarr D S, Johnson S, Brewah Y A, Woods R M, Patel N K, White W I, Young J F, Kiener P A., J. Mol. Biol. (2007) 368, 652-665
[Non-patent Document 8] Igawa T, et al., Nat. Biotechnol. (2010) 28, 1203-1207
[Non-patent Document 9] Scappaticci F A, Skillings J R, Holden S N, Gerber H P, Miller K, Kabbinavar F, Bergsland E, Ngai J, Holmgren E, Wang J, Hurwitz H., Arterial thromboembolic events in patients with metastatic carcinoma treated with chemotherapy and bevacizumab, J. Natl. Cancer Inst. (2007) 99 (16), 1232-1239
[Non-patent Document 10] Boumpas D T, Furie R, Manzi S, Illei G G, Wallace D J, Balow J E, Vaishnaw A, A short course of BG9588 (anti-CD40 ligand antibody) improves serologic activity and decreases hematuria in patients with proliferative lupus glomerulonephritis, Arthritis. Rheum. (2003) 48 (3), 719-727.
[Non-patent Document 11] Mackay M, Stanevsky A, Wang T, Aranow C, Li M, Koenig S, Ravetch J V, Diamond B., Selective dysregulation of the FcgammaIIB receptor on memory B cells in SLE, J. Exp. Med. (2006) 203 (9), 2157-2164
[Non-patent Document 12] Meyer T, Robles-Carrillo L, Robson T, Langer F, Desai H, Davila M, Amaya M, Francis J L, Amirkhosravi A., Bevacizumab immune complexes activate platelets and induce thrombosis in FCGR2A transgenic mice, J. Thromb. Haemost. (2009) 7 (1), 171-181
[Non-patent Document 13] Robles-Carrillo L, Meyer T, Hatfield M, Desai H, Davila M, Langer F, Amaya M, Garber E, Francis J L, Hsu Y M, Amirkhosravi A., Anti-CD40L immune complexes potently activate platelets in vitro and cause thrombosis in FCGR2A transgenic mice, J. Immunol. (2010) 185 (3), 1577-1583
[Non-patent Document 14] Duffau P, Seneschal J, Nicco C, Richez C, Lazaro E, Douchet I, Bordes C, Viallard J F, Goulvestre C, Pellegrin J L, Weil B, Moreau J F, Batteux F, Blanco P., Platelet CD154 potentiates interferon-alpha secretion by plasmacytoid dendritic cells in systemic lupus erythematosus, Sci. Transl. Med. (2010) 2 (47), 47-63
[Non-patent Document 15] Bruhns P., Properties of mouse and human IgG receptors and their contribution to disease models. Blood. (2012) 119, 5640-9.
[Non-patent Document 16] Hjelm F, Carlsson F, Getahun A, Heyman B., Antibody-mediated regulation of the immune response. Scand J Immunol. (2006) 64(3), 177-84.
[Non-patent Document 17] Wernersson S, Karlsson M C, Dahlstrom J, Mattsson R, Verbeek J S, Heyman B., IgG-mediated enhancement of antibody responses is low in Fc receptor gamma chain-deficient mice and increased in Fc gamma RII-deficient mice. J Immunol. (1999) 163, 618-22.

SUMMARY OF THE INVENTION

Problems to be Solved by the Invention

The present invention was achieved in view of the above circumstances. An objective of the present invention is to provide molecules that overcome the defect which originates from binding to activating FcγRs, by introducing an amino acid alteration into an antibody Fc region to accelerate antigen elimination. More specifically, an objective of the present invention is to provide Fc region variants whose binding activities to all activating FcγRs, in particular FcγRIIa (R type), can be reduced while their FcγRIIb-binding activity is maintained, as compared to those of a polypeptide containing a naturally-occurring IgG antibody Fc region; polypeptides comprising the Fc region variants; and pharmaceutical compositions comprising the polypeptides.

Means for Solving the Problems

The present inventors conducted dedicated research on Fc region variants whose binding activities to all activating FcγRs, in particular FcγRIIa (R type), can be decreased while their FcγRIIb-binding activity is maintained, when compared to a polypeptide containing a naturally-occurring IgG Fc region, by introducing amino acid alterations into an Fc region; and polypeptides comprising the Fc region variants. As a result, the present inventors discovered that binding activities to all activating FcγRs, in particular FcγRIIa (R type), can be decreased while maintaining FcγRIIb-binding activity by combining other amino acid alterations into an Fc region variant with alteration of the amino acid at position 238 in the Fc region according to EU numbering.

More specifically, the present invention relates to the following:

[1] an Fc region variant, wherein the variant comprises alteration of amino acid at position 238 of the Fc region according to EU numbering and any one of the amino acids of (a) to (k) below, wherein an FcγRIIb-binding activity of the variant is maintained and binding activities of the variant to all activating FcγRs are decreased when compared to those of a native IgG Fc region:
(a) amino acid at position 235 of the Fc region according to EU numbering;
(b) amino acid at position 237 of the Fc region according to EU numbering;
(c) amino acid at position 241 of the Fc region according to EU numbering;
(d) amino acid at position 268 of the Fc region according to EU numbering;
(e) amino acid at position 295 of the Fc region according to EU numbering;
(f) amino acid at position 296 of the Fc region according to EU numbering;
(g) amino acid at position 298 of the Fc region according to EU numbering;
(h) amino acid at position 323 of the Fc region according to EU numbering;
(i) amino acid at position 324 of the Fc region according to EU numbering;
(j) amino acid at position 330 of the Fc region according to EU numbering; and
(k) at least two amino acids selected from (a) to (j);

[2] the variant of [1] above, wherein at least two amino acids selected in (k) of [1] above are any one of the following amino acid combinations (1) to (3):
(1) amino acids at positions 241, 268, 296, and 324 of the Fc region according to EU numbering;
(2) amino acids at positions 237, 241, 296, and 330 of the Fc region according to EU numbering; and
(3) amino acids at positions 235, 237, 241, and 296 of the Fc region according to EU numbering;

[3] an Fc region variant, wherein the amino acid at position 238 of the Fc region according to EU numbering is Asp, and wherein the variant comprises any one of the amino acids of (a) to (k) below, wherein an FcγRIIb-binding activity of the variant is maintained and binding activities of the variant to all activating FcγRs are decreased when compared to those of a native IgG Fc region:
(a) Phe at amino acid position 235 of the Fc region according to EU numbering;
(b) Gln or Asp at amino acid position 237 of the Fc region according to EU numbering;
(c) Met or Leu at amino acid position 241 of the Fc region according to EU numbering;
(d) Pro at amino acid position 268 of the Fc region according to EU numbering;
(e) Met or Val at amino acid position 295 of the Fc region according to EU numbering;
(f) Glu, His, Asn, or Asp at amino acid position 296 of the Fc region according to EU numbering;
(g) Ala or Met at amino acid position 298 of the Fc region according to EU numbering;
(h) Ile at amino acid position 323 of the Fc region according to EU numbering;
(i) Asn or His at amino acid position 324 of the Fc region according to EU numbering;
(j) His or Tyr at amino acid position 330 of the Fc region according to EU numbering; and
(k) at least two amino acids selected from (a) to (j);

[4] an Fc region variant, wherein the amino acid at position 238 of the Fc region according to EU numbering is Asp, and wherein the variant comprises the amino acids of any one of (1) to (3) below:
(1) Met at amino acid position 241, Pro at amino acid position 268, Glu at amino acid position 296, and His at amino acid position 324 of the Fc region according to EU numbering;
(2) Gln or Asp at amino acid position 237, Met at amino acid position 241, Glu at amino acid position 296, and His at amino acid position 330 of the Fc region according to EU numbering; and
(3) Phe at amino acid position 235, Gln or Asp at amino acid position 237, Met at amino acid position 241, and Glu at amino acid position 296 of the Fc region according to EU numbering;

[5] an Fc region variant, wherein the variant comprises alterations of amino acids at positions 238 and 271 of the Fc region according to EU numbering and any one of the amino acids of (a) to (h) below, wherein an FcγRIIb-binding activity of the variant is maintained and binding activities of the variant to all activating FcγRs are decreased when compared to those of a native IgG Fc region:
(a) amino acid at position 234 of the Fc region according to EU numbering;
(b) amino acid at position 235 of the Fc region according to EU numbering;
(c) amino acid at position 236 of the Fc region according to EU numbering;
(d) amino acid at position 237 of the Fc region according to EU numbering;
(e) amino acid at position 239 of the Fc region according to EU numbering;
(f) amino acid at position 265 of the Fc region according to EU numbering;
(g) amino acid at position 267 of the Fc region according to EU numbering; and
(h) amino acid at position 297 of the Fc region according to EU numbering;

[6] the variant of [5] above, wherein the amino acid alteration is a combination of amino acid alterations of any one of (1) to (3) below:
(1) amino acids at positions 233, 238, 264, 267, 268, and 271 of the Fc region according to EU numbering;
(2) amino acids at positions 233, 237, 238, 264, 267, 268, 271, 296, 297, 330, and 396 of the Fc region according to EU numbering; and
(3) amino acids at positions 233, 238, 264, 267, 268, 271 and 296 of the Fc region according to EU numbering;

[7] an Fc region variant, wherein the amino acid at position 238 is Asp and the amino acid at position 271 is Gly in the Fc region according to EU numbering, and wherein the variant comprises any one of the amino acids of (a) to (h) below, wherein an FcγRIIb-binding activity of the variant is maintained and binding activities of the variant to all activating FcγRs are decreased when compared to those of a native IgG Fc region:
(a) Ala, His, Asn, Lys, or Arg at amino acid position 234 of the Fc region according to EU numbering;
(b) Ala at amino acid position 235 of the Fc region according to EU numbering;
(c) Gln at amino acid position 236 of the Fc region according to EU numbering;
(d) Arg or Lys at amino acid position 237 of the Fc region according to EU numbering;
(e) Lys at amino acid position 239 of the Fc region according to EU numbering;

(f) Lys, Asn, Arg, Ser, or Val at amino acid position 265 of the Fc region according to EU numbering;

(g) Lys, Arg, or Tyr at amino acid position 267 of the Fc region according to EU numbering; and (h) Ala at amino acid position 297 of the Fc region according to EU numbering;

[8] an Fc region variant, wherein the amino acid at position 238 is Asp and the amino acid at position 271 is Gly in the Fc region according to EU numbering, and wherein the variant comprises the amino acids of any one of (1) to (3) below:

(1) Asp at amino acid position 233, Asp at amino acid position 238, Ile at amino acid position 264, Arg at amino acid position 267, Glu at amino acid position 268, and Gly at amino acid position 271 of the Fc region according to EU numbering;

(2) Asp at amino acid position 233, Asp at amino acid position 237, Asp at amino acid position 238, Ile at amino acid position 264, Ala at amino acid position 267, Glu at amino acid position 268, Gly at amino acid position 271, Asp at amino acid position 296, Ala at amino acid position 297, Arg at amino acid position 330, and Met at amino acid position 396 of the Fc region according to EU numbering; and (3) Asp at amino acid position 233, Asp at amino acid position 238, Ile at amino acid position 264, Arg at amino acid position 267, Pro at amino acid position 268, Gly at amino acid position 271, and Glu at amino acid position 296 of the Fc region according to EU numbering;

[9] the Fc region variant of any one of [1] to [8] above, wherein its complement-binding is also decreased;

[10] the Fc region variant of [9] above, wherein the Fc region variant with decreased complement-binding comprises an amino acid alteration at position 322 of the Fc region according to EU numbering, or amino acid alterations at positions 327, 330, and 331 of the Fc region according to EU numbering;

[11] the Fc region variant of [9] above, wherein the amino acid at position 322 is Ala or Glu in the Fc region according to EU numbering; or the amino acid at position 327 is Gly, the amino acid at position 330 is Ser, and the amino acid at position 331 is Ser in the Fc region according to EU numbering;

[12] an Fc region variant, wherein the variant comprises alterations of amino acids at positions 238, 271, 327, 330, and 331 of the Fc region according to EU numbering, wherein an FcγRIIb-binding activity of the variant is maintained and binding activities of the variant to all activating FcγRs are decreased when compared to those of a native IgG Fc region;

[13] the variant of [12] above, wherein the variant further comprises an amino acid alteration of any one of (a) to (e) below:

(a) the amino acid at position 233 of the Fc region according to EU numbering;

(b) the amino acid at position 237 of the Fc region according to EU numbering;

(c) the amino acid at position 264 of the Fc region according to EU numbering;

(d) the amino acid at position 267 of the Fc region according to EU numbering; and (e) the amino acid at position 268 of the Fc region according to EU numbering;

[14] the variant of [13] above, wherein the amino acid alteration is a combination of amino acid alterations of any one of (1) to (4) below:

(1) amino acids at positions 237, 238, 268, 271, 327, 330, and 331 of the Fc region according to EU numbering;

(2) amino acids at positions 233, 237, 238, 268, 271, 327, 330, and 331 of the Fc region according to EU numbering;

(3) amino acids at positions 238, 267, 268, 271, 327, 330, and 331 of the Fc region according to EU numbering; and (4) amino acids at positions 238, 264, 267, 271, 327, 330, and 331 of the Fc region according to EU numbering;

[15] an Fc region variant, wherein the amino acid at position 238 is Asp, the amino acid at position 271 is Gly, the amino acid at position 327 is Gly, the amino acid at position 330 is Ser, and the amino acid at position 331 is Ser in the Fc region according to EU numbering, wherein an FcγRIIb-binding activity of the variant is maintained and binding activities of the variant to all activating FcγRs are decreased when compared to those of a native IgG Fc region;

[16] the variant of [15] above, wherein the variant further comprises any one of the amino acids of (a) to (e) below:

(a) Asp at amino acid position 233 of the Fc region according to EU numbering;

(b) Asp at amino acid position 237 of the Fc region according to EU numbering;

(c) Ile at amino acid position 264 of the Fc region according to EU numbering;

(d) Ala at amino acid position 267 of the Fc region according to EU numbering; and (e) Asp or Glu at amino acid position 268 of the Fc region according to EU numbering;

[17] an Fc region variant, wherein the amino acid at position 238 is Asp and the amino acid at position 271 is Gly in the Fc region according to EU numbering, wherein the variant also comprises the amino acids of any one of (1) to (4) below:

(1) Asp at amino acid position 237, Asp at amino acid position 238, Asp or Glu at amino acid position 268, Gly at amino acid position 271, Gly at amino acid position 327, Ser at amino acid position 330, and Ser at amino acid position 331 of the Fc region according to EU numbering;

(2) Asp at amino acid position 233, Asp at amino acid position 237, Asp at amino acid position 238, Asp at amino acid position 268, Gly at amino acid position 271, Gly at amino acid position 327, Ser at amino acid position 330, and, Ser at amino acid position 331 of the Fc region according to EU numbering;

(3) Asp at amino acid position 238, Ala at amino acid position 267, Glu at amino acid position 268, Gly at amino acid position 271, Gly at amino acid position 327, Ser at amino acid position 330, and Ser at amino acid position 331 of the Fc region according to EU numbering; and (4) Asp at amino acid position 238, Ile at amino acid position 264, Ala at amino acid position 267, Gly at amino acid position 271, Gly at amino acid position 327, Ser at amino acid position 330, and Ser at amino acid position 331 of the Fc region according to EU numbering;

[18] the Fc region variant of any one of [1] to [17] above, wherein the variant has an FcγRIIb-binding activity that is at least 80% of the binding amount of a native IgG Fc region, and has an FcγRIIaR-binding activity that is 30% or less of the binding amount of the native IgG Fc region;

[19] the Fc region variant of any one of [1] to [18] above, wherein a ratio of the FcγRIIb-binding activity of the variant relative to the binding activity of a polypeptide comprising the native IgG Fc region is at least 0.75, and the ratios of the binding activities to all activating FcγRs are 0.2 or less;

[20] the Fc region variant of [19] above, wherein additionally a ratio of an FcγRIIaR-binding activity of the variant relative to the binding activity of a polypeptide comprising the native IgG Fc region is 0.1 or less;

[21] a polypeptide comprising the Fc region variant of any one of [1] to [20] above;

[22] the polypeptide of [21] above, wherein the polypeptide comprising the Fc region variant is an IgG antibody;

[23] the polypeptide of [21] above, wherein the polypeptide comprising the Fc region variant is an Fc fusion protein molecule;

[24] a pharmaceutical composition comprising the polypeptide of any one of [21] to [23] above, and a medically acceptable carrier;

[25] the polypeptide of [21] above, which further comprises an antigen-binding domain whose antigen-binding activity changes depending on an ion concentration condition;

[26] the polypeptide of [25] above, wherein the ion concentration condition is a calcium ion concentration condition;

[27] the polypeptide of [26] above, wherein the aforementioned antigen-binding domain has a lower antigen-binding activity under a low calcium ion concentration condition than under a high calcium ion concentration condition;

[28] the polypeptide of any one of [25] to [27] above, wherein the ion concentration condition is a pH condition;

[29] the polypeptide of [28] above, wherein the antigen-binding domain has a lower antigen-binding activity in an acidic pH range condition than under a neutral pH range condition;

[30] the polypeptide of any one of [25] to [29] above, wherein the polypeptide comprising the Fc region variant is an IgG antibody;

[31] the polypeptide of any one of [25] to [29] above, wherein the polypeptide comprising the Fc region variant is an Fc fusion protein molecule;

[32] a pharmaceutical composition comprising the polypeptide of any one of [25] to [31] above and a medically acceptable carrier;

[33] the pharmaceutical composition of [32] above for promoting elimination of an antigen from plasma, wherein the antigen binds to the antigen-binding domain of the polypeptide of any one of [25] to [31] above, and is in the plasma;

[34] use of the polypeptide of any one of [25] to [31] above for promoting elimination of an antigen from plasma, wherein the antigen binds to the antigen-binding domain of the polypeptide, and is in the plasma;

[35] a method of reducing bindings of a polypeptide comprising an Fc region to all activating FcγRs while maintaining an FcγRIIb-binding activity of the polypeptide, which comprises altering the amino acid at position 238 of the Fc region according to EU numbering and at least one amino acid selected from the amino acids at positions 235, 237, 241, 268, 295, 296, 298, 323, 324, and 330 of the Fc region according to EU numbering to other amino acids;

[36] the method of [35] above, wherein the amino acid alteration of the Fc region is a substitution of the amino acid at position 238 with Asp, a substitution of the amino acid at position 235 with Phe, a substitution of the amino acid at position 237 with Gln, a substitution of the amino acid at position 241 with Met or Leu, a substitution of the amino acid at position 268 with Pro, a substitution of the amino acid at position 295 with Met or Val, a substitution of the amino acid at position 296 with Glu, His, Asn, or Asp, a substitution of the amino acid at position 298 with Ala or Met, a substitution of the amino acid at position 323 with Ile, a substitution of the amino acid at position 324 with Asn or His, and a substitution of the amino acid at position 330 with His or Tyr according to EU numbering;

[37] a method of producing a polypeptide comprising an Fc region variant, wherein the method comprises altering the amino acid at position 238 of the Fc region according to EU numbering and at least one amino acid selected from the amino acids at positions 235, 237, 241, 268, 295, 296, 298, 323, 324, and 330 of the Fc region according to EU numbering to other amino acids, wherein bindings to all activating FcγRs are decreased while an FcγRIIb-binding activity is maintained as compared to those of the polypeptide before the altering;

[38] the method of [37] above, wherein the amino acid alteration of the Fc region is a substitution of the amino acid at position 238 with Asp, substitution of the amino acid at position 235 with Phe, substitution of the amino acid at position 237 with Gln, substitution of the amino acid at position 241 with Met or Leu, substitution of the amino acid at position 268 with Pro, substitution of the amino acid at position 295 with Met or Val, substitution of the amino acid at position 296 with Glu, His, Asn, or Asp, substitution of the amino acid at position 298 with Ala or Met, substitution of the amino acid at position 323 with Ile, substitution of the amino acid at position 324 with Asn or His, and substitution of the amino acid at position 330 with His or Tyr according to EU numbering;

[39] a method of reducing binding activities of a polypeptide comprising an Fc region to all activating FcγRs while maintaining an FcγRIIb-binding activity at a similar level in comparison to those of a native IgG, wherein the method comprises combining and introducing an amino acid alteration(s) that increases the FcγRIIb-binding activity by two-fold or more as compared to that of a native IgG Fc region, and an amino acid alteration(s) that decreases the binding activities to all FcγRs;

[40] the method of [39] above, wherein the amino acid alteration(s) that increases the FcγRIIb-binding activity by two-fold or more as compared to that of the native IgG Fc region is an amino acid alteration(s) of Table 11;

[41] the method of [39] or [40] above, wherein the amino acid alteration(s) that decreases the binding activities to all FcγRs is an alteration(s) of at least one amino acid selected from the amino acids at positions 234, 235, 236, 237, 239, 265, 267, and 297 of the Fc region according to EU numbering to another amino acid;

[42] the method of any one of [39] to [41] above, wherein the amino acid alteration(s) of the Fc region is a substitution of the amino acid at position 234 with Ala, His, Asn, Lys, or Arg, a substitution of the amino acid at position 235 with Ala, a substitution of the amino acid at position 236 with Gln, a substitution of the amino acid at position 237 with Arg or Lys, a substitution of the amino acid at position 239 with Lys, a substitution of the amino acid at position 265 with Lys, Asn, Arg, Ser, or Val, a substitution of the amino acid at position 267 with Lys, Arg, or Tyr, and a substitution of the amino acid at position 297 with Ala according to EU numbering;

[43] the method of any one of [35], [36], and [39] to [42] above, wherein the FcγRIIb-binding activity is maintained with at least 80% of the binding amount of a native IgG Fc region, and an FcγRIIaR-binding activity is reduced to 30% or less of the binding amount of the native IgG Fc region;

[44] the method of any one of [35], [36], and [39] to [43] above, wherein a ratio of the FcγRIIb-binding activity relative to the binding activity of a polypeptide comprising the native IgG Fc region is maintained at 0.75 at least, and the ratios of the binding activities to all activating FcγRs are reduced to 0.2 or less;

[45] the method of [44] above, wherein additionally a ratio of an FcγRIIaR-binding activity relative to the binding activity of a polypeptide comprising the native IgG Fc region is reduced to 0.05 or less;

[46] a method of producing a polypeptide comprising an Fc region variant, wherein binding activities to all activating FcγRs are decreased while an FcγRIIb-binding activity is maintained at a similar level in comparison to those of a native IgG, wherein the method comprises combining and introducing an amino acid alteration(s) that increases the FcγRIIb-binding activity by two-fold or more as compared to that of a native IgG Fc region, and an amino acid alteration(s) that decreases the binding activities to all FcγRs;

[47] the method of [46] above, wherein the amino acid alteration(s) that increases the FcγRIIb-binding activity by two-fold or more as compared to that of the native IgG Fc region is an amino acid alteration of Table 11;

[48] the method of [46] or [47] above, wherein the amino acid alteration(s) that decreases the binding activities to all FcγRs is an alteration of at least one amino acid selected from the amino acids at positions 234, 235, 236, 237, 239, 265, 267, and 297 of an Fc region according to EU numbering to another amino acid;

[49] the method of any one of [46] to [48] above, wherein the amino acid alteration(s) of the Fc region is a substitution of the amino acid at position 234 with Ala, His, Asn, Lys, or Arg, a substitution of the amino acid at position 235 with Ala, a substitution of the amino acid at position 236 with Gln, a substitution of the amino acid at position 237 with Arg or Lys, a substitution of the amino acid at position 239 with Lys, a substitution of the amino acid at position 265 with Lys, Asn, Arg, Ser, or Val, a substitution of the amino acid at position 267 with Lys, Arg, or Tyr, and a substitution of the amino acid at position 297 with Ala according to EU numbering;

[50] the method of any one of [37], [38], and [46] to [49] above, wherein the FcγRIIb-binding activity is maintained with at least 80% of the binding amount of a native IgG Fc region, and the binding activities to all activating FcγRs are reduced to 30% or less of the binding amount of the native IgG Fc region;

[51] the method of any one of [37], [38], and [46] to [50] above, wherein a ratio of the FcγRIIb-binding activity relative to the binding activity of a polypeptide comprising the native IgG Fc region is maintained at 0.75 at least, and the ratios of binding activities to all activating FcγRs are decreased to 0.2 or less;

[52] the method of [51] above, wherein additionally a ratio of the FcγRIIaR-binding activity relative to the binding activity of a polypeptide comprising the native IgG Fc region is reduced to 0.1 or less;

[53] the method of any one of [37], [38], and [46] to [52] above, wherein the method further comprises combining and introducing an alteration(s) that decreases complement-binding;

[54] the method of [53] above, wherein the alteration(s) that decreases complement-binding is an amino acid alteration at position 322 of the Fc region according to EU numbering, or amino acid alterations at positions 327, 330, and 331 of the Fc region according to EU numbering;

[55] the method of [53] above, wherein the alteration(s) that decreases complement-binding is a substitution of the amino acid at position 322 with Ala or Glu in the Fc region according to EU numbering, or alternatively, a substitution of the amino acid at position 327 with Gly, a substitution of the amino acid at position 330 with Ser, and a substitution of the amino acid at position 331 with Ser in the Fc region according to EU numbering;

[56] a method of reducing bindings of a polypeptide comprising an Fc region to all activating FcγRs while maintaining an FcγRIIb-binding activity of the polypeptide, which comprises altering the amino acids at positions 238, 271, 327, 330, and 331 of the Fc region according to EU numbering to other amino acids, or further comprises altering at least one amino acid selected from the amino acids at positions 233, 237, 264, 267, and 268 of the Fc region according to EU numbering to another amino acid;

[57] the method of [56] above, wherein the amino acid alteration of the Fc region is a substitution of the amino acid at position 238 with Asp, a substitution of the amino acid at position 271 with Gly, a substitution of the amino acid at position 327 with Gly, a substitution of the amino acid at position 330 with Ser, a substitution of the amino acid at position 331 with Ser, a substitution of the amino acid at position 233 with Asp, a substitution of the amino acid at position 237 with Asp, a substitution of the amino acid at position 264 with Ile, a substitution of the amino acid at position 267 with Ala, and a substitution of the amino acid at position 268 with Asp or Glu in the Fc region according to EU numbering;

[58] a method of producing a polypeptide comprising an Fc region variant, wherein the method comprises altering the amino acids at positions 238, 271, 327, 330, and 331 of the Fc region according to EU numbering to other amino acids, or further comprising altering at least one amino acid selected from the amino acids at positions 233, 237, 264, 267, and 268 of the Fc region according to EU numbering to another amino acid, wherein bindings to all activating FcγRs are decreased and complement-binding is decreased while an FcγRIIb-binding activity is maintained as compared to those of the polypeptide before the altering; and

[59] the method of [58] above, wherein the amino acid alteration of the Fc region is a substitution of the amino acid at position 238 with Asp, a substitution of the amino acid at position 271 with Gly, a substitution of the amino acid at position 327 with Gly, a substitution of the amino acid at position 330 with Ser, a substitution of the amino acid at position 331 with Ser, a substitution of the amino acid at position 233 with Asp, a substitution of the amino acid at position 237 with Asp, a substitution of the amino acid at position 264 with Ile, a substitution of the amino acid at position 267 with Ala, and a substitution of the amino acid at position 268 with Asp or Glu in the Fc region according to EU numbering.

Furthermore, the present invention relates to methods of decreasing the binding activities of an Fc region to all activating FcγRs, in particular FcγRIIa (R type), while maintaining its FcγRIIb-binding activity by introducing the Fc-region amino-acid alterations of the present invention. The present invention also relates to methods for suppressing production of antibodies against polypeptides comprising the Fc region by introducing the Fc-region amino-acid alterations of the present invention.

Furthermore, the present invention relates to methods for promoting elimination of a disease-causing antigen in plasma, which are accomplished by an Fc region variant produced by introducing the Fc-region amino-acid alterations of the present invention, and a polypeptide which has an activity to bind to the antigen present in soluble form in plasma and comprises an antigen-binding domain whose binding activity towards the antigen changes according to the ion concentration condition. The present invention also relates to the use of an Fc region variant produced by introducing the Fc-region amino acid alterations of the present invention, and a polypeptide having an activity to bind to a disease-causing antigen present in soluble form in plasma and comprising an antigen-binding domain whose binding activity towards the antigen changes according to the ion concentration condition, wherein the use is for promoting elimination of the antigen in plasma.

The present invention also relates to a therapeutic or preventive agent for immune inflammatory diseases that comprises a polypeptide of the present invention. Furthermore, the present invention relates to a method for treating or preventing immune inflammatory diseases, which comprises the step of administering a polypeptide of the present invention to a subject. In addition, the present invention relates to a kit for use in the method of the present invention for treating or preventing immune inflammatory diseases, which comprises a polypeptide of the present invention. The present invention also relates to use of a polypeptide of the present invention in the production of a therapeutic or preventive agent for immune inflammatory diseases. Furthermore, the present invention relates to a polypeptide of the present invention for use in the method for treating or preventing immune inflammatory diseases of the present invention.

The present invention relates to an activation inhibitor for B cells, mast cells, dendritic cells, and/or basophils, which comprises a polypeptide of the present invention. Furthermore, the present invention relates to a method of inhibiting activation of B cells, mast cells, dendritic cells, and/or basophils, which comprises administering a polypeptide of the present invention to a subject. The present invention also relates to a kit for use in the method of inhibiting activation of B cells, mast cells, dendritic cells, and/or basophils, which comprises a polypeptide of the present invention. The present invention relates to a use of a polypeptide of the present invention in producing activation inhibitors for B cells, mast cells, dendritic cells, and/or basophils. The present invention also relates to a polypeptide of the present invention for use in the method of the present invention of inhibiting activation of B cells, mast cells, dendritic cells, and/or basophils.

Furthermore, the present invention relates to a therapeutic agent for diseases in which a protein necessary for an organism is deficient, wherein the agent comprises a polypeptide of the present invention. The present invention also relates to a method for treating diseases in which a protein necessary for an organism is deficient, which comprises administering a polypeptide of the present invention to a subject. Furthermore, the present invention relates to a kit for use in the method of the present invention for treating diseases in which a protein necessary for an organism is deficient, wherein the kit comprises a polypeptide of the present invention. The present invention relates to use of a polypeptide of the present invention in producing a therapeutic agent for diseases in which a protein necessary for an organism is deficient. The present invention also relates to a polypeptide of the present invention for use in the method of the present invention for treating diseases in which a protein necessary for an organism is deficient.

In addition, the present invention relates to an agent for suppressing virus proliferation, which comprises a polypeptide of the present invention. The present invention also relates to a method of suppressing virus proliferation, which comprises administering a polypeptide of the present invention to a subject. Furthermore, the present invention relates to a kit of the present invention for use in the method of suppressing virus proliferation, wherein the kit comprises a polypeptide of the present invention. The present invention relates to use of a polypeptide of the present invention in producing an agent for suppressing virus proliferation. The present invention also relates to a polypeptide of the present invention for use in the method of the present invention of suppressing virus proliferation.

Effects of the Invention

The present invention provides Fc region variants whose binding activities to all activating FcγRs, in particular FcγRIIa (R type), have been reduced, while their FcγRIIb binding activity is maintained, when compared to those of the naturally-occurring IgG Fc region. By using polypeptides containing the Fc region variants, it is possible to enhance the inflammatory immune response-suppressing signals produced by phosphorylation of ITIM of FcγRIIb, under conditions where the property of eliminating immune complexes via FcγRIIb is maintained to a similar degree as in a naturally-occurring IgG. Furthermore, by conferring an Fc region with the property of selectively binding to FcγRIIb, it may be possible to suppress anti-antibody production. Furthermore, by reducing binding to activating FcγRs, platelet activation mediated by interaction between FcγRIIa on the platelet and the immune complex, and dendritic cell activation by crosslinking of activating FcγRs can be avoided.

BRIEF DESCRIPTION OF THE DRAWINGS

FIG. 1 shows the results of analysis by gel filtration chromatography which confirm the pH-dependent formation of a large immune complex by human IgE and a pH-dependent anti-IgE antibody, clone 278.

FIG. 2 shows changes in the human IgE concentration in normal mouse plasma for the group to which human IgE alone was administered, the human IgE+clone 278 antibody-administered group, and the human IgE+Xolair antibody-administered group.

FIG. 3 shows changes in the antibody concentration in normal mouse plasma for the human IgE+clone 278-administered group and the human IgE+Xolair antibody-administered group.

FIG. 4 shows changes in the human IgE concentration in normal mouse plasma for the group to which human IgE alone was administered, the human IgE+278-IgG1 antibody-administered group, and the human IgE+278-F760 antibody-administered group.

FIG. 5 shows changes in the normal mouse antibody concentration for the human IgE+278-IgG1 antibody-administered group and the human IgE+278-F760 antibody-administered group.

FIG. 6 shows results of using the IL-8 expression level as an indicator to evaluate DC activation by an Fc variant.

FIG. 7 confirms the expression of CD62p (p-selectin) on the surface of a washed platelet membrane to which Fc variants were added. The case of 5c8-F648 addition and ADP stimulation is shown by a solid line, and the filled area shows the case of 5c8-F600 addition and ADP stimulation.

FIG. 8 confirms the expression of activated integrin (PAC-1) on the surface of a washed platelet membrane to which Fc variants were added. The case of 5c8-F648 addition and ADP stimulation is shown by a solid line, and the filled area shows the case of 5c8-F600 addition and ADP stimulation.

FIG. 9 shows how antibodies with a pH-dependent binding property bind repeatedly to soluble antigens: (i) an antibody binds to soluble antigens; (ii) the antibody is taken up non-specifically into the cell by pinocytosis; (iii) the antibody binds to FcRn in the endosome, and then the soluble antigens dissociate from the antibody; (iv) the soluble antigens translocate to the lysosome and are then degraded; (v) the antibody from which the soluble antigens have dissociated is recycled into the plasma by FcRn; and (vi) the recycled antibody can bind again to soluble antigens.

FIG. 10 shows how enhancing FcRn binding under neutral conditions further improves the effects of antibodies with a pH-dependent binding property to repeatedly bind to antigens: (i) an antibody binds to soluble antigens; (ii) the antibody is taken up into cells by pinocytosis via FcRn; (iii) the soluble antigens dissociate from the antibody in the endosome; (iv) the soluble antigens are degraded upon translocation to the lysosome; (v) the antibody from which the soluble antigens have dissociated is recycled into the plasma by FcRn; and (iv) the recycled antibody can bind again to soluble antigens.

MODE FOR CARRYING OUT THE INVENTION

The present invention provides Fc region variants that can lower binding activities to all activating FcγRs, in particular FcγRIIa (R type), while maintaining FcγRIIb-binding activity, when compared to a polypeptide containing a native IgG antibody Fc region, and polypeptides comprising the Fc region variants.

More specifically, the invention provides Fc region variants comprising an amino acid sequence in which the amino acid alteration at position 238 according to EU numbering is combined with other specific amino acid alterations, and polypeptides comprising the Fc region variants. Furthermore, the present invention provides methods of introducing the amino acid alterations into an Fc region for decreasing its binding activities to all activating FcγRs, in particular FcγRIIa (R type), while maintaining its FcγRIIb-binding activity in comparison to those of a polypeptide containing a native IgG antibody Fc region; and methods of introducing the amino acid alterations into an Fc region for producing polypeptides comprising an Fc region variant with reduced binding activities to all activating FcγRs, in particular FcγRIIa (R type), and maintained FcγRIIb-binding activity in comparison to those of polypeptides containing the native IgG Fc region. The invention also provides Fc region variants in which the amino acid alterations have been introduced into the Fc region, and polypeptides that have binding activity to a disease-causing antigen present in the plasma in soluble form, and comprise an antigen-binding domain whose binding activity to the antigen changes according to the ion concentration condition, and methods of using the polypeptides for promoting elimination of the antigen in the plasma.

"Polypeptides" of the present invention generally refers to peptides or proteins approximately ten amino acids or more in length. Furthermore, they are generally polypeptides derived from organisms, but are not particularly limited, and for example, they may be polypeptides comprising an artificially designed sequence. Furthermore, they may be any of naturally-occurring polypeptides, synthetic polypeptides, recombinant polypeptides, or such.

Preferred examples of the polypeptides of the present invention include antibodies. More preferred examples include naturally-occurring IgGs, particularly naturally-occurring human IgGs. "Naturally-occurring (native) IgGs" refers to polypeptides belonging to a class of antibodies practically encoded by immunoglobulin gamma genes and comprising an amino acid sequence identical to those of IgGs found in nature. For example, a naturally-occurring human IgG means a naturally-occurring human IgG1, naturally-occurring human IgG2, naturally-occurring human IgG3, naturally-occurring human IgG4, or such. Naturally-occurring IgGs also include mutants spontaneously produced from them.

Figure 18:
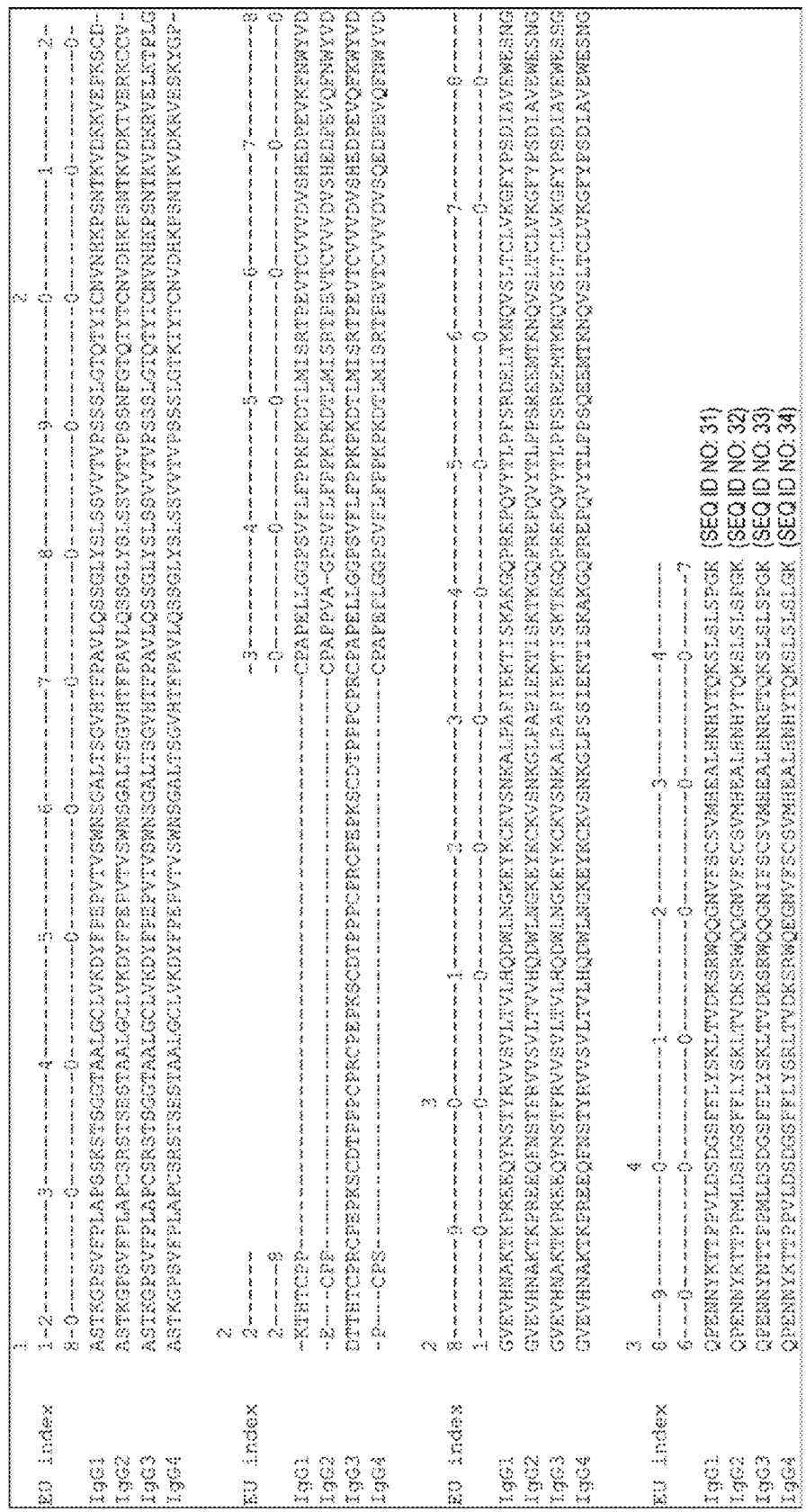
FIG. 18 shows the relationship between the amino acid residues constituting the constant regions of IgG1, IgG2, IgG3, and IgG4, and EU numbering (herein, also referred to as EU INDEX).

While an IgK (Kappa, κ chain), IgL1, IgL2, IgL3, IgL6, and IgL7 (Lambda, λ chain)-type constant region is present in the antibody light chain constant region, it may be any light chain constant region. For the human IgK (Kappa) constant region and human IgL7 (Lambda) constant region, a plurality of allotype sequences due to genetic polymorphism are described in "Sequences of proteins of immunological interest", NIH Publication No. 91-3242, and any of them may be used in the present invention. Furthermore, in the present invention, a light chain constant region may be a light chain constant region that has been altered with amino acid substitutions, additions, deletions, insertions, and/or modifications or such. For the antibody Fc region, for example, Fc regions of the IgA1, IgA2, IgD, IgE, IgG1, IgG2, IgG3, IgG4, and IgM types exist. For example, a human IgG antibody Fc region can be used as the antibody Fc region of the present invention, and human IgG1 antibody Fc regions are preferred. Fc regions that can be used as an Fc region of the present invention are, for example, those derived from naturally-occurring IgG constant regions, or specifically, a constant region derived from naturally-occurring human IgG1 (SEQ ID NO: 31), a constant region derived from naturally-occurring human IgG2 (SEQ ID NO: 32), a constant region derived from naturally-occurring human IgG3 (SEQ ID NO: 33), and a constant region derived from naturally-occurring human IgG4 (SEQ ID NO: 34). FIG. 18 shows the constant region sequences of the naturally-occurring IgG1, IgG2, IgG3, and IgG4. Constant regions of naturally-occurring IgGs also include mutants spontaneously produced from them. For the constant regions of human IgG1, human IgG2, human IgG3, and human IgG4 antibodies, a plurality of allotype sequences due to genetic polymorphism are described in "Sequences of proteins of immunological interest", NIH Publication No. 91-3242, and any of them may be used in the present invention. In particular, for the human IgG1 sequence, the amino acid sequence at positions 356 to 358 (EU numbering) may be either DEL or EEM.

"Fcγ receptors" (herein, referred to as Fcγ receptors, FcγR or FcgR) refers to receptors that may bind to the Fc region of IgG1, IgG2, IgG3, and IgG4 monoclonal antibodies, and practically means any member of the family of proteins encoded by the Fcγ receptor genes. In humans, this family includes FcγRI (CD64) including isoforms FcγRIa, FcγRIb, and FcγRIc; FcγRII (CD32) including isoforms FcγRIIa (including allotypes H131 (type H) and R131 (type R)), FcγRIIb (including FcγRIIb-1 and FcγRIIb-2), and FcγRIIc; and FcγRIII (CD16) including isoforms FcγRIIIa (including allotypes V158 and F158), and FcγRIIIb (including allotypes FcγRIIIb-NA1 and FcγRIIIb-NA2), and any human FcγRs, FcγR isoforms or allotypes yet to be discovered, but is not limited thereto. FcγRIIb1 and FcγRIIb2 have been reported as splicing variants of human FcγRIIb. In addition, a splicing variant named FcγRIIb3 has been reported (J. Exp. Med, 1989, 170: 1369). In addition to these splicing variants, human FcγRIIb includes all splicing variants registered in NCBI, which are NP_001002273.1, NP_001002274.1, NP_001002275.1, NP_001177757.1, and NP_003992.3. Furthermore, human FcγRIIb includes every previously-reported genetic polymorphism, as well as FcγRIIb (Arthritis Rheum, 2003, 48: 3242-52; Hum Mol Genet, 2005, 14: 2881-92; and Arthritis Rheum. 2002 May; 46(5): 1242-54), and every genetic polymorphism that will be reported in the future. The FcγR includes human, mouse, rat, rabbit, and monkey-derived FcγRs but is not limited thereto, and may be derived from any organism. Mouse FcγRs include FcγRI (CD64), FcγRII (CD32), FcγRIII (CD16), and FcγRIII-2 (CD16-2), and any mouse FcγRs, or FcγR isoforms or allotypes yet to be discovered, but are not limited thereto. Favorable examples of such Fcγ receptors include human FcγRI (CD64), FcγRIIA (CD32), FcγRIIB (CD32), FcγRIIIA (CD16), and/or FcγRIIIB (CD16).

The polynucleotide sequence and amino acid sequence of FcγRI are set forth in SEQ ID NOs: 35 (NM_000566.3) and 36 (NP_000557.1), respectively;
the polynucleotide sequence and amino acid sequence of FcγRIIA are set forth in SEQ ID NOs: 37 (BC020823.1) and 38 (AAH20823.1), respectively;
the polynucleotide sequence and amino acid sequence of FcγRIIB are set forth in SEQ ID NOs: 39 (BC146678.1) and 40 (AAI46679.1), respectively;
the polynucleotide sequence and amino acid sequence of FcγRIIIA are set forth in SEQ ID NOs: 41 (BC033678.1) and 42 (AAH33678.1), respectively; and
the polynucleotide sequence and amino acid sequence of FcγRIIIB are set forth in SEQ ID NOs 43 (BC128562.1) and 44 (AAI28563.1), respectively (the RefSeq Registration number is indicated inside the parentheses).

In FcγRIIa, there are two allotypes: one where the amino acid at position 131 of FcγRIIa is histidine (type H) and the other where this amino acid is substituted with arginine (type R) (J. Exp. Med, 172: 19-25, 1990).

In FcγRI (CD64) including FcγRIa, FcγRIb, and FcγRIc, and in FcγRIII (CD16) including isoform FcγRIIIa (including allotypes V158 and F158), the a chain that binds to the Fc portion of IgG is associated with the common γ chain having ITAM responsible for transducing activation signals inside cells. FcγRIIIb (including allotypes FcγRIIIb-NA1 and FcγRIIIb-NA2) is a GPI anchor protein. Meanwhile, the cytoplasmic domain of FcγRII (CD32) itself which includes isoforms FcγRIIa (including allotypes H131 and R131) and FcγRIIc, contains ITAM. These receptors are expressed on many immune cells such as macrophages, mast cells, and antigen-presenting cells. The activation signals transduced when these receptors bind to the Fc portion of IgG enhance the phagocytic ability of macrophages, inflammatory cytokine production, mast cell degranulation, and promotion of the function of antigen-presenting cells. Fcγ receptors having the ability to transduce the activation signals as described above are also referred to as activating Fcγ receptors in the present invention.

Meanwhile, the intracytoplasmic domain of FcγRIIb (including FcγRIIb-1 and FcγRIIb-2) itself contains ITIM responsible for transduction of inhibitory signals. The crosslinking between FcγRIIb and B cell receptor (BCR) on B cells suppresses the activation signals from BCR, which results in suppression of antibody production via BCR. The crosslinking of FcγRIII and FcγRIIb on macrophages suppresses the phagocytic ability and the ability to produce inflammatory cytokines. Fcγ receptors having the ability to transduce the inhibitory signals as described above are also referred to as inhibitory Fcγ receptors in the present invention.

In the present invention, an "Fc region variant" refers to an Fc region in which at least one amino acid of the present invention has been altered into another amino acid in an Fc region not introduced with the amino acid alteration of the present invention. Herein, an Fc region in which "at least one amino acid has been altered to another amino acid" includes an Fc region into which the amino acid alteration has been introduced, and an Fc region comprising an amino acid sequence identical to that of the Fc region comprising the amino acid alteration.

"Naturally-occurring IgGs (Native IgGs)" refers to polypeptides belonging to a class of antibodies substantially encoded by immunoglobulin gamma genes and comprising an amino acid sequence identical to those of IgGs found in nature. For example, a native human IgG refers to a native human IgG1, native human IgG2, native human IgG3, native human IgG4, or such. Native IgGs also include mutants spontaneously produced therefrom, and IgGs introduced with alterations that do not substantially affect the FcγR-binding activities.

The Fc region of a native IgG means an Fc region comprising an amino acid sequence identical to that of the Fc region derived from an IgG found in nature. The heavy chain constant region of the native IgG is shown in FIG. 18 (SEQ ID NOs: 31 to 34), and for example, it refers to Fc regions in the heavy chain constant regions derived from native human IgG1, Fc regions in the heavy chain constant regions derived from native human IgG2, Fc regions in the heavy chain constant regions derived from native human IgG3, and Fc regions in the heavy chain constant regions derived from native human IgG4. The Fc regions of native IgGs also include mutants spontaneously produced therefrom and Fc regions introduced with alterations that do not substantially affect the FcγR-binding activities.

In the present invention, whether or not the binding activity towards each type of FcγR is enhanced, or maintained or decreased in a polypeptide comprising an Fc region variant or an Fc region variant of the present invention can be determined, for example, by observing whether there is a decrease or an increase in the dissociation constant (KD) value obtained from the results of sensorgram analysis, where various FcγRs are subjected to interaction as an analyte with antibodies immobilized onto the sensor chips or captured onto the sensor chips using Protein A, Protein L, Protein A/G, Protein G, anti-lamda chain antibodies, anti-kappa chain antibodies, antigen peptides, antigen proteins, or such using BIACORE which is an interaction analyzer that utilizes the surface plasmon resonance (SPR) phenomena, as shown in the Examples or Reference Examples. Alternatively, it can also be determined by observing whether there is an increase or a decrease in the value obtained by dividing the amount of change in the resonance unit (RU) value on the sensorgram before and after various types of FcγRs are subjected to interaction as an analyte with antibodies immobilized onto the sensor chips or captured onto the sensor chips using Protein A, Protein L, Protein A/G, Protein G, anti-lamda chain antibodies, anti-kappa chain antibodies, antigen peptides, antigen proteins, or such, by the amount of change of resonance units (RU) before and after antibodies are immobilized or captured onto the sensor chip. Furthermore, it can be determined by observing an increase or a decrease in the dissociation constant (KD) values obtained from sensorgram analysis, where a sample such as an antibody to be evaluated is subjected to interaction as an analyte using a sensor chip onto which FcγR is immobilized directly or via an anti-tag antibody. Alternatively, it can be determined by observing whether the amount of change in sensorgram values increases or decreases before and after a sample such as an antibody to be evaluated is subjected to interaction as an analyte with the sensor chip onto which FcγR is immobilized directly or via an anti-tag antibody.

Specifically, the binding activity of an Fc region variant towards an Fcγ receptor can be measured by the Amplified Luminescent Proximity Homogeneous Assay (ALPHA) screening, the BIACORE method which utilizes the surface plasmon resonance (SPR) phenomena, or such, in addition to ELISA or fluorescence activated cell sorting (FACS) (Proc. Natl. Acad. Sci. USA (2006) 103 (11): 4005-4010).

ALPHA screening is performed by ALPHA technology which uses two beads, a donor and an acceptor, based on the following principles. Luminescent signals are detected only when molecules bound to donor beads physically interact with molecules bound to the acceptor beads, and the two beads are in close proximity to each other. Laser-excited photosensitizer in the donor beads converts ambient oxygen to excited-state singlet oxygen. Singlet oxygen is dispersed around the donor beads, and when it reaches the adjacent acceptor beads, chemiluminescent reaction is induced in the beads, and light is ultimately emitted. When the molecules bound to the donor beads do not interact with the molecules bound to the acceptor beads, the chemiluminescent reaction does not take place because singlet oxygen produced by the donor beads does not reach the acceptor beads.

For example, a biotinylated polypeptide complex is bound to the donor beads, and Fcγ receptor tagged with glutathione S transferase (GST) is linked to the acceptor beads. In the absence of a competing polypeptide complex comprising an Fc region variant, the polypeptide complex comprising a wild-type Fc region interacts with the Fcγ receptor and produces 520-620 nm signals. The polypeptide complex comprising an untagged mutant Fc region competes with the polypeptide complex comprising a wild-type Fc region for interaction with the Fcγ receptor. Relative binding activities can be determined by quantifying the decrease in fluorescence observed as a result of the competition. Biotinylation of polypeptide complexes such as antibodies using Sulfo-NHS-biotin and such is well known. The method of expressing the Fcγ receptor and GST in a cell carrying a fusion gene produced by fusing a polynucleotide encoding the Fcγ receptor in frame with a polynucleotide encoding GST in an expressible vector, and performing purification using a glutathione column is appropriately adopted as a method for tagging an Fcγ receptor with GST. The obtained signals are preferably analyzed, for example, by fitting them to a one-site competition model which uses a non-linear regression analysis using software such as GRAPHPAD PRISM (GraphPad, San Diego).

One of the substances (the ligand) in observation of an interaction is immobilized onto a gold thin film on a sensor chip, and by shining light from the reverse side of the sensor chip so that total reflection takes place at the interface between the gold thin film and glass, a portion of reduced reflection intensity is formed in part of the reflected light (SPR signal). When the other one of the substances (the analyte) in observation of an interaction is made to flow on the sensor chip surface and the ligand binds to the analyte, the mass of the immobilized ligand molecule increases and the refractive index of the solvent on the sensor chip surface changes. The position of the SPR signal shifts as a result of this change in refractive index (on the other hand, the signal position returns when this binding dissociates). The Biacore system indicates the amount of shift mentioned above, or more specifically the time variable of mass by plotting the change in mass on the sensor chip surface on the ordinate as the measurement data (sensorgram). The amount of analyte bound to the ligand trapped on the sensor chip surface is determined from the sensorgram. Kinetic parameters such as association rate constants (ka) and dissociation rate constants (kd) are determined from the curves of the sensorgram, and the dissociation constants (KD) are determined from the ratio of these constants. In the BIACORE method, a method for measuring inhibition is preferably used. An example of the method for measuring inhibition is described in Proc. Natl. Acad. Sci USA (2006) 103 (11): 4005-4010.

An Fc region whose FcγRIIb-binding activity is maintained or a polypeptide comprising such an Fc region refers to a polypeptide that binds to FcγRIIb with a binding activity equivalent to or substantially unchanged from the parent polypeptide when assay is performed with substantially the same amount of a polypeptide containing the Fc region of the native IgG (also referred to as a polypeptide containing the parent Fc region or a parent polypeptide) and a polypeptide comprising the amino acid alterations of the present invention in the Fc region (a polypeptide containing the Fc region variant). Specifically, it refers to an Fc region variant that maintains at least 55.5% of the FcγRIIb-binding property of the polypeptide containing the parent Fc region.

An Fc region whose binding activities to activating FcγRs have been decreased, lowered, or attenuated, or a polypeptide containing such an Fc region refers to an Fc region variant or a polypeptide containing the Fc region variant which binds to activating FcγRs with binding activities substantially weaker than those of polypeptides containing the parent Fc region when assay is performed with substantially the same amount of a polypeptide containing the Fc region of the native IgG (also referred to as a polypeptide containing the parent Fc region or a parent polypeptide) and a polypeptide which includes amino acid alterations of the present invention in the Fc region (a polypeptide containing an Fc region variant).

Whether or not an Fc region variant of the present invention maintains the FcγRIIb-binding activity of the Fc region of a native IgG can be determined by comparing the KD value for FcγRIIb of the polypeptide comprising the Fc region variant of the present invention with the KD value for FcγRIIb of the polypeptide containing the Fc region of a native IgG, which can be determined, for example, according to the above-mentioned examples. Specifically, when the KD value for the polypeptide containing an Fc region variant of the present invention is a value equivalent to or less than that of a polypeptide containing the parent Fc region, the polypeptide containing the Fc region variant of the present invention can be determined to have maintained its FcγRIIb-binding activity in comparison to a polypeptide containing the parent Fc region. Whether or not the activating FcγR-binding activity of an Fc region variant of the present invention is decreased in comparison to that of a native IgG Fc region can be determined in a similar manner, for example, by comparing the KD value for an activating FcγR of the polypeptide comprising the Fc region variant of the present invention with the KD value for the activating FcγR of the polypeptide containing the Fc region of a native IgG, as determined according to the above-mentioned examples. Specifically, when the KD value of the polypeptide comprising the Fc region variant of the present invention is enhanced compared to that of the polypeptide comprising the parent Fc region, the polypeptide comprising the Fc region variant of the present invention can be determined to have a reduced binding activity for activating FcγR in comparison to that of the polypeptide comprising the parent Fc region. In particular, since the FcγRIIa (R type)-binding activity is more easily correlated with the FcγRIIb-binding activity than with binding activities for other activating FcγRs, finding amino acid alterations that can decrease the FcγRIIa (R type)-binding activity while maintaining the FcγRIIb-binding activity is the most difficult task in selectively decreasing the binding activities for activating FcγRs other than FcγRIIb.

An equivalent or maintained FcγRIIb-binding activity means that, for example, in the KD values determined by the measurement method described above, the KD ratio of [KD value for FcγRIIb of the polypeptide comprising the parent Fc region]/[KD value for FcγRIIb of the polypeptide comprising the Fc region variant] is preferably at least 0.75, more preferably at least 0.8, even more preferably at least 0.9. Furthermore, a value of about 5 is sufficient for the KD ratio, and a higher value is not necessary for determining that the FcγRIIb-binding activity is equivalent or maintained.

Decrease, reduction or attenuation of binding activities for activating FcγRs means that, for example, in the KD value determined by the above-mentioned measurement method, the KD ratio for [KD value for an activating FcγR of the polypeptide comprising the parent Fc region]/[KD value for the activating FcγR of the polypeptide comprising the Fc region variant] is preferably 0.2 or less, more preferably 0.15 or less, or more preferably 0.1 or less.

In particular, since the extracellular region sequences of FcγRIIa and FcγRIIb have 93% identity and their structures are extremely similar, for the FcγRIIaR-binding activity, which is difficult to decrease while maintaining the FcγRIIb-binding activity, the KD ratio for [KD value for FcγRIIaR of the polypeptide comprising the parent Fc region]/[KD value for FcγRIIaR of the polypeptide comprising the Fc region variant] is preferably 0.1 or less, and more preferably 0.05.

Furthermore, whether or not the binding activities of the polypeptides of the present invention towards various FcγRs were maintained, enhanced, or decreased can be determined from the increase or decrease in the amount of binding of the various FcγRs to the polypeptides of the present invention, which were determined according to the examples described above. Here, the amount of binding of the various FcγRs to the polypeptides refers to values obtained by determining the difference in the RU values of sensorgrams that changed before and after interaction of various FcγRs as the analyte with each polypeptide, and dividing them by differences in the RU values of sensorgrams that changed before and after capturing polypeptides to the sensor chips.

Furthermore, an Fc region whose selectivity for FcγRIIb has been improved or a polypeptide comprising such an Fc region, or an Fc region whose binding activities to activating FcγRs have been selectively reduced or a polypeptide comprising such an Fc region refers to an Fc region whose binding activities to activating FcγRs have been decreased, lowered, or attenuated, while maintaining the FcγRIIb-binding activity, or a polypeptide comprising such an Fc region.

Fc region variants of the present invention are not particularly limited in terms of their KD values (mol/L) for FcγRIIb and activating FcγRs; however, for example, the value for FcγRIIb may be $7.0 \times 10^{-6}$ or less, preferably $6.0 \times 10^{-6}$ or less, or more preferably $5.0 \times 10^{-6}$ or less, and the values for activating FcγRs may be $2.5 \times 10^{-9}$ or higher, preferably $3.0 \times 10^{-9}$ or higher, or more preferably $3.5 \times 10^{-9}$ or higher, and the value for FcγRIIa (R type) in particular is preferably $2.0 \times 10^{-5}$ or higher.

An "Fc region" refers to a fragment consisting of a hinge portion or a part thereof, and CH2 and CH3 domains in an antibody molecule. According to EU numbering (herein, also referred to as EU INDEX) (see FIG. 18), an IgG-class Fc region refers to, for example, the region from cysteine at position 226 to the C terminus, or from proline at position 230 to the C terminus, but is not limited thereto.

The Fc region may be obtained suitably by re-eluting the fraction adsorbed onto a protein A column and a protein G column after partially digesting IgG1, IgG2, IgG3, IgG4 monoclonal antibodies or such using a protease such as pepsin. Such protease is not particularly limited as long as it can digest a full-length antibody so as to produce restrictively Fab and F(ab')$_2$ by appropriately setting the enzyme reaction conditions such as pH, and examples include pepsin and papain.

The present invention provides an Fc region variant which comprises amino acid alterations that combine an alteration of the amino acid at position 238 according to EU numbering to another amino acid with alteration of any one of the amino acids of (a) to (k) below to another amino acid in the Fc region of human IgG (IgG1, IgG2, IgG3, and IgG4). Introducing the alterations into an Fc region can provide a polypeptide comprising an Fc region variant with decreased binding activities to all activating FcγRs, in particular FcγRIIa (R type), while maintaining the FcγRIIb-binding activity as compared to those of a polypeptide comprising the Fc region of a native IgG:
(a) amino acid at position 235 of the Fc region according to EU numbering;
(b) amino acid at position 237 of the Fc region according to EU numbering;
(c) amino acid at position 241 of the Fc region according to EU numbering;
(d) amino acid at position 268 of the Fc region according to EU numbering;
(e) amino acid at position 295 of the Fc region according to EU numbering;
(f) amino acid at position 296 of the Fc region according to EU numbering;
(g) amino acid at position 298 of the Fc region according to EU numbering;
(h) amino acid at position 323 of the Fc region according to EU numbering;
(i) amino acid at position 324 of the Fc region according to EU numbering;
(j) amino acid at position 330 of the Fc region according to EU numbering; and
(k) at least two amino acids selected from (a) to (j).

A combination of at least two amino acids selected in the above-mentioned (k) is not particularly limited as long as binding activities to all activating FcγRs are decreased while the FcγRIIb-binding activity is maintained in comparison to those of a polypeptide comprising the native IgG Fc region, but the following combinations (1) to (3) are preferred:
(1) amino acids at positions 241, 268, 296, and 324 of the Fc region according to EU numbering;
(2) amino acids at positions 237, 241, 296, and 330 of the Fc region according to EU numbering; and
(3) amino acids at positions 235, 237, 241, and 296 of the Fc region according to EU numbering.

The amino acids selected to be present after alteration are not particularly limited as long as binding activities to all activating FcγRs are decreased while the FcγRIIb-binding activity is maintained in comparison to those of a polypeptide comprising the Fc region of a native IgG, but are preferably Asp at amino acid position 238, Phe at amino acid position 235, Gln or Asp at amino acid position 237, Met or Leu at amino acid position 241, Pro at amino acid position 268, Met or Val at amino acid position 295, Glu, His, Asn, or Asp at amino acid position 296, Ala or Met at amino acid position 298, Ile at amino acid position 323, Asn or His at amino acid position 324, and His or Tyr at amino acid position 330 according to EU numbering. Furthermore, the amino acids selected to be present after the alteration with regard to (1) to (3) described above are preferably:
(1) Met at amino acid position 241, Pro at amino acid position 268, Glu at amino acid position 296, and His at amino acid position 324 of the Fc region according to EU numbering;
(2) Gln or Asp at amino acid position 237, Met at amino acid position 241, Glu at amino acid position 296, and His at amino acid position 330 of the Fc region according to EU numbering; and
(3) Phe at amino acid position 235, Gln or Asp at amino acid position 237, Met at amino acid position 241, and Glu at amino acid position 296 of the Fc region according to EU numbering.

Furthermore, the present invention provides an Fc region variant comprising amino acid alterations which combine alterations of the amino acids at positions 238 and 271 of the human IgG Fc region according to EU numbering to other amino acids, with alteration of any one of the amino acids of (a) to (h) below to another amino acid. Introducing the alterations into the Fc region can provide a polypeptide comprising an Fc region variant with decreased binding activities to all activating FcγRs, in particular FcγRIIa (R type), while maintaining the FcγRIIb-binding activity in comparison to those of a polypeptide comprising the Fc region of a native IgG.
(a) amino acid at position 234 of the Fc region according to EU numbering;
(b) amino acid at position 235 of the Fc region according to EU numbering;
(c) amino acid at position 236 of the Fc region according to EU numbering;
(d) amino acid at position 237 of the Fc region according to EU numbering;
(e) amino acid at position 239 of the Fc region according to EU numbering;
(f) amino acid at position 265 of the Fc region according to EU numbering;
(g) amino acid at position 267 of the Fc region according to EU numbering; and
(h) amino acid at position 297 of the Fc region according to EU numbering.

Amino acid alterations to be combined with alterations of the amino acids at positions 238 and 271 according to EU numbering to other amino acids may further include alterations of other amino acids in addition to the amino acids of (a) to (h) described above. Such amino acid combinations are not particularly limited, but a combination of alterations selected from (1) to (3) below is preferred:
(1) amino acids at positions 233, 238, 264, 267, 268, and 271 of the Fc region according to EU numbering;
(2) amino acids at positions 233, 237, 238, 264, 267, 268, 271, 296, 297, 330, and 396 of the Fc region according to EU numbering; and
(3) amino acids at positions 233, 238, 264, 267, 268, 271 and 296 of the Fc region according to EU numbering.

The amino acids selected to be present after alteration are not particularly limited as long as binding activities to all activating FcγRs are decreased while the FcγRIIb-binding activity is maintained in comparison to those of a polypeptide comprising the Fc region of a native IgG, but are preferably Asp at amino acid position 238, Gly at amino acid position 271, Ala, His, Asn, Lys, or Arg at amino acid at 234, Ala at amino acid position 235, Gln at amino acid position 236, Arg or Lys at amino acid position 237, Lys at amino acid position 239, Lys, Asn, Arg, Ser, or Val at amino acid position 265, Lys, Arg, or Tyr at amino acid position 267, and Ala at amino acid position 297 according to EU numbering.

Furthermore, the amino acids selected to be present after the alterations in (1) to (3) described above are preferably:
(1) Asp at amino acid position 233, Asp at amino acid position 238, Ile at amino acid position 264, Arg at amino acid position 267, Glu at amino acid position 268, and Gly at amino acid position 271 of the Fc region according to EU numbering;
(2) Asp at amino acid position 233, Asp at amino acid position 237, Asp at amino acid position 238, Ile at amino acid position 264, Ala at amino acid position 267, Glu at amino acid position 268, Gly at amino acid position 271, Asp at amino acid position 296, Ala at amino acid position 297, Arg at amino acid position 330, and Met at amino acid position 396 of the Fc region according to EU numbering; and
(3) Asp at amino acid position 233, Asp at amino acid position 238, Ile at amino acid position 264, Arg at amino acid position 267, Pro at amino acid position 268, Gly at amino acid position 271, and Glu at amino acid position 296 of the Fc region according to EU numbering.

Furthermore, the present invention provides an Fc region variant comprising alterations of the amino acids at positions 238, 271, 327, 330, and 331 of the human IgG Fc region according to EU numbering to other amino acids. The present invention also provides an Fc region variant comprising amino acid alterations, where the variant further comprises alteration of a combination of the amino acids of any one of (a) to (e) below to other amino acids. Introducing the alterations into the Fc region can provide a polypeptide comprising an Fc region variant with decreased binding activities to all activating FcγRs, in particular FcγRIIa (R type), while maintaining FcγRIIb-binding activity as compared to those of a polypeptide comprising the Fc region of a native IgG.
(a) the amino acid at position 233 of the Fc region according to EU numbering;
(b) the amino acid at position 237 of the Fc region according to EU numbering;
(c) the amino acid at position 264 of the Fc region according to EU numbering;
(d) the amino acid at position 267 of the Fc region according to EU numbering; and
(e) the amino acid at position 268 of the Fc region according to EU numbering.

Amino acid alterations to be combined with the alterations of amino acids at positions 238 and 271 according to EU numbering to other amino acids may include alterations of other amino acids in addition to the amino acids of (a) to (e) described above. Such amino acid combinations are not particularly limited, but a combination of alterations selected from (1) to (4) below is preferred.
(1) amino acids at positions 237, 238, 268, 271, 327, 330, and 331 of the Fc region according to EU numbering;
(2) amino acids at positions 233, 237, 238, 268, 271, 327, 330, and 331 of the Fc region according to EU numbering;
(3) amino acids at positions 238, 267, 268, 271, 327, 330, and 331 of the Fc region according to EU numbering; and
(4) amino acids at positions 238, 264, 267, 271, 327, 330, and 331 of the Fc region according to EU numbering.

The amino acids selected to be present after alteration are not particularly limited as long as binding activities to all activating FcγRs are decreased while the FcγRIIb-binding activity is maintained in comparison to those of a polypeptide comprising the Fc region of a native IgG, but are preferably Asp at amino acid position 238, Gly at amino acid position 271, Gly at amino acid position 327, Ser at amino acid position 330, Ser at amino acid position 331, Asp at amino acid position 233, Asp at amino acid position 237, Ile at amino acid position 264, Ala at amino acid position 267, and Asp or Glu at amino acid position 268 according to EU numbering.

Furthermore, the amino acids selected to be present after the alterations in (1) to (4) described above are preferably:
(1) Asp at amino acid position 237, Asp at amino acid position 238, Asp or Glu at amino acid position 268, Gly at amino acid position 271, Gly at amino acid position 327, Ser at amino acid at position 330, and Ser at amino acid position 331 of the Fc region according to EU numbering;
(2) Asp at amino acid position 233, Asp at amino acid position 237, Asp at amino acid position 238, Asp at amino acid position 268, Gly at amino acid position 271, Gly at amino acid position 327, Ser at amino acid position 330, and Ser at amino acid position 331 of the Fc region according to EU numbering;
(3) Asp at amino acid position 238, Ala at amino acid position 267, Glu at amino acid position 268, Gly at amino acid position 271, Gly at amino acid position 327, Ser at amino acid position 330, and Ser at amino acid position 331 of the Fc region according to EU numbering; and
(4) Asp at amino acid position 238, Ile at amino acid position 264, Ala at amino acid position 267, Gly at amino acid position 271, Gly at amino acid position 327, Ser at amino acid position 330, and Ser at amino acid position 331 of the Fc region according to EU numbering.

In the present invention, at least another different alteration can be made to the Fc region in addition to these alterations. The alteration is not particularly limited as long as it decreases the binding activities to activating FcγRs while maintaining the FcγRIIb-binding activity.

Examples of such an alteration include those that decrease the complement-binding activity. Specific examples include amino acid alteration at position 322 of the Fc region according to EU numbering, or a combination of amino acid alterations at positions 327, 330, and 331 of the Fc region according to EU numbering. The amino acids selected to be present after alteration are not particularly limited as long as the complement-binding activity is decreased while binding activities to all activating FcγRs are decreased and the FcγRIIb-binding activity is maintained in comparison to those of a polypeptide comprising the Fc region of a native IgG, but are preferably Ala or Glu at amino acid position 322, Gly at amino acid position 327, Ser at amino acid position 330, and Ser at amino acid position 331 according to EU numbering.

In the present invention, whether the complement-binding activity of the Fc region variant or the polypeptide comprising the Fc region variant of the present invention is decreased can be confirmed by a method similar to the method described above for confirming whether the FcγR-binding activities have been decreased. Specifically, for example, the determination can be made by observing whether there is an increase in the dissociation constant (KD) value obtained from the results of sensorgram analysis, where the complement is interacted as an analyte with antibodies to be evaluated which are immobilized onto the sensor chips or captured onto the sensor chips using Protein A, Protein L, Protein A/G, Protein G, anti-lamda chain antibodies, anti-kappa chain antibodies, antigen peptides, antigen proteins, or such using BIACORE, which is an interaction analyzer that utilizes the surface plasmon resonance (SPR) phenomena, as shown in the Examples. Alternatively, it can also be determined by observing whether there is an increase in the value obtained by dividing the amount of change in the resonance unit (RU) value on the sensorgram before and after the complement is subjected to interaction as an analyte with antibodies to be evaluated immobilized onto the sensor chips or captured onto the sensor chips using Protein A, Protein L, Protein A/G, Protein G, anti-lamda chain antibodies, anti-kappa chain antibodies, antigen peptides, antigen proteins, or such, by the amount of change of resonance units (RU) before and after the antibodies are immobilized or captured onto the sensor chip. Furthermore, it can be determined by observing whether there is an increase in the dissociation constant (KD) values obtained from sensorgram analysis, where a sample such as an antibody to be evaluated is subjected to interaction as an analyte using a sensor chip onto which a complement has been immobilized directly or via an anti-tag antibody. Alternatively, it can be determined by observing whether the amount of change in sensorgram values increases or not before and after a sample such as an antibody to be evaluated is subjected to interaction as an analyte with the sensor chip onto which a complement is immobilized directly or via an anti-tag antibody. Otherwise, it can be determined by evaluating the amount of binding by ELISA which involves adding the complement to a plate onto which an antibody to be evaluated has been immobilized directly or via an antigen, and then adding an anti-human C1q antibody labeled with peroxidase or such.

Amino acid alterations carried out for other purposes may also be combined into the polypeptide comprising an Fc region variant of the present invention. For example, amino acid substitutions that improve the FcRn-binding activity (J. Immunol. 2006 Jan. 1; 176(1): 346-56; J Biol Chem. 2006 Aug. 18; 281(33): 23514-24; Int. Immunol. 2006 December; 18(12): 1759-69; Nat Biotechnol. 2010 February; 28(2): 157-9; WO 2006/019447; WO 2006/053301; and WO 2009/086320), and amino acid substitutions for improving antibody heterogeneity or stability (WO 2009/041613) may be introduced. Alternatively, polypeptides produced by conferring polypeptides comprising an Fc region variant of the present invention with the property of promoting antigen elimination, which are described in WO 2011/122011 or PCT/JP2011/072550, and polypeptides conferred with the property for repeatedly binding to multiple antigen molecules, which are described in WO 2009/125825 or PCT/JP2011/077619, are also included in the present invention. Alternatively, with the objective of increasing plasma retention, amino acid alterations that decrease the pI of the constant region (WO 2012/016227) may be combined into a polypeptide comprising an Fc region variant of the present invention. Otherwise, with the objective of conferring binding ability to other antigens, the amino acid alterations in CH3 described in EP1752471 and EP1772465 may be combined into a polypeptide comprising an Fc region variant of the present invention.

When a polypeptide comprising an Fc region variant of the present invention comprises an antigen-binding domain such as in an antibody, amino acid alteration for changing its antigen-binding activity according to the ion concentration condition can be combined to enhance the effect of the polypeptide to eliminate antigens from plasma.

Herein, an "antigen-binding domain" may be of any structure as long as it binds to an antigen of interest. Such domains preferably include, for example:
antibody heavy-chain and light-chain variable regions;
a module of about 35 amino acids called A domain which is contained in the in vivo cell membrane protein Avimer (WO 2004/044011, WO 2005/040229);
Adnectin containing the 10Fn3 domain which binds to the protein moiety of fibronectin, a glycoprotein expressed on cell membrane (WO 2002/032925);
Affibody which is composed of a 58-amino acid three-helix bundle based on the scaffold of the IgG-binding domain of Protein A (WO 1995/001937);
Designed Ankyrin Repeat proteins (DARPins) which are a region exposed on the molecular surface of ankyrin repeats (AR) having a structure in which a subunit consisting of a turn comprising 33 amino acid residues, two antiparallel helices, and a loop is repeatedly stacked (WO 2002/020565);
Anticalins and such, which are domains consisting of four loops that support one side of a barrel structure composed of eight circularly arranged antiparallel strands that are highly conserved among lipocalin molecules such as neutrophil gelatinase-associated lipocalin (NGAL) (WO 2003/029462); and
the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the system of acquired immunity in jawless vertebrate such as lampery and hagfish (WO 2008/016854). Preferred antigen-binding domains of the present invention include, for example, those having antibody heavy-chain and light-chain variable regions. Preferred examples of antigen-binding domains include "single chain Fv (scFv)", "single chain antibody", "Fv", "single chain Fv 2 (scFv2)", "Fab", and "F(ab')₂".

"Ion concentration" as used herein includes, for example, metal ion concentration. "Metal ions" refer to ions of group I elements except hydrogen such as alkaline metals and copper group elements, group II elements such as alkaline earth metals and zinc group elements, group III elements except boron, group IV elements except carbon and silicon, group VIII elements such as iron group and platinum group elements, elements belonging to subgroup A of groups V, VI, and VII, and metal elements such as antimony, bismuth, and polonium. Metal atoms have the property of releasing valence electrons to become cations. This is referred to as ionization tendency. Metals with strong ionization tendency are deemed to be chemically active. In the present invention, preferred metal ions include, for example, calcium ion.

Calcium ion is involved in modulation of many biological phenomena, including contraction of muscles such as skeletal, smooth, and cardiac muscles; activation of movement, phagocytosis, and the like of leukocytes; activation of shape change, secretion, and the like of platelets; activation of lymphocytes; activation of mast cells including secretion of histamine; cell responses mediated by catecholamine a receptor or acetylcholine receptor; exocytosis; release of transmitter substances from neuron terminals; and axoplasmic flow in neurons. Known intracellular calcium ion receptors include troponin C, calmodulin, parvalbumin, and myosin light chain, which have several calcium ion-binding sites and are believed to be derived from a common origin in terms of molecular evolution. There are also many known calcium-binding motifs. Such well-known motifs include, for example, cadherin domains, EF-hand of calmodulin, C2 domain of Protein kinase C, Gla domain of blood coagulation protein Factor IX, C-type lectins of acyaroglycoprotein receptor and mannose-binding receptor, A domains of LDL receptors, annexin, thrombospondin type 3 domain, and EGF-like domains.

In the present invention, when the metal ion is calcium ion, the conditions of calcium ion concentration include low calcium ion concentration conditions and high calcium ion concentration conditions. "The binding activity varies depending on calcium ion concentration conditions" means that the antigen-binding activity of an antigen-binding molecule varies due to the difference in the conditions between low and high calcium ion concentrations. For example, the antigen-binding activity of an antigen-binding molecule may be higher under a high calcium ion concentration condition than under a low calcium ion concentration condition. Alternatively, the antigen-binding activity of an antigen-binding molecule may be higher under a low calcium ion concentration condition than under a high calcium ion concentration condition.

Herein, the high calcium ion concentration is not particularly limited to a specific value; however, the concentration may preferably be selected between 100 µM and 10 mM. In another embodiment, the concentration may be selected between 200 µM and 5 mM. In an alternative embodiment, the concentration may be selected between 400 µM and 3 mM. In still another embodiment, the concentration may be selected between 200 µM and 2 mM. Furthermore, the concentration may be selected between 400 µM and 1 mM. In particular, a concentration selected between 500 µM and 2.5 mM, which is close to the plasma (blood) concentration of calcium ion in vivo, is preferred.

Herein, the low calcium ion concentration is not particularly limited to a specific value; however, the concentration may preferably be selected between 0.1 µM and 30 µM. In another embodiment, the concentration may be selected between 0.2 µM and 20 µM. In still another embodiment, the concentration may be selected between 0.5 µM and 10 µM. In an alternative embodiment, the concentration may be selected between 1 µM and 5 µM. Furthermore, the concentration may be selected between 2 µM and 4 µM. In particular, a concentration selected between 1 µM and 5 µM, which is close to the concentration of ionized calcium in early endosomes in vivo, is preferred.

In the present invention, "the antigen-binding activity is lower at a low calcium ion concentration condition than at a high calcium ion concentration condition" means that the antigen-binding activity of an antigen-binding molecule is weaker at a calcium ion concentration selected between 0.1 µM and 30 µM than at a calcium ion concentration selected between 100 µM and 10 mM. Preferably, it means that the antigen-binding activity of an antigen-binding molecule is weaker at a calcium ion concentration selected between 0.5 µM and 10 µM than at a calcium ion concentration selected between 200 µM and 5 mM. It particularly preferably means that the antigen-binding activity at the calcium ion concentration in the early endosome in vivo is weaker than that at the in vivo plasma calcium ion concentration; and specifically, it means that the antigen-binding activity of an antigen-binding molecule is weaker at a calcium ion concentration selected between 1 µM and 5 µM than at a calcium ion concentration selected between 500 µM and 2.5 mM.

Whether the antigen-binding activity of an antigen-binding molecule is changed depending on metal ion concentrations can be determined, for example, by the use of known measurement methods such as those described in the section "Binding Activity" above. For example, in order to confirm that the antigen-binding activity of an antigen-binding molecule becomes higher under a high calcium ion concentration condition than under a low calcium ion concentration condition, the antigen-binding activity of the antigen-binding molecule under low and high calcium ion concentration conditions is compared.

In the present invention, the expression "the antigen-binding activity is lower at a low calcium ion concentration condition than at a high calcium ion concentration condition" can also be expressed as "the antigen-binding activity of an antigen-binding molecule is higher under a high calcium ion concentration condition than under a low calcium ion concentration condition". In the present invention, "the antigen-binding activity is lower at a low calcium ion concentration condition than at a high calcium ion concentration condition" is sometimes written as "the antigen-binding ability is weaker under a low calcium ion concentration condition than under a high calcium ion concentration condition". Also, "the antigen-binding activity at a low calcium ion concentration condition is reduced to be lower than that at a high calcium ion concentration condition" may be written as "the antigen-binding ability under a low calcium ion concentration condition is made weaker than that under a high calcium ion concentration condition".

When determining the antigen-binding activity, the conditions other than calcium ion concentration can be appropriately selected by those skilled in the art, and are not particularly limited. For example, the activity can be determined at 37° C. in HEPES buffer. For example, Biacore (GE Healthcare) or such can be used for the determination. When the antigen is a soluble antigen, the antigen-binding activity of an antigen-binding molecule can be assessed by flowing the antigen as an analyte over a chip onto which the antigen-binding molecule is immobilized. When the antigen is a membrane antigen, the binding activity of an antigen-binding molecule to the membrane antigen can be assessed by flowing the antigen-binding molecule as an analyte over a chip onto which the antigen is immobilized.

As long as the antigen-binding activity of an antigen-binding molecule of the present invention at a low calcium ion concentration condition is weaker than that at a high calcium ion concentration condition, the ratio of the antigen-binding activity between that under a low calcium ion concentration condition and under a high calcium ion concentration condition is not particularly limited; and the value of KD (Ca 3 µM)/KD (Ca 2 mM), which is the ratio of the dissociation constant (KD) for an antigen at a low calcium ion concentration condition to the KD at a high calcium ion concentration condition, is preferably 2 or more; more preferably the value of KD (Ca 3 µM)/KD (Ca 2 mM) is 10 or more; and still more preferably the value of KD (Ca 3 µM)/KD (Ca 2 mM) is 40 or more. The upper limit of KD (Ca 3 µM)/KD (Ca 2 mM) value is not particularly limited, and may be any value such as 400, 1000, or 10000, as long as the molecule can be produced by the techniques of those skilled in the art.

When the antigen is a soluble antigen, KD (dissociation constant) can be used to represent the antigen-binding activity. Meanwhile, when the antigen is a membrane antigen, apparent KD (apparent dissociation constant) can be used to represent the activity. KD (dissociation constant) and apparent KD (apparent dissociation constant) can be determined by methods known to those skilled in the art, for example, using Biacore (GE healthcare), Scatchard plot, or flow cytometer.

Alternatively, for example, the dissociation rate constant (kd) can also be preferably used as an index to represent the ratio of the antigen-binding activity of an antigen-binding molecule of the present invention between low and high calcium concentration conditions. When the dissociation rate constant (kd) is used instead of the dissociation constant (KD) as an index to represent the binding activity ratio, the ratio of the dissociation rate constant (kd) between low and high calcium concentration conditions, i.e., the value of kd (low calcium concentration condition)/kd (high calcium concentration condition), is preferably 2 or more, more preferably 5 or more, still more preferably 10 or more, and yet more preferably 30 or more. The upper limit of the Kd (low calcium concentration condition)/kd (high calcium concentration condition) value is not particularly limited, and can be any value such as 50, 100, or 200 as long as the molecule can be produced by techniques known to those skilled in the art.

When the antigen is a soluble antigen, kd (dissociation rate constant) can be used to represent the antigen-binding activity. Meanwhile, when the antigen is a membrane antigen, apparent kd (apparent dissociation rate constant) can be used to represent the antigen-binding activity. The kd (dissociation rate constant) and apparent kd (apparent dissociation rate constant) can be determined by methods known to those skilled in the art, for example, using Biacore (GE healthcare) or flow cytometer. In the present invention, when the antigen-binding activity of an antigen-binding molecule is determined at different calcium ion concentrations, it is preferable to use the same conditions except for the calcium concentrations.

For example, an antigen-binding domain or antigen-binding molecule whose antigen-binding activity is lower at a low calcium ion concentration condition than at a high calcium ion concentration condition, which is one embodiment of the present invention, can be obtained via screening of antigen-binding domains or antibodies including the steps of (a) to (c) below:
(a) determining the antigen-binding activity of an antigen-binding domain or antigen-binding molecule at a low calcium concentration condition;
(b) determining the antigen-binding activity of an antigen-binding domain or antigen-binding molecule at a high calcium concentration condition; and
(c) selecting an antigen-binding domain or antigen-binding molecule whose antigen-binding activity is lower at a low calcium concentration condition than at a high calcium concentration condition.

Moreover, an antigen-binding domain or antigen-binding molecule whose antigen-binding activity is lower at a low calcium ion concentration condition than at a high calcium ion concentration condition, which is one embodiment of the present invention, can be obtained via screening of antigen-binding domains or antigen-binding molecules, or a library thereof, including the steps of (a) to (c) below:
(a) contacting an antigen with an antigen-binding domain or antigen-binding molecule, or a library thereof at a high calcium concentration condition;
(b) incubating under a low calcium concentration condition an antigen-binding domain or antigen-binding molecule that has bound to the antigen in step (a); and
(c) isolating an antigen-binding domain or antigen-binding molecule dissociated in step (b).

Furthermore, an antigen-binding domain or antigen-binding molecule whose antigen-binding activity is lower at a low calcium ion concentration condition than at a high calcium ion concentration condition, which is one embodiment of the present invention, can be obtained via screening of antigen-binding domains or antigen-binding molecules, or a library thereof, including the steps of (a) to (d) below:
(a) contacting an antigen with a library of antigen-binding domains or antigen-binding molecules under a low calcium concentration condition;
(b) selecting an antigen-binding domain or antigen-binding molecule which does not bind to the antigen in step (a);
(c) allowing the antigen-binding domain or antigen-binding molecule selected in step (b) to bind to the antigen under a high calcium concentration condition; and
(d) isolating an antigen-binding domain or antigen-binding molecule that has bound to the antigen in step (c).

In addition, an antigen-binding domain or antigen-binding molecule whose antigen-binding activity is lower at a low calcium ion concentration condition than at a high calcium ion concentration condition, which is one embodiment of the present invention, can be obtained by a screening method comprising the steps of (a) to (c) below:
(a) contacting under a high calcium concentration condition a library of antigen-binding domains or antigen-binding molecules with a column onto which an antigen is immobilized;
(b) eluting an antigen-binding domain or antigen-binding molecule that has bound to the column in step (a) from the column under a low calcium concentration condition; and
(c) isolating the antigen-binding domain or antigen-binding molecule eluted in step (b).

Furthermore, an antigen-binding domain or antigen-binding molecule whose antigen-binding activity is lower at a low calcium ion concentration condition than at a high calcium ion concentration condition, which is one embodiment of the present invention, can be obtained by a screening method comprising the steps of (a) to (d) below:
(a) allowing under a low calcium concentration condition a library of antigen-binding domains or antigen-binding molecules to pass through a column onto which an antigen is immobilized;
(b) collecting an antigen-binding domain or antigen-binding molecule that has been eluted without binding to the column in step (a);
(c) allowing the antigen-binding domain or antigen-binding molecule collected in step (b) to bind to the antigen under a high calcium concentration condition; and
(d) isolating an antigen-binding domain or antigen-binding molecule that has bound to the antigen in step (c).

Moreover, an antigen-binding domain or antigen-binding molecule whose antigen-binding activity is lower at a low calcium ion concentration condition than at a high calcium ion concentration condition, which is one embodiment of the present invention, can be obtained by a screening method comprising the steps of (a) to (d) below:
(a) contacting an antigen with a library of antigen-binding domains or antigen-binding molecules under a high calcium concentration condition;
(b) obtaining an antigen-binding domain or antigen-binding molecule that has bound to the antigen in step (a);
(c) incubating under a low calcium concentration condition the antigen-binding domain or antigen-binding molecule obtained in step (b); and
(d) isolating an antigen-binding domain or antigen-binding molecule whose antigen-binding activity in step (c) is weaker than the criterion for the selection of step (b).

The above-described steps may be repeated twice or more times. Thus, the present invention provides antigen-binding domains or antigen-binding molecules whose antigen-binding activity is lower at a low calcium ion concentration condition than at a high calcium ion concentration condition, which are obtained by screening methods that further comprises the step of repeating twice or more times steps (a) to (c) or (a) to (d) in the above-described screening methods. The number of cycles of steps (a) to (c) or (a) to (d) is not particularly limited, but generally is 10 or less.

In the above-mentioned screening methods, the antigen-binding activity of an antigen-binding domain or antigen-binding molecule under a low calcium concentration condition is not particularly limited as long as it is antigen-binding activity at an ionized calcium concentration of between 0.1 μM and 30 μM, but preferably is antigen-binding activity at an ionized calcium concentration of between 0.5 μM and 10 μM. More preferably, it is antigen-binding activity at the ionized calcium concentration in the early endosome in vivo, specifically, between 1 μM and 5 μM. Meanwhile, the antigen-binding activity of an antigen-binding domain or antigen-binding molecule under a high calcium concentration condition is not particularly limited, as long as it is antigen-binding activity at an ionized calcium concentration of between 100 μM and 10 mM, but preferably is antigen-binding activity at an ionized calcium concentration of between 200 μM and 5 mM. More preferably, it is antigen-binding activity at the ionized calcium concentration in plasma in vivo, specifically, between 0.5 mM and 2.5 mM.

The method described in WO 2012/073992 (for example, paragraphs 0200-0213) and such may be exemplified as a method of screening for an antigen-binding molecule or an antigen-binding domain having lower antigen-binding activity under low calcium ion concentration conditions than under high calcium ion concentration conditions, which is an embodiment provided by the present invention.

The antigen-binding activity of an antigen-binding domain or antigen-binding molecule can be measured by methods known to those skilled in the art. Conditions other than the ionized calcium concentration can be determined by those skilled in the art. The antigen-binding activity of an antigen-binding domain or antigen-binding molecule can be evaluated as a dissociation constant (KD), apparent dissociation constant (apparent KD), dissociation rate constant (kd), apparent dissociation constant (apparent kd), and such. These can be determined by methods known to those skilled in the art, for example, using Biacore (GE healthcare), Scatchard plot, or FACS.

In the present invention, the step of selecting an antigen-binding domain or antigen-binding molecule whose antigen-binding activity is higher under a high calcium concentration condition than under a low calcium concentration condition is synonymous with the step of selecting an antigen-binding domain or antigen-binding molecule whose antigen-binding activity is lower under a low calcium concentration condition than under a high calcium concentration condition.

As long as the antigen-binding activity is higher under a high calcium concentration condition than under a low calcium concentration condition, the difference in the antigen-binding activity between high and low calcium concentration conditions is not particularly limited; however, the antigen-binding activity under a high calcium concentration condition is preferably twice or more, more preferably 10 times or more, and still more preferably 40 times or more than that under a low calcium concentration condition.

Antigen-binding domains or antigen-binding molecules of the present invention to be screened by the screening methods described above may be any antigen-binding domains and antigen-binding molecules. For example, it is possible to screen the above-described antigen-binding domains or antigen-binding molecules. For example, antigen-binding domains or antigen-binding molecules having natural sequences or substituted amino acid sequences may be screened.

For example, in an embodiment provided by the present invention, the method described in WO 2012/073992 (for example, paragraphs 0200-0213) and such may be exemplified as a method of screening for an antigen-binding molecule or an antigen-binding domain having lower antigen-binding activity under a low calcium ion concentration condition than under a high calcium ion concentration condition.

Antigen-binding domains or antigen-binding molecules of the present invention whose antigen-binding activities change according to the calcium ion concentration condition, which are screened by the above-described screening methods, may be prepared in any manner. For example, when the metal ion concentration refers to calcium ion concentration, it is possible to use preexisting antigen-binding domains or antigen-binding molecules, preexisting libraries (phage library, etc.), antibodies or libraries prepared from hybridomas obtained by immunizing animals or from B cells of immunized animals, antibodies or libraries obtained by introducing amino acids capable of chelating calcium (for example, aspartic acid and glutamic acid) or introducing non-natural amino acid mutations into the above-described antibodies or libraries (libraries produced by increasing the content of amino acids capable of chelating calcium (such as aspartic acid and glutamic acid) or non-natural amino acids, libraries prepared by introducing amino acids capable of chelating calcium (such as aspartic acid and glutamic acid) or non-natural amino acid mutations at particular positions, or the like).

Examples of the amino acids that alter the antigen-binding activity of antigen-binding molecules according to the ion concentration condition as described above may be any types of amino acids as long as the amino acids form a calcium-binding motif. Calcium-binding motifs are well known to those skilled in the art and have been described in details (for example, Springer et al. (Cell (2000) 102, 275-277); Kawasaki and Kretsinger (Protein Prof (1995) 2, 305-490); Moncrief et al. (J. Mol. Evol. (1990) 30, 522-562); Chauvaux et al. (Biochem. J. (1990) 265, 261-265); Bairoch and Cox (FEBS Lett. (1990) 269, 454-456); Davis (New Biol. (1990) 2, 410-419); Schaefer et al. (Genomics (1995) 25, 638-643); Economou et al. (EMBO J. (1990) 9, 349-354); Wurzburg et al. (Structure. (2006) 14, 6, 1049-1058)). Specifically, any known calcium-binding motifs, including type C lectins such as ASGPR, CD23, MBR, and DC-SIGN, can be included in antigen-binding molecules of the present invention. Preferred examples of such preferred calcium-binding motifs also include, in addition to those described above, for example, the calcium-binding motif in the antigen-binding domain of SEQ ID NO: 45.

Furthermore, as amino acids that alter the antigen-binding activity of antigen-binding domains included in the antigen-binding molecules of the present invention depending on calcium ion concentration conditions, for example, amino acids having metal-chelating activity may also be preferably used. Examples of such metal-chelating amino acids include, for example, serine (Ser (S)), threonine (Thr (T)), asparagine (Asn (N)), glutamine (Gln (Q)), aspartic acid (Asp (D)), and glutamic acid (Glu (E)).

Positions in the antigen-binding domains at which the above-described amino acids are contained are not particularly limited to particular positions, and may be any positions within the heavy chain variable region or light chain variable region that forms an antigen-binding domain, as long as they alter the antigen-binding activity of antigen-binding molecules depending on calcium ion concentration conditions. In a non-limiting embodiment, antigen-binding domains of the present invention can be obtained from a library mainly composed of antigen-binding molecules whose sequences are different from one another and whose heavy chain antigen-binding domains contain amino acids that alter the antigen-binding activity of the antigen-binding molecules depending on calcium ion concentration conditions. In another non-limiting embodiment, antigen-binding domains of the present invention can be obtained from a library mainly composed of antigen-binding molecules whose sequences are different from one another and whose heavy chain CDR3 domains contain the above-mentioned amino acids. In still another embodiment, antigen-binding domains of the present invention can be obtained from a library mainly composed of antigen-binding molecules whose sequences are different from one another and whose heavy chain CDR3 domains contain the above-mentioned amino acids at positions 95, 96, 100a, and/or 101 as indicated according to the Kabat numbering system.

Meanwhile, in a non-limiting embodiment of the present invention, antigen-binding domains of the present invention can be obtained from a library mainly composed of antigen-binding molecules whose sequences are different from one another and whose light chain antigen-binding domains contain amino acids that alter the antigen-binding activity of antigen-binding molecules depending on calcium ion concentration conditions. In another non-limiting embodiment, antigen-binding domains of the present invention can be obtained from a library mainly composed of antigen-binding molecules whose sequences are different from one another and whose light chain CDR1 domains contain the above-mentioned amino acids. In still another embodiment, antigen-binding domains of the present invention can be obtained from a library mainly composed of antigen-binding molecules whose sequences are different from one another and whose light chain CDR1 domains contain the above-mentioned amino acids at positions 30, 31, and/or 32 as indicated according to the Kabat numbering system.

In another non-limiting embodiment, antigen-binding domains of the present invention can be obtained from a library mainly composed of antigen-binding molecules whose sequences are different from one another and whose light chain CDR2 domains contain the above-mentioned amino acid residues. In yet another non-limiting embodiment, the present invention provides libraries mainly composed of antigen-binding molecules whose sequences are different from one another and whose light chain CDR2 domains contain the above-mentioned amino acid residues at position 50 as indicated according to the Kabat numbering system.

In still another embodiment of the present invention, antigen-binding domains of the present invention can be obtained from a library mainly composed of antigen-binding molecules whose sequences are different from one another and whose light chain CDR3 domains contain the above-mentioned amino acid residues. In an alternative embodiment, antigen-binding domains of the present invention can be obtained from a library mainly composed of antigen-binding molecules whose sequences are different from one another and whose light chain CDR3 domains contain the above-mentioned amino acid residues at position 92 as indicated according to the Kabat numbering system.

Furthermore, in a different embodiment of the present invention, antigen-binding domains of the present invention can be obtained from a library mainly composed of antigen-binding molecules whose sequences are different from one another and in which two or three CDRs selected from the above-described light chain CDR1, CDR2, and CDR3 contain the aforementioned amino acid residues. Moreover, antigen-binding domains of the present invention can be obtained from a library mainly composed of antigen-binding molecules whose sequences are different from one another and whose light chains contain the aforementioned amino acid residues at any one or more of positions 30, 31, 32, 50, and/or 92 as indicated according to the Kabat numbering system.

In a particularly preferred embodiment, the framework sequences of the light chain and/or heavy chain variable region of an antigen-binding molecule preferably contain human germ line framework sequences. Thus, in an embodiment of the present invention, when the framework sequences are completely human sequences, it is expected that when such an antigen-binding molecule of the present invention is administered to humans (for example, to treat diseases), it induces little or no immunogenic response. In the above sense, the phrase "containing a germ line sequence" in the present invention means that a part of the framework sequences in the present invention is identical to a part of any human germ line framework sequences. For example, when the heavy chain FR2 sequence of an antigen-binding molecule in the present invention is a combination of heavy chain FR2 sequences of different human germ line framework sequences, such a molecule is also an antigen-binding molecule in the present invention "containing a germ line sequence".

Preferred examples of the frameworks include, for example, fully human framework region sequences currently known, which are included in the website of V-Base (http://vbase.mrc-cpe.cam.ac.uk/) or others. Those framework region sequences can be appropriately used as a germ line sequence contained in an antigen-binding molecule of the present invention. The germ line sequences may be categorized according to their similarity (Tomlinson et al. (J. Mol. Biol. (1992) 227, 776-798); Williams and Winter (Eur. J. Immunol. (1993) 23, 1456-1461); Cox et al. (Nat. Genetics (1994) 7, 162-168)). Appropriate germ line sequences can be selected from Vκ, which is grouped into seven subgroups; Vλ, which is grouped into ten subgroups; and VH, which is grouped into seven subgroups.

Fully human VH sequences preferably include, but are not limited to, for example, VH sequences of:
subgroup VH1 (for example, VH1-2, VH1-3, VH1-8, VH1-18, VH1-24, VH1-45, VH1-46, VH1-58, and VH1-69);
subgroup VH2 (for example, VH2-5, VH2-26, and VH2-70);
subgroup VH3 (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74);
subgroup VH4 (VH4-4, VH4-28, VH4-31, VH4-34, VH4-39, VH4-59, and VH4-61);
subgroup VH5 (VH5-51);
subgroup VH6 (VH6-1); and
subgroup VH7 (VH7-4 and VH7-81).
These are also described in known documents (Matsuda et al. (J. Exp. Med. (1998) 188, 1973-1975)) and such, and thus persons skilled in the art can appropriately design antigen-binding molecules of the present invention based on the information of these sequences. It is also preferable to use other fully human frameworks or framework sub-regions.

Fully human Vκ sequences preferably include, but are not limited to, for example:
A20, A30, L1, L4, L5, L8, L9, L11, L12, L14, L15, L18, L19, L22, L23, L24, O2, O4, O8, O12, O14, and O18 grouped into subgroup Vk1;
A1, A2, A3, A5, A7, A17, A18, A19, A23, O1, and O11, grouped into subgroup Vk2;
A11, A27, L2, L6, L10, L16, L20, and L25, grouped into subgroup Vk3;
B3, grouped into subgroup Vk4;
B2 (herein also referred to as Vk5-2), grouped into subgroup Vk5; and
A10, A14, and A26, grouped into subgroup Vk6
(Kawasaki et al. (Eur. J. Immunol. (2001) 31, 1017-1028); Schable and Zachau (Biol. Chem. Hoppe Seyler (1993) 374, 1001-1022); Brensing-Kuppers et al. (Gene (1997) 191, 173-181)).

Fully human Vλ sequences preferably include, but are not limited to, for example:

V1-2, V1-3, V1-4, V1-5, V1-7, V1-9, V1-11, V1-13, V1-16, V1-17, V1-18, V1-19, V1-20, and V1-22, grouped into subgroup VL1;
V2-1, V2-6, V2-7, V2-8, V2-11, V2-13, V2-14, V2-15, V2-17, and V2-19, grouped into subgroup VL1;
V3-2, V3-3, and V3-4, grouped into subgroup VL3;
V4-1, V4-2, V4-3, V4-4, and V4-6, grouped into subgroup VL4; and
V5-1, V5-2, V5-4, and V5-6, grouped into subgroup VL5 (Kawasaki et al. (Genome Res. (1997) 7, 250-261)).

Normally, these framework sequences are different from one another at one or more amino acid residues. These framework sequences can be used in combination with "at least one amino acid residue that alters the antigen-binding activity of an antigen-binding molecule depending on ion concentration conditions" in the present invention. Other examples of the fully human frameworks used in combination with "at least one amino acid residue that alters the antigen-binding activity of an antigen-binding molecule depending on ion concentration conditions" in the present invention include, but are not limited to, for example, KOL, NEWM, REI, EU, TUR, TEI, LAY, and POM (for example, Kabat et al. (1991) supra; Wu et al. (J. Exp. Med. (1970) 132, 211-250)).

Without being bound by a particular theory, one reason for the expectation that the use of germ line sequences precludes adverse immune responses in most individuals is believed to be as follows. As a result of the process of affinity maturation during normal immune responses, somatic mutation occurs frequently in the variable regions of immunoglobulin. Such mutations mostly occur around CDRs whose sequences are hypervariable, but also affect residues of framework regions. Such framework mutations do not exist on the germ line genes, and also they are less likely to be immunogenic in patients. On the other hand, the normal human population is exposed to most of the framework sequences expressed from the germ line genes. As a result of immunotolerance, these germ line frameworks are expected to have low or no immunogenicity in patients. To maximize the possibility of immunotolerance, variable region-encoding genes may be selected from a group of commonly occurring functional germ line genes.

Known methods such as site-directed mutagenesis (Kunkel et al. (Proc. Natl. Acad. Sci. USA (1985) 82, 488-492)) and overlap extension PCR can be appropriately employed to produce the antigen-binding molecules of the present invention in which the above-described variable region sequences, heavy or light chain variable region sequences, CDR sequences, or framework sequences contain amino acids that alter the antigen-binding activity of the antigen-binding molecules depending on calcium ion concentration conditions.

For example, a library which contains a plurality of antigen-binding molecules of the present invention whose sequences are different from one another can be constructed by combining heavy chain variable regions prepared as a randomized variable region sequence library with a light chain variable region selected as a framework sequence originally containing at least one amino acid residue that alters the antigen-binding activity of the antigen-binding molecule depending on calcium ion concentration conditions. As a non-limiting example, when the ion concentration is calcium ion concentration, such preferred libraries include, for example, those constructed by combining the light chain variable region sequence of SEQ ID NO: 45 (Vk5-2) and the heavy chain variable region produced as a randomized variable region sequence library.

Alternatively, a light chain variable region sequence selected as a framework region originally containing at least one amino acid residue that alters the antigen-binding activity of an antigen-binding domain or an antigen-binding molecule according to the calcium ion concentration condition as mentioned above can be designed to contain various amino acid residues other than the above amino acid residues. In the present invention, such residues are referred to as flexible residues. The number and position of flexible residues are not limited to particular embodiments as long as the antigen-binding activity of the antigen-binding domain or antigen-binding molecule of the present invention varies depending on the ion concentration condition. Specifically, the CDR sequences and/or FR sequences of the heavy chain and/or light chain may contain one or more flexible residues. For example, when the ion concentration is calcium ion concentration, non-limiting examples of flexible residues to be introduced into the light chain variable region sequence of SEQ ID NO: 45 (Vk5-2) include the amino acid residues listed in Tables 1 or 2.

TABLE 1

| CDR | Kabat NUMBERING | 70% OF AMINO ACID OF THE TOTAL | | | |
|---|---|---|---|---|---|
| CDR1 | 28 | S: 100% | | | |
|  | 29 | I: 100% | | | |
|  | 30 | E: 72% | N: 14% | S: 14% | |
|  | 31 | D: 100% | | | |
|  | 32 | D: 100% | | | |
|  | 33 | L: 100% | | | |
|  | 34 | A: 70% | N: 30% | | |
| CDR2 | 50 | E: 100% | | | |
|  | 51 | A: 100% | | | |
|  | 52 | S: 100% | | | |
|  | 53 | H: 5% | N: 25% | S: 45% | T: 25% |
|  | 54 | L: 100% | | | |
|  | 55 | Q: 100% | | | |
|  | 56 | S: 100% | | | |
| CDR3 | 90 | Q: 100% | | | |
|  | 91 | H: 25% | S: 15% | R: 15% | Y: 45% |
|  | 92 | D: 80% | N: 10% | S: 10% | |
|  | 93 | D: 5% | G: 10% | N: 25% | S: 50% | R: 10% |
|  | 94 | S: 50% | Y: 50% | | |
|  | 95 | P: 100% | | | |
|  | 96 | L: 50% | Y: 50% | | |

(Position indicates Kabat numbering.)

TABLE 2

| CDR | Kabat NUMBERING | 30% OF AMINO ACID OF THE TOTAL | | |
|---|---|---|---|---|
| CDR1 | 28 | S: 100% | | |
|  | 29 | I: 100% | | |
|  | 30 | E: 83% | S: 17% | |
|  | 31 | D: 100% | | |
|  | 32 | D: 100% | | |
|  | 33 | L: 100% | | |
|  | 34 | A: 70% | N: 30% | |
| CDR2 | 50 | H: 100% | | |
|  | 51 | A: 100% | | |
|  | 52 | S: 100% | | |
|  | 53 | H: 5% | N: 25% | S: 45% | T: 25% |
|  | 54 | L: 100% | | |
|  | 55 | Q: 100% | | |
|  | 56 | S: 100% | | |

TABLE 2-continued

| CDR | Kabat NUMBERING | 30% OF AMINO ACID OF THE TOTAL | | | |
|---|---|---|---|---|---|
| CDR3 | 90 | Q: 100% | | | |
| | 91 | H: 25% | S: 15% | R: 15% | Y: 45% |
| | 92 | D: 80% | N: 10% | S: 10% | |
| | 93 | D: 5% | G: 10% | N: 25% | S: 50% | R: 10% |
| | 94 | S: 50% | Y: 50% | | |
| | 95 | P: 100% | | | |
| | 96 | L: 50% | Y: 50% | | |

(Position indicates Kabat numbering.)

Herein, flexible residues refer to amino acid residue variations present at hypervariable positions at which several different amino acids are present on the light chain and heavy chain variable regions when the amino acid sequences of known and/or native antibodies or antigen-binding domains are compared. Hypervariable positions are generally located in the CDR. In an embodiment, the data provided by Kabat, Sequences of Proteins of Immunological Interest (National Institute of Health Bethesda Md.) (1987 and 1991) is useful to determine hypervariable positions in known and/or native antibodies. Furthermore, several databases on the Internet (http://vbase.mrc-cpe.cam.ac.uk/, http://www.bioinf.org.uk/abs/index.html) provide the collected sequences of many human light chains and heavy chains and their locations. The information on the sequences and locations is useful to determine hypervariable positions in the present invention. According to the present invention, when a certain amino acid position has preferably about 2 to about 20 possible amino acid residue variations, preferably about 3 to about 19, preferably about 4 to about 18, preferably 5 to 17, preferably 6 to 16, preferably 7 to 15, preferably 8 to 14, preferably 9 to 13, and preferably 10 to 12 possible different amino acid residue variations, the position is hypervariable. In some embodiments, a certain amino acid position may have preferably at least about 2, preferably at least about 4, preferably at least about 6, preferably at least about 8, preferably about 10, and preferably about 12 possible different amino acid residue variations.

Alternatively, a library containing a plurality of antigen-binding molecules of the present invention whose sequences are different from one another can be constructed by combining heavy chain variable regions produced as a randomized variable region sequence library with light chain variable regions into which at least one amino acid residue that alters the antigen-binding activity of antigen-binding molecules depending on ion concentration conditions as mentioned above is introduced. When the ion concentration is calcium ion concentration, non-limiting examples of such libraries preferably include, for example, libraries in which heavy chain variable regions produced as a randomized variable region sequence library are combined with light chain variable region sequences in which a particular residue(s) in a germ line sequence such as SEQ ID NO: 46 (Vk1), SEQ ID NO: 47 (Vk2), SEQ ID NO: 48 (Vk3), or SEQ ID NO: 49 (Vk4) has been substituted with at least one amino acid residue that alters the antigen-binding activity of an antigen-binding molecule depending on calcium ion concentration conditions. Non-limiting examples of such amino acid residues include amino acid residues in light chain CDR1. Furthermore, non-limiting examples of such amino acid residues include amino acid residues in light chain CDR2. In addition, non-limiting, other examples of such amino acid residues also include amino acid residues in light chain CDR3.

Non-limiting examples of such amino acid residues contained in light chain CDR1 include those at positions 30, 31, and/or 32 in the CDR1 of light chain variable region as indicated by EU numbering. Furthermore, non-limiting examples of such amino acid residues contained in light chain CDR2 include an amino acid residue at position 50 in the CDR2 of light chain variable region as indicated by Kabat numbering. Moreover, non-limiting examples of such amino acid residues contained in light chain CDR3 include an amino acid residue at position 92 in the CDR3 of light chain variable region as indicated by Kabat numbering. These amino acid residues can be contained alone or in combination as long as they form a calcium-binding motif and/or as long as the antigen-binding activity of an antigen-binding molecule varies depending on calcium ion concentration conditions. Meanwhile, as troponin C, calmodulin, parvalbumin, and myosin light chain, which have several calcium ion-binding sites and are believed to be derived from a common origin in terms of molecular evolution, are known, the light chain CDR1, CDR2, and/or CDR3 can be designed to have their binding motifs. For example, it is possible to use cadherin domains, EF hand of calmodulin, C2 domain of Protein kinase C, Gla domain of blood coagulation protein FactorIX, C type lectins of acyaroglycoprotein receptor and mannose-binding receptor, A domains of LDL receptors, annexin, thrombospondin type 3 domain, and EGF-like domains in an appropriate manner for the above purposes.

When heavy chain variable regions produced as a randomized variable region sequence library and light chain variable regions into which at least one amino acid residue that alters the antigen-binding activity of an antigen-binding molecule depending on ion concentrations has been introduced are combined as described above, the sequences of the light chain variable regions can be designed to contain flexible residues in the same manner as described above. The number and position of such flexible residues are not limited to particular embodiments as long as the antigen-binding activity of antigen-binding molecules of the present invention varies depending on ion concentration conditions. Specifically, the CDR sequences and/or FR sequences of heavy chain and/or light chain can contain one or more flexible residues. For example, when the ion concentration is calcium ion concentration, non-limiting examples of flexible residues to be introduced into the sequence of light chain variable region include the amino acid residues listed in Tables 1 and 2.

The preferred heavy chain variable regions to be combined include, for example, randomized variable region libraries. Known methods are combined as appropriate to produce a randomized variable region library. In a non-limiting embodiment of the present invention, an immune library constructed based on antibody genes derived from lymphocytes of animals immunized with a specific antigen, patients with infections, persons with an elevated antibody titer in blood as a result of vaccination, cancer patients, or auto immune disease patients, may be preferably used as a randomized variable region library.

In another non-limiting embodiment of the present invention, a synthetic library produced by replacing the CDR sequences of V genes in genomic DNA or functional reshaped V genes with a set of synthetic oligonucleotides containing sequences encoding codon sets of an appropriate length can also be preferably used as a randomized variable region library. In this case, since sequence diversity is observed in the heavy chain CDR3 sequence, it is also possible to replace the CDR3 sequence only. A criterion of giving rise to diversity in amino acids in the variable region of an antigen-binding molecule is that diversity is given to amino acid residues at surface-exposed positions in the antigen-binding molecule. The surface-exposed position refers to a position that is considered to be able to be exposed on the surface and/or contacted with an antigen, based on structure, ensemble of structures, and/or modeled structure of an antigen-binding molecule. In general, such positions are CDRs. Preferably, surface-exposed positions are determined using coordinates from a three-dimensional model of an antigen-binding molecule using a computer program such as the InsightII program (Accelrys). Surface-exposed positions can be determined using algorithms known in the art (for example, Lee and Richards (J. Mol. Biol. (1971) 55, 379-400); Connolly (J. Appl. Cryst. (1983) 16, 548-558)). Determination of surface-exposed positions can be performed using software suitable for protein modeling and three-dimensional structural information obtained from an antibody. Software that can be used for these purposes preferably includes SYBYL Biopolymer Module software (Tripos Associates). Generally or preferably, when an algorithm requires a user input size parameter, the "size" of a probe which is used in the calculation is set at about 1.4 Angstrom or smaller in radius. Furthermore, methods for determining surface-exposed regions and areas using software for personal computers are described by Pacios (Comput. Chem. (1994) 18 (4), 377-386; J. Mol. Model. (1995) 1, 46-53).

In another non-limiting embodiment of the present invention, a naive library, which is constructed from antibody genes derived from lymphocytes of healthy persons and whose repertoire comprises naive sequences, which are antibody sequences with no bias, can also be particularly preferably used as a randomized variable region library (Gejima et al. (Human Antibodies (2002) 11, 121-129); Cardoso et al. (Scand. J. Immunol. (2000) 51, 337-344)). Herein, an amino acid sequence comprising a naive sequence refers to an amino acid sequence obtained from such a naive library.

In one embodiment of the present invention, an antigen-binding domain of the present invention can be obtained from a library containing a plurality of antigen-binding molecules of the present invention whose sequences are different from one another, prepared by combining light chain variable regions constructed as a randomized variable region sequence library with a heavy chain variable region selected as a framework sequence that originally contains "at least one amino acid residue that alters the antigen-binding activity of an antigen-binding molecule depending on ion concentration conditions". When the ion concentration is calcium ion concentration, non-limiting examples of such libraries preferably include those constructed by combining light chain variable regions constructed as a randomized variable region sequence library with the sequence of heavy chain variable region of SEQ ID NO: 50 (6RL #9-IgG1) or SEQ ID NO: 51 (6KC4-1 #85-IgG1). Alternatively, such a library can be constructed by selecting appropriate light chain variable regions from those having germ line sequences, instead of light chain variable regions constructed as a randomized variable region sequence library. Such preferred libraries include, for example, those in which the sequence of heavy chain variable region of SEQ ID NO: 50 (6RL #9-IgG1) or SEQ ID NO: 51 (6KC4-1 #85-IgG1) is combined with light chain variable regions having germ line sequences.

Alternatively, the sequence of a heavy chain variable region selected as a framework sequence that originally contains "at least one amino acid residue that alters the antigen-binding activity of an antigen-binding molecule depending on ion concentration condition" as mentioned above can be designed to contain flexible residues. The number and position of the flexible residues are not particularly limited as long as the antigen-binding activity of an antigen-binding molecule of the present invention varies depending on ion concentration conditions. Specifically, the CDR and/or FR sequences of heavy chain and/or light chain can contain one or more flexible residues. When the ion concentration is calcium ion concentration, non-limiting examples of flexible residues to be introduced into the sequence of heavy chain variable region of SEQ ID NO: 50 (6RL #9-IgG1) include all amino acid residues of heavy chain CDR1 and CDR2 and the amino acid residues of the heavy chain CDR3 except those at positions 95, 96, and/or 100a. Alternatively, non-limiting examples of flexible residues to be introduced into the sequence of heavy chain variable region of SEQ ID NO: 51 (6KC4-1 #85-IgG1) include all amino acid residues of heavy chain CDR1 and CDR2 and the amino acid residues of the heavy chain CDR3 except those at amino acid positions 95 and/or 101.

Alternatively, a library containing a plurality of antigen-binding molecules whose sequences are different from one another can be constructed by combining light chain variable regions constructed as a randomized variable region sequence library or light chain variable regions having germ line sequences with heavy chain variable regions into which "at least one amino acid residue that alters the antigen-binding activity of an antigen-binding molecule depending on ion concentration condition" has been introduced as mentioned above. When the ion concentration is calcium ion concentration, non-limiting examples of such libraries preferably include those in which light chain variable regions constructed as a randomized variable region sequence library or light chain variable regions having germ line sequences are combined with the sequence of a heavy chain variable region in which a particular residue(s) has been substituted with at least one amino acid residue that alters the antigen-binding activity of an antigen-binding molecule depending on calcium ion concentration conditions. Non-limiting examples of such amino acid residues include amino acid residues of the heavy chain CDR1. Further non-limiting examples of such amino acid residues include amino acid residues of the heavy chain CDR2. In addition, non-limiting examples of such amino acid residues also include amino acid residues of the heavy chain CDR3. Non-limiting examples of such amino acid residues of heavy chain CDR3 include the amino acids of positions 95, 96, 100a, and/or 101 in the CDR3 of heavy chain variable region as indicated by the Kabat numbering. Furthermore, these amino acid residues can be contained alone or in combination as long as they form a calcium-binding motif and/or the antigen-binding activity of an antigen-binding molecule varies depending on calcium ion concentration conditions.

When light chain variable regions constructed as a randomized variable region sequence library or light chain variable regions having germ line sequence are combined with a heavy chain variable region into which at least one amino acid residue that alter the antigen-binding activity of an antigen-binding molecule depending on ion concentration conditions as mentioned above has been introduced, the sequence of the heavy chain variable region can also be designed to contain flexible residues in the same manner as described above. The number and position of flexible residues are not particularly limited as long as the antigen-binding activity of an antigen-binding molecule of the present invention varies depending on ion concentration conditions. Specifically, the heavy chain CDR and/or FR sequences may contain one or more flexible residues. Furthermore, randomized variable region libraries can be preferably used as amino acid sequences of CDR1, CDR2, and/or CDR3 of the heavy chain variable region other than the amino acid residues that alter the antigen-binding activity of an antigen-binding molecule. When germ line sequences are used as light chain variable regions, non-limiting examples of such sequences include those of SEQ ID NO: 46 (Vk1), SEQ ID NO: 47 (Vk2), SEQ ID NO: 48 (Vk3), and SEQ ID NO: 49 (Vk4).

Any of the above-described amino acids that alter the antigen-binding activity of an antigen-binding molecule depending on calcium ion concentration conditions can be preferably used, as long as they form a calcium-binding motif. Specifically, such amino acids include electron-donating amino acids. Preferred examples of such electron-donating amino acids include serine, threonine, asparagine, glutamic acid, aspartic acid, and glutamic acid.

An example of the "ion concentration condition" of the present invention includes a "pH condition". A pH condition may also be referred to as a hydrogen ion concentration condition. In the present invention, the condition of concentration of proton, i.e., the nucleus of hydrogen atom, is treated as synonymous with a hydrogen index (pH) condition. When the activity of hydrogen ion in an aqueous solution is represented as aH+, pH is defined as $-\log 10aH+$. When the ionic strength of the aqueous solution is low (for example, lower than $10^{-3}$), aH+ is nearly equal to the hydrogen ion strength. For example, the ionic product of water at 25° C. and 1 atmosphere is $Kw=aH+aOH=10^{-14}$, and therefore in pure water, $aH+=aOH=10^{-7}$. In this case, pH=7 is neutral; an aqueous solution whose pH is lower than 7 is acidic or whose pH is greater than 7 is alkaline.

In the present invention, when pH condition is used as the ion concentration condition, pH conditions include conditions of high hydrogen ion concentration or low pHs, i.e., an acidic pH range condition, and conditions of low hydrogen ion concentration or high pHs, i.e., a neutral pH range condition. "The antigen-binding activity of an antigen-binding domain contained in the antigen-binding molecule of the present invention varies depending on pH condition" means that the antigen-binding activity of an antigen-binding domain contained in an antigen-binding molecule varies due to the difference in conditions of a high hydrogen ion concentration or low pH (an acidic pH range) and a low hydrogen ion concentration or high pH (a neutral pH range). This includes, for example, the case where the antigen-binding activity of an antigen-binding molecule is higher under a neutral pH range condition than under an acidic pH range condition and the case where the antigen-binding activity of an antigen-binding molecule is higher under an acidic pH range condition than under a neutral pH range condition.

Herein, neutral pH range is not limited to a specific value and is preferably selected from between pH 6.7 and pH 10.0. In another embodiment, the pH can be selected from between pH 6.7 and pH 9.5. In still another embodiment, the pH can be selected from between pH 7.0 and pH 9.0. In yet another embodiment, the pH can be selected from between pH 7.0 and pH 8.0. In particular, the preferred pH includes pH 7.4, which is close to the pH of plasma (blood) in vivo.

Herein, an acidic pH range is not limited to a specific value and is preferably selected from between pH 4.0 and pH 6.5. In another embodiment, the pH can be selected from between pH 4.5 and pH 6.5. In still another embodiment, the pH can be selected from between pH 5.0 and pH 6.5. In yet another embodiment, the pH can be selected from between pH 5.5 and pH 6.5. In particular, the preferred pH includes pH 5.8, which is close to the ionized calcium concentration in the early endosome in vivo.

In the present invention, "the antigen-binding activity under a condition of a high hydrogen ion concentration or low pH (an acidic pH range) is lower than that under a condition of a low hydrogen ion concentration or high pH (a neutral pH range)" means that the antigen-binding activity of antigen-binding domain or antigen-binding molecule comprising the domain of the present invention at a pH selected from between pH 4.0 and pH 6.5 is weaker than that at a pH selected from between pH 6.7 and pH 10.0; preferably means that the antigen-binding activity of an antigen-binding domain or antigen-binding molecule comprising the domain at a pH selected from between pH 4.5 and pH 6.5 is weaker than that at a pH selected from between pH 6.7 and pH 9.5; more preferably, means that the antigen-binding activity of an antigen-binding molecule at a pH selected from between pH 5.0 and pH 6.5 is weaker than that at a pH selected from between pH 7.0 and pH 9.0; still more preferably means that the antigen-binding activity of an antigen-binding molecule at a pH selected from between pH 5.5 and pH 6.5 is weaker than that at a pH selected from between pH 7.0 and pH 8.0; particularly preferably means that the antigen-binding activity at the pH in the early endosome in vivo is weaker than the antigen-binding activity at the pH of plasma in vivo; and specifically means that the antigen-binding activity of an antigen-binding molecule at pH 5.8 is weaker than the antigen-binding activity at pH 7.4.

Whether the antigen-binding activity of an antigen-binding domain or antigen-binding molecule comprising the domain has changed by the pH condition can be determined, for example, by the use of known measurement methods such as those described in the section "Binding Activity" above. For example, the binding activity is measured under different pH conditions using the measurement methods described above. For example, the antigen-binding activity of an antigen-binding domain or antigen-binding molecule comprising the domain is compared under the conditions of acidic pH range and neutral pH range to confirm that binding activity of the domain or the molecule changes to be higher under the condition of neutral pH range than that under the condition of acidic pH range.

Furthermore, in the present invention, the expression "the antigen-binding activity under a condition of high hydrogen ion concentration or low pH, i.e., under an acidic pH range condition, is lower than that under a condition of low hydrogen ion concentration or high pH, i.e., under a neutral pH range condition" can also be expressed as "the antigen-binding activity of an antigen-binding domain or antigen-binding molecule comprising the domain under a condition of low hydrogen ion concentration or high pH, i.e., under a neutral pH range condition, is higher than that under a condition of high hydrogen ion concentration or low pH, i.e., under an acidic pH range condition". In the present invention, "the antigen-binding activity under a condition of high hydrogen ion concentration or low pH, i.e., under an acidic pH range condition, is lower than that under a condition of low hydrogen ion concentration or high pH, i.e., under a neutral pH range condition" may be described as "the antigen-binding activity under a condition of high hydrogen ion concentration or low pH, i.e., under an acidic pH range condition, is weaker than the antigen-binding ability under a condition of low hydrogen ion concentration or high pH, i.e., under a neutral pH range condition". Alternatively, "the antigen-binding activity under a condition of high hydrogen ion concentration or low pH, i.e., under an acidic pH range condition, is reduced to be lower than that under a condition of low hydrogen ion concentration or high pH, i.e., under a neutral pH range condition" may be described as "the antigen-binding activity under a condition of high hydrogen ion concentration or low pH, i.e., under an acidic pH range condition, is reduced to be weaker than the antigen-binding ability under a condition of low hydrogen ion concentration or high pH, i.e., under a neutral pH range condition".

The conditions other than hydrogen ion concentration or pH for measuring the antigen-binding activity may be suitably selected by those skilled in the art and are not particularly limited. Measurements can be carried out, for example, at 37° C. using HEPES buffer. Measurements can be carried out, for example, using Biacore (GE Healthcare). When the antigen is a soluble antigen, the antigen-binding activity of antigen-binding domain or antigen-binding molecule comprising the domain can be determined by assessing the binding activity to the soluble antigen by flowing the antigen as an analyte into a chip immobilized with the antigen-binding domain or the antigen-binding molecule comprising the domain. When the antigen is a membrane antigen, the binding activity to the membrane antigen can be assessed by flowing the antigen-binding domain or the antigen-binding molecule comprising the domain as an analyte into a chip immobilized with the antigen.

As long as the antigen-binding activity of an antigen-binding molecule of the present invention at a condition of high hydrogen ion concentration or low pH, i.e., in an acidic pH range condition is weaker than that at a condition of low hydrogen ion concentration or high pH, i.e., in a neutral pH range condition, the ratio of the antigen-binding activity between that under a condition of high hydrogen ion concentration or low pH, i.e., under an acidic pH range condition, and under a condition of low hydrogen ion concentration or high pH, i.e., under a neutral pH range condition is not particularly limited, and the value of KD (pH 5.8)/KD (pH 7.4), which is the ratio of the dissociation constant (KD) for an antigen at a condition of high hydrogen ion concentration or low pH, i.e., in an acidic pH range condition to the KD at a condition of low hydrogen ion concentration or high pH, i.e., in a neutral pH range condition, is preferably 2 or more; more preferably the value of KD (pH 5.8)/KD (pH 7.4) is 10 or more; and still more preferably the value of KD (pH 5.8)/KD (pH 7.4) is 40 or more. The upper limit of KD (pH 5.8)/KD (pH 7.4) value is not particularly limited, and may be any value such as 400, 1000, or 10000, as long as the molecule can be produced by the techniques of those skilled in the art.

Alternatively, for example, the dissociation rate constant (kd) can be suitably used as an index for indicating the ratio of the antigen-binding activity of an antigen-binding domain or antigen-binding molecule comprising the domain of the present invention between that at a condition of high hydrogen ion concentration or low pH, i.e., in an acidic pH range condition and at a condition of low hydrogen ion concentration or high pH, i.e., in a neutral pH range condition. When kd (dissociation rate constant) is used as an index for indicating the binding activity ratio instead of KD (dissociation constant), the value of kd (in an acidic pH range condition)/kd (in a neutral pH range condition), which is the ratio of kd (dissociation rate constant) for the antigen at a condition of high hydrogen ion concentration or low pH, i.e., in an acidic pH range condition to kd (dissociation rate constant) at a condition of low hydrogen ion concentration or high pH, i.e., in a neutral pH range condition, is preferably 2 or more, more preferably 5 or more, still more preferably 10 or more, and yet more preferably 30 or more. The upper limit of kd (in an acidic pH range condition)/kd (in a neutral pH range condition) value is not particularly limited, and may be any value such as 50, 100, or 200, as long as the molecule can be produced by the techniques of those skilled in the art.

When the antigen is a soluble antigen, the dissociation rate constant (kd) can be used as the value for antigen-binding activity and when the antigen is a membrane antigen, the apparent dissociation rate constant (kd) can be used. The dissociation rate constant (kd) and apparent dissociation rate constant (kd) can be determined by methods known to those skilled in the art, and Biacore (GE healthcare), flow cytometer, and such may be used. In the present invention, when the antigen-binding activity of an antigen-binding domain or antigen-binding molecule comprising the domain is measured at different hydrogen ion concentrations, i.e., pHs, conditions other than the hydrogen ion concentration, i.e., pH, are preferably the same.

For example, an antigen-binding domain or antigen-binding molecule whose antigen-binding activity at a condition of high hydrogen ion concentration or low pH, i.e., in an acidic pH range condition is lower than that at a condition of low hydrogen ion concentration or high pH, i.e., in a neutral pH range condition, which is one embodiment provided by the present invention, can be obtained via screening of antigen-binding domains or antigen-binding molecules, comprising the following steps (a) to (c):

(a) obtaining the antigen-binding activity of an antigen-binding domain or antigen-binding molecule in an acidic pH range condition;

(b) obtaining the antigen-binding activity of an antigen-binding domain or antigen-binding molecule in a neutral pH range condition; and (c) selecting an antigen-binding domain or antigen-binding molecule whose antigen-binding activity in the acidic pH range condition is lower than that in the neutral pH range condition.

Alternatively, an antigen-binding domain or antigen-binding molecule whose antigen-binding activity at a condition of high hydrogen ion concentration or low pH, i.e., in an acidic pH range condition, is lower than that at a condition of low hydrogen ion concentration or high pH, i.e., in a neutral pH range condition, which is one embodiment provided by the present invention, can be obtained via screening of antigen-binding domains or antigen-binding molecules, or a library thereof, comprising the following steps (a) to (c):

(a) contacting an antigen-binding domain or antigen-binding molecule, or a library thereof, in a neutral pH range condition with an antigen;

(b) placing in an acidic pH range condition the antigen-binding domain or antigen-binding molecule bound to the antigen in step (a); and (c) isolating the antigen-binding domain or antigen-binding molecule dissociated in step (b).

An antigen-binding domain or antigen-binding molecule whose antigen-binding activity at a condition of high hydrogen ion concentration or low pH, i.e., in an acidic pH range condition is lower than that at a condition of low hydrogen ion concentration or high pH, i.e., in a neutral pH range condition, which is another embodiment provided by the present invention, can be obtained via screening of antigen-binding domains or antigen-binding molecules, or a library thereof, comprising the following steps (a) to (d):
(a) contacting in an acidic pH range condition an antigen with a library of antigen-binding domains or antigen-binding molecules;
(b) selecting the antigen-binding domain or antigen-binding molecule which does not bind to the antigen in step (a);
(c) allowing the antigen-binding domain or antigen-binding molecule selected in step (b) to bind with the antigen in a neutral pH range condition; and
(d) isolating the antigen-binding domain or antigen-binding molecule bound to the antigen in step (c).

An antigen-binding domain or antigen-binding molecule whose antigen-binding activity at a condition of high hydrogen ion concentration or low pH, i.e., in an acidic pH range condition, is lower than that at a condition of low hydrogen ion concentration or high pH, i.e., in a neutral pH range condition, which is even another embodiment provided by the present invention, can be obtained by a screening method comprising the following steps (a) to (c):
(a) contacting in a neutral pH range condition a library of antigen-binding domains or antigen-binding molecules with a column immobilized with an antigen;
(b) eluting in an acidic pH range condition from the column the antigen-binding domain or antigen-binding molecule bound to the column in step (a); and
(c) isolating the antigen-binding domain or antigen-binding molecule eluted in step (b).

An antigen-binding domain or antigen-binding molecule whose antigen-binding activity at a condition of high hydrogen ion concentration or low pH, i.e., in an acidic pH range condition, is lower than that at a condition of low hydrogen ion concentration or high pH, i.e., in a neutral pH range condition, which is still another embodiment provided by the present invention, can be obtained by a screening method comprising the following steps (a) to (d):
(a) allowing, in an acidic pH range condition, a library of antigen-binding domains or antigen-binding molecules to pass a column immobilized with an antigen;
(b) collecting the antigen-binding domain or antigen-binding molecule eluted without binding to the column in step (a);
(c) allowing the antigen-binding domain or antigen-binding molecule collected in step (b) to bind with the antigen in a neutral pH range condition; and
(d) isolating the antigen-binding domain or antigen-binding molecule bound to the antigen in step (c).

An antigen-binding domain or antigen-binding molecule whose antigen-binding activity at a high hydrogen ion concentration or low pH, i.e., in an acidic pH range condition, is lower than that at a low hydrogen ion concentration or high pH, i.e., in a neutral pH range condition, which is yet another embodiment provided by the present invention, can be obtained by a screening method comprising the following steps (a) to (d):
(a) contacting an antigen with a library of antigen-binding domains or antigen-binding molecules in a neutral pH range condition;
(b) obtaining the antigen-binding domain or antigen-binding molecule bound to the antigen in step (a);
(c) placing in an acidic pH range condition the antigen-binding domain or antigen-binding molecule obtained in step (b); and
(d) isolating the antigen-binding domain or antigen-binding molecule whose antigen-binding activity in step (c) is weaker than the standard selected in step (b).

The above-described steps may be repeated twice or more times. Thus, the present invention provides antigen-binding domains and antigen-binding molecules whose antigen-binding activity in an acidic pH range condition is lower than that in a neutral pH range condition, which are obtained by a screening method that further comprises the steps of repeating steps (a) to (c) or (a) to (d) in the above-described screening methods. The number of times that steps (a) to (c) or (a) to (d) is repeated is not particularly limited; however, the number is 10 or less in general.

In the screening methods of the present invention, the antigen-binding activity of an antigen-binding domain or antigen-binding molecule at a condition of a high hydrogen ion concentration or low pH, i.e., in an acidic pH range, is not particularly limited, as long as it is the antigen-binding activity at a pH of between 4.0 and 6.5, and includes the antigen-binding activity at a pH of between 4.5 and 6.6 as the preferred pH. The antigen-binding activity also includes that at a pH of between 5.0 and 6.5, and that at a pH of between 5.5 and 6.5 as another preferred pH. The antigen-binding activity also includes that at the pH in the early endosome in vivo as the more preferred pH, and specifically, that at pH 5.8. Meanwhile, the antigen-binding activity of an antigen-binding domain or antigen-binding molecule at a condition of a low hydrogen ion concentration or high pH, i.e., in a neutral pH range, is not particularly limited, as long as it is the antigen-binding activity at a pH of between 6.7 and 10, and includes the antigen-binding activity at a pH of between 6.7 and 9.5 as the preferred pH. The antigen-binding activity also includes that at a pH of between 7.0 and 9.5 and that at a pH of between 7.0 and 8.0 as another preferred pH. The antigen-binding activity also includes that at the pH of plasma in vivo as the more preferred pH, and specifically, that at pH 7.4.

The antigen-binding activity of an antigen-binding domain or antigen-binding molecule can be measured by methods known to those skilled in the art. Those skilled in the art can suitably determine conditions other than ionized calcium concentration. The antigen-binding activity of an antigen-binding domain or antigen-binding molecule can be assessed based on the dissociation constant (KD), apparent dissociation constant (KD), dissociation rate constant (kd), apparent dissociation rate constant (kd), and such. These can be determined by methods known to those skilled in the art, for example, using Biacore (GE healthcare), Scatchard plot, or FACS.

In the present invention, the step of selecting an antigen-binding domain or antigen-binding molecule whose antigen-binding activity at a condition of low hydrogen ion concentration or high pH, i.e., in a neutral pH range condition, is higher than that at a condition of high hydrogen ion concentration or low pH, i.e., in an acidic pH range condition, is synonymous with the step of selecting an antigen-binding domain or antigen-binding molecule whose antigen-binding activity at a condition of high hydrogen ion concentration or low pH, i.e., in an acidic pH range condition, is lower than that at a condition of low hydrogen ion concentration or high pH, i.e., in a neutral pH range condition.

As long as the antigen-binding activity at a condition of low hydrogen ion concentration or high pH, i.e., in a neutral pH range condition, is higher than that at a condition of high hydrogen ion concentration or low pH, i.e., in an acidic pH range condition, the difference between the antigen-binding activity at a condition of low hydrogen ion concentration or high pH, i.e., in a neutral pH range condition, and that at a condition of high hydrogen ion concentration or low pH, i.e., in an acidic pH range condition, is not particularly limited; however, the antigen-binding activity at a condition of low hydrogen ion concentration or high pH, i.e., in a neutral pH range condition, is preferably twice or more, more preferably 10 times or more, and still more preferably 40 times or more than that at a condition of high hydrogen ion concentration or low pH, i.e., in an acidic pH range condition.

The antigen-binding domain or antigen-binding molecule whose antigen-binding activity varies depending on hydrogen ion concentration conditions of the present invention to be screened by the above-described screening methods may be prepared in any manner. For example, conventional antigen-binding molecules, conventional libraries (phage library, etc.), antibodies or libraries prepared from B cells of immunized animals or from hybridomas obtained by immunizing animals, antibodies or libraries (libraries with increased content of amino acids with a side chain pKa of 4.0-8.0 (for example, histidine and glutamic acid) or unnatural amino acids, libraries introduced with amino acids with a side chain pKa of 4.0-8.0 (for example, histidine and glutamic acid) or unnatural amino acid mutations at specific positions, etc.) obtained by introducing amino acids with a side chain pKa of 4.0-8.0 (for example, histidine and glutamic acid) or unnatural amino acid mutations into the above-described antibodies or libraries may be used.

Methods for obtaining an antigen-binding domain or antigen-binding molecule whose antigen-binding activity at a low hydrogen ion concentration or high pH, i.e., in a neutral pH range condition, is higher than that at a high hydrogen ion concentration or low pH, i.e., in an acidic pH range condition, from an antigen-binding domains or antigen-binding molecules prepared from hybridomas obtained by immunizing animals or from B cells of immunized animals preferably include, for example, the antigen-binding molecule or antigen-binding molecule in which at least one of the amino acids of the antigen-binding domain or antigen-binding molecule is substituted with an amino acid with a side chain pKa of 4.0-8.0 (for example, histidine and glutamic acid) or an unnatural amino acid mutation, or the antigen-binding domain or antigen-binding molecule inserted with an amino acid with a side chain pKa of 4.0-8.0 (for example, histidine and glutamic acid) or unnatural amino acid, such as those described in WO 2009/125825.

The sites of introducing mutations of amino acids with a side chain pKa of 4.0-8.0 (for example, histidine and glutamic acid) or unnatural amino acids are not particularly limited, and may be any position as long as the antigen-binding activity in an acidic pH range becomes weaker than that in a neutral pH range (the value of KD (in an acidic pH range)/KD (in a neutral pH range) or kd (in an acidic pH range)/kd (in a neutral pH range) is increased) as compared to before substitution or insertion. For example, when the antigen-binding molecule is an antibody, antibody variable region and CDRs are suitable. Those skilled in the art can appropriately determine the number of amino acids to be substituted with or the number of amino acids with a side chain pKa of 4.0-8.0 (for example, histidine and glutamic acid) or unnatural amino acids to be inserted. It is possible to substitute with a single amino acid having a side chain pKa of 4.0-8.0 (for example, histidine and glutamic acid) or a single unnatural amino acid; it is possible to insert a single amino acid having a side chain pKa of 4.0-8.0 (for example, histidine and glutamic acid) or a single unnatural amino acid; it is possible to substitute with two or more amino acids having a side chain pKa of 4.0-8.0 (for example, histidine and glutamic acid) or two or more unnatural amino acids; and it is possible to insert two or more amino acids having a side chain pKa of 4.0-8.0 (for example, histidine and glutamic acid) or two or more unnatural amino acids. Alternatively, other amino acids can be deleted, added, inserted, and/or substituted concomitantly, aside from the substitution into amino acids having a side chain pKa of 4.0-8.0 (for example, histidine and glutamic acid) or unnatural amino acids, or the insertion of amino acids having a side chain pKa of 4.0-8.0 (for example, histidine and glutamic acid) or unnatural amino acids. Substitution into or insertion of amino acids with a side chain pKa of 4.0-8.0 (for example, histidine and glutamic acid) or unnatural amino acids can performed randomly by methods such as histidine scanning, in which the alanine of alanine scanning known to those skilled in the art is replaced with histidine. Antigen-binding molecules exhibiting a greater value of KD (in an acidic pH range)/KD (in a neutral pH range) or kd (in an acidic pH range)/kd (in a neutral pH range) as compared to before the mutation can be selected from antigen-binding domains or antibodies introduced with random insertions or substitution mutations of amino acids with a side chain pKa of 4.0-8.0 (for example, histidine and glutamic acid) or unnatural amino acids.

Preferred examples of antigen-binding molecules containing the mutation into amino acids with a side chain pKa of 4.0-8.0 (for example, histidine and glutamic acid) or unnatural amino acids as described above and whose antigen-binding activity in an acidic pH range is lower than that in a neutral pH range include, antigen-binding molecules whose antigen-binding activity in the neutral pH range after the mutation into amino acids with a side chain pKa of 4.0-8.0 (for example, histidine and glutamic acid) or unnatural amino acids is comparable to that before the mutation into amino acids with a side chain pKa of 4.0-8.0 (for example, histidine and glutamic acid) or unnatural amino acids. Herein, "an antigen-binding molecule after the mutation with amino acids having a side chain pKa of 4.0-8.0 (for example, histidine and glutamic acid) or unnatural amino acids has an antigen-binding activity comparable to that before the mutation with amino acids having a side chain pKa of 4.0-8.0 (for example, histidine and glutamic acid) or unnatural amino acids" means that, when taking the antigen-binding activity of an antigen-binding molecule before the mutation with amino acids having a side chain pKa of 4.0-8.0 (for example, histidine and glutamic acid) or unnatural amino acids as 100%, the antigen-binding activity of an antigen-binding molecule after the mutation with amino acids having a side chain pKa of 4.0-8.0 (for example, histidine and glutamic acid) or unnatural amino acids is at least 10% or more, preferably 50% or more, more preferably 80% or more, and still more preferably 90% or more. The antigen-binding activity after the mutation of amino acids with a side chain pKa of 4.0-8.0 (for example, histidine and glutamic acid) or unnatural amino acids at pH 7.4 may be higher than that before the mutation of amino acids with a side chain pKa of 4.0-8.0 (for example, histidine and glutamic acid) or unnatural amino acids at pH 7.4. If the antigen-binding activity of an antigen-binding molecule is decreased due to insertion of or substitution into amino acids with a side chain pKa of 4.0-8.0 (for example, histidine and glutamic acid) or unnatural amino acids, the antigen-binding activity can be made to be comparable to that before the insertion of or substitution into amino acids with a side chain pKa of 4.0-8.0 (for example, histidine and glutamic acid) or unnatural amino acids, by introducing a substitution, deletion, addition, and/or insertion of one or more amino acids of the antigen-binding molecule. The present invention also includes antigen-binding molecules whose binding activity has been adjusted to be comparable by substitution, deletion, addition, and/or insertion of one or more amino acids after substitution or insertion of amino acids with a side chain pKa of 4.0-8.0 (for example, histidine and glutamic acid) or unnatural amino acids.

In one embodiment of the present invention, a library containing multiple antigen-binding domains or antigen-binding molecules of the present invention whose sequences are different from one another can also be constructed by combining heavy chain variable regions, produced as a randomized variable region sequence library, with light chain variable regions introduced with "at least one amino acid residue that changes the antigen-binding activity of antigen-binding domain or antigen-binding molecule depending on the hydrogen ion concentration condition".

Such amino acid residues include, but are not limited to, for example, amino acid residues contained in the light chain CDR1. The amino acid residues also include, but are not limited to, for example, amino acid residues contained in the light chain CDR2. The amino acid residues also include, but are not limited to, for example, amino acid residues contained in the light chain CDR3.

The above-described amino acid residues contained in the light chain CDR1 include, but are not limited to, for example, amino acid residue(s) of position(s) 24, 27, 28, 31, 32, and/or 34 according to Kabat numbering in the CDR1 of light chain variable region. Meanwhile, the amino acid residues contained in the light chain CDR2 include, but are not limited to, for example, amino acid residue(s) of position(s) 50, 51, 52, 53, 54, 55, and/or 56 according to Kabat numbering in the CDR2 of light chain variable region. Furthermore, the amino acid residues in the light chain CDR3 include, but are not limited to, for example, amino acid residues of position(s) 89, 90, 91, 92, 93, 94, and/or 95A according to Kabat numbering in the CDR3 of light chain variable region. Moreover, the amino acid residues can be contained alone or can be contained in combination of two or more amino acids as long as they allow the change in the antigen-binding activity of an antigen-binding molecule depending on the hydrogen ion concentration condition.

Even when the heavy chain variable region produced as a randomized variable region sequence library is combined with the above-described light chain variable region introduced with "at least one amino acid residue that changes the antigen-binding activity of an antigen-binding molecule depending on the hydrogen ion concentration condition", it is possible to design so that the flexible residues are contained in the sequence of the light chain variable region in the same manner as described above. The number and position of the flexible residues are not particularly limited to a specific embodiment, as long as the antigen-binding activity of antigen-binding domain or antigen-binding molecule of the present invention changes depending on the hydrogen ion concentration condition. Specifically, the CDR and/or FR sequences of heavy chain and/or light chain can contain one or more flexible residues. For example, flexible residues to be introduced into the sequences of the light chain variable regions include, but are not limited to, for example, the amino acid residues listed in Tables 3 and 4. Meanwhile, amino acid sequences of light chain variable regions other than the flexible residues and amino acid residues that change the antigen-binding activity of an antigen-binding domain or antigen-binding molecule depending on the hydrogen ion concentration condition suitably include, but are not limited to, germ line sequences such as Vk1 (SEQ ID NO: 46), Vk2 (SEQ ID NO: 47), Vk3 (SEQ ID NO: 48), and Vk4 (SEQ ID NO: 49).

TABLE 3

| POSITION | AMINO ACID | | | | | | | |
|---|---|---|---|---|---|---|---|---|
| CDR1 | | | | | | | | |
| 28 | S: 100% | | | | | | | |
| 29 | I: 100% | | | | | | | |
| 30 | N: 25% | S: 25% | R: 25% | H: 25% | | | | |
| 31 | S: 100% | | | | | | | |
| 32 | H: 100% | | | | | | | |
| 33 | L: 100% | | | | | | | |
| 34 | A: 50% | N: 50% | | | | | | |
| CDR2 | | | | | | | | |
| 50 | H: 100% | | | | OR | A: 25% | D: 25% | G: 25% | K: 25% |
| 51 | A: 100% | | | | | A: 100% | | | |
| 52 | S: 100% | | | | | S: 100% | | | |
| 53 | K: 33.3% | N: 33.3% | S: 33.3% | | | H: 100% | | | |
| 54 | L: 100% | | | | | L: 100% | | | |
| 55 | Q: 100% | | | | | Q: 100% | | | |
| 56 | S: 100% | | | | | S: 100% | | | |
| CDR3 | | | | | | | | |
| 90 | Q: 100% | | | | OR | Q: 100% | | | |
| 91 | H: 100% | | | | | S: 33.3% | R: 33.3% | Y: 33.3% | |
| 92 | G: 25% | N: 25% | S: 25% | Y: 25% | | H: 100% | | | |
| 93 | H: 33.3% | N: 33.3% | S: 33.3% | | | H: 33.3% | N: 33.3% | S: 33.3% | |
| 94 | S: 50% | Y: 50% | | | | S: 50% | Y: 50% | | |
| 95 | P: 100% | | | | | P: 100% | | | |
| 96 | L: 50% | Y: 50% | | | | L: 50% | Y: 50% | | |

(Position indicates Kabat numbering)

TABLE 4

| CDR | POSITION | AMINO ACID | |
|---|---|---|---|
| CDR1 | 28 | S: 100% | |
| | 29 | I: 100% | |

TABLE 4-continued

| CDR | POSITION | AMINO ACID | | | |
|---|---|---|---|---|---|
| | 30 | H: 30% | N: 10% | S: 50% | R: 1.0% |
| | 31 | N: 35% | S: 65% | | |
| | 32 | H: 40% | N: 20% | Y: 40% | |
| | 33 | L: 100% | | | |
| | 34 | A: 70% | N: 30% | | |
| CDR2 | 50 | A: 25% | D: 15% | G: 25% | H: 30% K: 5% |
| | 51 | A: 100% | | | |
| | 52 | S: 100% | | | |
| | 53 | H: 30% | K: 10% | N: 15% | S: 45% |
| | 54 | L: 100% | | | |
| | 55 | Q: 100% | | | |
| | 56 | S: 100% | | | |
| CDR3 | 90 | Q: 100% | | | |
| | 91 | H: 30% | S: 15% | R: 10% | Y: 45% |
| | 92 | G: 20% | H: 30% | N: 20% | S: 15% Y: 15% |
| | 93 | H: 30% | N: 25% | S: 45% | |
| | 94 | S: 50% | Y: 50% | | |
| | 95 | P: 100% | | | |
| | 96 | L: 50% | Y: 50% | | |

(Position indicates Kabat numbering)

Any amino acid residue may be suitably used as the above-described amino acid residues that change the antigen-binding activity of an antigen-binding domain or antigen-binding molecule depending on the hydrogen ion concentration conditions. Specifically, such amino acid residues include amino acids with a side chain pKa of 4.0-8.0. Such electron-releasing amino acids preferably include, for example, naturally occurring amino acids such as histidine and glutamic acid, as well as unnatural amino acids such as histidine analogs (US2009/0035836), m-NO2-Tyr (pKa 7.45), 3,5-Br2-Tyr (pKa 7.21), and 3,5-12-Tyr (pKa 7.38) (Bioorg. Med. Chem. (2003) 11 (17), 3761-3768). Particularly preferred amino acid residues include, for example, amino acids with a side chain pKa of 6.0-7.0. Such electron-releasing amino acid residues preferably include, for example, histidine.

The preferred heavy chain variable region that is used in combination includes, for example, randomized variable region libraries. Known methods are appropriately combined as a method for producing a randomized variable region library. In a non-limiting embodiment of the present invention, an immune library constructed based on antibody genes derived from animals immunized with specific antigens, patients with infection or persons with an elevated antibody titer in blood as a result of vaccination, cancer patients, or lymphocytes of autoimmune diseases may be suitably used as a randomized variable region library.

In another non-limiting embodiment of the present invention, in the same manner as described above, a synthetic library in which the CDR sequences of V genes from genomic DNA or functional reconstructed V genes are replaced with a set of synthetic oligonucleotides containing the sequences encoding codon sets of an appropriate length can also be suitably used as a randomized variable region library. In this case, the CDR3 sequence alone may be replaced because variety in the gene sequence of heavy chain CDR3 is observed. The basis for giving rise to amino acid variations in the variable region of an antigen-binding molecule is to generate variations of amino acid residues of surface-exposed positions of the antigen-binding molecule. The surface-exposed position refers to a position where an amino acid is exposed on the surface and/or contacted with an antigen based on the conformation, structural ensemble, and/or modeled structure of an antigen-binding molecule, and in general, such positions are the CDRs. The surface-exposed positions are preferably determined using the coordinates derived from a three-dimensional model of the antigen-binding molecule using computer programs such as InsightII program (Accelrys). The surface-exposed positions can be determined using algorithms known in the art (for example, Lee and Richards (J. Mol. Biol. (1971) 55, 379-400); Connolly (J. Appl. Cryst. (1983) 16, 548-558)). The surface-exposed positions can be determined based on the information on the three dimensional structure of antibodies using software suitable for protein modeling. Software which is suitably used for this purpose includes the SYBYL biopolymer module software (Tripos Associates). When the algorithm requires the input size parameter from the user, the "size" of probe for use in computation is generally or preferably set at about 1.4 angstrom or less in radius. Furthermore, a method for determining surface-exposed region and area using personal computer software is described by Pacios (Comput. Chem. (1994) 18 (4), 377-386; and J. Mol. Model. (1995) 1, 46-53).

In still another non-limiting embodiment of the present invention, a naive library constructed from antibody genes derived from lymphocytes of healthy persons and comprising naive sequences, which are unbiased repertoire of antibody sequences, can also be particularly suitably used as a randomized variable region library (Gejima et al. (Human Antibodies (2002) 11, 121-129); and Cardoso et al. (Scand. J. Immunol. (2000) 51, 337-344)).

Furthermore, amino acid alterations for enhancing the human FcRn-binding activity under an acidic pH-range condition can be combined in addition. More specifically, alterations used to enhance human FcRn-binding activity under an acidic pH range condition may be carried out on an IgG antibody, for example, by a method of substituting Leu for Met at position 428, and substituting Ser for Asn at position 434, according to EU numbering (Nat Biotechnol, 2010 28: 157-159); a method of substituting Ala for Asn at position 434 (Drug Metab Dispos. 2010 April; 38(4): 600-5); a method of substituting Tyr for Met at position 252, substituting Thr for Ser at position 254, and substituting Glu for Thr at position 256 (J Biol Chem, 2006, 281: 23514-23524); a method for substituting Gln for Thr at position 250, and substituting Leu for Met at position 428 (J Immunol. 2006, 176(1): 346-56); method of substituting His for Asn at position 434 (Clinical Pharmacology & Therapeutics (2011) 89(2): 283-290), or by using alterations such as those described in WO2010106180, WO2010045193, WO2009058492, WO2008022152, WO2006050166, WO2006053301, WO2006031370, WO2005123780, WO2005047327, WO2005037867, WO2004035752, WO2002060919, or such.

Furthermore, an antibody molecule produced by substituting His for Asn at position 434 (EU numbering) in humanized anti-CD4 antibody to enhance human FcRn-binding activity under an acidic pH range condition and to improve plasma retention properties was recently reported to bind to rheumatoid factors (RF) (Clin Pharmacol Ther. 2011 February; 89(2): 283-90). This antibody has a human IgG1 Fc region, but by substituting His for Asn at position 434 which is positioned at the FcRn-binding site, it has been shown to bind to rheumatoid factors that recognize this substituted site.

As described above, various alterations have been reported as alterations for enhancing human FcRn-binding activity under an acidic pH range condition; however, by introducing these alterations into the FcRn-binding site in an Fc region, affinity to rheumatoid factors which recognize this site may become enhanced.

However, by introducing alterations which do not reduce FcRn-binding activity and reduce only binding activity to rheumatoid factors into the site in the Fc region, antigen-binding molecules with enhanced human FcRn-binding activity under an acidic pH range condition and without affinity to rheumatoid factors can be produced.

For alterations that reduce binding activity to rheumatoid factors, alterations to positions 248-257, 305-314, 342-352, 380-386, 388, 414-421, 423, 425-437, 439, and 441-444 according to EU numbering are used. Preferably, alterations to positions 387, 422, 424, 426, 433, 436, 438, and 440 are used. Particularly preferably, alteration of substituting Glu or Ser for Val at position 422, alteration of substituting Arg for Ser at position 424, alteration of substituting Asp for His at position 433, alteration of substituting Thr for Tyr at position 436, alteration of substituting Arg or Lys for Gln at position 438, and alteration of substituting Glu or Asp for Ser at position 440 are used. These alterations may be used alone or by combining alterations at multiple positions.

Alternatively, to decrease binding activity to rheumatoid factors, an N-type glycosylation sequence may be introduced into this site. Specifically, Asn-Xxx-Ser/Thr (Xxx is any amino acid other than Pro) is known as an N-type glycosylation sequence. Adding an N-type sugar chain by introducing this sequence into the site in the Fc region enables inhibition of binding to RF by steric hindrance due to the N-type sugar chain. Alterations used to add an N-type sugar chain are preferably alteration which substitutes Asn for Lys at position 248, alteration which substitutes Asn for Ser at position 424, alteration which substitutes Asn for Tyr at position 436 and substitutes Thr for Gln at position 438, and alteration which substitutes Asn for Gln at position 438. Particularly preferably, the alteration which substitutes Asn for Ser at position 424 is used.

A preferred example of a polypeptide comprising an Fc region variant of the present invention includes at least one of polypeptides comprising two associated Fc region variants like an IgG antibody. When an IgG antibody is used as the antibody, the type of constant region is not limited, and an IgG isotype (subclasses) such as IgG1, IgG2, IgG3, and IgG4 can be used. IgG antibodies of the present invention are preferably human IgGs, and more preferably human IgG1 and human IgG4. The amino acid sequences of the heavy-chain constant regions of human IgG1 and human IgG4 are known. A plurality of allotype sequences due to genetic polymorphisms have been described in the Sequences of Proteins of Immunological Interest, NIH Publication No. 91-3242 for the human IgG1 constant region, and any of the sequences may be used in the present invention.

In the present invention, amino acid alteration means any of substitution, deletion, addition, insertion, and modification, or a combination thereof. In the present invention, amino acid alteration may be rephrased as amino acid mutation, and they are used synonymously.

When substituting amino acid residues, substitution to a different amino acid residue is carried out with the objective of altering aspects such as (a)-(c) described below:

(a) polypeptide backbone structure in the sheet-structure or helical-structure region;

(b) electric charge or hydrophobicity at the target site; or (c) size of the side chain.

Amino acid residues are classified into the following groups based on their general side chain properties:

(1) hydrophobic: norleucine, met, ala, val, leu, and ile;

(2) neutral hydrophilic: cys, ser, thr, asn, and gln;

(3) acidic: asp and glu;

(4) basic: his, lys, and arg;

(5) residues that affect the chain orientation: gly and pro; and (6) aromatic: tip, tyr, and phe.

Substitution between amino acid residues within each of these amino acid groups is referred to as conservative substitution, and amino acid residue substitution between different groups is referred to as non-conservative substitution. Substitutions in the present invention may be conservative substitutions or non-conservative substitutions, or a combination of conservative substitutions and non-conservative substitutions.

Amino acid sequence alterations are produced by various methods known to those skilled in the art. Such methods include the site-directed mutagenesis method (Hashimoto-Gotoh, T, Mizuno, T, Ogasahara, Y, and Nakagawa, M. (1995) An oligodeoxyribonucleotide-directed dual amber method for site-directed mutagenesis. Gene 152: 271-275; Zoller, M J, and Smith, M. (1983) Oligonucleotide-directed mutagenesis of DNA fragments cloned into M13 vectors. Methods Enzymol. 100: 468-500; Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12: 9441-9456; Kramer W, and Fritz H J (1987) Oligonucleotide-directed construction of mutations via gapped duplex DNA Methods. Enzymol. 154, 350-367; and Kunkel, TA (1985) Rapid and efficient site-specific mutagenesis without phenotypic selection. Proc Natl Acad Sci USA. 82: 488-492), the PCR mutation method, and the cassette mutation method, but are not limited thereto.

Amino acid modification of the present invention includes post-translational modification. A specific post-translational modification may be addition or deletion of a sugar chain. For example, in the IgG1 constant region comprising the amino acid sequence of SEQ ID NO: 31, the amino acid residue at position 297 (EU numbering) may be sugar chain-modified. The sugar-chain structure for the modification is not limited. Generally, antibodies expressed in eukaryotic cells comprise glycosylation in the constant region. Therefore, antibodies expressed in cells such as those below are normally modified by some type of sugar chain:

antibody-producing cells of mammals eukaryotic cells transformed with an expression vector comprising a DNA encoding an antibody Eukaryotic cells shown here include yeast and animal cells. For example, CHO cells and HEK293H cells are representative animal cells used in transformation with an expression vector comprising an antibody-encoding DNA. On the other hand, those without glycosylation at this site are also included in the constant region of the present invention. Antibodies whose constant region is not glycosylated can be obtained by expressing an antibody-encoding gene in prokaryotic cells such as *Escherichia coli.*

Specifically, for example, sialic acid may be added to the sugar chain of an Fc region (MAbs. 2010 September-October; 2(5): 519-27).

Furthermore, the present invention provides antibodies comprising any of Fc region variant described above.

The term "antibody/antibodies" in the present invention is used in the broadest sense, and as long as the desired biological activity is shown, it comprises any antibody such as monoclonal antibodies (including full-length monoclonal antibodies), polyclonal antibodies, antibody variants, antibody fragments, polyspecific antibodies (multi-specific antibodies) (for example, bispecific antibodies (diabodies)), chimeric antibodies, and humanized antibodies.

Regarding the antibodies of the present invention, the antigen type and antibody origin are not limited, and they may be any type of antibodies. The origin of the antibodies is not particularly limited, but examples include human antibodies, mouse antibodies, rat antibodies, and rabbit antibodies.

Methods for producing the antibodies are well known to those skilled in the art, and for example, monoclonal antibodies may be produced by the hybridoma method (Kohler and Milstein, Nature 256: 495 (1975)), or the recombination method (U.S. Pat. No. 4,816,567). Alternatively, they may be isolated from a phage antibody library (Clackson et al., Nature 352: 624-628 (1991); Marks et al., J. Mol. Biol. 222: 581-597 (1991)).

A humanized antibody is also called a reshaped human antibody. Specifically, humanized antibodies prepared by grafting the CDRs of a non-human animal antibody such as a mouse antibody to a human antibody and such are known. Common genetic engineering techniques for obtaining humanized antibodies are also known. Specifically, for example, overlap extension PCR is known as a method for grafting mouse antibody CDRs to human FRs.

A vector for expressing a humanized antibody can be produced by inserting a DNA encoding an antibody variable region in which three CDRs and four FRs are ligated and a DNA encoding a human antibody constant region into an expression vector so that these DNAs are fused in frame. After this integration vector is transfected into a host to establish recombinant cells, these cells are cultured, and the DNA encoding the humanized antibody is expressed to produce the humanized antibody in the culture of the cells (see, European Patent Publication No. EP 239,400, and International Patent Publication No. WO 1996/002576).

As necessary, an amino acid residue in an FR may be substituted so that the CDRs of a reshaped human antibody form an appropriate antigen-binding site. For example, a mutation can be introduced into the amino acid sequence of an FR by applying the PCR method used for grafting mouse CDRs to human FRs.

A desired human antibody can be obtained by DNA immunization using a transgenic animal having the complete repertoire of human antibody genes (see International Publication Nos. WO 1993/012227, WO 1992/003918, WO 1994/002602, WO 1994/025585, WO 1996/034096, and WO 1996/033735) as an animal for immunization.

Furthermore, technologies for obtaining a human antibody by panning using a human antibody library are known. For example, a human antibody V region is expressed on the surface of a phage as a single-chain antibody (scFv) by the phage display method. The scFv-expressing phage that binds to the antigen can be selected. The DNA sequence that encodes the V region of the antigen-bound human antibody can be determined by analyzing the genes of the selected phage. After determining the DNA sequence of the scFv that binds to the antigen, an expression vector can be prepared by fusing the V-region sequence in-frame with the sequence of a desired human antibody C region, and then inserting this into a suitable expression vector. The expression vector is introduced into suitable expression cells such as those described above, and the human antibody can be obtained by expressing the human antibody-encoding gene. These methods are already known (see, International Publication Nos. WO 1992/001047, WO 1992/020791, WO 1993/006213, WO 1993/011236, WO 1993/019172, WO 1995/001438, and WO 1995/15388).

Variable regions constituting the antibodies of the present invention can be variable regions that recognize any antigen.

Herein, there is no particular limitation on the antigen, and it may be any antigens. Examples of such antigens preferably include ligands (cytokines, chemokines, and such), receptors, cancer antigens, MHC antigens, differentiation antigens, immunoglobulins, and immune complexes partly containing immunoglobulins.

Examples of cytokines include interleukins 1 to 18, colony stimulating factors (G-CSF, M-CSF, GM-CSF, etc.), interferons (IFN-$\alpha$, IFN-$\beta$, IFN-$\gamma$, etc.), growth factors (EGF, FGF, IGF, NGF, PDGF, TGF, HGF, etc.), tumor necrosis factors (TNF-$\alpha$ and TNF-$\beta$), lymphotoxin, erythropoietin, leptin, SCF, TPO, MCAF, and BMP.

Examples of chemokines include CC chemokines such as CCL1 to CCL28, CXC chemokines such as CXCL1 to CXCL17, C chemokines such as XCL1 to XCL2, and CX3C chemokines such as CX3CL1.

Examples of receptors include receptors belonging to receptor families such as the hematopoietic growth factor receptor family, cytokine receptor family, tyrosine kinase-type receptor family, serine/threonine kinase-type receptor family, TNF receptor family, G protein-coupled receptor family, GPI anchor-type receptor family, tyrosine phosphatase-type receptor family, adhesion factor family, and hormone receptor family. The receptors belonging to these receptor families and their characteristics have been described in many documents such as Cooke B A., King R J B., van der Molen H J. ed. New Comprehesive Biochemistry Vol. 18B "Hormones and their Actions Part II" pp. 1-46 (1988) Elsevier Science Publishers BV; Patthy (Cell (1990) 61 (1): 13-14); Ullrich et al. (Cell (1990) 61 (2): 203-212); Massagué (Cell (1992) 69 (6): 1067-1070); Miyajima et al. (Annu. Rev. Immunol. (1992) 10: 295-331); Taga et al. (FASEB J. (1992) 6, 3387-3396); Fantl et al. (Annu. Rev. Biochem. (1993), 62: 453-481); Smith et al. (Cell (1994) 76 (6): 959-962); and Flower D R. Flower (Biochim. Biophys. Acta (1999) 1422 (3): 207-234).

Examples of specific receptors belonging to the above-mentioned receptor families preferably include human or mouse erythropoietin (EPO) receptors (Blood (1990) 76 (1): 31-35; and Cell (1989) 57 (2): 277-285), human or mouse granulocyte-colony stimulating factor (G-CSF) receptors (Proc. Natl. Acad. Sci. USA. (1990) 87 (22): 8702-8706, mG-CSFR; Cell (1990) 61 (2): 341-350), human or mouse thrombopoietin (TPO) receptors (Proc Natl Acad Sci USA. (1992) 89 (12): 5640-5644; EMBO J. (1993) 12(7): 2645-53), human or mouse insulin receptors (Nature (1985) 313 (6005): 756-761), human or mouse Flt-3 ligand receptors (Proc. Natl. Acad. Sci. USA. (1994) 91 (2): 459-463), human or mouse platelet-derived growth factor (PDGF) receptors (Proc. Natl. Acad. Sci. USA. (1988) 85 (10): 3435-3439), human or mouse interferon (IFN)-$\alpha$ and $\beta$ receptors (Cell (1990) 60 (2): 225-234; and Cell (1994) 77 (3): 391-400), human or mouse leptin receptors, human or mouse growth hormone (GH) receptors, human or mouse interleukin (IL)-10 receptors, human or mouse insulin-like growth factor (IGF)-I receptors, human or mouse leukemia inhibitory factor (LIF) receptors, and human or mouse ciliary neurotrophic factor (CNTF) receptors.

Cancer antigens are antigens that are expressed as cells become malignant, and they are also called tumor-specific antigens. Abnormal sugar chains that appear on cell surfaces or protein molecules when cells become cancerous are also cancer antigens, and they are also called sugar-chain cancer antigens. Examples of cancer antigens preferably include GPC3 which is a receptor belonging to the GPI anchor-type receptor family mentioned above, and is also expressed in several cancers including liver cancer (Int J Cancer. (2003)

103 (4): 455-65), as well as EpCAM which is expressed in several cancers including lung cancer (Proc Natl Acad Sci USA. (1989) 86 (1): 27-31), CA19-9, CA15-3, and sialyl SSEA-1 (SLX).

MHC antigens are roughly classified into MHC class I antigens and MHC class II antigens. MHC class I antigens include HLA-A, -B, -C, -E, -F, -G, and -H, and MHC class II antigens include HLA-DR, -DQ, and -DP.

Differentiation antigens may include CD1, CD2, CD4, CD5, CD6, CD7, CD8, CD10, CD11a, CD11b, CD11c, CD13, CD14, CD15s, CD16, CD18, CD19, CD20, CD21, CD23, CD25, CD28, CD29, CD30, CD32, CD33, CD34, CD35, CD38, CD40, CD41a, CD41b, CD42a, CD42b, CD43, CD44, CD45, CD45RO, CD48, CD49a, CD49b, CD49c, CD49d, CD49e, CD49f, CD51, CD54, CD55, CD56, CD57, CD58, CD61, CD62E, CD62L, CD62P, CD64, CD69, CD71, CD73, CD95, CD102, CD106, CD122, CD126, and CDw130.

Immunoglobulins include IgA, IgM, IgD, IgG, and IgE Immune complexes include a component of at least any of the immunoglobulins.

Other antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAM8, ADAM9, ADAMTS, ADAMTS4, ADAMTS5, addressin, aFGF, ALCAM, ALK, ALK-1, ALK-7,alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Ax1, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gash, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGD2, PIN, PLA2, placental alkaline phosphatase (PLAP), PlGF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, 5100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEM5, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaRIIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alphabeta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACT), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and S1P; and receptors for hormone and growth factors.

One or more amino acid residue alterations are allowed in the amino acid sequences constituting the variable regions as long as their antigen-binding activities are maintained. When altering a variable region amino acid sequence, there is no particularly limitation on the site of alteration and number of amino acids altered. For example, amino acids present in CDR and/or FR can be altered appropriately. When altering amino acids in a variable region, the binding activity is preferably maintained without particular limitation; and for example, as compared to before alteration, the binding activity is 50% or more, preferably 80% or more, and more preferably 100% or more. Furthermore, the binding activity may be increased by amino acid alterations. For example, the binding activity may be 2-, 5-, 10-times higher or such than that before alteration. In the antibodies of the present invention, alteration of amino acid sequence may be at least one of amino acid residue substitution, addition, deletion, and modification.

For example, the modification of the N-terminal glutamine of a variable region into pyroglutamic acid by pyroglutamylation is a modification well known to those skilled in the art. Thus, when the heavy-chain N terminus is glutamine, the antibodies of the present invention comprise the variable regions in which the glutamine is modified to pyroglutamic acid.

Antibody variable regions of the present invention may have any sequences, and they may be antibody variable regions of any origin, such as mouse antibodies, rat antibodies, rabbit antibodies, goat antibodies, camel antibodies, humanized antibodies produced by humanizing these non-human antibodies, and human antibodies. "Humanized antibodies", also referred to as "reshaped human antibodies", are antibodies in which the complementarity determining regions (CDRs) of an antibody derived from a non-human mammal, for example, a mouse antibody, are transplanted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342: 877). Their common genetic recombination techniques are also known (see, European Patent Application Publication No. EP 125023 and WO 96/02576). Furthermore, these antibodies may have various amino acid substitutions introduced into their variable regions to improve their antigen binding, pharmacokinetics, stability, and antigenicity. Variable regions of the antibodies of the present invention may be able to bind antigens repeatedly due to their pH dependability in antigen binding (WO 2009/125825).

κ chain and λ chain-type constant regions are present in antibody light-chain constant regions, but either one of the light chain constant regions is acceptable. Furthermore, light-chain constant regions of the present invention may be light-chain constant regions with amino acid alterations such as substitutions, deletions, additions, and/or insertions.

For example, for the heavy chain constant regions of an antibody of the present invention, heavy chain constant regions of human IgG antibodies may be used and heavy chain constant regions of human IgG1 antibodies and those of human IgG4 antibodies are preferred.

Furthermore, Fc region variants of the present invention may be made into Fc fusion protein molecules by linking to other proteins, physiologically active peptides, and such. Herein, fusion protein refers to a chimeric polypeptide comprising at least two different polypeptides, which do not spontaneously link with each other in natural. Examples of the other proteins and biologically active peptides include receptors, adhesion molecules, ligands, and enzymes, but are not limited thereto.

Preferred examples of Fc fusion protein molecules of the present invention include proteins with Fc region fused to a receptor protein that binds to a target, and such examples include TNFR-Fc fusion protein, IL1R-Fc fusion protein, VEGFR-Fc fusion protein, and CTLA4-Fc fusion protein (Nat Med. 2003 January; 9(1): 47-52; BioDrugs. 2006; 20(3): 151-60). Furthermore, a protein to be fused to a polypeptide of the present invention may be any molecule as long as it binds to a target molecule, and examples include scFv molecules (WO 2005/037989), single-domain antibody molecules (WO 2004/058821; WO 2003/002609), antibody-like molecules (Current Opinion in Biotechnology 2006, 17: 653-658; Current Opinion in Biotechnology 2007, 18: 1-10; Current Opinion in Structural Biology 1997, 7: 463-469; and Protein Science 2006, 15: 14-27) such as DARPins (WO 2002/020565), Affibody (WO 1995/001937), Avimer (WO 2004/044011; WO 2005/040229), and Adnectin (WO 2002/032925). Furthermore, antibodies and Fc fusion protein molecules may be multispecific antibodies that bind to multiple types of target molecules or epitopes.

Furthermore, the antibodies of the present invention include antibody modification products. Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. Bispecific antibody refers to an antibody that has in a single molecule variable regions that recognize different epitopes. The epitopes may be present in a single molecule or in different molecules.

The polypeptides of the present invention can be prepared by the methods known to those skilled in the art. For example, the antibodies can be prepared by the methods described below, but the methods are not limited thereto.

A DNA encoding an antibody heavy chain in which one or more amino acid residues in the Fc region have been substituted with other amino acids of interest and DNA encoding an antibody light chain, are expressed. A DNA encoding a heavy chain in which one or more amino acid residues in the Fc region are substituted with other amino acids of interest can be prepared, for example, by obtaining a DNA encoding the Fc region of a natural heavy chain, and introducing an appropriate substitution so that a codon encoding a particular amino acid in the Fc region encodes another amino acid of interest.

Alternatively, a DNA encoding a heavy chain in which one or more amino acid residues in the Fc region are substituted with other amino acids of interest can also be prepared by designing and then chemically synthesizing a DNA encoding a protein in which one or more amino acid residues in the Fc region of the natural heavy chain are substituted with other amino acids of interest. The position and type of amino acid substitution are not particularly limited. Furthermore, alteration is not limited to substitution, and alteration may be any of deletion, addition, or insertion, or combination thereof.

Alternatively, a DNA encoding a heavy chain in which one or more amino acid residues in the Fc region are substituted with other amino acids of interest can be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc region, but are not limited thereto. Furthermore, a DNA encoding a light chain can similarly be prepared as a combination of partial DNAs.

Methods for expressing the above-described DNAs include the methods described below. For example, a heavy chain expression vector is constructed by inserting a DNA encoding a heavy chain variable region into an expression vector along with a DNA encoding a heavy chain constant region. Likewise, a light chain expression vector is constructed by inserting a DNA encoding a light chain variable region into an expression vector along with a DNA encoding a light chain constant region. Alternatively, these heavy and light chain genes may be inserted into a single vector.

When inserting a DNA encoding the antibody of interest into an expression vector, the DNA is inserted so that the antibody is expressed under the control of an expression-regulating region such as an enhancer or promoter. Next, host cells are transformed with this expression vector to express the antibody. In such cases, an appropriate combination of host and expression vector may be used.

Examples of the vectors include M13 vectors, pUC vectors, pBR322, pBluescript, and pCR-Script. Alternatively, when aiming to subclone and excise cDNA, in addition to the vectors described above, pGEM-T, pDIRECT, pT7, and such can be used.

Expression vectors are particularly useful when using vectors for producing the polypeptides of the present invention. For example, when a host cell is $E.\ coli$ such as JM109, DH5α, HB101, and XL1-Blue, the expression vectors must carry a promoter that allows efficient expression in $E.\ coli$, for example, lacZ promoter (Ward et al., Nature (1989) 341: 544-546; FASEB J. (1992) 6: 2422-2427; its entirety are incorporated herein by reference), araB promoter (Better et al., Science (1988) 240: 1041-1043; its entirety are incorporated herein by reference), T7 promoter, or such. Such vectors include pGEX-5X-1 (Pharmacia), "QIAexpress system" (QIAGEN), pEGFP, or pET (in this case, the host is preferably BL21 that expresses T7 RNA polymerase) in addition to the vectors described above.

The vectors may contain signal sequences for polypeptide secretion. As a signal sequence for polypeptide secretion, a pelB signal sequence (Lei, S. P. et al J. Bacteriol. (1987) 169: 4397; its entirety are incorporated herein by reference) may be used when a polypeptide is secreted into the $E.\ coli$ periplasm. The vector can be introduced into host cells by lipofectin method, calcium phosphate method, and DEAE-Dextran method, for example.

In addition to $E.\ coli$ expression vectors, the vectors for producing the polypeptides of the present invention include mammalian expression vectors (for example, pcDNA3 (Invitrogen), pEGF-BOS (Nucleic Acids. Res. 1990, 18(17): p5322; its entirety are incorporated herein by reference), pEF, and pCDM8), insect cell-derived expression vectors (for example, the "Bac-to-BAC baculovirus expression system" (GIBCO-BRL) and pBacPAK8), plant-derived expression vectors (for example, pMH1 and pMH2), animal virus-derived expression vectors (for example, pHSV, pMV, and pAdexLcw), retroviral expression vectors (for example, pZIPneo), yeast expression vectors (for example, "Pichia Expression Kit" (Invitrogen), pNV11, and SP-Q01), and *Bacillus subtilis* expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277: 108; its entirety are incorporated herein by reference), MMTV-LTR promoter, EF1α promoter (Mizushima et al., Nucleic Acids Res. (1990) 18: 5322; its entirety are incorporated herein by reference), CAG promoter (Gene. (1990) 18: 5322; its entirety are incorporated herein by reference), and CMV promoter, and more preferably they have a gene for selecting transformed cells (for example, a drug resistance gene that allows evaluation using an agent (neomycin, G418, or such)). Vectors with such characteristics include pMAM, pDR2, pBK-RSV, pBK-CMV, pOPRSV, and pOP13, for example.

In addition, the following method can be used for stable gene expression and gene copy number amplification in cells: CHO cells deficient in a nucleic acid synthesis pathway are introduced with a vector that carries a DHFR gene which compensates for the deficiency (for example, pCHOI), and the vector is amplified using methotrexate (MTX). Alternatively, the following method can be used for transient gene expression: COS cells with a gene expressing SV40 T antigen on their chromosome are transformed with a vector with an SV40 replication origin (pcD and such). Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

Antibodies can be collected, for example, by culturing transformed cells, and then separating the antibodies from the inside of the transformed cells or from the culture media. Antibodies can be separated and purified using an appropriate combination of methods such as centrifugation, ammonium sulfate fractionation, salting out, ultrafiltration, 1q, FcRn, protein A, protein G column, affinity chromatography, ion exchange chromatography, and gel filtration chromatography.

Furthermore, the present invention provides methods of promoting elimination of a disease-causing antigen in plasma by using a polypeptide comprising an Fc region variant of the present invention and an antigen-binding domain having a binding activity to the antigen and whose binding activity to the antigen changes depending on the ion concentration condition, wherein the antigen exists in a soluble form in plasma.

As described in WO2011/122011, a pH-dependent antigen-binding molecule produced by further modifying a pH-dependent antigen-binding molecule to enhance its FcRn binding under a neutral condition (pH 7.4) has been reported to be able to eliminate antigens from plasma by administration of a polypeptide comprising such an antigen-binding domain, since the molecule has an effect of enabling repeated antigen binding and an effect of eliminating antigens from plasma (WO2011/122011). However, so far there are no reports on methods for accelerating antigen elimination besides the method of enhancing FcRn binding under neutral conditions.

In the Examples, a polypeptide comprising an antigen-binding domains whose antigen-binding activity changes depending on the pH condition was found to show accelerated elimination of antigens in plasma through FcγR binding as compared to when only the antigen exists, even though the polypeptide comprises a native IgG1-derived Fc region whose binding to FcRn in the neutral pH range is not enhanced. Without being restricted to a particular theory, the following mechanism is an example of the reason why such phenomena occurs in clone 278 and such.

Figure 9:
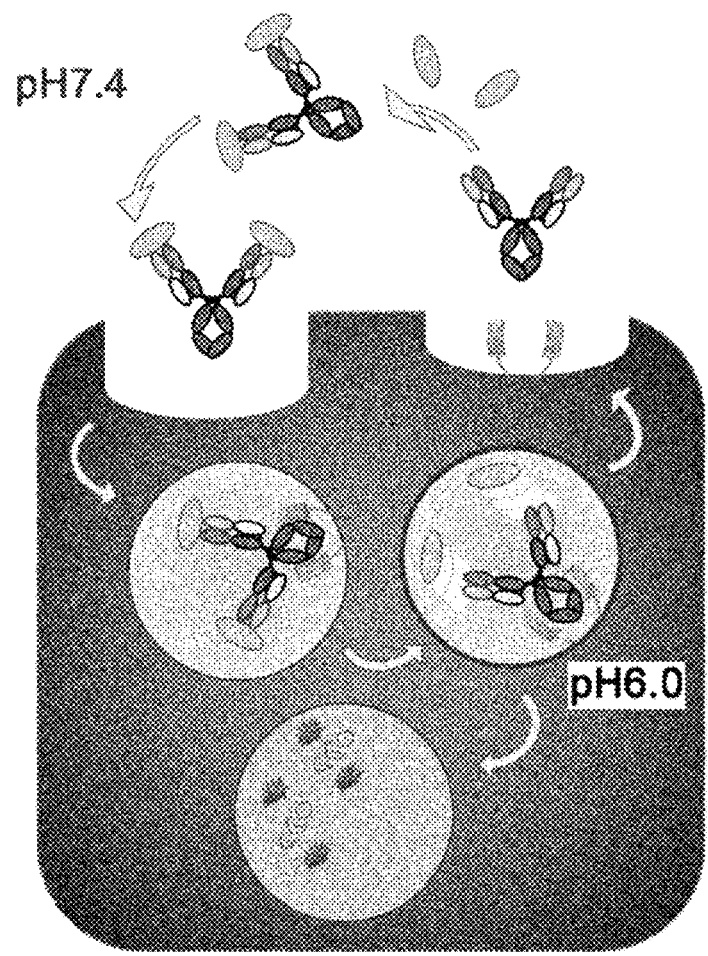

When the site to which the antigen-binding domain can bind is one (that is, a homo-monomer) such as in sIL-6R, two molecules of antigens bind to one antibody molecule comprising divalent antigen-binding domains, and one anti-sIL-6R antibody molecule and two antigen molecules comprising two antigen-binding units form a complex. Therefore, this type of antigen-antibody complex has only one Fc region (native IgG1 Fc region) as shown in FIG. 9. Since the complex binds to two molecules of FcRn or one molecule of FcγR via a single Fc region, affinities for these receptors are the same as those of normal IgG antibodies, and uptake into cells can be considered to take place mostly non-specifically.

On the other hand, when epitopes to which the antigen-binding domain binds are present at two sites in an antigen such as when an antigen is a heterodimeric complex of heavy and light chains, e.g., human IgE, binding of each of the bivalent antigen-binding domains in a single anti-IgE antibody molecule to each of the two units of epitopes in a single IgE molecule may be difficult in terms of epitope placement and such. As a result, it is considered that an antigen-antibody complex (immune complex) comprising at least four molecules (that is, two molecules of IgE, which are antigen molecules, and two molecules of anti-IgE antibodies, which are polypeptides comprising the antigen-binding domain) is formed by the binding of a separate anti-IgE antibody molecule to two antigen-binding units present in two IgE molecules that bind to the bivalent antigen-binding domain present in a single anti-IgE antibody molecule.

When a polypeptide comprising an antigen-binding domain such as an antibody that binds to an antigen molecule comprising two or more sites to which an antigen-binding domain can bind forms a large immune complex which is at least a tetramer, such immune complex can bind strongly with avidity via at least two or more multivalent Fc regions to FcγR, FcRn, complement receptor, and such. On the other hand, when an antigen molecule has one site to which the antigen-binding domain can bind, the Fc region-mediated affinity of immune complexes formed between the antigen molecule and the polypeptide comprising an antigen-binding domain for these receptors is insufficient compared to when the above-mentioned immune complexes are formed. More specifically, the immune complex is incorporated highly efficiently by cells expressing these receptors.

When an antigen molecule comprises two or more sites that bind to an antigen-binding domain, a polypeptide of the present invention, in case when the polypeptide is, for example, an antibody, forms antigen-antibody complexes (immune complexes) comprising at least four molecules (two antigen molecules and two antibody molecules) in plasma, and when the immune complexes are incorporated into cells, antigens dissociate from the antibodies in the endosome where the ion concentration condition is different from that in plasma as the polypeptide of the present invention has an antigen-binding domain whose antigen binding varies depending on the ion concentration condition such as pH-dependent binding. Therefore, the formed immune complexes are eliminated in the endosome of cells into which the immune complexes were incorporated. Since the dissociated antigens cannot bind to FcRn in the endosome, they are degraded after being transferred to the lysosome. On the other hand, antibodies that dissociate from the antigen may be recycled into the plasma after binding to FcRn in the endosome. Similar recycling is possible using an ion concentration condition other than the pH condition as described in the Examples, and Reference Examples 3 to 6 show that elimination of antigens in plasma can be accelerated using an antigen-binding domain whose antigen-binding activity changes depending on the calcium concentration condition instead of the pH-dependent condition.

Therefore, when an immune complex formed by antigens and polypeptides comprising an antigen-binding domain for the antigen is a complex comprising two or more multivalent Fc regions for FcγR, FcRn, complement receptor, and such, the complex can accelerate elimination of the antigens.

In addition, the examinations of Reference Examples 7 to 9 show that among the FcγRs, FcγRIIB which is an inhibitory FcγR makes the largest contribution to elimination of antigens via FcγR. More specifically, even if FcγR binding is decreased, the ability of an antibody to eliminate antigens via FcγR can be maintained as long as FcγRIIB binding can be maintained.

To date, side effects due to interactions between IgG and FcγR have been reported for several therapeutic antibodies. For example, in the group of patients who were administered with bevacizumab, an antibody against VEGF, frequency for developing thromboembolism is known to increase (J. Natl. Cancer Inst. (2007) 99 (16), 1232-1239). Furthermore, thromboembolism has been observed similarly in clinical development tests of antibodies against the CD40 ligand, and the clinical trial was discontinued (Arthritis. Rheum. (2003) 48 (3), 719-727). FcγRIIa, an activating Fcγ receptor, is expressed on platelet cells, while FcγRIIb, an inhibitory Fcγ receptor, is not expressed (J. Exp. Med. (2006) 203 (9), 2157-2164); and later studies using animal models and such have suggested that both of the administered antibodies aggregate platelets via binding to FcγRIIa on the platelets, resulting in the formation of blood clots (J. Thromb. Haemost. (2009) 7 (1), 171-181; and J. Immunol. (2010) 185 (3), 1577-1583). In patients with systemic lupus erythematosus which is an autoimmune disease, platelets are activated through an FcγRIIa-dependent mechanism, and platelet activation has been reported to correlate with the severity of symptoms (Sci. Transl. Med. (2010) 2 (47), 47-63).

Furthermore, it has been reported to date that through studies using animal models, an immune complex formed between an antibody and a multivalent antigen induced anaphylaxis via activating FcγRs (Bruhns P., Blood. (2012) 119(24): 5640-9).

Uptake of immune complexes formed between a multivalent antigen and an antibody via activating FcγR has been reported to increase antibody titer production for the antigen (Scand J Immunol. (2006) 64(3): 177-84; J Immunol. (1999) 163: 618-22). This suggests the possibility that antibodies against the therapeutic antibody itself are likely to be produced for therapeutic antibodies that recognize multivalent antigens. When antibodies against a therapeutic antibody are produced, kinetics in blood worsens and effects may be weakened.

This way, by binding of antibodies with multivalent antigens to form immune complexes, these immune complexes may induce various side effects by interacting with activating FcγR, and lowers the value of the antibody as pharmaceutical. Examples of multivalent antigens (multimeric antigens) include GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), TNF, TNF-alpha, TNF-alpha/beta, TNF-beta 2, TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), VEGF, IgE, IgA, IgG, IgM, RANKL, TGF-alpha, TGF-beta, TGF-beta Pan Specific, and IL-8.

Methods for solving these issues may be methods of attenuating FcγR binding. However, if binding to all FcγRs is attenuated, acceleration of antigen elimination via FcγRs may not be possible using that antibody.

As described earlier, since from among the FcγRs, FcγRIIB plays a main role in FcγR-mediated antigen elimination by antibodies and side effects due to FcγR interactions are caused by interactions with activating FcγRs, it is possible to produce excellent antibodies with decreased side effects by activating FcγRs without losing the ability to eliminate antigens by selectively attenuating binding to other activating FcγRs while maintaining FcγRIIB binding.

Therefore, an excellent effect of promoting elimination of disease-causing soluble antigens from the plasma can be achieved by polypeptides comprising an Fc region variant of the present invention and an antigen-binding domain whose binding activity to the antigen changes according to the ion concentration condition.

Furthermore, by using the polypeptides of the present invention, similar effects can be achieved even if antigens to which the polypeptides bind have only one site that can bind to an antigen-binding domain (monomeric antigen).

Such an example includes the method of promoting elimination of monomeric antigens from plasma using a cocktail of polypeptides comprising antigen-binding domains.

As described above, when an antigen is a multimeric antigen (a non-limiting example is an immunoglobulin such as IgA or IgE, or a member of the TNF superfamily such as TNF or CD154), a large immune complex comprising two or more antigen-binding molecules and two or more antigen-binding units may be formed. On the other hand, even when an antigen is a monomeric antigen, a mixture of polypeptides comprising two or more appropriate antigen-binding domains that individually bind to different epitopes present in the monomeric antigen, where binding to the epitopes varies depending on the ion concentration condition (such as pH or Ca), may also be able to form large immune complexes comprising a polypeptide having two or more antigen-binding domains, and two or more binding sites for antigen-binding domains (monomeric antigens). Herein, a mixture of polypeptides comprising two or more appropriate antigen-binding domains that individually bind to different epitopes present in the monomeric antigen, where binding of the antigen-binding molecules to the epitopes varies depending on the ion concentration condition (such as pH or Ca) is called an antigen-binding-molecule cocktail. Among these antigen-binding domain-comprising polypeptides, at least one of the (antigen-binding domains contained in) the polypeptides forming the immune complex has to be an antigen-binding domain whose antigen-binding activity varies according to the ion concentration condition.

Other examples include methods of promoting elimination of monomeric antigens from plasma using a polypeptide comprising multispecific or multiparatopic antigen-binding domains.

Figure 19:
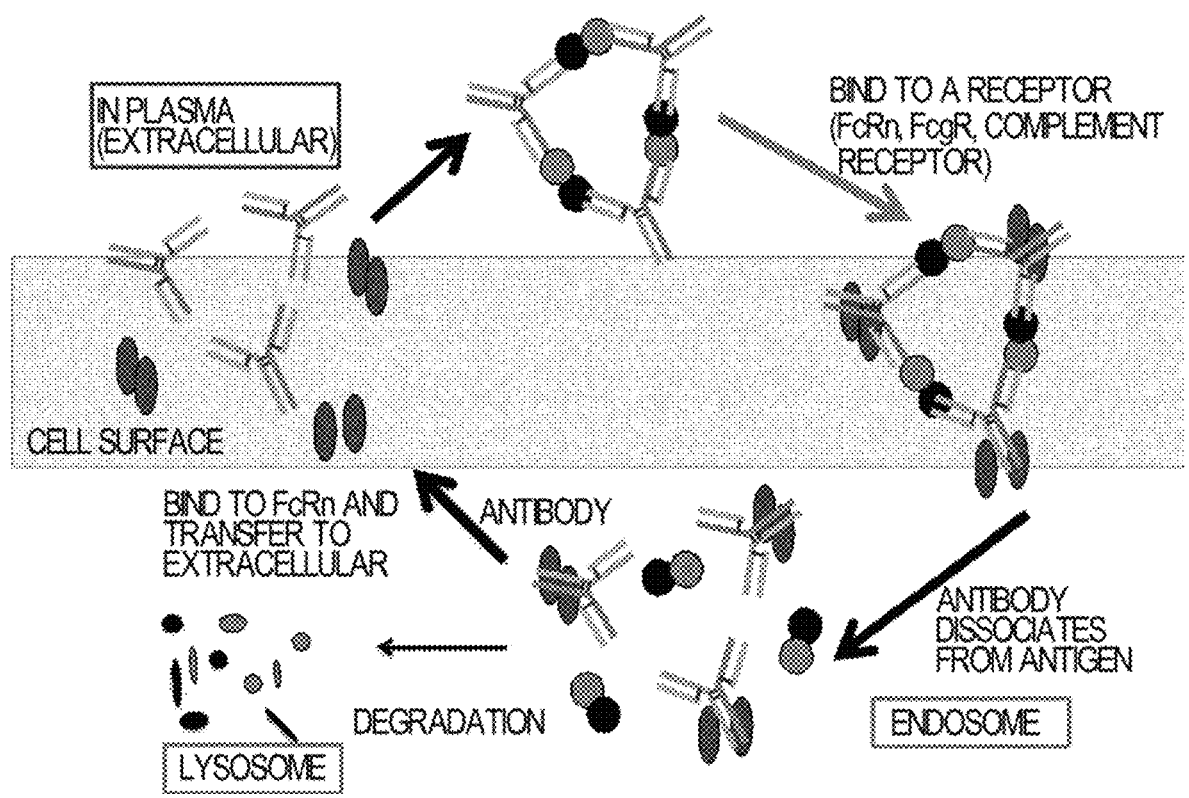
FIG. 19 is a figure exemplifying the antigen elimination efficiency by a single molecule of a multispecific pH/Ca-dependent antibody that recognizes two or more epitopes present on an antigen monomer and is suitable for forming large immune complexes.

Alternatively, even when the antigen is a monomeric antigen, each antigen-binding domain contained in a polypeptide comprising antigen-binding domains that individually bind to different epitopes present in the monomeric antigen, and antigen-binding molecules comprising antigen-binding domains in which the epitope binding of the individual antigen-binding domains varies according to the ion concentration condition (such as pH or Ca), may also be able to form a large immune complex comprising a polypeptide containing two or more antigen-binding domains and two or more antigen binding units (monomeric antigens). Examples of a non-limiting embodiment of such a polypeptide include multispecific or multiparatopic antibodies comprising appropriate variable regions that individually bind to different epitopes present on a monomeric antigen. As a non-limiting embodiment of such multispecific antibodies or multiparatopic antibodies, antibodies whose variable regions show pH- or Ca-dependent binding (bispecific antibodies or biparatopic antibodies comprising a right-arm variable region which recognizes epitope A and a left-arm variable region that recognizes epitope B, as shown in FIG. 19) may also be able to form large immune complexes comprising two or more antibodies and two or more antigen-binding units (monomeric antigens).

An antigen-binding molecule that further accelerates elimination of monomeric antigens from plasma can be obtained by screening for combinations of antigen-binding domains targeting different epitopes of a monomeric antigen, where the activity to bind to each of the epitopes varies depending on the ion concentration condition, and the antigen-binding domains can bind with avidity to the above-mentioned receptors. The ion concentration condition that changes the binding activity of the multispecific or multiparatopic antigen-binding domain to each of the epitopes may be the same ion concentration condition or a different ion concentration condition. For example, an antigen-binding molecule comprising bispecific or biparatopic antigen-binding domains, where the epitope-binding activity of one of the antigen-binding domains varies depending on the pH condition or metal ion concentration condition such as Ca ion concentration, may be exemplified as a non-limiting embodiment of the antigen-binding molecule of the present invention. Furthermore, for example, an antigen-binding molecule comprising bispecific or biparatopic antigen-binding domains, where the epitope-binding activity of one of the antigen-binding domains varies depending on the pH condition and the epitope-binding activity of the other antigen-binding domain varies depending on the condition of metal ion concentration such as Ca ion concentration, may also be exemplified as a non-limiting embodiment of the antigen-binding molecule of the present invention. An antigen-binding molecule comprising bispecific or biparatopic antigen-binding domains, where the epitope-binding activity of one of the antigen-binding domains varies depending on the pH condition and the epitope-binding activity of the other antigen-binding domain also varies depending on the pH condition, may also be exemplified as a non-limiting embodiment of the antigen-binding molecule of the present invention. A polypeptide antigen-binding molecule comprising bispecific or biparatopic antigen-binding domains, where the epitope-binding activity of one of the antigen-binding domains varies depending on the condition of metal ion concentration such as Ca ion concentration, and the epitope-binding activity of the other antigen-binding domain also varies depending on the condition of metal ion concentration such as Ca ion concentration, may also be exemplified as a non-limiting embodiment of the antigen-binding molecule of the present invention.

As for a polypeptide comprising multispecific antigen-binding domains or a polypeptide molecule comprising multiparatopic antigen-binding domains of the present invention, a polypeptide comprising at least two antigen-binding domains, wherein at least one of the antigen-binding domains binds to a first epitope in an antigen molecule, and at least another one of the antigen-binding domains binds to a second epitope in the antigen molecule, is called a multispecific antigen-binding molecule from the viewpoint of its reaction specificity. When a single antigen-binding molecule binds to two different epitopes through two types of antigen-binding domains comprised in the antigen-binding molecule, this molecule is called a bispecific antigen-binding molecule. When a single antigen-binding molecule binds to three different epitopes through three types of antigen-binding domains comprised in the antigen-binding molecule, this molecule is called a trispecific antigen-binding molecule.

A paratope in the antigen-binding domain that binds to the first epitope in the antigen molecule and a paratope in the antigen-binding domain that binds to the second epitope structurally different from the first epitope are paratopes that have different structures. Therefore, an antigen-binding molecule comprising at least two antigen-binding domains, wherein at least one of the antigen-binding domains binds to a first epitope in an antigen molecule, and at least another one of the antigen-binding domains binds to a second epitope in the antigen molecule, is called a multiparatopic antigen-binding molecule from the viewpoint of its structural specificity. When a single antigen-binding molecule binds to two different epitopes through two types of antigen-binding domains comprised in the antigen-binding molecule, this molecule is called a biparatopic antigen-binding molecule. When a single antigen-binding molecule binds to three different epitopes through three types of antigen-binding domains comprised in the antigen-binding molecule, this molecule is called a triparatopic antigen-binding molecule.

Multivalent multispecific or multiparatopic antigen-binding molecules comprising one or more antigen-binding domains and their preparation methods are described in non-patent documents such as Conrath et al., (J. Biol. Chem. (2001) 276 (10) 7346-7350), Muyldermans (Rev. Mol. Biotech. (2001) 74, 277-302), and Kontermann R. E. (2011) Bispecific Antibodies (Springer-Verlag), and in Patent Documents such as WO1996/034103 and WO1999/023221. Antigen-binding molecules of the present invention can be produced using multispecific or multiparatopic antigen-binding molecules and preparation methods described in these documents.

Bispecific antibodies and methods of producing them are presented below as examples of an embodiment of the aforementioned multispecific or multiparatopic antigen-binding molecules and their preparation methods. Bispecific antibodies are antibodies comprising two types of variable regions that bind specifically to different epitopes. IgG-type bispecific antibodies can be secreted from a hybrid hybridoma (quadroma) produced by fusing two types of hybridomas that produce IgG antibodies (Milstein et al., Nature (1983) 305, 537-540).

When a bispecific antibody is produced by using recombination techniques such as those described in the above-mentioned section on antibodies, one may adopt a method that introduces genes encoding heavy chains containing the two types of variable regions of interest into cells to co-express them. However, even when only the heavy-chain combination is considered, such a co-expression method will produce a mixture of (i) a combination of a pair of heavy chains in which one of the heavy chains contains a variable region that binds to a first epitope and the other heavy chain contains a variable region that binds to a second epitope, (ii) a combination of a pair of heavy chains which include only heavy chains containing a variable region that binds to the first epitope, and (iii) a combination of a pair of heavy chains which include only heavy chains containing a variable region that binds to the second epitope, which are present at a molecular ratio of 2:1:1. It is difficult to purify antigen-binding molecules containing the desired combination of heavy chains from the mixture of three types of heavy chain combinations.

When producing bispecific antibodies using recombination techniques such as described above, bispecific antibodies comprising the hetero combination of heavy chains can be preferentially secreted by altering the CH3 domain that constitutes a heavy chain using appropriate amino acid substitutions. Specifically, it is a method of enhancing heterogeneous heavy chain formation and inhibiting homogeneous heavy chain formation by substituting amino acid side chain in one heavy chain CH3 domain with a bulker side chain (knob (meaning "projection")) while substituting amino acid side chain in the other heavy chain CH3 domain with a smaller side chain (hole (meaning "void")) so that the "knob" is placed in the "hole" (WO 1996/027011, Ridgway et al. (Protein Engineering (1996) 9, 617-621), Merchant et al. (Nat. Biotech. (1998) 16, 677-681)).

Furthermore, known techniques for producing bispecific antibodies include those in which a means for regulating polypeptide association or association to form heteromeric multimers constituted by polypeptides is applied to the association of heavy chains. Specifically, to produce bispecific antibodies, one can use methods for regulating heavy chain association by altering amino acid residues forming interface between heavy chains so as to form two heavy chains with different sequences, while inhibiting the association of heavy chains having an identical sequence (WO 2006/106905). Such methods can be used to produce bispecific antibodies.

Furthermore, a technique for obtaining bispecific antibodies by individually obtaining two types of monoclonal antibodies, and combining them in vitro in the presence of a reducing agent has been reported (WO2008/119353). In this technique, two types of monoclonal antibodies are cleaved into half molecules by the reducing agent, and by reassembling them, bispecific antibodies are obtained at a certain rate. Furthermore, methods of obtaining bispecific antibodies more efficiently by substituting amino acids present in the CH3 domain to regulate the reassembly of the half molecules have been reported (WO2011/131746). Such methods may also be employed when producing bispecific antibodies.

In the present invention, "promoting elimination of antigens from plasma" refers to improvement of the ability to eliminate antigens from plasma when a polypeptide comprising the antigen-binding domains (hereinafter also referred to as antigen-binding molecule) is administered in vivo or when an antigen-binding molecule is secreted in vivo. Accordingly, it means that when the antigen-binding molecules are administered, the rate of antigen elimination from plasma is accelerated as compared to when an antigen-binding molecule comprising an antigen-binding domain whose antigen-binding activity does not vary depending on ion concentrations, an antigen-binding molecule comprising an FcRn-binding domain without FcRn-binding activity under an acidic pH range condition, or an antigen-binding molecule comprising an Fcγ receptor-binding domain without selective binding activity to an Fcγ receptor is administered. Whether or not the ability of an antigen-binding molecule to eliminate antigens in the plasma increased can be determined, for example, by administering soluble antigens and the antigen-binding molecule in vivo, and then measuring the plasma concentration of the soluble antigen after administration. When the concentration of the soluble antigens in the plasma is decreased after administration of the soluble antigens and the antigen-binding molecules comprising an antigen-binding domain whose antigen-binding activity varies depending on ion concentration conditions, the FcRn-binding domain having FcRn-binding activity under an acidic pH range condition, and an Fcγ receptor-binding domain having selective binding activity to an Fcγ receptor (a selective FcγR-binding domain), the ability of the antigen-binding molecules to eliminate antigens in the plasma is judged to be increased. Here, selective FcγR-binding domain refers to a domain whose binding to activating FcγRs is decreased while binding to FcγRIIb is maintained. The soluble antigen may be an antigen that is bound to an antigen-binding molecule or an antigen that is not bound to an antigen-binding molecule in the plasma, and its concentration can be determined as a "plasma concentration of the antigen bound to the antigen-binding molecule" or as a "plasma concentration of the antigen not bound to the antigen-binding molecule", respectively (the latter is synonymous with "free antigen concentration in plasma"). The "total antigen concentration in plasma" means the sum of concentrations of the antigen-binding molecule-bound antigen and the antigen not bound by an antigen-binding molecule, or the "free antigen concentration in plasma" which is the concentration of the antigen not bound by an antigen-binding molecule. Thus, the soluble antigen concentration can be determined as the "total antigen concentration in plasma". Various methods for measuring the "total antigen concentration in plasma" or the "free antigen concentration in plasma" are well known in the art as described hereinafter.

In the present invention, "enhancement of pharmacokinetics", "improvement of pharmacokinetics", and "superior pharmacokinetics" can be restated as "enhancement of plasma (blood) retention", "improvement of plasma (blood) retention", "superior plasma (blood) retention", and "prolonged plasma (blood) retention". These terms are synonymous.

In the present invention, "improvement of pharmacokinetics" means not only prolongation of the period until elimination from the plasma (for example, until the antigen-binding molecule is degraded intracellularly or the like and cannot return to the plasma) after administration of the antigen-binding molecule to humans, or non-human animals such as mice, rats, monkeys, rabbits, and dogs, but also prolongation of the plasma retention of the antigen-binding molecule in a form that allows antigen binding (for example, in an antigen-free form of the antigen-binding molecule) during the period of administration to elimination due to degradation. Human IgG having native Fc region can bind to FcRn from non-human animals. For example, mouse can be preferably used to be administered in order to confirm the property of the antigen-binding molecule of the invention since human IgG having native Fc region can bind to mouse FcRn stronger than to human FcRn (Int Immunol. (2001) 13(12): 1551-1559). As another example, mouse in which its native FcRn genes are disrupted and a transgene for human FcRn gene is harbored to be expressed (Methods Mol Biol. 2010; 602: 93-104) can also be preferably used to be administered in order to confirm the property of the antigen-binding molecule of the invention described hereinafter. Specifically, "improvement of pharmacokinetics" also includes prolongation of the period until elimination due to degradation of the antigen-binding molecule not bound to antigens (the antigen-free form of antigen-binding molecule). The antigen-binding molecule in plasma cannot bind to a new antigen if the antigen-binding molecule has already bound to an antigen. Thus, the longer the period that the antigen-binding molecule is not bound to an antigen, the longer the period that it can bind to a new antigen (the higher the chance of binding to another antigen). This enables reduction of the time period that an antigen is free of the antigen-binding molecule in vivo and prolongation of the period that an antigen is bound to the antigen-binding molecule. The plasma concentration of the antigen-free form of antigen-binding molecule can be increased and the period that the antigen is bound to the antigen-binding molecule can be prolonged by accelerating the antigen elimination from the plasma by administration of the antigen-binding molecule. Specifically, "improvement of the pharmacokinetics of antigen-binding molecule" in the present invention includes the improvement of a pharmacokinetic parameter of the antigen-free form of the antigen-binding molecule (any of prolongation of the half-life in plasma, prolongation of mean retention time in plasma, and impairment of plasma clearance), prolongation of the period that the antigen is bound to the antigen-binding molecule after administration of the antigen-binding molecule, and acceleration of antigen-binding molecule-mediated antigen elimination from the plasma. The improvement of pharmacokinetics of antigen-binding molecule can be assessed by determining any one of the parameters, half-life in plasma, mean plasma retention time, and plasma clearance for the antigen-binding molecule or the antigen-free form thereof ("Pharmacokinetics: Enshu-niyoru Rikai (Understanding through practice)" Nanzando). For example, the plasma concentration of the antigen-binding molecule or antigen-free form thereof is determined after administration of the antigen-binding molecule to mice, rats, monkeys, rabbits, dogs, or humans. Then, each parameter is determined. When the plasma half-life or mean plasma retention time is prolonged, the pharmacokinetics of the antigen-binding molecule can be judged to be improved. The parameters can be determined by methods known to those skilled in the art. The parameters can be appropriately assessed, for example, by noncompartmental analysis using the pharmacokinetics analysis software WinNonlin (Pharsight) according to the appended instruction manual. The plasma concentration of antigen-free antigen-binding molecule can be determined by methods known to those skilled in the art, for example, using the assay method described in Clin Pharmacol. 2008 April; 48 (4): 406-417.

In the present invention, "improvement of pharmacokinetics" also includes prolongation of the period that an antigen is bound to an antigen-binding molecule after administration of the antigen-binding molecule. Whether the period that an antigen is bound to the antigen-binding molecule after administration of the antigen-binding molecule is prolonged can be assessed by determining the plasma concentration of free antigen. The prolongation can be judged based on the determined plasma concentration of free antigen or the time period required for an increase in the ratio of free antigen concentration to the total antigen concentration.

The plasma concentration of free antigen not bound to the antigen-binding molecule or the ratio of free antigen concentration to the total concentration can be determined by methods known to those skilled in the art, for example, by the method used in Pharm Res. 2006 January; 23 (1): 95-103. Alternatively, when an antigen exhibits a particular function in vivo, whether the antigen is bound to an antigen-binding molecule that neutralizes the antigen function (antagonistic molecule) can be assessed by testing whether the antigen function is neutralized. Whether the antigen function is neutralized can be assessed by assaying an in vivo marker that reflects the antigen function. Whether the antigen is bound to an antigen-binding molecule that activates the antigen function (agonistic molecule) can be assessed by assaying an in vivo marker that reflects the antigen function.

Determination of the plasma concentration of free antigen and ratio of the amount of free antigen in plasma to the amount of total antigen in plasma, in vivo marker assay, and such measurements are not particularly limited; however, the assays are preferably carried out after a certain period of time has passed after administration of the antigen-binding molecule. In the present invention, the period after administration of the antigen-binding molecule is not particularly limited; those skilled in the art can determine the appropriate period depending on the properties and the like of the administered antigen-binding molecule. Such periods include, for example, one day after administration of the antigen-binding molecule, three days after administration of the antigen-binding molecule, seven days after administration of the antigen-binding molecule, 14 days after administration of the antigen-binding molecule, and 28 days after administration of the antigen-binding molecule. In the present invention, the concept "plasma antigen concentration" comprises both "total antigen concentration in plasma" which is the sum of antigen-binding molecule bound antigen and non-bound antigen concentration or "free antigen concentration in plasma" which is antigen-binding molecule non-bound antigen concentration.

The total antigen concentration in the plasma can be lowered by administration, as antigen-binding molecule, of the antigen-binding molecule of the present invention by 2-fold, 5-fold, 10-fold, 20-fold, 50-fold, 100-fold, 200-fold, 500-fold, 1,000-fold, or even higher as compared to administration of an antigen-binding molecule containing an antigen-binding domain whose antigen-binding activity is ion concentration-independent or an antigen-binding molecule containing an Fc region with an impaired FcγR-binding activity, or compared to when the antigen-binding domain molecule of the present invention is not administered.

Molar antigen/antigen-binding molecule ratio can be calculated as shown below:
value A: Molar antigen concentration at each time point
value B: Molar antigen-binding molecule concentration at each time point
value C: Molar antigen concentration per molar antigen-binding molecule concentration (molar antigen/antigen-binding molecule ratio) at each time point $$C=A/B.$$

Smaller value C indicates higher efficiency of antigen elimination per antigen-binding molecule whereas higher value C indicates lower efficiency of antigen elimination per antigen-binding molecule.

Molar antigen/antigen-binding molecule ratio can be calculated as described above.

A 2-fold, 5-fold, 10-fold, 20-fold, 50-fold, 100-fold, 200-fold, 500-fold, 1,000-fold or even greater reduction of molar antigen/antigen-binding molecule ratio can be achieved by administration of an antigen-binding molecule of the present invention as compared to when an antigen-binding molecule comprising an antigen-binding domain whose antigen-binding activity does not vary depending on ion concentrations, an antigen-binding molecule comprising an FcRn-binding domain without FcRn-binding activity under an acidic pH range condition, or an antigen-binding molecule comprising an Fcγ receptor-binding domain without selective binding activity to an Fcγ receptor is administered as the antigen-binding molecule.

In the present invention, an antigen-binding molecule comprising an antigen-binding domain whose antigen-binding activity does not vary depending on ion concentrations, an antigen-binding molecule comprising an FcRn-binding domain without FcRn-binding activity under an acidic pH range condition, or an antigen-binding molecule comprising an Fcγ receptor-binding domain without selective binding activity to an Fcγ receptor is used as a reference antigen-binding molecule to be compared with the antigen-binding molecules of the present invention.

When evaluating the effect of an FcRn-binding domain having FcRn-binding activity under an acidic pH range condition, reduction of total antigen concentration in plasma or molar antigen/antibody ratio can be assessed by either antigen and antibody co-injection model or steady-state antigen infusion model using human FcRn transgenic mouse line 32 or line 276 (Jackson Laboratories, Methods Mol. Biol. (2010) 602, 93-104), when the antigen-binding molecule does not cross-react with the mouse counterpart antigen. When an antigen-binding molecule cross-react with mouse counterpart, they can be assessed by simply injecting antigen-binding molecule to human FcRn transgenic mouse line 32 or line 276 (Jackson Laboratories). In co-injection model, mixture of antigen-binding molecule and antigen is administered to the mouse. In steady-state antigen infusion model, infusion pump containing antigen solution is implanted to the mouse to achieve constant plasma antigen concentration, and then antigen-binding molecule is injected to the mouse. Test antigen-binding molecule is administered at same dosage. Total antigen concentration in plasma, free antigen concentration in plasma and plasma antigen-binding molecule concentration is measured at appropriate time point using method known to those skilled in the art.

For assessing the effects of an Fcγ receptor-binding domain having selective binding activity to Fcγ receptors, when an antigen-binding molecule does not cross-react with a mouse counterpart antigen, total antigen concentration in plasma or decrease in antigen/antibody mole ratio can be assessed by either the antigen-antibody simultaneous injection model or the steady-state antigen injection model using the conventionally used C57BL/6J mice (Charles River Japan). When an antigen-binding molecule cross-reacts with the mouse counterpart, the antigen-binding molecule can simply be injected to conventionally used C57BL/6J mice (Charles River Japan) to carry out the assessment.

In the co-injection model, a mixture of the antigen-binding molecule and antigen is administered to mice. In the steady-state antigen infusion model, an infusion pump filled with an antigen solution is embedded into mice to achieve a constant plasma antigen concentration, and then the antigen-binding molecule is injected into the mice. Test antigen-binding molecules are administered at the same dose. The total antigen concentration in plasma, free antigen concentration in plasma, and antigen-binding molecule concentration in plasma are measured at appropriate time points using methods known to those skilled in the art.

Total or free antigen concentration in plasma and molar antigen/antigen-binding molecule ratio can be measured at 2 days, 4 days, 7 days, 14 days, 28 days, 56 days, or 84 days after administration to evaluate the long-term effect of the present invention. In other words, a long term plasma antigen concentration is determined by measuring total or free antigen concentration in plasma and molar antigen/antigen-binding molecule ratio at 2 days, 4 days, 7 days, 14 days, 28 days, 56 days, or 84 days after administration of an antigen-binding molecule in order to evaluate the property of the antigen-binding molecule of the present invention. Whether the reduction of plasma antigen concentration or molar antigen/antigen-binding molecule ratio is achieved by antigen-binding molecule described in the present invention can be determined by the evaluation of the reduction at any one or more of the time points described above.

Total or free antigen concentration in plasma and molar antigen/antigen-binding molecule ratio can be measured at 15 minutes, 1 hour, 2 hours, 4 hours, 8 hours, 12 hours, or 24 hours after administration to evaluate the short-term effect of the present invention. In other words, a short term plasma antigen concentration is determined by measuring total or free antigen concentration in plasma and molar antigen/antigen-binding molecule ratio at 15 minutes, 1 hour, 2 hours, 4 hours, 8 hours, 12 hours, or 24 hours after administration of an antigen-binding molecule in order to evaluate the property of the antigen-binding molecule of the present invention.

Route of administration of an antigen-binding molecule of the present invention can be selected from intradermal, intravenous, intravitreal, subcutaneous, intraperitoneal, parenteral and intramuscular injection.

In the present invention, improvement of pharmacokinetics of antigen-binding molecule in human is preferred. When the plasma retention in human is difficult to determine, it may be predicted based on the plasma retention in mice (for example, normal mice, human antigen-expressing transgenic mice, human FcRn-expressing transgenic mice) or monkeys (for example, cynomolgus monkeys).

"The improvement of the pharmacokinetics and prolonged plasma retention of an antigen-binding molecule" in the present invention means improvement of any pharmacokinetic parameter (any of prolongation of the half-life in plasma, prolongation of mean retention time in plasma, reduction of plasma clearance, and bioavailability) after in vivo administration of the antigen-binding molecule, or an increase in the concentration of the antigen-binding molecule in the plasma in an appropriate time after administration. It may be determined by measuring any parameter such as half-life in plasma, mean retention time in plasma, plasma clearance, and bioavailability of the antigen-binding molecule (Pharmacokinetics: Enshu-niyoru Rikai (Understanding through practice), (Nanzando)). For example, when an antigen-binding molecule is administered to mice (normal mice and human FcRn transgenic mice), rats, monkeys, rabbits, dogs, humans, and so on, and the concentration of the antigen-binding molecule in the plasma is determined and each of the parameters is calculated, the pharmacokinetics of the antigen-binding molecule can be judged to be improved when the plasma half-life or mean retention time in the plasma is prolonged. These parameters can be determined by methods known to those skilled in the art. For example, the parameters can be appropriately assessed by non-compartmental analysis using pharmacokinetics analysis software WinNonlin (Pharsight) according to the attached instruction manual.

Four types of FcγRs, FcγRI, FcγRIIb, FcγRIII, and FcγRIV, have been identified in mice. In humans as well, as corresponding FcγRs, FcγRI, FcγRIIa, FcγRIIb, FcγRIIIa, FcγRIIIa, and FcγRIIIb have been identified. FcγRIIb which is considered to be the only inhibitory type among these FcγRs is conserved in both humans and mice. The other FcγRs, except for FcγRIIIb, transmit activation signals via the immunoreceptor tyrosine-based activating motif (ITAM), whereas FcγRIIb transmits inhibitory signals via the immunoreceptor tyrosine-based inhibitory motif (ITIM) present inside the cells (Nat. Rev. Immunol. (2008) 8, 34-47).

FcγRIIb1 and FcγRIIb2 have been reported as splicing variants of FcγRIIb. In both humans and mice, FcγRIIb1 has a longer intracellular domain than FcγRIIb2. FcγRIIb1 has been confirmed to be expressed in B cells, and FcγRIIb2 has been confirmed to be expressed in macrophages, mast cells, dendritic cells, basophils, neutrophils, and eosinophils (J. Clin. Immunol. (2005) 25 (1), 1-18).

So far, in humans, dysfunction and decreased expression of FcγRIIb have been reported to be correlated with onset of autoimmune diseases. For example, it has been reported that in some SLE patients, binding of transcriptional activators is attenuated due to polymorphism in an expression promoter region of FcγRIIb, which results in the decreased FcγRIIb expression (Hum. Genet. (2005) 117, 220-227; J. Immunol. (2004) 172, 7192-7199; and J. Immunol. (2004) 172, 7186-7191). Furthermore, among SLE patients, two types of allotypes have been reported, where the amino acid at position 233 is Ile or Thr in FcγRIIb. This position exists in the transmembrane region of FcγRIIb, and it is reported that FcγRIIb is less likely to exist in the lipid raft when the amino acid at position 233 is Thr compared to when this amino acid is Ile, and as a result, signal transduction function of FcγRIIb decreases (Nat. Med. (2005) 11, 1056-1058; Hum. Mol. Genet., (2005) 14, 2881-2892). In mice as well, knockout mice produced by disrupting the FcγRIIb gene in C57BL/6 mice has been reported to present SLE-like symptoms such as autoantibody production and glomerulonephritis (Immunity 13 (2000) 277-285; J. Exp. Med. (2002) 195, 1167-1174). Furthermore, so far, reduced expression level of FcγRIIb and such have been reported in mice considered to be models with natural onset of SLE (Immunogenetics (2000) 51, 429-435; Int. Immunol. (1999) 11, 1685-1691; Curr. Biol. (2000) 10, 227-230; J. Immunol. (2002) 169, 4340-4346). From these reports, FcγRIIb is considered to regulate humoral immunity in mice as in humans.

When an antibody carrying an Fc of the present invention eliminates antigens via FcγRIIb, the endocytosis function of FcγRIIb is considered to be making the most important contribution among the functions of FcγRIIb. As described above, FcγRIIb1 and FcγRIIb2 exist as splicing variants of FcγRIIb, but it is reported that the latter is mainly involved in the endocytosis of an immune complex of an antibody and antigen (J. Immunol. (1994), 152 574-585; Science (1992) 256, 1808-1812; Cell (1989) 58, 317-327). So far, mouse FcγRIIb2 has been reported to be incorporated into a clathrin-coated pit and endocytosed (Cell (1989) 58, 317-327). Furthermore, it has been reported that a dileucine motif is necessary for FcγRIIb2-mediated endocytosis, and the dileucine motif is conserved in both humans and mice (EMBO J. (1994) 13 (13), 2963-2969). From these, FcγRIIb2 may have an endocytotic ability in humans as in mice.

On the other hand, unlike FcγRIIb2, it has been reported that FcγRIIb1 does not cause endocytosis. FcγRIIb1 has an inserted sequence in its intracellular domain that is not found in FcγRIIb2. It is considered that this sequence inhibits the uptake of FcγRIIb1 into a clathrin-coated pit, and as a result endocytosis is inhibited (J. Cell. Biol. (1992) 116, 875-888; J. Cell. Biol. (1989) 109, 3291-3302). In humans as well, FcγRIIb1 has an insertion sequence at a site similar to that of FcγRIIb2 as in mice; therefore, difference in the endocytotic ability between FcγRIIb1 and FcγRIIb2 is presumed to be caused by a similar mechanism. Furthermore, in both humans and mice, approximately 40% of immune complexes on the cell surface is reported to be taken up into the cell in 20 minutes (Mol. Immunol. (2011) 49, 329-337; Science (1992) 256, 1808-1812). Therefore, in humans as well, FcγRIIb2 is presumed to uptake immune complexes into cells at rates similar to those in mice.

Since FcγRIIb is the only one that has ITIM inside the cell in both humans and mice among the FcγR family and the distribution of expressing cells are the same, it is presumed that its function in immune control is similar. Furthermore, considering the fact that immune complexes are taken up into cells at similar rates in humans and mice, antigen elimination effects of antibodies mediated by FcγRIIb in humans may be predictable using mice. Antigen-binding molecules mF44 and mF46 have properties of binding to soluble antigens in a pH-dependent manner, and have enhanced affinity to mouse FcγRIIb and FcγRIII compared to mIgG1 which is an antigen-binding molecule having the property of binding to a soluble antigen in a pH-dependent manner. Indeed, it is shown in Reference Example 7 that antigen clearance increased when mF44 or mF46 was administered to normal mice compared to when mIgG1 was administered.

Furthermore, in the later-described Reference Example 8, a similar experiment was carried out using Fc receptor γ chain-deficient mice. It has been reported that FcγRs other than FcγRIIb are expressed only in the co-presence of a gamma chain in mice. Thus, only FcγRIIb is expressed in the Fc receptor γ chain-deficient mice. Administration of mF44 or mF46, which are antigen-binding molecules having the property of binding to soluble antigens in a pH-dependent manner, to Fc receptor γ chain-deficient mice enables assessment of antigen elimination-acceleration effects when FcγRIIb-binding is selectively enhanced. From the results of Reference Example 8, when mF44 or mF46 (which are antigen-binding molecules having the property of binding to soluble antigens in a pH-dependent manner) was administered to Fc receptor γ chain-deficient mice, antigen clearance was shown to increase compared to when mIgG1 (which is an antigen-binding molecule having the property of binding to soluble antigens in a pH-dependent manner) was administered to the mice. Furthermore, the results of Reference Example 8 shows that when administered to Fc receptor γ chain-deficient mice, mF44 or mF46 cause similar degrees of antigen elimination as when administered to normal mice.

In Reference Example 8, a similar experiment was performed using FcγRIII-deficient mice. Since mIgG1, mF44, and mF46 bind only to FcγRIIb and FcγRIII among the mFcγRs, administration of the antibodies to FcγRIII-deficient mice enables assessment of antigen elimination-accelerating effects when FcγRIIb-binding is selectively enhanced. The results of Reference Example 8 indicate that when mF44 or mF46 was administered to FcγRIII-deficient mice, antigen clearance was increased compared to when mIgG1 was administered to the mice antigen clearance. Furthermore, the results of Reference Example 8 showed that when administered to FcγRIII-deficient mice, mF44 and mF46 cause similar degrees of antigen elimination as when administered to Fc receptor γ chain-deficient mice and when administered to normal mice.

These results revealed that antigen elimination can be accelerated by selectively enhancing only the binding to FcγRIIb without enhancing the binding to activating FcγRs. More specifically, this shows that FcγRIIb is mainly involved in the FcγR-mediated elimination of immune complexes, and as long as the binding to FcγRIIb among the FcγRs is maintained, the efficiency of FcγR-mediated elimination of immune complexes by the antibody may also be maintained.

In addition to the reported documents discussed so far, based on the above-mentioned assessment results using mice, it is considered that uptake of immune complexes into cells via FcγRIIb takes place in vivo in humans as in mice, and as a result, antibodies that have Fc with selectively enhanced binding to human FcγRIIb can accelerate elimination of its antigens. Furthermore, as discussed above, since uptake of immune complexes into cells via FcγRIIb is considered to take place at similar rates in mice and humans, effects of accelerating antigen elimination comparable to those of antibodies having Fc with enhanced affinity to mouse FcγRIIb may be achieved in vivo in humans by using Fc in which affinity to human FcγRIIb is enhanced to a similar extent.

The present invention also provides a method of producing a polypeptide comprising an antibody Fc region variant with decreased binding activities to activating FcγRs while maintaining its FcγRIIb-binding activity, in comparison to those of a polypeptide comprising a parent Fc region, wherein the method comprises adding at least one amino acid alteration to the Fc region variant in a polypeptide comprising the Fc region variant.

Examples include a production method comprising the following steps:
(a) adding at least one amino acid alteration to an Fc region in a polypeptide comprising the Fc region;
(b) measuring the FcγRIIb-binding activity and binding activities to activating FcγRs of the polypeptide altered in step (a); and
(c) selecting a polypeptide comprising an Fc region variant with decreased binding activities to activating FcγRs while maintaining its FcγRIIb-binding activity in comparison to those of a polypeptide comprising the parent Fc region.

A preferred embodiment is a method of producing a polypeptide comprising an Fc region variant, which comprises the steps of:
(a) altering a nucleic acid encoding a polypeptide comprising a parent Fc region so that binding activities to activating FcγRs are decreased while the FcγRIIb-binding activity is maintained in comparison to those of the polypeptide;
(b) introducing the nucleic acid into a host cell and culturing the cell to express a polypeptide; and
(c) collecting the polypeptide from the host cell culture.

Antibodies and Fc fusion protein molecules produced by this production method are also included in this invention.

Furthermore, the present invention provides methods of decreasing the binding activities to all activating FcγRs, in particular FcγRIIa (R type), while maintaining the FcγRIIb-binding activity compared to those of a polypeptide comprising the parent Fc region, wherein the method comprises the step of adding at least one amino acid alteration to an antibody Fc region variant in a polypeptide comprising the antibody Fc region variant; or a method of producing a polypeptide comprising the Fc region variant of the present invention.

An example includes a method comprising the following steps of:
(a) adding at least one amino acid alteration to an Fc region in a polypeptide comprising the Fc region;
(b) measuring the FcγRIIa-binding activity and the FcγRIIb-binding activity of the polypeptide altered in step (a); and
(c) selecting a polypeptide comprising an Fc region variant with a decreased binding activity to FcγRIIa (R type) while maintaining its FcγRIIb-binding activity in comparison to those of a polypeptide comprising the parent Fc region.

A preferred embodiment is a method of decreasing the binding activities to all FcγRs, in particular FcγRIIa (R type), while maintaining the FcγRIIb-binding activity of a polypeptide comprising a parent Fc region, or a method of producing a polypeptide comprising an Fc region variant, which comprises the steps of:
(a) altering a nucleic acid encoding a polypeptide comprising a parent Fc region so that its binding activity to FcγRIIa (R type) is decreased while its FcγRIIb-binding activity is maintained in comparison to those of the polypeptide;
(b) introducing the nucleic acid into a host cell and culturing the cell to express a polypeptide; and
(c) collecting the polypeptide from the host cell culture.

Furthermore, antibodies and Fc fusion protein molecules produced by the production method are also included in the present invention.

Furthermore, the present invention provides a method of suppressing production of antibodies against a polypeptide in comparison to a polypeptide comprising a parent Fc region when the polypeptide is administered in vivo, wherein the method comprises adding at least one amino acid alteration to an Fc region in a polypeptide comprising the Fc region, or a method of producing polypeptides, wherein production of antibodies against the polypeptide is suppressed.

An example includes a method comprising the following steps of:
(a) adding at least one amino acid alteration to an Fc region in a polypeptide comprising the Fc region; and
(b) confirming that administration of the polypeptide comprising the Fc region altered in step (a) in vivo suppresses antibody production as compared to when a polypeptide comprising the parent Fc region is administered.

Such polypeptides may be useful as pharmaceuticals since they can suppress antibody production without activation of activating FcγRs.

In the above-mentioned method, it is preferred that the binding activities to all activating FcγRs, in particular FcγRIIa (R type), are decreased while the FcγRIIb-binding activity is maintained.

In a preferred embodiment of the above-mentioned method, for example, in a human IgG Fc region, the Fc region is altered so that the amino acid at position 238 according to EU numbering is altered to another amino acid, and at least one amino acid selected from among the amino acids at positions 235, 237, 241, 268, 295, 296, 298, 323, 324, and 330 of the Fc region, according to EU numbering, is altered to another amino acid. Two or more amino acids may be selected from the above and combined as the other amino acid alterations to be combined with the amino acid alteration at position 238 according to EU numbering. Preferred combinations include (1) to (3) below:

(1) amino acids at positions 241, 268, 296, and 324 of the Fc region according to EU numbering;
(2) amino acids at positions 237, 241, 296, and 330 of the Fc region according to EU numbering; and
(3) amino acids at positions 235, 237, 241, and 296 of the Fc region according to EU numbering.

The amino acids selected to be present after alteration are not particularly limited as long as binding selectivity for all activating FcγRs, in particular FcγRIIa(R), are decreased while the FcγRIIb-binding activity is maintained in comparison to those before the alteration, and are preferably Asp at amino acid position 238 according to EU numbering, and also Phe at amino acid position 235, Gln or Asp at amino acid position 237, Met or Leu at amino acid position 241, Pro at amino acid position 268, Met or Val at amino acid position 295, Glu, His, Asn, or Asp at amino acid position 296, Ala or Met at amino acid position 298, Ile at amino acid position 323, Asn or His at amino acid position 324, and His or Tyr at amino acid position 330 according to EU numbering.

Furthermore, in a preferred embodiment of the above-mentioned method, for example, an Fc region in a human IgG Fc region is altered so that amino acid alteration(s) that increases the FcγRIIb-binding activity by two-fold or more as compared to that of a native IgG Fc region is introduced in combination with amino acid alteration(s) that decreases the binding activities to all FcγRs.

In the present invention, "amino acid alterations that increase the FcγRIIb-binding activity by two-fold or more as compared to that of a native IgG Fc region" is not particularly limited, but examples include the amino acid alterations shown in Table 11.

Furthermore, in the present invention, "amino acid alterations that decrease the binding activities to all FcγRs" is not particularly limited, but examples include at least one amino acid selected from among amino acids at positions 234, 235, 236, 237, 239, 265, 267, and 297 of the Fc region according to EU numbering.

A preferred combination includes, for example, a combination of alterations of the amino acids at positions 238 and 271 of the Fc region according to EU numbering that increase the FcγRIIb-binding activity by two-fold or more compared to that of a native IgG Fc region, with alteration of at least one amino acid selected from among the amino acids at positions 234, 235, 236, 237, 239, 265, 267, and 297 of the Fc region according to EU numbering that reduces the binding activities to all FcγRs.

Specifically, preferred combinations of alterations include the combinations of amino acids (1) to (3) below:
(1) amino acids at positions 233, 238, 264, 267, 268, and 271 of the Fc region according to EU numbering;
(2) amino acids at positions 233, 237, 238, 264, 267, 268, 271, 296, 297, 330, and 396 of the Fc region according to EU numbering; and
(3) amino acids at positions 233, 238, 264, 267, 268, 271 and 296 of the Fc region according to EU numbering.

The amino acids selected to be present after alteration are not particularly limited as long as binding selectivities for all activating FcγRs, in particular FcγRIIa(R), are decreased while the FcγRIIb-binding activity is maintained in comparison to those before the alteration, and are preferably Asp at amino acid position 238, Gly at amino acid position 271, Ala, His, Asn, Lys, or Arg at amino acid 234, Ala at amino acid position 235, Gln at amino acid position 236, Arg or Lys at amino acid position 237, Lys at amino acid position 239, Lys, Asn, Arg, Ser, or Val at amino acid position 265, Lys, Arg, or Tyr at amino acid position 267, and Ala at amino acid position 297 according to EU numbering.

Alternatively, in a preferred embodiment of the above-mentioned method, for example, the Fc region is altered so that alterations of the amino acids at positions 238, 271, 327, 330, and 331 according to EU numbering to other amino acids are introduced into the human IgG Fc region. Furthermore, the Fc region is altered so that alterations of at least one amino acid selected from the amino acids at positions 233, 237, 264, 267, and 268 to other amino acids are introduced. For other amino acid alterations to be combined, two or more amino acids from the above may be selected and combined. Examples of the preferred combination include (1) to (4) below:
(1) amino acids at positions 237, 238, 268, 271, 327, 330, and 331 of the Fc region according to EU numbering;
(2) amino acids at positions 233, 237, 238, 268, 271, 327, 330, and 331 of the Fc region according to EU numbering;
(3) amino acids at positions 238, 267, 268, 271, 327, 330, and 331 of the Fc region according to EU numbering; and
(4) amino acids at positions 238, 264, 267, 271, 327, 330, and 331 of the Fc region according to EU numbering.

The amino acids selected to be present after alteration are not particularly limited as long as binding selectivities for all activating FcγRs, in particular FcγRIIa(R), are decreased while the FcγRIIb-binding activity is maintained in comparison to before the alteration, and are preferably Asp at amino acid position 238, Gly at amino acid position 271, Gly at amino acid position 327, Ser at amino acid position 330, Ser at amino acid position 331, Asp at amino acid position 233, Asp at amino acid position 237, Ile at amino acid position 264, Ala at amino acid position 267, and Asp or Glu at amino acid position 268 according to EU numbering.

Furthermore, the present invention provides methods of altering polypeptides for producing polypeptides whose binding activities to activating FcγRs, in particular FcγRIIa (R type), are decreased while the FcγRIIb-binding activity is maintained in comparison to those of a polypeptide comprising the parent Fc region. Alternatively, the present invention provides methods of altering polypeptides for producing polypeptides whose binding activities to activating FcγRs, in particular FcγRIIa (R type), are decreased while the FcγRIIb-binding activity is maintained in comparison to those of a polypeptide comprising the parent Fc region.

The present invention also provides methods of altering polypeptides for producing a polypeptide that results in suppressed antibody production when the polypeptide is administered in vivo, in comparison to when a polypeptide comprising the parent Fc region is administered.

An example of a preferred embodiment includes a combination of amino acid alterations described in the above-described method of producing a polypeptide comprising an Fc region variant with decreased binding activities to activating FcγRs, in particular FcγRIIa (R type), while maintaining its FcγRIIb-binding activity.

For the various types of methods described above, other amino acid alterations may be used in combination as long as binding activities to all activating FcγRs are decreased and the FcγRIIb-binding activity is maintained in comparison to those of a polypeptide comprising the native IgG Fc region. Examples of such alterations include alterations that decrease the complement-binding activity. Specific examples include alteration of the amino acid at position 322 of the Fc region according to EU numbering, or a combination of amino acid alterations at positions 327, 330, and 331 of the Fc region according to EU numbering. The amino acids selected to be present after the alteration are not particularly limited as long as the complement-binding activity is decreased, while binding activities to all activating FcγRs are decreased and the FcγRIIb-binding activity is maintained in comparison to those of a polypeptide comprising the Fc region of a native IgG, and are preferably Ala or Glu at amino acid position 322, Gly at amino acid position 327, Ser at amino acid position 330, and Ser at amino acid position 331 according to EU numbering.

Furthermore, the present invention provides a nucleic acid encoding a polypeptide comprising an Fc region variant with decreased binding activities to activating FcγRs, in particular FcγRIIa (R type), while maintaining the FcγRIIb-binding activity in comparison to those of a polypeptide comprising the parent Fc region, wherein the Fc region-containing polypeptide has at least one altered amino acid. The present invention also provides a nucleic acid encoding a polypeptide comprising an Fc region variant with decreased binding activities to activating FcγRs, in particular FcγRIIa (R type), while maintaining the FcγRIIb-binding activity in comparison to those of a polypeptide comprising the parent Fc region, wherein the Fc region-containing polypeptide has at least one altered amino acid. The nucleic acids of the present invention may be in any form such as DNA or RNA.

The present invention also provides vectors carrying the above-described nucleic acids of the present invention. The type of vector can be appropriately selected by those skilled in the art depending on the host cells to be introduced with the vector. The vectors include, for example, those described above.

Furthermore, the present invention relates to host cells transformed with the above-described vectors of the present invention. Appropriate host cells can be selected by those skilled in the art. The host cells include, for example, those described above. Specific examples include the following host cells.

When eukaryotic cells are used as host cells, animal cells, plant cells, or fungal cells can be appropriately used. Specifically, the animal cells include, for example, the following cells.

(1) mammalian cells: CHO (Chinese hamster ovary cell line), COS (Monkey kidney cell line), myeloma (Sp2/O, NS0, and such), BHK (baby hamster kidney cell line), Hela, Vero, HEK293 (human embryonic kidney cell line with sheared adenovirus (Ad)5 DNA), Freestyle293, PER.C6 cell (human embryonic retinal cell line transformed with the Adenovirus Type 5 (Ad5) E1A and E1B genes), and such (Current Protocols in Protein Science (May, 2001, Unit 5.9, Table 5.9.1));

(2) amphibian cells: *Xenopus* oocytes, or such; and (3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:

yeasts: the *Saccharomyces* genus such as *Saccharomyces serevisiae*, and the *Pichia* genus such as *Pichia pastoris*; and filamentous fungi: the *Aspergillus* genus such as *Aspergillus niger*.

Furthermore, the present invention provides a method of decreasing binding activities to activating FcγRs, in particular FcγRIIa (R type), while maintaining its FcγRIIb-binding activity in comparison to those of a polypeptide comprising the parent Fc region, which comprises adding at least one amino acid alteration to the Fc region in a polypeptide comprising the Fc region.

The present invention further provides a method comprising the step of adding at least one amino acid alteration to an Fc region in a polypeptide comprising the Fc region, which is a method that results in suppressed production of antibodies against the polypeptide when the polypeptide is administered in vivo, in comparison to when a polypeptide comprising the parent Fc region is administered.

A preferred embodiment includes, for example, a combination of amino acid alterations described in the above-described method of producing a polypeptide comprising an Fc region variant with decreased binding activities to activating FcγRs, in particular FcγRIIa (R type), while maintaining its FcγRIIb-binding activity.

Polypeptides produced by any of the above-mentioned methods are also included in the present invention.

The present invention provides pharmaceutical compositions comprising the polypeptide comprising an Fc region variant of the present invention.

The pharmaceutical compositions of the present invention can be formulated, in addition to the antibody or Fc-fusion protein molecules of the present invention described above, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies or Fc-fusion protein molecules with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, polyoxyethylene hardened castor oil 60, saccharose, carboxymethyl cellulose, corn starch, inorganic salt, and such. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dosage of the pharmaceutical composition containing an antibody or a polynucleotide encoding an antibody can be selected, for example, from the range of 0.0001 mg to 1000 mg per kg of body weight. Alternatively, the dosage may be, for example, in the range of 0.001 to 100000 mg/body. However, the dosage is not limited to these values. The dosage and method of administration vary depending on the patient's body weight, age, and symptoms, and can be appropriately selected by those skilled in the art.

The above-mentioned polypeptides comprising an Fc region variant of the present invention are useful as active ingredients of pharmaceutical agents that suppress the activation of B cells, mast cells, dendritic cells, and/or basophils. Polypeptides comprising an Fc region variant of the present invention can suppress the activation of B cells, mast cells, dendritic cells, and/or basophils, by selectively working on FcγRIIb without activating FcγRs. B cell activation includes proliferation, IgE production, IgM production, and IgA production. The above-mentioned polypeptides comprising an Fc region variant of the present invention cross-link FcγRIIb with IgE to suppress IgE production of B cells, with IgM to suppress IgM production of B cells, and with IgA to suppress IgA production. Other than the above, suppressive effects similar to those mentioned above are exhibited by directly or indirectly cross-linking FcγRIIb with molecules that are expressed on B cells and comprise the ITAM domain inside the cell or interact with the ITAM domain such as BCR, CD19, and CD79b. Furthermore, activation of mast cells includes proliferation, activation by IgE and such, and degranulation. In mast cells, the above-mentioned polypeptides comprising an Fc region variant of the present invention can suppress proliferation, activation by IgE and such, and degranulation by directly or indirectly cross-linking FcγRIIb with IgE receptor molecules that are expressed on mast cells and comprise the ITAM domain or interact with the ITAM domain such as FcεRI, DAP12, and CD200R3. Activation of basophils includes proliferation and degranulation of basophils. Also in basophils, the above-mentioned polypeptides comprising an Fc region variant of the present invention can suppress proliferation, activation, and degranulation by directly or indirectly cross-linking FcγRIIb with molecules on the cell membrane, which comprise the ITAM domain inside the cell or interact with the ITAM domain. Activation of dendritic cells includes proliferation and degranulation of dendritic cells. Also in dendritic cells, the above-mentioned polypeptides comprising an Fc region variant of the present invention can suppress activation, degranulation, and proliferation by directly or indirectly cross-linking FcγRIIb with molecules on the cell membrane, which comprise the ITAM domain inside the cell or interact with the ITAM domain.

In the present invention, the polypeptides comprising an Fc region variant of the present invention mentioned above are useful as an active ingredient of therapeutic agents or preventive agents for immunological inflammatory diseases. As described above, since polypeptides comprising an Fc region variant of the present invention can suppress activation of B cells, mast cells, dendritic cells and/or basophils, administration of the polypeptides comprising an Fc region variant of the present invention as a result can treat or prevent immunological inflammatory diseases. Without being limited thereto, the term "immunological inflammatory diseases" comprises, rheumatoid arthritis, autoimmune hepatitis, autoimmune thyroiditis, autoimmune blistering diseases, autoimmune adrenocortical disease, autoimmune hemolytic anemia, autoimmune thrombocytopenic purpura, megalocytic anemia, autoimmune atrophic gastritis, autoimmune neutropenia, autoimmune orchitis, autoimmune encephalomyelitis, autoimmune receptor disease, autoimmune infertility, chronic active hepatitis, glomerulonephritis, interstitial pulmonary fibrosis, multiple sclerosis, Paget's disease, osteoporosis, multiple myeloma, uveitis, acute and chronic spondylitis, gouty arthritis, inflammatory bowel disease, adult respiratory distress syndrome (ARDS), psoriasis, Crohn's disease, Basedow's disease, juvenile diabetes, Addison's disease, myasthenia gravis, lens-induced uveitis, systemic lupus erythematosus, allergic rhinitis, allergic dermatitis, ulcerative colitis, hypersensitivity, muscle degeneration, cachexia, systemic scleroderma, localized scleroderma, Sjogren's syndrome, Behchet's disease, Reiter's syndrome, type I and type II diabetes, bone resorption disorder, graft-versus-host reaction, ischemia-reperfusion injury, atherosclerosis, brain trauma, cerebral malaria, sepsis, septic shock, toxic shock syndrome, fever, malgias due to staining, aplastic anemia, hemolytic anemia, idiopathic thrombocytopenia, Goodpasture's syndrome, Guillain-Barre syndrome, Hashimoto's thyroiditis, pemphigus, IgA nephropathy, pollinosis, antiphospholipid antibody syndrome, polymyositis, Wegener's granulomatosis, arteritis nodosa, mixed connective tissue disease, fibromyalgia, asthma, atopic dermatitis, chronic atrophic gastritis, primary biliary cirrhosis, primary sclerosing cholangitis, autoimmune pancreatitis, aortitis syndrome, rapidly progressive glomerulonephritis, megaloblastic anemia, idiopathic thrombocytopenic purpura, primary hypothyroidism, idiopathic Addison's disease, insulin-dependent diabetes mellitus, chronic discoid lupus erythematosus, pemphigoid, herpes gestationis, linear IgA bullous dermatosis, epidermolysis bullosa acquisita, alopecia areata, vitiligo vulgaris, leukoderma acquisitum centrifugum of Sutton, Harada's disease, autoimmune optic neuropathy, idiopathic azoospermia, habitual abortion, hypoglycemia, chronic urticaria, ankylosing spondylitis, psoriatic arthritis, enteropathic arthritis, reactive arthritis, spondyloarthropathy, enthesopathy, irritable bowel syndrome, chronic fatigue syndrome, dermatomyositis, inclusion body myositis, Schmidt's syndrome, Graves' disease, pernicious anemia, lupoid hepatitis, presenile dementia, Alzheimer's disease, demyelinating disorder, amyotrophic lateral sclerosis, hypoparathyroidism, Dressler's syndrome, Eaton-Lambert syndrome, dermatitis herpetiformis, alopecia, progressive systemic sclerosis, CREST syndrome (calcinosis, Raynaud's phenomenon, esophageal dysmotility, sclerodactyly, and telangiectasia), sarcoidosis, rheumatic fever, erythema multiforme, Cushing's syndrome, transfusion reaction, Hansen's disease, Takayasu arteritis, polymyalgia rheumatica, temporal arteritis, giant cell arthritis, eczema, lymphomatoid granulomatosis, Kawasaki disease, endocarditis, endomyocardial fibrosis, endophthalmitis, fetal erythroblastosis, eosinophilic fasciitis, Felty syndrome, Henoch-Schonlein purpura, transplant rejection, mumps, cardiomyopathy, purulent arthritis, familial Mediterranean fever, Muckle-Wells syndrome, and hyper-IgD syndrome.

Furthermore, in autoimmune diseases which may be caused by production of antibodies against autoantigens (autoantibodies), the polypeptides comprising an Fc region variant of the present invention mentioned above are useful as an active ingredient of pharmaceutical agents for treating or preventing the autoimmune diseases by suppressing production of those autoantibodies. Use of a molecule produced by fusing an antibody Fc portion with AchR (an autoantigen of myasthenia gravis) has been reported to suppress proliferation of B cells which express AchR-recognizing BCR, and induce apoptosis (J. Neuroimmunol, 227: 35-43, 2010). Use of a fusion protein formed between an antigen recognized by an autoantibody and an antibody Fc region of the present invention enables crosslinking of FcγRIIb with BCR of a B cell expressing BCR for that autoantigen, suppression of proliferation of B cells expressing BCR for the autoantigen, and induction of apoptosis. Such autoimmune diseases include Guillain-Barre syndrome, myasthenia gravis, chronic atrophic gastritis, autoimmune hepatitis, primary biliary cirrhosis, primary sclerosing cholangitis, autoimmune pancreatitis, aortitis syndrome, Goodpasture's syndrome, rapidly progressive glomerulonephritis, megaloblastic anemia, autoimmune hemolytic anemia, autoimmune neutropenia, idiopathic thrombocytopenic purpura, Basedow's disease, Hashimoto's thyroiditis, primary hypothyroidism, idiopathic Addison's disease, insulin-dependent diabetes mellitus, chronic discoid lupus erythematosus, localized scleroderma, pemphigus, pemphigoid, herpes gestationis, linear IgA bullous dermatosis, epidermolysis bullosa acquisita, alopecia areata, vitiligo vulgaris, leukoderma acquisitum centrifugum of Sutton, Harada's disease, autoimmune optic neuropathy, idiopathic azoospermia, habitual abortion, type II diabetes, hypoglycemia, and chronic urticaria; but are not limited thereto.

Furthermore, the above-mentioned polypeptides comprising an Fc Region variant of the present invention are useful as an active ingredient in therapeutic agents for diseases with deficiency of a biologically essential protein. For diseases with deficiency of a biologically essential protein, therapeutic methods that administer and supplement the protein as a pharmaceutical agent are used. However, since the patient lacks the protein from the beginning, the externally supplemented protein is recognized as a foreign substance and antibodies against that protein are produced. As a result, the protein becomes easily removed, and the effect as a pharmaceutical is reduced. Use of a fusion protein comprising such a protein and an antibody Fc region of the present invention enables crosslinking between FcγRIIb and BCR on B cells that recognize the protein, and enables suppression of antibody production against the protein. The proteins to be supplemented include Factor VIII, Factor IX, TPO, EPO, α-iduronidase, iduronate sulfatase, A-type heparan N-sulfatase, B type α-N-acetylglucosaminidase, C type acetyl CoA: α-glucosaminidase acetyltransferase, D type N-acetylglucosamine 6-sulfatase, galactose 6-sulfatase, N-acetylgalactosamine 4-sulfatase, β-glucuronidase, α-galactosidase, acidic α-galactosidase, and glucocerebrosidase. These proteins may be supplemented for diseases such as hemophilia, idiopathic thrombocytopenic purpura, renal anemia, and lysosomal disease (mucopolysaccharidosis, Fabry's disease, Pompe disease, and Gaucher's disease), without being limited thereto.

Furthermore, the above-mentioned polypeptides comprising an Fc region variant of the present invention are useful as an active ingredient for antiviral agents. Antibodies that comprise an Fc region of the present invention and are anti-virus antibodies can suppress antibody-dependent enhancement observed with anti-virus antibodies. Antibody-dependent enhancement is a phenomenon where a virus uses neutralizing antibodies against the virus to become phagocytosed via activating FcγRs, and infects FcγR-expressing cells so that the infection spreads. Binding of anti-dengue-virus neutralizing antibodies to FcγRIIb has been reported to play an important role in suppressing antibody-dependent enhancement (Proc. Natl. Acad. Sci. USA, 108: 12479-12484, 2011). Crosslinking FcγRIIb with an immune complex with dengue virus, which is formed by the anti-dengue-virus neutralizing antibodies, inhibits FcγR-mediated phagocytosis, resulting in the suppression of antibody-dependent enhancement. Examples of such viruses include dengue virus (DENV1, DENV2, and DENV4) and HIV, but are not limited thereto.

Furthermore, polypeptides comprising an Fc region variant of the present invention described above are useful as an active ingredient in preventive agents or therapeutic agents for arteriosclerosis. Antibodies against oxidized LDL, i.e., a cause for arteriosclerosis, which are antibodies comprising an Fc region of the present invention, can prevent FcγRIIa-dependent adhesion of inflammatory cells. It has been reported that while anti-oxidized LDL antibodies inhibit the interaction between oxidized LDL and CD36, anti-oxidized LDL antibodies bind to endothelial cells, and monocytes recognize their Fc portion in an FcγRIIa-dependent or FcγRI-dependent manner; and this leads to adhesion (Immunol. Lett., 108: 52-61, 2007). Using antibodies comprising an Fc region of the present invention for such antibodies may inhibit FcγRIIa-dependent binding and suppress monocyte adhesion by FcγRIIb-mediated inhibitory signals.

In the present invention, the above-mentioned polypeptides comprising the Fc region variants of the present invention are useful as active ingredients for therapeutic agents or prophylactic agents against cancer. As described above, by decreasing binding to all activating FcγRs and maintaining binding to FcγRIIb, platelet activation through the FcγRIIa-dependent mechanism can be suppressed while maintaining agonistic activity of agonist antibodies, and risk of thromboembolism and such may be reduced. Therefore, agonist antibodies using the Fc region variant of the present invention are useful for treatment or prevention of cancer. Specifically, the Fc region variant of the present invention enhances the agonistic activity of agonist antibodies against, for example, receptors of the TNF receptor family such as Aliases, CD120a, CD120b, Lymphotoxin β receptor, CD134, CD40, FAS, TNFRSF6B, CD27, CD30, CD137, TNFRSF10A, TNFRSF10B, TNFRSF10C, TNFRSF10D, RANK, Osteoprotegerin, TNFRSF12A, TNFRSF13B, TNFRSF13C, TNFRSF14, Nerve growth factor receptor, TNFRSF17, TNFRSF18, TNFRSF19, TNFRSF21, TNFRSF25, and Ectodysplasin A2 receptor and can be used for treating or preventing cancer. Furthermore, in addition to the above, agonistic activity is also enhanced for agonist antibodies against molecules which need to interact with FcγRIIb for exhibiting its agonistic activity. In addition, by incorporating the Fc region variant of the present invention into a polypeptide having binding activity to a molecule such as Kit, a type of receptor tyrosine kinase (RTK), which suppresses cell proliferation upon crosslinking with FcγRIIb, inhibitory effect against cells expressing such molecule may be enhanced. Without being limited thereto, cancer includes lung cancer (including small cell lung cancer, non-small cell lung cancer, pulmonary adenocarcinoma, and squamous cell carcinoma of the lung), large intestine cancer, rectal cancer, colon cancer, breast cancer, liver cancer, gastric cancer, pancreatic cancer, renal cancer, prostate cancer, ovarian cancer, thyroid cancer, cholangiocarcinoma, peritoneal cancer, mesothelioma, squamous cell carcinoma, cervical cancer, endometrial cancer, bladder cancer, esophageal cancer, head and neck cancer, nasopharyngeal cancer, salivary gland tumor, thymoma, skin cancer, basal cell tumor, malignant melanoma, anal cancer, penile cancer, testicular cancer, Wilms' tumor, acute myeloid leukemia (including acute myeloleukemia, acute myeloblastic leukemia, acute promyelocytic leukemia, acute myelomonocytic leukemia, and acute monocytic leukemia), chronic myelogenous leukemia, acute lymphoblastic leukemia, chronic lymphatic leukemia, Hodgkin's lymphoma, non-Hodgkin's lymphoma (Burkitt's lymphoma, chronic lymphocytic leukemia, mycosis fungoides, mantle cell lymphoma, follicular lymphoma, diffuse large-cell lymphoma, marginal zone lymphoma, pilocytic leukemia plasmacytoma, peripheral T-cell lymphoma, and adult T cell leukemia/lymphoma), Langerhans cell histiocytosis, multiple myeloma, myelodysplastic syndrome, brain tumor (including glioma, astroglioma, glioblastoma, meningioma, and ependymoma), neuroblastoma, retinoblastoma, osteosarcoma, Kaposi's sarcoma, Ewing's sarcoma, angiosarcoma, and hemangiopericytoma.

Furthermore, the present invention relates to methods for treating or preventing immunological inflammatory diseases, which comprise the step of administering to a subject (patient) a polypeptide comprising an Fc region variant of the present invention or a polypeptide comprising an Fc region variant produced by production methods of the present invention.

The present invention also provides kits for use in the therapeutic methods or preventive methods of the present invention, which comprises at least a polypeptide comprising an Fc region variant of the present invention or a polypeptide comprising an Fc region variant produced by production methods of the present invention, or a pharmaceutical composition of the present invention. In addition, pharmaceutically acceptable carriers, media, instructions on the method of use, and such may be included in the kit. Furthermore, the present invention relates to use of a polypeptide comprising an Fc region variant of the present invention or a polypeptide comprising an Fc region variant produced by production methods of the present invention in the production of agents for treating or preventing immunological inflammatory diseases. The present invention also relates to polypeptides comprising an Fc region variant of the present invention or polypeptides comprising an Fc region variant produced by production methods of the present invention for use in the therapeutic methods or preventive methods of the present invention.

As used herein, the three-letter and single-letter codes for respective amino acids are as follows:
Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

Herein below, the present invention will be specifically described further with reference to the Examples, but it is not to be construed as being limited thereto.

Example 1

Preparation of a pH-Dependent Anti-IgE Antibody (1-1) Preparation of an Anti-Human IgE Antibody In order to prepare a pH-dependent anti-human IgE antibody, human IgE (heavy chain, SEQ ID NO: 13; light chain, SEQ ID NO: 14) (its variable region is from an anti-human glypican 3 antibody) was expressed as an antigen using FreeStyle293 (Life Technologies). The expressed human IgE was prepared and purified by a general column chromatographic method known to those skilled in the art.

Antibodies that form large immune complexes comprising two or more anti-IgE antibody molecules and two or more IgE molecules, which show pH-dependent binding to human IgE, were selected from among the multiple antibodies obtained. Expression and purification of the selected anti-human IgE antibodies were carried out using the human IgG1 heavy chain constant regions and the human light chain constant regions. The produced antibody was named clone 278 (IgG1) (heavy chain SEQ ID NO: 10, light chain SEQ ID NO: 11).

(1-2) Evaluation of Binding Activities and pH-Dependent Binding Activities of Anti-Human IgE Antibodies Antibodies that can release antigens in the endosome can be produced using not only pH-dependent antigen binding but also Ca-dependent binding. Accordingly, the pH-dependent ability and pH/Ca-dependent ability to bind to human IgE (hIgE) were evaluated for clone 278 and Xolair (omalizumab, Novartis) used as a control which does not have pH-dependent IgE-binding ability.

More specifically, hIgE-binding activities (dissociation constant $K_D$ (M)) of clone 278 and Xolair were evaluated using Biacore T200 (GE Healthcare). Measurements were carried out using the following three types as running buffer:

1.2 mmol/l $CaCl_2$/0.05% tween20, 20 mmol/l ACES, 150 mmol/l NaCl, pH 7.4

1.2 mmol/l $CaCl_2$/0.05% tween20, 20 mmol/l ACES, 150 mmol/l NaCl, pH 5.8

3 μmol/l $CaCl_2$/0.05% tween20, 20 mmol/l ACES, 150 mmol/l NaCl, pH 5.8

A peptide produced by adding biotin to Lys present at the C terminus of a chemically synthesized human glypican 3 protein-derived sequence (SEQ ID NO: 12) (hereinafter written as "biotinylated GPC3 peptide") added at an appropriate amount was immobilized onto Sensor chip SA (GE Healthcare) utilizing the affinity between streptavidin and biotin. An appropriate concentration of human IgE was injected and trapped with the biotinylated GPC3 peptide to immobilize human IgE onto the chip. An appropriate concentration of clone 278 was injected as an analyte, and allowed to interact with human IgE on the sensor chip. Then, 10 mmol/L glycine-HCl (pH 1.5) was injected to regenerate the sensor chip. All of the assay for the interaction was performed at 37° C. Using Biacore T200 Evaluation Software (GE Healthcare), the assay results were analyzed by curve fitting to determine the binding rate constant ka (1/Ms) and dissociation rate constant kd (1/s). Dissociation constant KD (M) was calculated from the above constants. Then, the pH-dependent binding was assessed by calculating the KD ratio of each antibody between the conditions of pH 5.8/1.2 mM Ca and pH 7.4/1.2 mM Ca. The pH/Ca-dependent binding was assessed by calculating the KD ratio of each antibody between the conditions of pH 5.8/3 µM Ca and pH 7.4/1.2 mM Ca. The results are shown in Table 5.

method as described in Example 1. hIgE (Asp6) is a molecule in which asparagine has been replaced with aspartic acid in the six N-glycosylation sites in human IgE, so that time-dependent changes in the concentration of human IgE as an antigen in the plasma does not affect the heterogeneity of N-linked sugar chains of human IgE.

(2-2) Verification of the Effects of Clone 278 and Xolair to Accelerate Human IgE Elimination Using Normal Mice To C57BL/6J mice (Charles river Japan), hIgE (Asp6) alone was administered, or hIgE (Asp6) and an anti-hIgE

TABLE 5

| Antibody name (abbreviated) | Buffer condition | ka (1/Ms) | kd (1/s) | KD (M) | pH dependency KD(ph 5.8, 1.2 mM Ca)/ KD(pH 7.4, 1.2 mM Ca) | pH/Ca dependency KD(ph 5.8, 3 µM Ca)/ KD(pH 7.4, 1.2 mM Ca) |
|---|---|---|---|---|---|---|
| Clone 278 | pH 7.4, 1.2 mM Ca | 1.5E+06 | 3.6E−03 | 2.4E−09 | 842.5 | 1636.5 |
|  | pH 5.8, 1.2 mM Ca | 1.2E+05 | 2.3E−01 | 2.0E−06 |  |  |
|  | pH 5.8, 3 µM Ca | 6.2E+04 | 2.4E−01 | 3.9E−06 |  |  |
| Xolair | pH 7.4, 1.2 mM Ca | 2.5E+06 | 1.1E−02 | 4.4E−09 | 2.3 | 2.9 |
|  | pH 5.8, 1.2 mM Ca | 2.4E+06 | 2.4E−02 | 9.9E−09 |  |  |
|  | pH 5.8, 3 µM Ca | 1.4E+06 | 1.7E−02 | 1.3E−08 |  |  |

(1-3) Evaluation of the Formation of Immune Complexes with Clone 278 and Xolair

Figure 1:
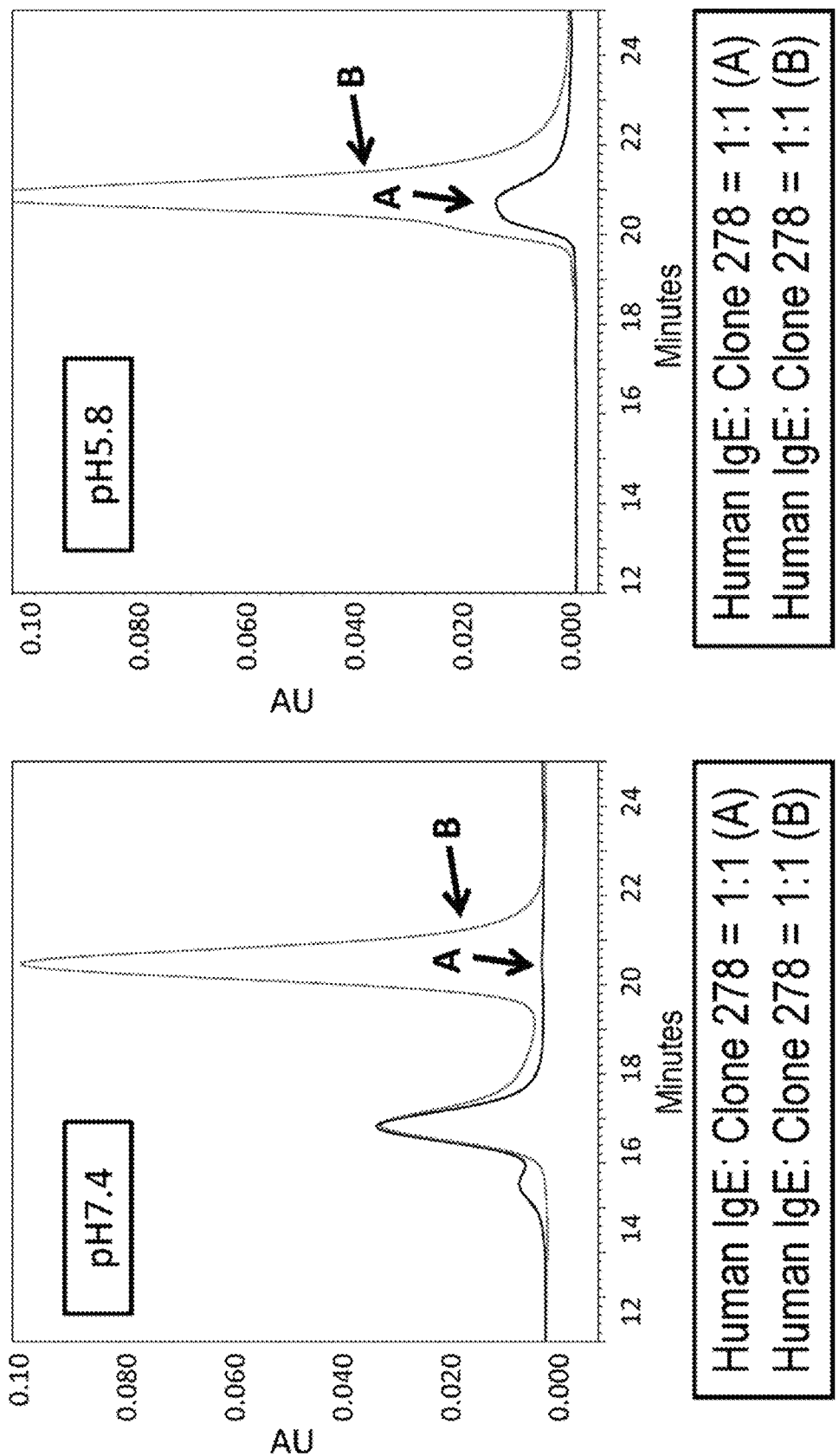

Formation of a large immune complex comprising two or more anti-IgE antibody molecules and two or more IgE molecules under a neutral condition (pH 7.4) by clone 278 and human IgE, and dissociation of that immune complex under an acidic condition (pH 5.8) were evaluated by gel filtration chromatography. Clone 278 dialyzed against 100 mM NaCl was diluted using a 20 mM Tris-HCl, 150 mM NaCl, 1.2 mM CaCl$_2$, pH 7.4 buffer to prepare samples under neutral conditions, or a 20 mM Bis-tris-HCl, 150 mM NaCl, 3 µM CaCl$_2$, pH 5.8 buffer to prepare samples under acidic conditions. Mixed solutions produced by mixing 100 µg/mL (0.06 µM) of hIgE (Asp6), which is a human IgE, and clone 278 at 1:1 and 1:6 molar ratios were left to stand at room temperature or in a 25° C. auto-sampler for two hours or longer, and then they were analyzed by gel filtration chromatography. For the mobile phase, 20 mM Tris-HCl, 300 mM NaCl, 1.2 mM CaCl$_2$, pH 7.4 and 20 mM Bis-tris-HCl, 300 mM NaCl, 3 µM CaCl$_2$, pH 5.8 were used under a neutral condition and an acidic condition, respectively. G4000SWxl (TOSOH) was used for the column and analyses were carried out at a flow rate of 0.5 mL/min at 25° C. The results are shown in FIG. 1. As shown in FIG. 1, clone 278 and human IgE were found to form large immune complexes comprising a tetramer having an apparent molecular weight of approximately 670 kDa (supposing that a single antibody molecule is a monomer) and larger multimers under a neutral condition. Such immune complexes were not observed under acidic conditions. Therefore, in a similar manner to the above-mentioned evaluation of binding using Biacore, these immune complexes were found to show pH-dependent dissociation.

Example 2

In Vivo Assessment of Clone 278 and Xolair (2-1) Preparation of Human IgE (hIgE (Asp6)) for In Vivo Assessment hIgE (Asp6) (its variable region is from an anti-human glypican 3 antibody), which is a human IgE for in vivo assessment, comprising the heavy chain (SEQ ID NO: 15) and light chain (SEQ ID NO: 14), was prepared by the same antibody (clone 278 or Xolair) were administered simultaneously, and then the in vivo kinetics of hIgE (Asp6) and anti-human IgE antibodies were evaluated. hIgE (Asp6) (20 µg/mL) or a mixed solution of hIgE (Asp6) and the anti-human IgE antibody (concentrations are shown in Table 6) was administered once at 10 mL/kg from the tail vein. Since each antibody is present sufficiently in excess with respect to hIgE (Asp6) at this point, most of the hIgE (Asp6) is considered to be bound to the antibody. Blood was collected from the mice 5 minutes, 2 hours, 7 hours, 1 day, 2 days, 4 days or 5 days, 7 days, 14 days, 21 days, and 28 days after administration. The collected blood samples were immediately subjected to centrifugation at 15,000 rpm for 5 minutes at 4° C. to obtain the plasma. The separated plasma samples were stored in a freezer set to −20° C. or lower until measurements were performed.

TABLE 6

| Anti-hIgE antibody | hIgE (Asp6) concentration in the administered solution (µg/mL) | Anti-hIgE antibody concentration in the administered solution (µg/mL) |
|---|---|---|
| Clone 278 | 20 | 100 |
| Xolair | 20 | 308 |

(2-3) Measurement of Plasma hIgE (Asp6) Concentration in Normal Mice

Plasma hIgE (Asp6) concentrations in mice were measured by ELISA. Calibration curve samples were prepared at plasma concentrations of 192, 96, 48, 24, 12, 6, and 3 ng/mL. To make the immune complexes formed between hIgE (Asp6) and an anti-hIgE antibody homogeneous, Xolair (Novartis) was added to the calibration curve samples and the mouse plasma measurement samples at 10 µg/mL, and these were left to stand at room temperature for 30 minutes. Subsequently, the calibration curve samples and the mouse plasma measurement samples were dispensed onto an anti-human IgE-immobilized immunoplate (MABTECH) or an anti-human IgE (clone 107, MABTECH)-immobilized immunoplate (Nunc F96 MicroWell Plate (Nalge nunc International)), and this was left to stand for two hours at room temperature or overnight at 4° C. Thereafter, the human GPC3 core protein (SEQ ID NO: 16), an anti-GPC3 antibody (prepared in-house) biotinylated with NHS-PEG4-

Figure 2:
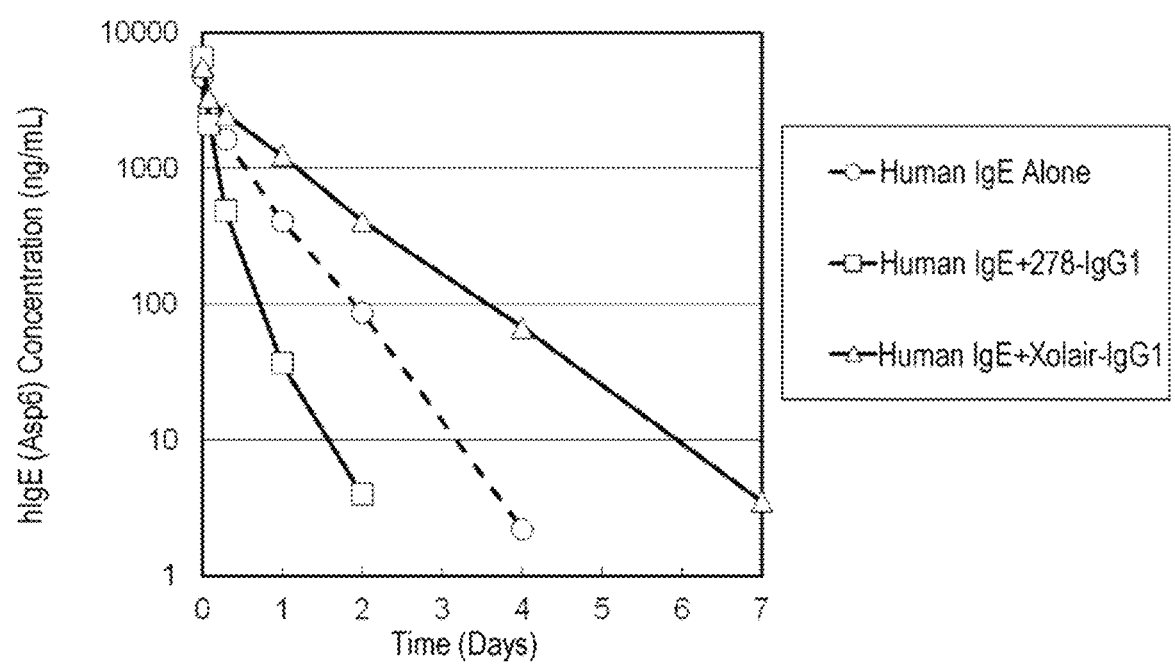

Biotin (Thermo Fisher Scientific), and Sterptavidin-PolyHRP80 (Stereospecific Detection Technologies) were individually reacted for one hour in a sequential manner. Concentrations in mouse plasma were measured using a method of measuring the absorbance at 450 nm with a microplate reader for color developed in a coloring reaction that uses TMB One Component HRP Microwell Substrate (BioFX Laboratories) as a substrate after the reaction is stopped with 1N-Sulfuric acid (Showa Chemical), or a method of measuring the luminescence intensity with a microplate reader after a luminescent reaction performed using SuperSignal® ELISA Pico Chemiluminescent Substrate (Thermo Fisher Scientific) as the substrate. The concentrations in mouse plasma were calculated from a calibration curve of luminescence intensity or absorbance values using the SOFTmax PRO analysis software (Molecular Devices). The change in plasma hIgE (Asp6) concentration after intravenous administration measured by this method is shown in FIG. 2. In the figure, clone 278 is noted as 278-IgG1 and Xolair as Xolair-IgG1.

Figure 3:
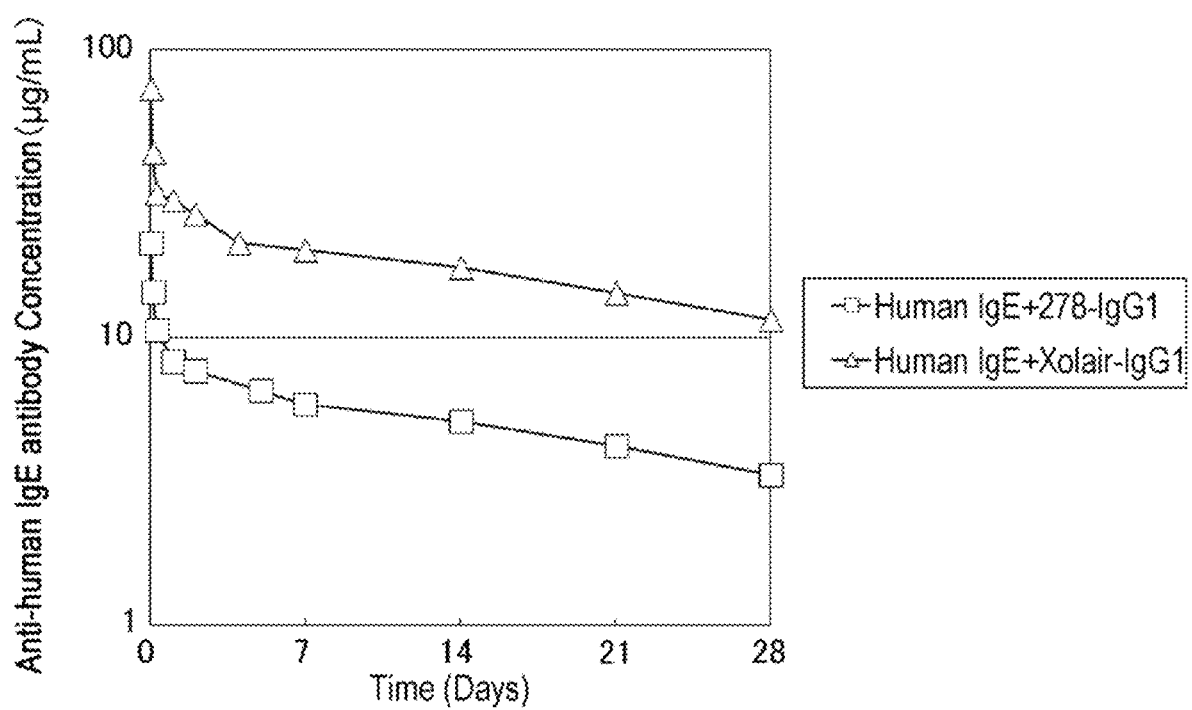

(2-4) Measurement of Plasma Anti-Human IgE Antibody Concentration in Normal Mice The anti-hIgE antibody concentration in mouse plasma was measured by ELISA. Calibration curve samples were prepared at plasma concentrations of 0.4, 0.2, 0.1, 0.05, 0.025, 0.0125, and 0.00625 µg/mL. To homogenize the immune complexes formed between hIgE (Asp6) and an anti-hIgE antibody, the calibration curve samples and the mouse plasma measurement samples were left to stand at room temperature for 30 minutes after addition of hIgE (Asp6) at 1 µg/mL. Subsequently, the calibration curve samples and the mouse plasma measurement samples were dispensed onto an anti-human kappa light chain antibody (Bethyl Laboratories)-immobilized immunoplate (Nunc-Immuno Plate, MaxiSorp (Nalge nunc International)), and this was left to stand for two hours at room temperature or overnight at 4° C. Thereafter, a rabbit anti-human IgG (Fc) secondary antibody, biotin conjugate (Pierce Biotechnology), and Streptavidin-PolyHRP80 (Stereospecific Detection Technologies) were individually reacted for one hour in a sequential manner. Concentrations in mouse plasma were determined using a method of measuring the absorbance at 450 nm with a microplate reader for color developed in a coloring reaction that uses TMB One Component HRP Microwell Substrate (BioFX Laboratories) as substrate after the reaction is stopped with 1N-sulfuric acid (Showa Chemical). The concentrations in mouse plasma were calculated from a calibration curve of absorbance values using the SOFTmax PRO analysis software (Molecular Devices). The change in plasma IgE antibody concentration after intravenous administration measured by this method is shown in FIG. 3. In the figure, clone 278 is noted as 278-IgG1 and Xolair as Xolair-IgG1.

As a result, when human IgE and Xolair which is the control anti-IgE antibody were administered simultaneously, elimination of human IgE became slow in comparison to elimination when human IgE was administered alone. On the other hand, with simultaneous administration of clone 278 which has a pH-dependent binding activity to human IgE, elimination of human IgE was found to be greatly accelerated compared to when human IgE was administered alone.

In WO2011/122011, a similar experiment has been performed using human IL-6 receptor (hsIL-6R) and antibodies that bind to hsIL-6R, but the results were different from the results of the present Examples. In Example 3 of WO2011/122011, when an IgG1 antibody which is an antibody (H54L28-IgG1) that binds to the human IL-6 receptor (hsIL-6R) but not in a pH-dependent manner had been administered simultaneously with an antigen to a normal mouse (C57BL/6J mouse), elimination of the human IL-6 receptor (the antigen) was not accelerated and was in fact slowed down in comparison to the case when the antigen alone was administered. When an antibody (Fv4-IgG1) that shows pH-dependent antigen binding had been administered simultaneously with an antigen, antigen elimination was slowed down in comparison to when the antigen alone was administered while antigen elimination was accelerated in comparison to when H54L28-IgG1 had been administered. This may have taken place since the antibody administration resulted in binding of the antibody to the antigen, which caused the antigen to move with the antibody, become recycled via FcRn in the same way as the antibody, and caused elimination from the blood to become difficult.

The result obtained from the present Examples is that simultaneous administration of an antigen with an antibody accelerates antigen elimination in comparison to when the antigen is administered alone, and appears to contradict previous reports. However, IgE used in the Examples as the antigen is a divalent antigen, and is different in the aspect that hsIL-6R is a monovalent antigen. When an anti-IgE antibody is added to IgE, a single antigen may be bound by two antibodies, and this leads to formation of an immune complex comprising multiple antigens and antibodies as observed in Example (1-3). By itself the antibody can only bind monovalently (with affinity) to FcγR which is an IgG receptor, but in the case of the above-described immune complex comprising multiple antigens and antibodies, it is possible to bind multivalently (with avidity) to FcγR. On the other hand, in the case of hsIL-6R, a single antigen can be bound by only one antibody; therefore, an immune complex comprising that antigen and antibody can only bind with FcγR monovalently (with affinity), and the interaction is very weak in comparison to when binding takes place with avidity. More specifically, an immune complex formed by IgE and its antibody binds strongly to FcγR with avidity, and as a result, it could be removed quickly from the blood via the liver or such that expresses FcγR.

Furthermore, when an antibody binds to the antigen, IgE, in a pH-dependent manner, the antigen-antibody immune complex is taken up into cells, and then the antigen dissociates in the endosome. Then, the antigen is not recycled with the antibody via FcRn, and the dissociated antigen is degraded in the lysosome. As a result, the antigen is considered to be eliminated more rapidly in comparison to when the antigen-antibody binding is not pH dependent.

Example 3

In Vivo Evaluation of Xolair and Clone 278 which has Reduced FcγR Binding (3-1) Obtaining Anti-Human IgE Antibodies with Reduced FcγR Binding Next, to verify whether the acceleration of antigen elimination observed in Example 2 comes from interaction between the immune complex and FcγR, a variant that has reduced binding to mouse FcγRs was produced from 278-IgG1 which binds to human IgE in a pH-dependent manner. To lower the binding to mouse FcγRs, Leu at position 235 was substituted with Arg, and Ser at position 239 was substituted with Lys in 278-IgG1, according to EU numbering, to produce 278-F760 (light chain SEQ ID NO: 11). DNA sequences encoding these genes were inserted into plasmids for expression in animals by a method known to those skilled in the art. These antibody variants expressed by the above-mentioned method using the animal cells introduced with the plasmids were purified, and then their concentrations were determined.

(3-2) Verification of the Effect of Xolair and Clone 278 which has Reduced FcγR Binding to Accelerate Human IgE Elimination Using Normal Mice By a method similar to that of (2-2), normal mice were used to verify the IgE elimination effect obtained when 278-F760 (light chain SEQ ID NO: 11) which has reduced binding to mouse FcγR was administered.

(3-3) Measurement of Plasma hIgE (Asp6) Concentration in Normal Mice

Figure 4:
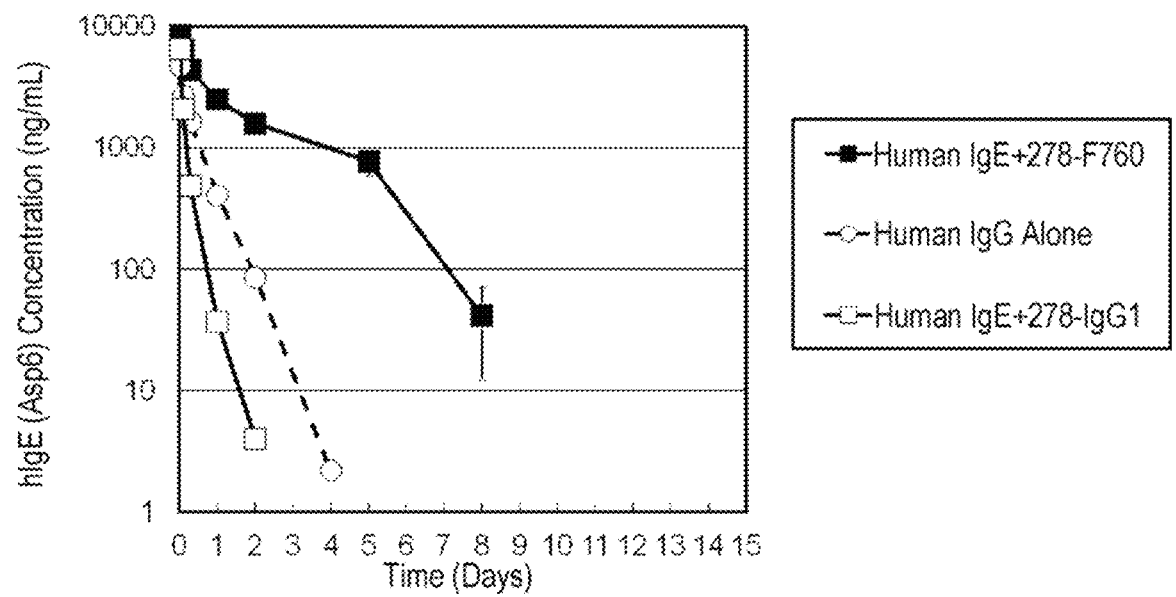

Plasma hIgE concentrations in normal mice were measured by a method similar to that of (2-3). The change in plasma hIgE concentration after intravenous administration measured by this method is shown in FIG. 4. For comparison, the change in plasma hIgE concentration upon administration of 278-IgG1 obtained in (2-3) is also shown in the figure.

(3-4) Measurement of Plasma Anti-Human IgE Antibody Concentration in Normal Mice The plasma anti-hIgE antibody concentration in normal mice was measured by a method similar to that of (2-4).

Figure 5:
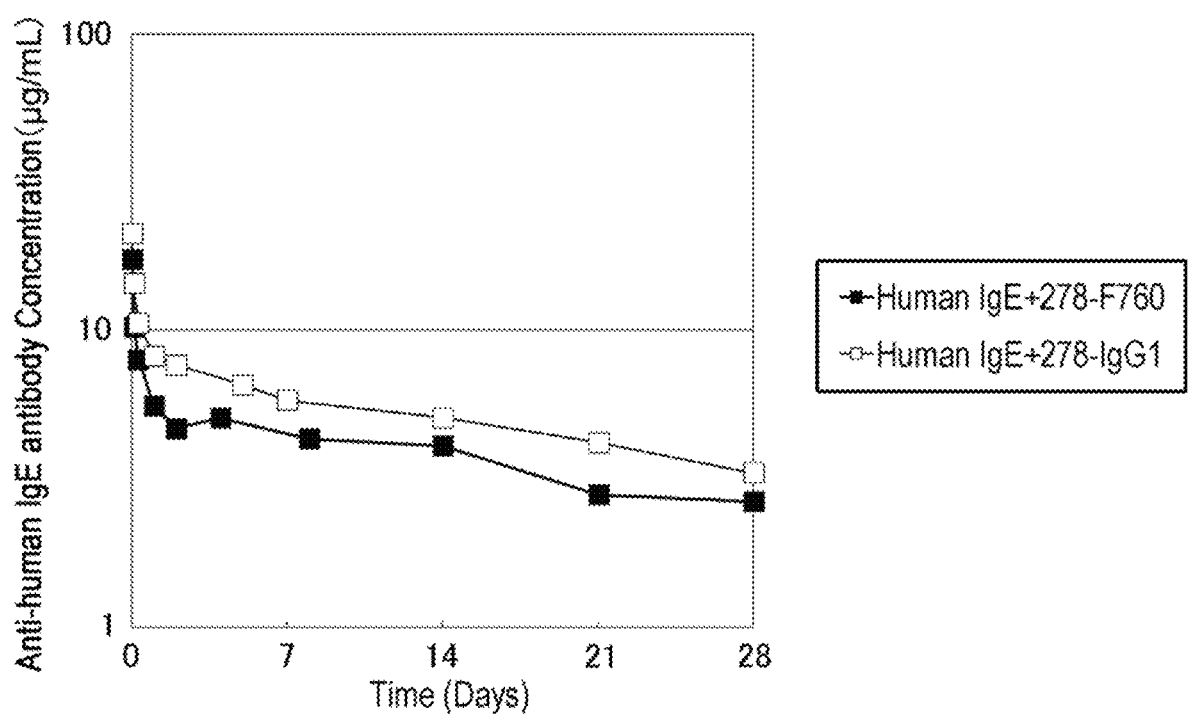
Figure 6:
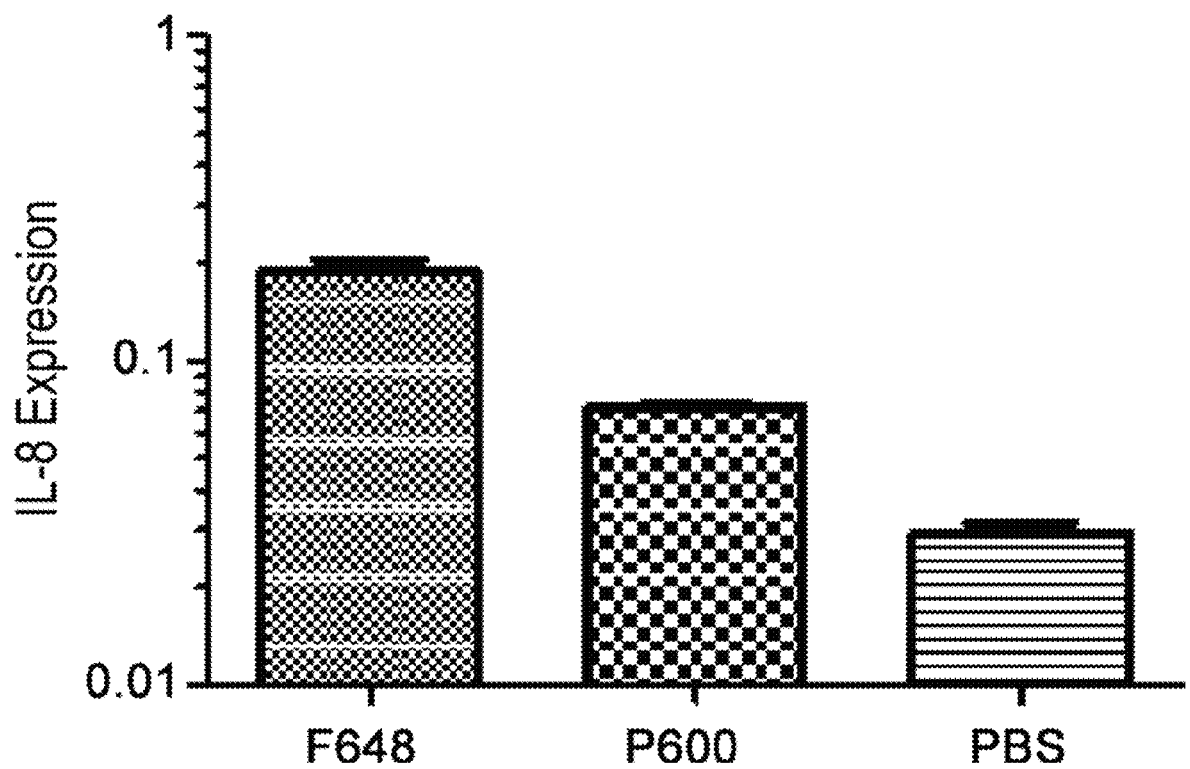

The change in plasma antibody concentration after intravenous administration measured by this method is shown in FIG. 5. For comparison, the change in plasma antibody concentration regarding 278-IgG1 obtained in (2-3) is also shown in the figure.

In the results of the present Examples, no major change in the shift of plasma antibody concentration was observed by reducing antibody binding to FcγR; however, the antigen elimination-accelerating effect of clone 278 upon administration of IgG1 antibody observed in Example 2 was remarkably attenuated. More specifically, acceleration of IgE elimination observed upon simultaneous administration with an anti-IgE antibody in Example 2 was shown to be derived from interaction between the administered antibody and FcγR.

Accordingly, to efficiently remove target antigens using antibodies, it may be necessary to form an immune complex comprising multiple antigens and antibodies, maintain FcγR binding of the antibody to a degree similar to that of a native IgG1 antibody, and preferably have pH-dependent binding of the antibody to antigen (antigen binding under acidic pH conditions is lowered in comparison to the binding under neutral conditions).

Example 4

Production of Variants Whose Binding to FcgRIIb is Maintained at a Level Similar to that of the Native Type while Binding to Other FcgRs has been Attenuated (4-1) Investigation of Alterations to be Combined with the P238D Alteration to Maintain Binding to FcgRIIb and Lower Binding to FcgRIIaR In the production of an antibody with selectively lowered binding only to activating FcgRs and while binding to FcgRIIb is maintained at a level similar to that of a native IgG1, the most difficult problem is to differentiate between FcgRIIa and FcgRIIb which have very high amino acid sequence homology in order to selectively reduce the binding activity. FcgRIIa has polymorphic forms, one where the amino acid at position 131 is Arg, and the other where this amino acid is His. The residue in FcgRIIb corresponding to this residue is Arg, and therefore, the sequence of FcgRIIb is more similar to the FcgRIIa R type sequence. Therefore, between the FcgRIIas, differentiating the FcgRIIa R type from FcgRIIb was considered to be a particularly difficult problem. As an alteration for improving binding selectivity for FcgRIIb over FcgRIIaR, the alteration of substituting Asp for Pro at position 238 according to EU numbering has been reported in WO2012/115241. The present investigation aims to use an antibody containing this alteration as the template to produce variants whose binding to FcgRIIb is maintained at a level similar to that of the native IgG1 while binding to other FcgRs is attenuated as much as possible.

Based on the results of X ray crystal structure analyses of a complex formed between Fc(P238D) and the extracellular region of FcγRIIb obtained in Example 5 of WO2012/115241, alterations were introduced comprehensively into an altered Fc with substitution of Asp for Pro at position 238 according to EU numbering at sites predicted to affect the interaction with FcγRIIb (the residues of positions 233, 234, 235, 236, 237, 239, 240, 241, 263, 265, 266, 267, 268, 271, 273, 295, 296, 298, 300, 323, 325, 326, 327, 328, 330, 332, and 334 according to EU numbering); and interaction with each FcγR was evaluated.

The variable region of IL6R-H (SEQ ID NO: 17), which is the variable region of the antibody against the human interleukin 6 receptor disclosed in WO 2009/125825, was produced as the antibody H chain variable region, and IL6R-G1d (SEQ ID NO: 3) comprising G1d prepared by deleting the C-terminal Gly and Lys of human IgG1, was produced as the antibody H chain constant region. Next, the method of Reference Example 1 was followed for substituting Asp for Pro at position 238 in IL6R-G1d, according to EU numbering, to produce IL6R-F648. Two types of H chains were prepared as the template H chain for introducing comprehensive alterations: IL6R-F652 (SEQ ID NO: 1) produced by introducing M252Y and N434Y to IL6R-F648; and IL6R-BF648 (SEQ ID NO: 2) produced by introducing K439E to IL6R-F648. The above-mentioned site of IL6R-F652 or IL6R-BF648 was introduced with 18 types of amino acids excluding the original amino acid and Cys. IL6R-L (SEQ ID NO: 6) was utilized as a common antibody L chain, and together with the respective H chain, the antibodies were expressed and purified according to the method of Reference Example 1. These antibody variants were expressed and purified according to the method of Reference Example 1, and binding to each of the FcγRs (FcγRIa, FcγRIIa H type, FcγRIIa R type, FcγRIIb, FcγRIIIa V type) was comprehensively evaluated by the method of Reference Example 2.

As a result, L235F, G237Q, F241M, F241L, H268P, Q295M, Q295V, Y296E, Y296H, Y296N, Y296D, S298A, S298M, V323I, S324N, S324H, A330H, and A330Y were found to be alterations that lower binding to FcgRIIaR without greatly decreasing binding to FcgRIIb when combined with the P238D alteration (Tables 7 and 8).

Table 7 and Table 8 show respectively the relative FcgRIIaR- and FcgRIIb-binding activities of variants discovered by comprehensively introducing alterations into IL6R-F652/IL6R-L and into IL6R-BF648/IL6R-L. These values are obtained by dividing values for the amount of each variant bound to FcgRIIaR or FcgRIIb by the values for the amount of IL6R-F652/IL6R-L or IL6R-BF648/IL6R-L bound to the respective FcgR, and then multiplying these values by 100.

TABLE 7

| Variant Name | Alterations introduced into IL6R-F652 | Relative FcgRIIaR-binding Activity | Relative FcgRIIb-binding Activity |
|---|---|---|---|
| IL6R-F652/IL6R-L | | 100.0 | 100.0 |
| IL6R-PD023/IL6R-L | A330H | 73.9 | 101.5 |
| IL6R-PD024/IL6R-L | A330Y | 60.0 | 74.4 |
| IL6R-PD089/IL6R-L | G237Q | 65.0 | 66.0 |
| IL6R-PD004/IL6R-L | H268P | 77.0 | 80.5 |
| IL6R-PD047/IL6R-L | L235F | 89.9 | 95.4 |
| IL6R-PD013/IL6R-L | S324H | 90.8 | 91.9 |
| IL6R-PD012/IL6R-L | S324N | 92.5 | 102.2 |

TABLE 8

| Variant Name | Alterations introduced into IL6R-BF648 | Relative FcgRIIaR-binding Activity | Relative FcgRIIb-binding Activity |
|---|---|---|---|
| IL6R-BF648/IL6R-L | | 100.0 | 100.0 |
| IL6R-2B044/IL6R-L | F241L | 55.7 | 65.5 |
| IL6R-2B045/IL6R-L | F241M | 64.7 | 81.1 |
| IL6R-2B118/IL6R-L | Q295M | 93.4 | 96.3 |
| IL6R-2B124/IL6R-L | Q295V | 65.2 | 72.9 |
| IL6R-2B128/IL6R-L | Y296D | 88.1 | 102.1 |
| IL6R-2B129/IL6R-L | Y296E | 68.4 | 93.3 |
| IL6R-2B132/IL6R-L | Y296H | 66.9 | 89.1 |
| IL6R-2B137/IL6R-L | Y296N | 77.7 | 98.3 |
| IL6R-2B145/IL6R-L | S298A | 45.1 | 55.5 |
| IL6R-2B154/IL6R-L | S298M | 77.5 | 79.4 |
| IL6R-2B169/IL6R-L | V323I | 90.8 | 102.9 |

From the results shown in Tables 7 and 8, all of these alterations were found to be those that lower FcgRIIaR binding while maintaining FcgRIIb binding to at least 55.5% or more in comparison to before introducing the alteration.

Therefore, the present investigation examined the production of variants whose FcgRIIaR binding is lowered as much as possible while FcgRIIb binding is maintained at a level similar to that of IgG1 by further combining these alterations. Specifically, alterations considered to selectively lower the binding to activating FcgRs in comparison to before introduction of the alterations in Tables 7 and 8, or combinations thereof were introduced into IL6R-F648. IL6R-L (SEQ ID NO: 6) was utilized as a common antibody L chain, and together with the respective H chain, the antibodies were expressed and purified according to the method of Reference Example 1. Binding of the obtained variants to FcgRIa, FcgRIIaR, FcgRIIaH, FcgRIIb, and FcgRIIIaV was evaluated according to the method of Reference Example 2. Table 9 shows the relative binding activities of each variant for FcgRIIaR and FcgRIIb. These are values obtained by dividing values for the amount of each variant bound to FcgRIIaR or FcgRIIb by values for the amount of IL6R-G1d/IL6R-L bound to FcgRIIaR or FcgRIIb, and then multiplying these values by 100.

TABLE 9

| Variant Name | Alteration(s) introduced into G1d | Relative FcgRIIaR-binding Activity | Relative FcgRIIb-binding Activity |
|---|---|---|---|
| IL6R-G1d/IL6R-L | | 100.0 | 100.0 |
| IL6R-F648/IL6R-L | P238D | 29.9 | 138.5 |
| IL6R-P589/IL6R-L | P238D/Y296E | 27.0 | 142.4 |
| IL6R-P590/IL6R-L | P238D/F241M | 20.6 | 126.2 |
| IL6R-P591/IL6R-L | P238D/F241M/Y296E | 20.0 | 131.2 |
| IL6R-P594/IL6R-L | P238D/F241L | 19.8 | 111.3 |
| IL6R-P595/IL6R-L | P238D/Q295V | 23.5 | 112.5 |
| IL6R-P596/IL6R-L | P238D/Q295M | 32.2 | 143.7 |
| IL6R-P597/IL6R-L | P238D/Y296H | 27.3 | 140.4 |
| IL6R-P598/IL6R-L | P238D/Y296N | 31.6 | 148.6 |
| IL6R-P599/IL6R-L | P238D/V323I | 30.9 | 148.9 |
| IL6R-P600/IL6R-L | P238D/S298A | 16.5 | 112.4 |
| IL6R-P601/IL6R-L | P238D/S298M | 27.3 | 131.7 |
| IL6R-P602/IL6R-L | P238D/F241M/Q295V/Y296E | 18.1 | 111.6 |
| IL6R-P603/IL6R-L | P238D/F241M/Y296E/V323I | 16.9 | 129.6 |
| IL6R-P604/IL6R-L | P238D/F241M/Y296E/S298A | 13.0 | 92.3 |
| IL6R-P605/IL6R-L | P238D/Y296D/S298A | 13.5 | 82.0 |
| IL6R-P653/IL6R-L | P238D/F241M/H268P/Y296E | 14.5 | 116.3 |
| IL6R-P654/IL6R-L | P238D/F241M/Y296E/S324N | 18.2 | 128.3 |
| IL6R-P655/IL6R-L | P238D/F241M/Y296E/S324H | 17.1 | 127.0 |
| IL6R-P656/IL6R-L | P238D/F241M/Y296E/A330H | 18.2 | 137.9 |
| IL6R-P657/IL6R-L | P238D/F241M/Y296E/A330Y | 15.4 | 115.0 |
| IL6R-P658/IL6R-L | L235F/P238D/F241M/Y296E | 20.8 | 149.2 |
| IL6R-P659/IL6R-L | G237Q/P238D/F241M/Y296E | 9.1 | 87.0 |
| IL6R-P660/IL6R-L | P238D/S298A/S324N | 14.7 | 100.4 |
| IL6R-P661/IL6R-L | P238D/S298A/A330H | 17.5 | 109.1 |
| IL6R-P662/IL6R-L | P238D/Y296D/S298A/S324N | 11.2 | 73.3 |
| IL6R-P663/IL6R-L | P238D/Y296D/S298A/A330H | 10.1 | 79.7 |
| IL6R-P687/IL6R-L | P238D/S298A/S324N/A330H | 12.6 | 100.2 |
| IL6R-P688/IL6R-L | P238D/F241M/H268P/Y296E/S324N | 13.3 | 113.7 |
| IL6R-P689/IL6R-L | P238D/F241M/H268P/Y296E/S324H | 10.1 | 102.9 |
| IL6R-P690/IL6R-L | G237Q/P238D/F241M/Y296E/A330H | 10.5 | 102.3 |
| IL6R-P691/IL6R-L | L235F/G237Q/P238D/F241M/Y296E | 10.7 | 103.6 |
| IL6R-P692/IL6R-L | L235F/G237Q/P238D/F241M/Y296E/A330H | 13.7 | 126.9 |

TABLE 9-continued

| Variant Name | Alteration(s) introduced into G1d | Relative FcgRIIaR-binding Activity | Relative FcgRIIb-binding Activity |
|---|---|---|---|
| IL6R-P693/IL6R-L | P238D/Y296E/S298A | 11.4 | 87.9 |
| IL6R-P718/IL6R-L | P238D/H268P | 20.5 | 122.9 |
| IL6R-P719/IL6R-L | P238D/S324N | 24.0 | 0.2 |
| IL6R-P720/IL6R-L | P238D/S324H | 21.5 | 125.6 |
| IL6R-P721/IL6R-L | P238D/A330H | 24.1 | 140.2 |
| IL6R-P722/IL6R-L | P238D/A330Y | 22.5 | 130.0 |
| IL6R-P723/IL6R-L | L235F/P238D | 24.0 | 128.5 |
| IL6R-P724/IL6R-L | G237Q/P238D | 17.8 | 101.2 |
| IL6R-P725/IL6R-L | P238D/Y296D | 24.5 | 135.7 |
| IL6R-P726/IL6R-L | G237Q/P238D/F241M/Y296E/S324H/A330H | 12.0 | 123.0 |
| IL6R-P727/IL6R-L | G237Q/P238D/F241M/H268P/Y296E/A330H | 8.3 | 107.9 |
| IL6R-P728/IL6R-L | L235F/G237Q/P238D/F241M/Y296E/S324H | 11.0 | 126.0 |
| IL6R-P729/IL6R-L | L235F/G237Q/P238D/F241M/H268P/Y296E | 10.0 | 126.6 |
| IL6R-P731/IL6R-L | G237Q/P238D/F241M/H268P/Y296E/S324H | 8.1 | 85.8 |
| IL6R-P732/IL6R-L | L235F/P238D/F241M/H268P/Y296E/S324H | 11.9 | 165.3 |
| IL6R-P733/IL6R-L | L235F/G237Q/P238D/F241M/H268P/Y296E/S324H | 6.3 | 103.5 |
| IL6R-P734/IL6R-L | L235F/G237Q/P238D/F241M/Y296E/S324H/A330H | 12.5 | 169.1 |
| IL6R-P735/IL6R-L | L235F/G237Q/P238D/F241M/H268P/Y296E/A330H | 11.3 | 173.1 |
| IL6R-P737/IL6R-L | G237Q/P238D/F241M/H268P/Y296E/S324H/A330H | 7.2 | 99.5 |

From among the variants shown in Table 9, variants whose FcgRIIaR binding has been lowered to 30% or less and FcgRIIb binding has been maintained at 80% or more in comparison to those of IL6R-G1d/IL6R-L are shown in Table 10 along with their KD values for each FcgR. Relative binding activity in the Table is a value obtained by dividing the KD value of IL6R-G 1 d/IL6R-L by the KD value of each variant, and represents the relative binding activity of each variant when the KD value of IL6R-G1d/IL6R-L for each FcgR is defined as 1. Among the KD values shown in the table, the values in the solid gray boxes are values calculated by utilizing Equation 2 of Reference Example 2, as the binding of FcgR to each variant is very weak and cannot be accurately analyzed by kinetic analysis.

$$KD = C \cdot R_{max}/(R_{eq} - RI) - C \quad \text{[Equation 2]}$$

TABLE 10

| Variant Name | Alteration(s) introduced into IL6R-G1d | KD (M) for FcgRIa | KD (M) for FcgRIIaR | KD (M) for FcgRIIaH | KD (M) for FcgRIIb |
|---|---|---|---|---|---|
| IL6R-G1d/IL6R-L | | 3.3E−10 | 1.2E−06 | 9.6E−07 | 5.1E−06 |
| IL6R-F648/IL6R-L | P238D | 8.0E−09 | 1.9E−05 | 7.9E−05 | 1.9E−06 |
| IL6R-P589/IL6R-L | P238D/Y296E | 1.0E−08 | 2.7E−05 | 8.3E−05 | 1.8E−06 |
| IL6R-P590/IL6R-L | P238D/F241M | 1.7E−08 | 3.6E−05 | 9.1E−05 | 2.8E−06 |
| IL6R-P591/IL6R-L | P238D/F241M/Y296E | 2.4E−08 | 3.7E−05 | 8.6E−05 | 3.1E−06 |
| IL6R-P594/IL6R-L | P238D/F241L | 1.4E−08 | 3.9E−05 | 1.1E−04 | 2.9E−06 |
| IL6R-P595/IL6R-L | P238D/Q295V | 1.1E−08 | 3.2E−05 | 1.0E−04 | 2.2E−06 |
| IL6R-P597/IL6R-L | P238D/Y296H | 1.7E−08 | 2.6E−05 | 8.3E−05 | 2.0E−06 |
| IL6R-P600/IL6R-L | P238D/S298A | 3.5E−09 | 4.8E−05 | 1.4E−04 | 4.4E−06 |
| IL6R-P601/IL6R-L | P238D/S298M | 4.0E−09 | 2.6E−05 | 9.7E−05 | 2.6E−06 |
| IL6R-P602/IL6R-L | P238D/F241M/Q295V/Y296E | 1.9E−08 | 4.4E−05 | 1.0E−04 | 2.4E−06 |
| IL6R-P603/IL6R-L | P238D/F241M/Y296E/V323I | 2.2E−08 | 4.7E−05 | 1.1E−04 | 2.7E−06 |
| IL6R-P604/IL6R-L | P238D/F241M/Y296E/S298A | 1.3E−08 | 6.4E−05 | 1.2E−04 | 5.5E−06 |
| IL6R-P605/IL6R-L | P238D/Y296D/S298A | 8.6E−09 | 6.0E−05 | 1.3E−04 | 5.3E−06 |
| IL6R-P653/IL6R-L | P238D/F241M/H268P/Y296E | 1.8E−08 | 5.1E−05 | 1.1E−04 | 3.5E−06 |
| IL6R-P654/IL6R-L | P238D/F241M/Y296E/S324N | 1.6E−08 | 3.9E−05 | 6.8E−05 | 2.6E−06 |
| IL6R-P655/IL6R-L | P238D/F241M/Y296E/S324H | 1.8E−08 | 4.2E−05 | 5.8E−05 | 2.7E−06 |
| IL6R-P656/IL6R-L | P238D/F241M/Y296E/A330H | 2.8E−08 | 3.9E−05 | 8.4E−05 | 1.9E−06 |
| IL6R-P657/IL6R-L | P238D/F241M/Y296E/A330Y | 1.7E−08 | 4.7E−05 | 1.1E−04 | 3.1E−06 |
| IL6R-P658/IL6R-L | L235F/P238D/F241M/Y296E | 8.3E−07 | 3.3E−05 | 9.6E−05 | 1.4E−06 |
| IL6R-P659/IL6R-L | G237Q/P238D/F241M/Y296E | 8.0E−08 | 8.5E−05 | 1.6E−04 | 6.4E−06 |
| IL6R-P660/IL6R-L | P238D/S298A/S324N | 7.4E−09 | 5.0E−05 | 1.1E−04 | 5.3E−06 |
| IL6R-P661/IL6R-L | P238D/S298A/A330H | 1.0E−08 | 4.1E−05 | 9.4E−05 | 4.0E−06 |
| IL6R-P687/IL6R-L | P238D/S298A/S324N/A330H | 7.0E−09 | 8.1E−05 | 1.3E−04 | 5.1E−06 |
| IL6R-P688/IL6R-L | P238D/F241M/H268P/Y296E/S324N | 1.3E−08 | 5.8E−05 | 1.1E−04 | 4.1E−06 |
| IL6R-P689/IL6R-L | P238D/F241M/H268P/Y296E/S324H | 2.8E−08 | 7.8E−05 | 1.2E−04 | 4.7E−06 |
| IL6R-P690/IL6R-L | G237Q/P238D/F241M/Y296E/A330H | 3.1E−07 | 7.4E−05 | 1.4E−04 | 4.0E−06 |
| IL6R-P691/IL6R-L | L235F/G237Q/P238D/F241M/Y296E | 7.6E−07 | 7.2E−05 | 1.3E−04 | 4.3E−06 |
| IL6R-P692/IL6R-L | L235F/G237Q/P238D/F241M/Y296E/A330H | 5.3E−07 | 5.6E−05 | 1.2E−04 | 2.7E−06 |
| IL6R-P693/IL6R-L | P238D/Y296E/S298A | 7.8E−09 | 6.8E−05 | 1.5E−04 | 5.6E−06 |
| IL6R-P718/IL6R-L | P238D/H268P | 1.3E−08 | 3.4E−05 | 1.1E−04 | 3.2E−06 |
| IL6R-P719/IL6R-L | P238D/S324N | 8.3E−09 | 2.8E−05 | 7.9E−05 | 2.2E−06 |
| IL6R-P720/IL6R-L | P238D/S324H | 9.7E−09 | 3.2E−05 | 7.3E−05 | 2.6E−06 |
| IL6R-P721/IL6R-L | P238D/A330H | 1.8E−08 | 2.8E−05 | 8.8E−05 | 1.8E−06 |
| IL6R-P722/IL6R-L | P238D/A330Y | 1.4E−08 | 3.0E−05 | 9.7E−05 | 2.9E−06 |
| IL6R-P723/IL6R-L | L235F/P238D | 8.6E−07 | 2.8E−05 | 8.5E−05 | 2.1E−06 |

TABLE 10-continued

| | | | | | |
|---|---|---|---|---|---|
| IL6R-P724/IL6R-L | G237Q/P238D | 3.3E−08 | 4.0E−05 | 1.2E−04 | 4.6E−06 |
| IL6R-P725/IL6R-L | P238D/Y296D | 1.6E−08 | 2.7E−05 | 9.0E−05 | 1.9E−06 |
| IL6R-P726/IL6R-L | G237Q/P238D/F241M/Y296E/S324H/A330H | 1.9E−07 | 6.6E−05 | 6.1E−05 | 4.1E−06 |
| IL6R-P727/IL6R-L | G237Q/P238D/F241M/H268P/Y296E/A330H | 2.3E−07 | 1.0E−04 | 1.5E−04 | 4.8E−06 |
| IL6R-P728/IL6R-L | L235F/G237Q/P238D/F241M/Y296E/S324H | 5.8E−07 | 7.4E−05 | 8.1E−05 | 3.9E−06 |
| IL6R-P729/IL6R-L | L235F/G237Q/P238D/F241M/H268P/Y296E | 6.6E−07 | 8.3E−05 | 1.8E−04 | 4.4E−06 |
| IL6R-P731/IL6R-L | G237Q/P238D/F241M/H268P/Y296E/S324H | 6.8E−08 | 1.1E−04 | 1.5E−04 | 1.0E−05 |
| IL6R-P732/IL6R-L | L235F/P238D/F241M/H268P/Y296E/S324H | 7.0E−07 | 7.2E−05 | 1.0E−04 | 2.9E−06 |
| IL6R-P733/IL6R-L | L235F/G237Q/P238D/F241M/H268P/Y296E/S324H | 2.5E−06 | 1.3E−04 | 1.8E−04 | 4.7E−06 |
| IL6R-P734/IL6R-L | L235F/G237Q/P238D/F241M/Y296E/S324H/A330H | 2.2E−07 | 6.8E−05 | 8.4E−05 | 2.5E−06 |
| IL6R-P735/IL6R-L | L235F/G237Q/P238D/F241M/H268P/Y296E/A330H | 2.6E−07 | 5.9E−05 | 1.4E−04 | 2.3E−06 |
| IL6R-P737/IL6R-L | G237Q/P238D/F241M/H268P/Y296E/S324H/A330H | 1.7E−07 | 1.2E−04 | 1.6E−04 | 6.4E−06 |

| Variant Name | KD (M) for FcgRIIIaV | Relative FcgRIa-binding Activity | Relative FcgRIIaR-binding Activity | Relative FcgRIIaH-binding Activity | Relative FcgRIIb-binding Activity | Relative FcgRIIIaV-binding Activity |
|---|---|---|---|---|---|---|
| IL6R-G1d/IL6R-L | 3.4E−07 | 1.0000 | 1.000 | 1.000 | 1.000 | 1.000 |
| IL6R-F648/IL6R-L | 6.9E−05 | 0.0413 | 0.065 | 0.012 | 2.749 | 0.005 |
| IL6R-P589/IL6R-L | 4.1E−05 | 0.0330 | 0.046 | 0.012 | 2.856 | 0.008 |
| IL6R-P590/IL6R-L | 6.6E−05 | 0.0194 | 0.034 | 0.011 | 1.836 | 0.005 |
| IL6R-P591/IL6R-L | 4.4E−05 | 0.0138 | 0.034 | 0.011 | 1.647 | 0.008 |
| IL6R-P594/IL6R-L | 6.4E−05 | 0.0236 | 0.032 | 0.009 | 1.766 | 0.005 |
| IL6R-P595/IL6R-L | 7.1E−05 | 0.0300 | 0.039 | 0.010 | 2.315 | 0.005 |
| IL6R-P597/IL6R-L | 4.5E−05 | 0.0194 | 0.048 | 0.012 | 2.636 | 0.008 |
| IL6R-P600/IL6R-L | 6.1E−05 | 0.0943 | 0.026 | 0.007 | 1.163 | 0.006 |
| IL6R-P601/IL6R-L | 5.4E−05 | 0.0825 | 0.048 | 0.010 | 2.000 | 0.006 |
| IL6R-P602/IL6R-L | 6.1E−05 | 0.0174 | 0.028 | 0.010 | 2.133 | 0.006 |
| IL6R-P603/IL6R-L | 8.3E−05 | 0.0150 | 0.026 | 0.009 | 1.897 | 0.004 |
| IL6R-P604/IL6R-L | 4.0E−05 | 0.0254 | 0.019 | 0.008 | 0.938 | 0.008 |
| IL6R-P605/IL6R-L | 4.4E−05 | 0.0384 | 0.021 | 0.007 | 0.977 | 0.008 |
| IL6R-P653/IL6R-L | 5.0E−05 | 0.0183 | 0.024 | 0.009 | 1.456 | 0.007 |
| IL6R-P654/IL6R-L | 4.8E−05 | 0.0206 | 0.032 | 0.014 | 2.016 | 0.007 |
| IL6R-P655/IL6R-L | 4.6E−05 | 0.0183 | 0.030 | 0.017 | 1.890 | 0.007 |
| IL6R-P656/IL6R-L | 5.0E−05 | 0.0118 | 0.032 | 0.011 | 2.677 | 0.007 |
| IL6R-P657/IL6R-L | 6.5E−05 | 0.0194 | 0.026 | 0.009 | 1.637 | 0.005 |
| IL6R-P658/IL6R-L | 7.1E−05 | 0.0004 | 0.038 | 0.010 | 3.807 | 0.005 |
| IL6R-P659/IL6R-L | 7.3E−05 | 0.0041 | 0.015 | 0.006 | 0.807 | 0.005 |
| IL6R-P660/IL6R-L | 3.0E−05 | 0.0446 | 0.025 | 0.009 | 0.972 | 0.011 |
| IL6R-P661/IL6R-L | 2.9E−05 | 0.0330 | 0.030 | 0.010 | 1.285 | 0.012 |
| IL6R-P687/IL6R-L | 4.2E−05 | 0.0471 | 0.020 | 0.007 | 1.006 | 0.008 |
| IL6R-P688/IL6R-L | 4.4E−05 | 0.0254 | 0.021 | 0.009 | 1.269 | 0.008 |
| IL6R-P689/IL6R-L | 5.2E−05 | 0.0118 | 0.016 | 0.008 | 1.091 | 0.007 |
| IL6R-P690/IL6R-L | 6.3E−05 | 0.0011 | 0.017 | 0.007 | 1.279 | 0.005 |
| IL6R-P691/IL6R-L | 4.8E−05 | 0.0004 | 0.017 | 0.007 | 1.187 | 0.007 |
| IL6R-P692/IL6R-L | 5.7E−05 | 0.0006 | 0.022 | 0.008 | 1.890 | 0.006 |
| IL6R-P693/IL6R-L | 4.0E−05 | 0.0423 | 0.018 | 0.006 | 0.918 | 0.008 |
| IL6R-P718/IL6R-L | 4.2E−05 | 0.0254 | 0.036 | 0.009 | 1.616 | 0.008 |
| IL6R-P719/IL6R-L | 5.6E−05 | 0.0398 | 0.044 | 0.012 | 2.358 | 0.006 |
| IL6R-P720/IL6R-L | 6.4E−05 | 0.0340 | 0.039 | 0.013 | 2.008 | 0.005 |
| IL6R-P721/IL6R-L | 6.2E−05 | 0.0183 | 0.044 | 0.011 | 2.840 | 0.006 |
| IL6R-P722/IL6R-L | 4.9E−05 | 0.0236 | 0.041 | 0.010 | 1.760 | 0.007 |
| IL6R-P723/IL6R-L | 3.9E−05 | 0.0300 | 0.044 | 0.011 | 2.448 | 0.009 |
| IL6R-P724/IL6R-L | 4.7E−05 | 0.0100 | 0.031 | 0.008 | 1.130 | 0.007 |
| IL6R-P725/IL6R-L | 4.5E−05 | 0.0206 | 0.046 | 0.011 | 2.749 | 0.008 |
| IL6R-P726/IL6R-L | 3.6E−05 | 0.0017 | 0.019 | 0.016 | 1.251 | 0.009 |
| IL6R-P727/IL6R-L | 6.6E−05 | 0.0014 | 0.012 | 0.007 | 1.064 | 0.005 |
| IL6R-P728/IL6R-L | 5.0E−05 | 0.0006 | 0.017 | 0.012 | 1.311 | 0.007 |
| IL6R-P729/IL6R-L | 5.6E−05 | 0.0005 | 0.015 | 0.005 | 1.166 | 0.006 |
| IL6R-P731/IL6R-L | 5.3E−05 | 0.0049 | 0.012 | 0.007 | 0.499 | 0.006 |
| IL6R-P732/IL6R-L | 7.6E−05 | 0.0005 | 0.017 | 0.010 | 1.748 | 0.004 |
| IL6R-P733/IL6R-L | 7.7E−05 | 0.0001 | 0.009 | 0.006 | 1.089 | 0.004 |
| IL6R-P734/IL6R-L | 1.0E−04 | 0.0015 | 0.018 | 0.011 | 2.073 | 0.003 |
| IL6R-P735/IL6R-L | 7.3E−05 | 0.0013 | 0.021 | 0.007 | 2.264 | 0.005 |
| IL6R-P737/IL6R-L | 6.8E−05 | 0.0020 | 0.011 | 0.006 | 0.802 | 0.005 |

Among the alterations introduced in this examination, it was shown that P589 produced by introducing Y296E, P590 produced by introducing F241M, P594 produced by introducing F241L, P595 produced by introducing Q295V, P597 produced by introducing Y296H, P600 produced by introducing S298A, P601 produced by introducing S298M, P718 produced by introducing H268P, P719 produced by introducing S324N, P720 produced by introducing S324H, P721 produced by introducing A330H, P722 produced by introducing A330Y, P723 produced by introducing L235F, P724 produced by introducing G237Q, and P725 produced by introducing Y296D have an effect of lowering FcgRIIaR binding in comparison to binding by F648 before introducing the alteration, while maintaining FcgRIIb binding to the same level as or stronger than the binding by G1d. Among these, P600 produced by introducing S298A had the most reduced FcgRIIaR binding. The FcgRIIaR-binding was lowered to 0.026-fold while FcgRIIb-binding was maintained at 1.2 times that of G1d.

As a result of examining combinations of alterations that showed an effect of selectively lowering binding to activating FcgRs, P727 was found to have 1.0-fold or higher FcgRIIb-binding in comparison to that of G1d, and the most reduced FcgRIIaR binding. In P727, the FcgRIIb binding was maintained at 1.1 times that of G1d, and the FcgRIIaR-binding was attenuated to 0.012 times. Furthermore, since its FcgRIa-binding was 0.0014 times that of G1d, FcgRIIaH-binding was attenuated to 0.007 times, and FcgRIIIaV binding was attenuated to 0.005 times, this was found to be an excellent variant having very selectively attenuated binding to activating FcgRs other than FcgRIIb.

(4-2) Examination of Lowering FcgRIIaR Binding of Variants with Enhanced FcgRIIb Binding Next, variants whose FcgRIIb binding is maintained at a level similar to that of IgG1 while binding to other FcgRs is lowered in comparison to those of IgG1 were expected to be obtainable by introducing alterations that lower binding to all FcgRs including FcgRIIb into a template variant with selectively enhanced FcgRIIb binding but whose binding to other FcgRs has not been enhanced or has been lowered.

First, IL6R-B3 (SEQ ID NO: 4) was produced by introducing K439E into IL6R-G1d (SEQ ID NO: 3). Introducing FcgRIIb-selective binding in combination into IL6R-B3 produced variants with selectively enhanced FcgRIIb binding. IL6R-L (SEQ ID NO: 6) was utilized as a common antibody L chain, and together with the respective H chain, the antibodies were expressed and purified according to the method of Reference Example 1. Binding of the obtained variants to FcgRIa, FcgRIIaR, FcgRIIaH, FcgRIIb, and FcgRIIIaV was evaluated according the method of Reference Example 2. Binding activities of the produced variants for each FcgR are shown in Table 11. Relative binding activities shown in the table are values obtained by dividing the KD value of IL6R-B3/IL6R-L by the KD value of each variant, and represent the relative binding activities for each variant when the KD value of IL6R-B3/IL6R-L for each FcgR is defined as 1. "KD(IIaR)/KD(IIb)" is a value obtained by dividing the KD value of each variant for FcgRIIaR by the KD value of the variant for FcgRIIb; and the greater this value, the higher the selectivity for FcgRIIb. Among the KD values shown in the table, the values in the solid gray boxes are values calculated by utilizing Equation 2 of Reference Example 2, as the binding of FcgR to each variant is very weak and cannot be accurately analyzed by kinetic analysis.

$$KD = C \cdot R_{max}/(R_{eq} - RI) - C \quad \text{[Equation 2]}$$

TABLE 11

| Variant Name | Alteration(s) introduced into IL6R-B3 | KD (mol/L) for FcgRIa | KD (mol/L) for FcgRIIaR | KD (mol/L) for FcgRIIaH | KD (mol/L) for FcgRIIb | KD (mol/L) for FcgRIIIaV | KD(IIaR)/KD(IIb) | Relative FcgRIIaR-binding Activity | Relative FcgRIIb-binding Activity |
|---|---|---|---|---|---|---|---|---|---|
| IL6R-G1d/IL6R-L |  | 3.2E−10 | 1.0E−06 | 6.7E−07 | 2.6E−06 | 3.5E−07 | 0.4 | 1.1 | 1.2 |
| IL6R-B3/IL6R-L | * | 4.2E−10 | 1.1E−06 | 7.7E−07 | 3.1E−06 | 3.3E−07 | 0.3 | 1.0 | 1.0 |
| IL6R-BF648/IL6R-L | P238D | 1.1E−08 | 1.5E−05 | 4.0E−05 | 1.2E−06 | 7.0E−05 | 13.0 | 0.1 | 2.6 |
| IL6R-2B253/IL6R-L | P238D/V323M/E233D | 1.4E−09 | 5.0E−06 | 1.3E−05 | 4.3E−07 | 5.0E−05 | 11.6 | 0.2 | 7.2 |
| IL6R-2B261/IL6R-L | P238D/E233D/Y296D | 9.0E−09 | 2.2E−05 | 3.3E−05 | 1.0E−06 | 7.3E−05 | 22.0 | 0.2 | 3.1 |
| IL6R-BP082/IL6R-L | E233D/P238D/A330K | 1.8E−08 | 1.2E−05 | 3.7E−05 | 5.4E−07 | 8.1E−05 | 22.8 | 0.1 | 5.8 |
| IL6R-BP083/IL6R-L | P238D/Y296D/A330K | 3.8E−08 | 2.3E−05 | 4.4E−05 | 7.9E−07 | 6.6E−05 | 29.0 | 0.0 | 3.9 |
| IL6R-BP084/IL6R-L | P238D/V323M/A330K | 7.0E−09 | 7.2E−06 | 2.4E−05 | 5.0E−07 | 6.7E−05 | 14.3 | 0.1 | 6.1 |
| IL6R-BP085/IL6R-L | G237D/P238D/A330K | 2.9E−07 | 4.2E−06 | 2.4E−05 | 3.2E−07 | 6.8E−05 | 13.1 | 0.3 | 9.6 |
| IL6R-BP086/IL6R-L | P238D/K326A/A330K | 2.7E−08 | 9.7E−06 | 3.4E−05 | 5.7E−07 | 5.7E−05 | 17.1 | 0.1 | 5.4 |
| IL6R-BP087/IL6R-L | L234Y/P238D/A330K | 3.8E−08 | 9.7E−06 | 2.1E−05 | 6.1E−07 | 4.4E−05 | 16.0 | 0.1 | 5.1 |
| IL6R-BP088/IL6R-L | G237D/P238D/K326A/A330K | 3.9E−07 | 2.9E−06 | 2.3E−05 | 2.2E−07 | 5.7E−05 | 13.3 | 0.4 | 14.3 |
| IL6R-BP089/IL6R-L | L234Y/P238D/K326A/A330K | 6.3E−08 | 6.4E−06 | 2.0E−05 | 3.9E−07 | 5.1E−05 | 16.6 | 0.2 | 8.0 |
| IL6R-BP129/IL6R-L | E233D/P238D/Y296D/A330K | 2.5E−08 | 5.3E−06 | 4.0E−05 | 5.2E−07 | 7.5E−05 | 29.3 | 0.1 | 6.0 |
| IL6R-BP130/IL6R-L | E233D/P238D/V323M/A330K | 1.8E−09 | 5.3E−06 | 2.6E−05 | 3.0E−07 | 7.1E−05 | 17.5 | 0.2 | 10.2 |
| IL6R-BP131/IL6R-L | E233D/G237D/P238D/A330K | 1.2E−07 | 3.1E−06 | 1.4E−05 | 2.5E−07 | 5.9E−05 | 12.5 | 0.4 | 12.6 |
| IL6R-BP132/IL6R-L | E233D/P238D/K326A/A330K | 1.5E−08 | 8.0E−06 | 3.0E−05 | 3.7E−07 | 5.8E−05 | 21.5 | 0.1 | 8.4 |
| IL6R-BP133/IL6R-L | E233D/L234Y/P238D/A330K | 1.3E−07 | 8.6E−06 | 2.6E−05 | 5.6E−07 | 6.2E−05 | 15.5 | 0.1 | 5.6 |
| IL6R-BP143/IL6R-L | L234Y/P238D/K326A | 1.6E−08 | 5.7E−06 | 2.7E−05 | 5.7E−07 | 6.2E−05 | 10.0 | 0.2 | 5.4 |
| IL6R-BP144/IL6R-L | G237D/P238D/K326A | 3.7E−08 | 6.9E−06 | 3.6E−05 | 7.9E−07 | 5.4E−05 | 8.7 | 0.2 | 3.9 |
| IL6R-BP145/IL6R-L | L234Y/G237D/P238D | 1.2E−07 | 3.4E−06 | 1.7E−05 | 3.4E−07 | 4.5E−05 | 9.9 | 0.3 | 9.1 |
| IL6R-BP146/IL6R-L | L234Y/G237D/P238D/K326A | 7.4E−08 | 2.1E−06 | 1.8E−05 | 2.3E−07 | 3.8E−05 | 9.3 | 0.5 | 13.7 |
| IL6R-BP147/IL6R-L | E233D/G237D/P238D/K326A/A330K | 1.4E−07 | 8.9E−07 | 5.1E−06 | 6.6E−08 | 3.3E−05 | 13.6 | 1.2 | 47.1 |
| IL6R-BP148/IL6R-L | E233D/L234Y/G237D/P238D/K326A/A330K | 8.9E−08 | 1.1E−06 | 7.0E−06 | 7.5E−08 | 3.0E−05 | 14.5 | 1.0 | 41.4 |
| IL6R-BP149/IL6R-L | E233D/L234Y/G237D/P238D/Y296D/K326A/A330K | 1.2E−08 | 1.4E−06 | 8.4E−06 | 9.3E−08 | 3.7E−05 | 15.0 | 0.8 | 33.1 |
| IL6R-BP150/IL6R-L | E233D/P238D/P271G/Y296D/A330K | 1.0E−08 | 2.6E−06 | 3.4E−05 | 3.1E−07 | 5.8E−05 | 17.7 | 0.4 | 28.3 |
| IL6R-BP151/IL6R-L | E233D/P238D/P271G/K326A/A330K | 3.2E−07 | 5.5E−07 | 4.7E−06 | 4.0E−08 | 3.1E−05 | 16.9 | 2.0 | 99.0 |
| IL6R-BP152/IL6R-L | E233D/L234Y/P238D/K326A/A330R | 8.4E−08 | 6.7E−07 | 5.6E−06 | 4.1E−08 | 4.8E−05 | 19.5 | 1.6 | 77.4 |
| IL6R-BP176/IL6R-L | E233D/L234Y/G237D/P238D/Y296D/K326A/A330R | 7.3E−08 | 8.1E−07 | 3.0E−05 | 3.6E−07 | 5.3E−05 | 19.1 | 1.3 | 75.0 |
| IL6R-BP177/IL6R-L | E233D/P238D/K326D/A330K | 7.3E−09 | 6.9E−06 | 8.2E−06 | 5.2E−08 | 3.7E−05 | 13.8 | 0.2 | 8.6 |
| IL6R-BP178/IL6R-L | E233D/G237D/P238D/P271G/K326D/A330K | 3.3E−08 | 7.1E−07 | 1.4E−05 | 5.1E−08 | 6.4E−05 | 18.1 | 1.5 | 60.0 |
| IL6R-BP179/IL6R-L | E233D/G237D/P238D/P271G/K326A/A330K | 4.3E−08 | 9.3E−07 | 1.6E−05 | 8.4E−08 | 5.6E−05 | 16.7 | 1.2 | 60.1 |
| IL6R-BP180/IL6R-L | G237D/P238D/P271G/K326A/A330K | 6.4E−08 | 1.4E−06 | 1.8E−05 | 6.2E−08 | 7.0E−05 | 18.6 | 0.8 | 36.9 |
| IL6R-BP181/IL6R-L | G237D/P238D/P271G/A330K | 9.8E−08 | 1.2E−06 | 2.6E−05 | 1.6E−07 | 5.7E−05 | 20.3 | 0.9 | 49.9 |
| IL6R-BP182/IL6R-L | E233D/P238D/P271G/K326A/A330K | 7.5E−09 | 3.2E−06 | 2.8E−05 | 5.8E−08 | 5.8E−05 | 23.5 | 0.3 | 19.3 |
| IL6R-BP183/IL6R-L | E233D/P238D/P271G/Y296D/A330K | 1.0E−08 | 2.6E−06 | 1.5E−05 | 1.1E−07 | 3.4E−05 | 10.8 | 0.4 | 28.3 |
| IL6R-BP184/IL6R-L | E233D/L234Y/P238D/P271G/K326A/A330K | 1.7E−08 | 2.6E−06 | 3.0E−05 | 2.4E−07 | 5.6E−05 | 18.2 | 0.4 | 12.9 |
| IL6R-BP185/IL6R-L | E233D/P238D/P271G/A330K | 1.1E−08 | 2.3E−06 | 7.3E−06 | 1.3E−07 | 6.6E−05 | 12.6 | 0.5 | 24.5 |
| IL6R-BP186/IL6R-L | E233D/L234Y/G237D/P238D/P271G/K326A/A330K | 6.3E−08 | 8.8E−07 | 9.3E−06 | 6.9E−08 | 3.6E−05 | 15.8 | 1.2 | 44.5 |
| IL6R-BP187/IL6R-L | E233D/L234Y/G237D/P238D/P271G/Y296D/K326A/A330K | 4.5E−08 | 9.6E−07 | 6.1E−06 | 4.9E−08 | 4.9E−05 | 9.7 | 1.1 | 50.7 |
| IL6R-BP188/IL6R-L | L234Y/P238D/P271G/K326A/A330K | 2.5E−08 | 2.8E−06 | 1.8E−05 | 2.9E−07 | 5.6E−05 | 21.9 | 0.4 | 10.7 |
| IL6R-BP189/IL6R-L | E233D/G237D/P238D/H268D/P271G/A330K | 2.1E−08 | 1.0E−06 | 4.6E−06 | 7.4E−08 | 5.8E−05 | 18.5 | 1.1 | 67.6 |
| IL6R-BP190/IL6R-L | G237D/P238D/H268D/P271G/K326A/A330K | 4.2E−08 | 1.4E−06 | 2.1E−05 | 1.1E−07 | 4.9E−05 | 19.3 | 0.8 | 41.8 |
| IL6R-BP191/IL6R-L | E233D/P238D/H268D/P271G/K326A/A330K | 6.3E−08 | 1.1E−06 | 1.7E−05 | 5.8E−08 | 4.5E−05 | 20.3 | 1.0 | 53.2 |
| IL6R-BP192/IL6R-L | E233D/P238D/H268D/P271G/K326A/A330K | 4.0E−09 | 3.0E−06 | 2.7E−05 | 1.5E−07 | 4.9E−05 | 23.1 | 0.4 | 21.2 |
| IL6R-BP193/IL6R-L | E233D/L234Y/P238D/P271G/Y296D/A330K | 6.6E−09 | 2.6E−06 | 3.2E−05 | 1.1E−07 | 5.9E−05 | 18.3 | 0.4 | 27.3 |
| IL6R-BP194/IL6R-L | E233D/P238D/H268D/P271G/K326A/A330K | 6.3E−09 | 2.2E−06 | 2.5E−05 | 1.2E−07 | 5.1E−05 | 15.8 | 0.5 | 25.5 |
| IL6R-BP195/IL6R-L | E233D/L234Y/G237D/P238D/H268D/P271G/K326A/A330K | 2.4E−08 | 8.2E−07 | 8.5E−06 | 5.2E−08 | 2.7E−05 | 15.8 | 1.3 | 59.4 |

TABLE 11-continued

| Variant Name | Alteration(s) introduced into IL6R-B3 | KD (mol/L) for FcgRIa | KD (mol/L) for FcgRIIaR | KD (mol/L) for FcgRIIaH | KD (mol/L) for FcgRIIb | KD (mol/L) for FcgRIIIaV | KD(IIaR)/KD(IIb) | Relative FcgRIIaR-binding Activity | Relative FcgRIIb-binding Activity |
|---|---|---|---|---|---|---|---|---|---|
| IL6R-BP195/IL6R-L | E233D/L234Y/G237D/P238D/H268D/P271G/Y296D/K326A/A330K | 2.3E-08 | 9.1E-07 | 1.0E-05 | 5.0E-08 | 3.1E-05 | 18.2 | 1.2 | 62.0 |
| IL6R-BP196/IL6R-L | L234Y/P238D/H268D/P271G/Y296D/K326A/A330K | 1.4E-08 | 3.0E-06 | 1.9E-05 | 2.2E-07 | 5.1E-05 | 13.4 | 0.4 | 13.9 |
| IL6R-BP197/IL6R-L | E233D/L234Y/G237D/P238D/H268D/P271G/Y296D/K326D/A330K | 1.9E-08 | 9.8E-07 | 1.2E-05 | 5.8E-08 | 3.3E-05 | 17.1 | 1.1 | 53.7 |
| IL6R-BP198/IL6R-L | E233D/L234Y/P238D/H268D/P271G/K326D/A330K | 1.1E-08 | 2.2E-06 | 2.0E-05 | 2.0E-07 | 4.4E-05 | 11.0 | 0.5 | 15.7 |
| IL6R-BP199/IL6R-L | E233D/P238D/K326D/A330K | 6.4E-09 | 8.6E-06 | 2.6E-05 | 4.9E-07 | 6.1E-05 | 17.6 | 0.1 | 6.3 |
| IL6R-BP200/IL6R-L | E233D/L234Y/G237D/P238D/P271G/K326D/A330K | 3.3E-08 | 6.3E-07 | 4.2E-06 | 3.4E-08 | 3.8E-05 | 18.5 | 1.7 | 90.9 |
| IL6R-BP201/IL6R-L | E233D/L234Y/G237D/P238D/P271G/A330K | 5.1E-08 | 8.4E-07 | 6.9E-06 | 4.0E-08 | 5.2E-05 | 21.0 | 1.3 | 77.3 |
| IL6R-BP202/IL6R-L | E233D/L234Y/G237D/P238D/P271G/K326A/A330K | 9.5E-08 | 1.2E-06 | 9.2E-06 | 6.4E-08 | 5.9E-05 | 18.8 | 1.3 | 48.3 |
| IL6R-BP203/IL6R-L | G237D/P238D/P271G/K326A/A330R | 1.8E-07 | 9.9E-07 | 1.1E-05 | 4.9E-08 | 7.2E-05 | 20.2 | 1.1 | 63.1 |
| IL6R-BP204/IL6R-L | E233D/P238D/P271G/K326A/A330R | 7.6E-08 | 4.5E-06 | 2.1E-05 | 2.5E-07 | 5.2E-05 | 18.0 | 0.2 | 12.4 |
| IL6R-BP205/IL6R-L | G237D/P238D/P271G/Y296D/A330R | 7.7E-08 | 3.5E-06 | 2.8E-05 | 1.6E-07 | 6.8E-05 | 21.9 | 0.3 | 19.3 |
| IL6R-BP206/IL6R-L | E233D/P238D/P271G/Y296D/A330R | 8.2E-08 | 3.1E-06 | 2.4E-05 | 2.0E-07 | 6.9E-05 | 15.5 | 0.3 | 15.5 |
| IL6R-BP207/IL6R-L | E233D/P238D/A330R | 2.2E-08 | 1.9E-05 | 2.9E-05 | 8.4E-07 | 6.5E-05 | 22.6 | 0.1 | 3.7 |
| IL6R-BP208/IL6R-L | E233D/G237D/P238D/H268D/P271G/Y296D/A330K | 1.9E-08 | 8.5E-07 | 8.3E-06 | 3.2E-08 | 5.3E-05 | 26.6 | 1.3 | 96.6 |
| IL6R-BP209/IL6R-L | G237D/P238D/H268D/P271G/Y296D/A330R | 3.9E-08 | 1.2E-06 | 1.0E-05 | 5.1E-08 | 4.1E-05 | 23.5 | 0.9 | 60.6 |
| IL6R-BP210/IL6R-L | E233D/G237D/P238D/H268D/P271G/Y296D/K326D/A330R | 6.5E-08 | 1.0E-06 | 9.5E-06 | 3.9E-08 | 4.6E-05 | 25.6 | 1.1 | 79.2 |
| IL6R-BP211/IL6R-L | E233D/P238D/H268D/P271G/K326A/A330K | 4.2E-09 | 4.1E-06 | 2.7E-05 | 2.2E-07 | 7.3E-05 | 18.6 | 0.3 | 14.0 |
| IL6R-BP212/IL6R-L | E233D/P238D/H268D/P271G/Y296D/A330R | 5.2E-09 | 3.5E-06 | 2.2E-05 | 1.7E-07 | 5.2E-05 | 20.6 | 0.3 | 18.2 |
| IL6R-BP213/IL6R-L | E233D/P238D/H268D/P271G/A330R | 4.1E-09 | 3.1E-06 | 2.4E-05 | 1.8E-07 | 6.3E-05 | 17.2 | 0.3 | 17.2 |
| IL6R-BP214/IL6R-L | E233D/L234Y/G237D/P238D/Y296D/K326D/A330K | 5.9E-08 | 1.7E-06 | 9.2E-06 | 1.2E-07 | 3.8E-05 | 14.2 | 0.6 | 25.8 |
| IL6R-BP215/IL6R-L | G237D/P238D/H268D/P271G/Y296D/A330R | 4.3E-08 | 1.3E-06 | 1.4E-05 | 4.1E-08 | 6.7E-05 | 31.7 | 0.8 | 75.4 |
| IL6R-BP216/IL6R-L | G237D/P238D/S267Q/H268D/P271G/A330K | 6.2E-07 | 2.9E-06 | 2.6E-05 | 1.4E-07 | 5.3E-05 | 20.7 | 0.4 | 22.1 |
| IL6R-BP217/IL6R-L | G237D/P238D/S267Q/H268D/P271G/Y296D/A330R | 2.8E-08 | 1.2E-06 | 2.8E-05 | 1.5E-07 | 6.0E-05 | 24.0 | 0.3 | 20.6 |
| IL6R-BP218/IL6R-L | G237D/P238D/H268D/P271G/K326D/A330K | 3.7E-08 | 1.5E-06 | 1.2E-05 | 7.6E-08 | 3.8E-05 | 19.7 | 0.7 | 40.7 |
| IL6R-BP219/IL6R-L | E233D/P238D/H268D/P271G/K326A/A330R | 4.6E-08 | 6.1E-07 | 2.5E-06 | 3.4E-08 | 2.9E-05 | 17.9 | 1.8 | 90.9 |
| IL6R-BP220/IL6R-L | E233D/G237D/P238D/H268D/P271G/Y296D/A330K | 2.0E-08 | 1.1E-06 | 1.2E-05 | 3.6E-08 | 5.8E-05 | 30.6 | 1.0 | 85.8 |
| IL6R-BP221/IL6R-L | E233D/L234Y/G237D/P238D/Y296D/K326A/A330R | 1.3E-07 | 7.1E-07 | 2.5E-06 | 2.8E-08 | 4.6E-05 | 25.4 | 1.5 | 110.4 |
| IL6R-BP222/IL6R-L | L234Y/G237D/P238D/P271G/K326A/A330R | 5.1E-08 | 7.1E-07 | 2.6E-06 | 3.4E-08 | 4.7E-05 | 20.9 | 1.5 | 90.9 |
| IL6R-BP223/IL6R-L | E233D/L234Y/G237D/P238D/H268D/P271G/K326A/A330R | 2.7E-08 | 6.0E-07 | 2.8E-06 | 2.5E-08 | 3.2E-05 | 24.0 | 1.8 | 123.6 |
| IL6R-BP224/IL6R-L | E233D/L234Y/G237D/P238D/H268D/S267Q/H268D/P271G/K326A/A330R | 6.2E-09 | 4.5E-07 | 9.5E-06 | 3.5E-08 | 4.1E-05 | 12.9 | 2.4 | 88.3 |
| IL6R-BP225/IL6R-L | L234Y/G237D/P238D/K326D/A330R | 9.5E-08 | 6.9E-07 | 2.8E-06 | 3.5E-08 | 3.2E-05 | 19.7 | 1.6 | 88.3 |
| IL6R-BP226/IL6R-L | E233D/L234Y/G237D/P238D/P271G/K326D/A330R | 5.2E-08 | 5.7E-07 | 2.4E-06 | 3.3E-08 | 3.6E-05 | 17.3 | 1.9 | 93.6 |
| IL6R-BP227/IL6R-L | L234Y/G237D/P238D/P271G/A330R | 2.7E-08 | 6.2E-07 | 2.9E-06 | 3.2E-08 | 2.6E-05 | 19.4 | 1.7 | 96.6 |
| IL6R-BP228/IL6R-L | E233D/L234Y/G237D/P238D/S267Q/H268D/P271G/K326D/A330R | 4.2E-08 | 4.2E-07 | 1.1E-05 | 4.0E-08 | 3.2E-05 | 10.5 | 2.6 | 77.3 |
| IL6R-BP229/IL6R-L | E233D/L234Y/G237D/P238D/H268D/P271G/Y296D/K326D/A330R | 5.6E-08 | 8.1E-07 | 3.3E-06 | 4.2E-08 | 3.7E-05 | 19.3 | 1.3 | 73.6 |
| IL6R-BP230/IL6R-L | E233D/L234Y/G237D/P238D/P271G/Y296D/K326A/A330R | 1.4E-08 | 5.7E-07 | 9.6E-06 | 2.1E-08 | 3.5E-05 | 27.1 | 1.9 | 147.1 |
| IL6R-BP231/IL6R-L | E233D/G237D/P238D/H268D/S267Q/H268D/P271G/K326A/A330R | 9.4E-09 | 7.4E-07 | 1.1E-05 | 2.3E-08 | 4.0E-05 | 32.2 | 1.5 | 134.3 |
| IL6R-BP232/IL6R-L | L234Y/G237D/P238D/P271G/Y296D/A330R | 7.6E-08 | 8.4E-07 | 3.3E-06 | 5.6E-08 | 4.5E-05 | 15.0 | 1.3 | 55.2 |
| IL6R-BP233/IL6R-L | L234Y/G237D/P238D/P271G/A330R | 7.0E-08 | 6.9E-07 | 2.8E-06 | 3.7E-08 | 5.1E-05 | 18.6 | 1.3 | 83.5 |
| IL6R-BP234/IL6R-L | E233D/L234Y/G237D/P238D/S267Q/H268D/P271G/Y296D/K326D/A330R | 6.5E-09 | 1.2E-06 | 2.0E-05 | 1.2E-07 | 3.1E-05 | 10.0 | 0.9 | 25.8 |
| IL6R-BP235/IL6R-L | E233D/L234Y/G237D/P238D/H268D/P271G/Y296D/K326D/A330R | 3.5E-09 | 6.8E-07 | 7.5E-06 | 4.4E-08 | 2.5E-05 | 15.5 | 1.6 | 70.2 |
| IL6R-BP236/IL6R-L | E233D/L234Y/G237D/P238D/S267Q/H268D/P271G/K326D/A330R | 2.7E-08 | 8.4E-07 | 1.9E-05 | 6.5E-08 | 3.9E-05 | 12.9 | 1.3 | 47.5 |
| IL6R-BP237/IL6R-L | E233D/L234Y/G237D/P238D/S267Q/H268D/P271G/K326A/A330K | 7.7E-09 | 8.4E-07 | 3.3E-05 | 1.0E-07 | 3.5E-05 | 11.0 | 1.3 | 30.9 |
| IL6R-BP238/IL6R-L | E233D/L234Y/G237D/P238D/S267Q/H268D/P271G/Y296D/K326A/A330K | 4.1E-09 | 1.1E-06 | 9.6E-06 | 3.6E-08 | 2.7E-05 | 17.8 | 1.7 | 85.8 |
| IL6R-BP239/IL6R-L | E233D/L234Y/G237D/P238D/P271G/Y296D/K326D/A330R | 7.6E-09 | 6.4E-07 | 7.0E-06 | 3.6E-08 | 2.9E-05 | 13.5 | 1.3 | 51.5 |
| IL6R-BP240/IL6R-L | E233D/L234Y/G237D/P238D/P271G/Y296D/K326A/A330R | 7.6E-09 | 8.1E-07 | 1.7E-05 | 6.0E-08 | 4.8E-05 | 15.8 | 1.3 | 32.5 |
| IL6R-BP241/IL6R-L | E233D/L234Y/G237D/P238D/P271G/A330R | 1.1E-09 | 1.5E-06 | 2.6E-05 | 9.5E-08 | 5.2E-05 | 15.1 | 0.7 | 68.7 |
| IL6R-BP242/IL6R-L | E233D/L234Y/G237D/P238D/H268D/P271G/K326D/A330R | 1.9E-09 | 6.8E-07 | 9.0E-06 | 4.5E-08 | 3.1E-05 | 14.7 | 1.6 | 60.6 |
| IL6R-BP243/IL6R-L | E233D/L234Y/G237D/P238D/H268D/P271G/K326A/A330R | 3.0E-09 | 5.4E-07 | 6.0E-06 | 3.6E-08 | 2.5E-05 | 15.0 | 2.0 | 85.8 |

TABLE 11-continued

| Variant Name | Alteration(s) introduced into IL6R-B3 | KD (mol/L) for FcgRIa | KD (mol/L) for FcgRIIaR | KD (mol/L) for FcgRIIaH | KD (mol/L) for FcgRIIb | KD (mol/L) for FcgRIIIaV | KD(IIaR)/ KD(IIb) | Relative FcgRIIaR-binding Activity | Relative FcgRIIb-binding Activity |
|---|---|---|---|---|---|---|---|---|---|
| IL6R-BP244/IL6R-L | E233D/G237D/P238D/S267Q/H268D/P271G/Y296D/A330R | 7.8E−09 | 1.8E−06 | 2.6E−05 | 1.1E−07 | 4.6E−05 | 16.4 | 0.6 | 28.1 |
| IL6R-BP245/IL6R-L | E233D/G237D/P238D/S267Q/H268D/P271G/Y296D/K326D/A330R | 6.3E−09 | 1.4E−06 | 2.5E−05 | 8.3E−08 | 3.9E−05 | 16.9 | 0.8 | 37.2 |
| IL6R-BP246/IL6R-L | E233D/G237D/P238D/S267Q/H268D/P271G/Y296D/K326A/A330R | 8.0E−09 | 1.6E−06 | 2.3E−05 | 9.2E−08 | 4.4E−05 | 17.4 | 0.7 | 33.6 |
| IL6R-BP247/IL6R-L | E233D/G237D/P238D/H268D/P271G/Y296D/K326D/A330R | 7.5E−09 | 8.1E−07 | 1.2E−05 | 3.7E−08 | 4.4E−05 | 21.9 | 1.3 | 83.5 |
| IL6R-BP248/IL6R-L | E233D/G237D/P238D/H268D/P271G/Y296D/K326A/A330R | 1.7E−09 | 8.2E−07 | 1.1E−05 | 3.5E−08 | 4.4E−05 | 23.4 | 1.3 | 88.3 |
| IL6R-BP249/IL6R-L | E233D/L234Y/G237D/P238D/H268D/P271G/Y296D/A330R | 7.0E−09 | 6.2E−07 | 7.2E−06 | 3.7E−08 | 2.8E−05 | 16.8 | 1.7 | 83.5 |
| IL6R-BP262/IL6R-L | G237D/P238D/H268E/P271G | 1.0E−08 | 2.0E−06 | 4.5E−05 | 1.2E−07 | 5.6E−05 | 17.0 | 0.5 | 25.8 |
| IL6R-BP264/IL6R-L | E233D/G237D/P238D/H268E/P271G/Y296D/A330R | 7.4E−09 | 3.5E−07 | 2.8E−06 | 1.2E−08 | 2.6E−05 | 28.3 | 3.1 | 251.2 |
| IL6R-BP265/IL6R-L | G237D/P238D/H268E/P271G/Y296D/A330R | 2.3E−08 | 6.3E−07 | 1.2E−05 | 1.5E−08 | 9.6E−05 | 41.2 | 1.7 | 203.3 |
| IL6R-BP266/IL6R-L | E233D/G237D/P238D/H268E/P271G/A330R | 1.4E−08 | 3.2E−07 | 1.1E−05 | 1.8E−08 | 4.0E−05 | 18.0 | 3.4 | 174.6 |
| IL6R-BP268/IL6R-L | E233D/G237D/P238D/H268E/P271G/Y296D | 4.5E−09 | 1.8E−06 | 2.1E−05 | 9.2E−08 | 2.8E−05 | 19.6 | 0.6 | 33.6 |
| IL6R-BP269/IL6R-L | G237D/P238D/H268E/P271G/Y296D | 1.4E−08 | 2.2E−06 | 7.2E−05 | 1.1E−07 | 1.4E−04 | 19.6 | 0.5 | 27.3 |
| IL6R-BP423/IL6R-L | E233D/G237D/P238D/S267A/H268E/P271G/A330R | 7.7E−10 | 1.8E−07 | 2.0E−06 | 5.1E−09 | 1.6E−05 | 34.2 | 6.2 | 603.5 |
| IL6R-BP425/IL6R-L | E233D/G237D/P238D/V266L/S267A/H268E/P271G/A330R | 4.1E−09 | 2.2E−07 | 1.5E−05 | 9.1E−09 | 4.2E−05 | 23.6 | 5.0 | 338.8 |
| IL6R-BP426/IL6R-L | E233D/G237D/P238D/S267A/H268E/E269D/P271G/A330R | 1.0E−09 | 1.6E−07 | 4.9E−05 | 5.9E−09 | 4.1E−05 | 27.6 | 6.7 | 527.3 |
| IL6R-BP428/IL6R-L | E233D/G237D/P238D/S267G/H268E/P271G/A330R | 4.9E−09 | 3.9E−07 | 4.2E−05 | 1.4E−08 | 3.6E−05 | 28.0 | 2.8 | 220.7 |
| IL6R-BP429/IL6R-L | E233D/G237D/P238D/V264I/S267G/H268E/P271G/A330R | 6.2E−09 | 1.7E−07 | 3.5E−06 | 5.4E−09 | 6.8E−05 | 31.5 | 6.4 | 572.2 |
| IL6R-BP430/IL6R-L | E233D/G237D/P238D/V266L/S267G/H268E/P271G/A330R | 1.7E−08 | 2.2E−07 | 1.1E−05 | 1.2E−08 | 3.5E−05 | 18.5 | 4.8 | 255.4 |
| IL6R-BP431/IL6R-L | E233D/G237D/P238D/S267G/H268E/E269D/P271G/A330R | 3.6E−09 | 4.1E−07 | 7.6E−06 | 1.2E−08 | 3.2E−05 | 34.6 | 2.7 | 264.1 |
| IL6R-BP433/IL6R-L | E233D/G237D/P238D/H268D/P271G/Y296D/A330K/I332T | 7.5E−10 | 6.8E−07 | 7.3E−06 | 3.4E−08 | 2.6E−05 | 20.0 | 1.6 | 91.4 |
| IL6R-BP434/IL6R-L | E233D/G237D/P238D/H268D/P271G/Y296D/K326D/A330R/I332T | 5.5E−10 | 3.4E−07 | 4.1E−06 | 1.2E−08 | 2.5E−05 | 27.2 | 3.2 | 251.2 |
| IL6R-BP435/IL6R-L | E233D/G237D/P238D/H268D/P271G/Y296D/K326A/A330R/I332T | 1.0E−09 | 4.2E−07 | 3.4E−06 | 1.6E−08 | 2.2E−05 | 27.1 | 2.6 | 198.1 |
| IL6R-BP436/IL6R-L | E233D/G237D/P238D/S267A/H268E/P271G/Y296D/A330R/I332T | 2.6E−10 | 2.2E−07 | 2.1E−06 | 5.1E−09 | 1.3E−05 | 43.8 | 4.8 | 604.7 |
| IL6R-BP437/IL6R-L | G237D/P238D/S267A/H268E/P271G/Y296D/A330R/I332T | 7.5E−10 | 2.2E−07 | 1.4E−06 | 5.9E−09 | 1.1E−05 | 37.7 | 4.8 | 522.0 |
| IL6R-BP438/IL6R-L | E233D/G237D/P238D/S267A/H268E/P271G/A330R/I332T | 2.1E−10 | 1.8E−07 | 1.6E−06 | 5.5E−09 | 6.8E−06 | 32.7 | 6.1 | 567.0 |
| IL6R-BP439/IL6R-L | E233D/G237D/P238D/V264I/V266L/S267A/H268E/P271G/A330R | 8.7E−09 | 1.3E−07 | 2.8E−06 | 6.1E−09 | 6.6E−05 | 20.9 | 8.5 | 508.2 |
| IL6R-BP440/IL6R-L | E233D/G237D/P238D/V264I/H268E/P271G/A330R | 8.7E−09 | 1.3E−07 | 1.6E−06 | 5.2E−09 | 2.8E−05 | 24.0 | 8.6 | 593.1 |
| IL6R-BP441/IL6R-L | E233D/G237D/P238D/V266L/H268E/P271G/A330R | 1.7E−08 | 3.6E−07 | 8.8E−06 | 1.5E−08 | 3.7E−05 | 24.0 | 3.0 | 204.6 |
| IL6R-BP442/IL6R-L | E233D/G237D/P238D/H268E/E269D/P271G/A330R | 4.5E−09 | 3.8E−07 | 4.7E−06 | 1.2E−08 | 2.5E−05 | 30.6 | 2.8 | 249.2 |
| IL6R-BP443/IL6R-L | E233D/G237D/P238D/V266L/H268E/E269D/P271G/A330R | 1.8E−08 | 5.1E−07 | 9.5E−06 | 2.3E−08 | 2.3E−05 | 21.7 | 2.1 | 132.1 |
| IL6R-BP445/IL6R-L | E233D/G237D/P238D/V264I/S267A/H268E/P271G/A330R | 2.0E−09 | 8.0E−08 | 1.5E−06 | 2.6E−09 | 2.4E−05 | 31.0 | 13.5 | 1197.7 |
| IL6R-BP479/IL6R-L | E233D/G237D/P238D/V264I/V266L/S267A/H268E/P271G | 5.3E−09 | 9.0E−07 | 1.5E−05 | 5.6E−08 | 4.0E−05 | 16.1 | 1.2 | 55.3 |
| IL6R-BP480/IL6R-L | E233D/G237D/P238D/V266L/H268E/E269D/P271G | 1.3E−08 | 6.3E−06 | 2.1E−05 | 2.0E−07 | 4.6E−05 | 32.1 | 0.2 | 15.8 |
| IL6R-BP481/IL6R-L | E233D/G237D/P238D/V264I/S267A/H268E/P271G | 1.0E−09 | 4.0E−07 | 6.8E−06 | 1.9E−08 | 2.4E−05 | 20.5 | 2.7 | 159.3 |
| IL6R-BP483/IL6R-L | E233D/G237D/P238D/V266L/S267A/H268E/P271G | 1.3E−09 | 1.3E−06 | 1.8E−05 | 7.8E−08 | 2.5E−05 | 16.8 | 0.8 | 39.6 |
| IL6R-BP484/IL6R-L | E233D/G237D/P238D/S267A/H268E/E269D/P271G | 8.2E−10 | 7.8E−07 | 1.1E−05 | 4.6E−08 | 2.5E−05 | 17.1 | 1.4 | 67.6 |
| IL6R-BP487/IL6R-L | E233D/G237D/P238D/V264I/S267A/H268E/P271G/A330R/P396M | 1.2E−09 | 3.9E−08 | 8.4E−07 | 1.2E−09 | 1.0E−05 | 33.8 | 27.8 | 2687.0 |
| IL6R-BP488/IL6R-L | E233D/G237D/P238D/V264I/S267A/H268E/P271G/Y296D/A330R | 2.2E−09 | 7.4E−08 | 1.6E−06 | 1.9E−09 | 2.0E−05 | 40.1 | 14.6 | 1670.3 |
| IL6R-BP489/IL6R-L | E233D/G237D/P238D/V264I/S267A/H268E/P271G/Y296D/A330R/P396M | 1.3E−09 | 4.3E−08 | 8.7E−07 | 1.0E−09 | 1.2E−05 | 42.8 | 25.2 | 3090.0 |
| IL6R-BP490/IL6R-L | G237D/P238D/V264I/S267A/H268E/P271G/A330R | 4.5E−09 | 1.1E−07 | 2.4E−06 | 2.4E−09 | 2.3E−05 | 46.7 | 9.6 | 1287.5 |
| IL6R-BP491/IL6R-L | G237D/P238D/V264I/S267A/H268E/P271G/Y296D/A330R | 5.3E−09 | 1.2E−07 | 2.2E−06 | 3.0E−09 | 2.1E−05 | 38.8 | 9.2 | 1016.4 |
| IL6R-BP492/IL6R-L | P238D/V264I/S267A/H268E/P271G | 7.9E−10 | 9.2E−07 | 1.6E−05 | 2.4E−08 | 3.6E−05 | 38.8 | 1.2 | 130.9 |
| IL6R-BP493/IL6R-L | P238D/V264I/S267A/H268E/P271G/Y296D | 8.2E−10 | 1.1E−06 | 1.9E−05 | 2.1E−08 | 3.5E−05 | 52.1 | 1.0 | 146.4 |
| IL6R-BP494/IL6R-L | G237D/P238D/S267A/H268E/P271G/Y296D/A330R | 3.9E−09 | 2.5E−07 | 5.4E−06 | 6.6E−09 | 4.0E−05 | 38.6 | 4.3 | 469.6 |
| IL6R-BP495/IL6R-L | G237D/P238D/S267G/H268E/P271G/Y296D/A330R | 8.3E−09 | 4.9E−07 | 1.2E−05 | 9.7E−09 | 3.3E−05 | 50.9 | 2.2 | 320.2 |
| IL6R-BP496/IL6R-L | E233D/G237D/P238D/V264I/S267A/H268E/P271G/Y296D | 1.2E−09 | 4.7E−07 | 3.7E−06 | 1.8E−08 | 3.0E−05 | 25.5 | 2.3 | 167.9 |
| IL6R-BP497/IL6R-L | E233D/G237D/P238D/V264I/S267A/H268E/P271G/A327G/A330R | 2.1E−09 | 8.5E−08 | 9.6E−07 | 4.1E−09 | 2.8E−05 | 21.0 | 12.6 | 761.1 |
| IL6R-BP498/IL6R-L | E233D/G237D/P238D/V264I/S267A/H268E/P271G/A330R/P396L | 1.3E−09 | 5.1E−08 | 9.3E−07 | 1.7E−09 | 1.0E−05 | 30.8 | 21.3 | 1872.7 |
| IL6R-BP499/IL6R-L | E233D/G237D/P238D/V264I/S267A/H268E/P271G/Y296D/A330R/P396L | 1.2E−09 | 4.9E−08 | 1.0E−06 | 1.5E−09 | 1.2E−05 | 33.8 | 21.9 | 2116.4 |

TABLE 11-continued

| Variant Name | Alteration(s) introduced into IL6R-B3 | KD (mol/L) for FcgRIa | KD (mol/L) for FcgRIIaR | KD (mol/L) for FcgRIIaH | KD (mol/L) for FcgRIIb | KD (mol/L) for FcgRIIIaV | KD(IIaR)/ KD(IIb) | Relative FcgRIIaR-binding Activity | Relative FcgRIIb-binding Activity |
|---|---|---|---|---|---|---|---|---|---|
| IL6R-BP500/IL6R-L | G237D/P238D/V264I/S267A/H268E/P271G/Y296D | 2.3E-09 | 7.2E-07 | 2.5E-05 | 2.4E-08 | 3.9E-05 | 29.9 | 1.5 | 127.7 |
| IL6R-BP501/IL6R-L | G237D/P238D/V264I/S267A/H268E/P271G | 2.1E-09 | 6.3E-07 | 1.4E-05 | 2.5E-08 | 1.9E-05 | 25.1 | 1.7 | 122.6 |
| IL6R-BP502/IL6R-L | E233D/G237D/P238D/V264I/S267A/H268E/P271G | 2.1E-09 | 1.1E-07 | 1.3E-06 | 3.7E-09 | 2.4E-05 | 29.5 | 9.9 | 837.4 |
| IL6R-BP503/IL6R-L | E233D/G237D/P238D/V264I/S267A/H268E/P271G/Y296D/A327G/A330R | 1.2E-09 | 5.7E-08 | 8.6E-07 | 1.7E-09 | 2.1E-05 | 33.2 | 19.0 | 1807.0 |
| IL6R-BP504/IL6R-L | E233D/G237D/P238D/V264I/S267A/H268E/P271G/Y296D/A327G/A330R/P396M | 1.4E-09 | 4.5E-07 | 1.6E-05 | 2.4E-08 | 3.4E-05 | 18.5 | 2.4 | 127.2 |
| IL6R-BP505/IL6R-L | E233D/G237D/P238D/V264I/S267A/H268E/P271G/E272P | 1.1E-09 | 4.3E-07 | 1.1E-05 | 2.1E-08 | 3.8E-05 | 20.0 | 2.5 | 144.4 |
| IL6R-BP506/IL6R-L | E233D/G237D/P238D/V264I/S267A/H268E/P271G/E272D | 3.1E-09 | 1.2E-07 | 2.5E-06 | 3.4E-09 | 5.5E-05 | 35.1 | 9.0 | 903.5 |
| IL6R-BP507/IL6R-L | E233D/G237D/P238D/V264I/S267A/H268E/P271G/E272P/Y296D/A330R | 2.6E-09 | 1.0E-07 | 1.8E-06 | 2.9E-09 | 2.6E-05 | 34.2 | 10.9 | 1061.9 |
| IL6R-BP508/IL6R-L | E233D/G237D/P238D/V264I/S267A/H268E/P271G/E272P/Y296D | 1.4E-09 | 5.4E-07 | 2.0E-05 | 2.1E-08 | 6.1E-05 | 26.0 | 2.0 | 148.6 |
| IL6R-BP509/IL6R-L | E233D/G237D/P238D/V264I/S267A/H268E/P271G/E272P/Y296D | 1.1E-09 | 5.2E-07 | 7.9E-06 | 1.8E-08 | 2.3E-05 | 29.2 | 2.1 | 173.6 |
| IL6R-BP510/IL6R-L | E233D/G237D/P238D/V264I/S267A/H268E/P271G/E272P/A330R | 6.0E-09 | 1.7E-07 | 4.0E-06 | 3.8E-09 | 2.5E-05 | 43.5 | 6.5 | 804.7 |
| IL6R-BP511/IL6R-L | G237D/P238D/V264I/S267A/H268E/P271G/E272P/Y296D/A330R | 6.0E-09 | 1.8E-07 | 4.3E-06 | 3.5E-08 | 7.1E-05 | 50.6 | 6.1 | 887.9 |
| IL6R-BP531/IL6R-L | E233D/G237D/P238D/V264I/S267A/H268E/P271G/Y296D/A330R/P396M | 9.4E-09 | 1.2E-07 | 3.5E-06 | 3.8E-09 | 2.7E-05 | 33.1 | 8.7 | 824.0 |
| IL6R-BP532/IL6R-L | E233D/G237D/P238D/V264I/H268E/P271G/Y296D/A330R/P396M | 1.2E-08 | 9.4E-08 | 1.9E-06 | 3.2E-09 | 2.6E-05 | 29.3 | 11.5 | 965.6 |
| IL6R-BP533/IL6R-L | E233D/G237D/P238D/V264I/S267G/H268E/P271G/Y296D/A330R/P396L | 7.7E-08 | 1.2E-07 | 2.6E-06 | 4.1E-09 | 2.7E-05 | 29.3 | 9.0 | 753.7 |
| IL6R-BP534/IL6R-L | E233D/G237D/P238D/V264I/S267G/H268E/P271G/Y296D/A330R/P396L | 9.3E-08 | 9.1E-08 | 1.8E-06 | 3.0E-09 | 2.5E-05 | 30.7 | 11.8 | 1040.4 |
| IL6R-BP535/IL6R-L | E233D/G237D/P238D/V264I/S267G/H268E/P271G/Y296D/A327G/A330R/P396M | 1.1E-08 | 9.2E-08 | 3.2E-06 | 4.0E-09 | 3.3E-05 | 23.2 | 11.7 | 778.3 |
| IL6R-BP536/IL6R-L | E233D/G237D/P238D/V264I/S267G/H268E/P271G/Y296D/A327G/A330R | 8.9E-08 | 7.9E-08 | 1.3E-06 | 3.0E-09 | 2.3E-05 | 26.6 | 13.7 | 1040.4 |
| IL6R-BP537/IL6R-L | E233D/G237D/P238D/V264I/H268E/P271G/Y296D/A330R/P396M | 2.9E-08 | 3.1E-07 | 3.1E-06 | 6.9E-09 | 3.6E-05 | 39.1 | 4.0 | 445.9 |
| IL6R-BP538/IL6R-L | G237D/P238D/V264I/H268E/P271G/A330R | 5.5E-08 | 2.0E-07 | 3.0E-06 | 5.3E-09 | 3.3E-05 | 38.6 | 5.3 | 585.2 |
| IL6R-BP539/IL6R-L | G237D/P238D/V264I/S267G/H268E/P271G/E272P/Y296D/A330R | 6.4E-08 | 3.3E-07 | 5.6E-06 | 8.4E-09 | 3.4E-05 | 39.0 | 3.3 | 367.9 |
| IL6R-BP540/IL6R-L | E233D/G237D/P238D/V264I/H268E/P271G/E272P/Y296D/A330R | 9.6E-08 | 2.1E-07 | 4.6E-06 | 5.7E-09 | 3.9E-05 | 36.6 | 5.1 | 539.3 |
| IL6R-BP549/IL6R-L | E233D/G237D/P238D/S267G/H268E/P271G/A330R | 1.8E-08 | 5.7E-07 | 1.1E-05 | 1.6E-08 | 2.4E-05 | 35.9 | 1.9 | 195.6 |
| IL6R-BP550/IL6R-L | E233D/G237D/P238D/V264I/S267G/H268E/P271G/E272D/Y296D/A330R | 2.5E-08 | 3.4E-07 | 5.0E-06 | 7.6E-09 | 4.8E-05 | 45.0 | 3.2 | 405.0 |
| IL6R-BP551/IL6R-L | E233D/G237D/P238D/V264I/H268E/P271G/E272D/Y296D/A330R | 3.2E-08 | 2.5E-07 | 2.8E-06 | 6.4E-09 | 4.8E-05 | 38.1 | 4.4 | 480.6 |
| IL6R-BP552/IL6R-L | E233D/G237D/P238D/V264I/S267A/H268E/P271G/E272D/Y296D/A330R | 3.2E-09 | 9.7E-08 | 1.9E-06 | 2.6E-09 | 3.0E-05 | 37.3 | 11.2 | 1193.1 |
| IL6R-BP553/IL6R-L | E233D/G237D/P238D/V264I/S267A/H268E/P271G/E272P/Y296D/A330R | 3.4E-08 | 8.6E-08 | 1.4E-06 | 3.1E-09 | 2.0E-05 | 27.8 | 12.6 | 1000.0 |
| IL6R-BP554/IL6R-L | E233D/G237D/P238D/V264I/S267A/H268E/P271G/E272D/A330R | 8.0E-09 | 1.5E-07 | 2.3E-06 | 4.4E-09 | 2.4E-05 | 32.7 | 7.4 | 695.9 |
| IL6R-BP555/IL6R-L | G237D/P238D/V264I/S267A/H268E/P271G/E272D/Y296D/A330R | 9.4E-09 | 1.6E-07 | 3.2E-06 | 4.1E-09 | 3.0E-05 | 39.7 | 6.6 | 751.8 |
| IL6R-BP556/IL6R-L | G237D/P238D/V264I/S267A/H268E/P271G/Y296D/A330R | 4.3E-08 | 3.0E-07 | 5.8E-06 | 8.4E-09 | 6.0E-05 | 35.4 | 3.6 | 368.7 |
| IL6R-BP557/IL6R-L | G237D/P238D/S267G/H268D/P271G/Y296D/A330R | 1.3E-08 | 8.5E-07 | 1.5E-05 | 2.0E-08 | 2.9E-05 | 42.0 | 1.3 | 153.7 |
| IL6R-BP558/IL6R-L | G237D/P238D/V264I/S267A/H268E/P271G/E272D/A330R | 1.3E-08 | 3.3E-07 | 4.9E-06 | 9.0E-09 | 3.6E-05 | 36.4 | 3.3 | 342.6 |
| IL6R-BP559/IL6R-L | P238D/V264I/S267A/H268E/P271G/Y296D | 1.1E-09 | 1.6E-06 | 2.0E-05 | 2.8E-08 | 4.4E-05 | 58.4 | 0.7 | 110.0 |
| IL6R-BP560/IL6R-L | P238D/S267G/H268E/P271G/Y296D/A330R | 5.6E-09 | 4.2E-06 | 3.1E-05 | 1.8E-07 | 4.1E-05 | 22.8 | 0.3 | 16.8 |
| IL6R-BP561/IL6R-L | E233D/G237D/P238D/H268D/P271G/E272D/Y296D/A330R | 9.4E-09 | 5.1E-07 | 5.3E-06 | 1.8E-08 | 3.7E-05 | 28.0 | 2.1 | 169.8 |
| IL6R-BP562/IL6R-L | E233D/G237D/P238D/H268D/P271G/E272D/Y296D/A330R | 2.5E-08 | 6.8E-07 | 1.1E-05 | 2.4E-08 | 5.3E-05 | 29.0 | 1.6 | 130.9 |
| IL6R-BP563/IL6R-L | E233D/G237D/P238D/H268D/P271G/E272D/Y296D/A330R | 1.2E-08 | 4.6E-07 | 8.3E-06 | 1.6E-08 | 3.8E-05 | 29.1 | 2.4 | 195.6 |
| IL6R-BP564/IL6R-L | G237D/P238D/H268E/P271G/E272D/Y296D/A330R | 3.1E-08 | 5.8E-07 | 1.0E-05 | 2.2E-08 | 4.9E-05 | 26.2 | 1.9 | 140.5 |
| IL6R-BP565/IL6R-L | E233D/G237D/P238D/S267A/H268E/P271G/Y296D/A330R | 2.4E-10 | 2.3E-07 | 4.7E-06 | 5.5E-09 | 2.1E-05 | 41.5 | 4.7 | 562.8 |
| IL6R-BP567/IL6R-L | E233D/G237D/P238D/V264I/S267A/H268E/P271G/Y296D | 2.1E-10 | 8.9E-07 | 1.7E-05 | 1.4E-08 | 3.9E-05 | 64.4 | 1.2 | 223.9 |
| IL6R-BP568/IL6R-L | E233D/G237D/P238D/V264I/S267A/H268E/P271G | 1.9E-10 | 6.8E-07 | 1.1E-05 | 1.5E-08 | 2.5E-05 | 46.1 | 1.6 | 210.2 |

All of the variants in Table 11 had enhanced FcgRIIb binding in comparison to that of IL6R-B3/IL6R-L, and the degree of enhancement of FcgRIIb binding compared to that of IL6R-B3/IL6R-L was 2.6 times to 3090 times. Furthermore, while KD(IIaR)/KD(IIb) for IL6R-B3/IL6R-L was 0.3, those of the variants shown in Table 11 ranged from 8.7 to 64.4, and the selectivities (KD(IIaR)/KD(IIb)) of all the variants for FcgRIIb were improved in comparison to those of IL6R-B3/IL6R-L.

Introducing alterations that lower binding to all FcgRs into these variants with selectively enhanced FcgRIIb binding was predicted to yield variants whose FcgRIIb-binding is maintained at a level similar to that of IgG1 while binding to other activating FcgRs is selectively lowered in comparison to those of IgG1. Then, it was verified whether variants can be obtained as predicted above, by actually using two types of alterations introduced into IL6R-BP568/IL6R-L and IL6R-BP489/IL6R-L that selectively enhance FcgRIIb binding. Specifically, variants introduced with the above-mentioned two alterations which selectively enhance FcgRIIb binding were used as templates to confirm that it is possible to obtain variants with FcgRIIb binding maintained at a level similar to that of IgG1 but whose binding to other activating FcgRs is selectively lowered in comparison to those of IgG1. More specifically, by introducing into IL6R-G1d alterations that enhance FcgRIIb binding as used in IL6R-BP568/IL6R-L and IL6R-BP489/IL6R-L, two types of variants with selectively enhanced FcgRIIb binding, IL6R-P577 and IL6R-P587, were produced. IL6R-L (SEQ ID NO: 6) was utilized as a common antibody L chain, and together with the respective H chain, the antibodies were expressed and purified according to the method of Reference Example 1. KD values of these two variants for each FcgR are shown in Table 12.

TABLE 12

| Variant Name | Introduced Alterations | KD (M) for FcgRIa | KD (M) for FcgRIIaR | KD (M) for FcgRIIaH | KD (M) for FcgRIIb | KD (M) for FcgRIIIaV | KD of G1d for FcgRIIaR/ KD of Each Variant for FcgRIIaR | KD of G1d for FcgRIIb/ KD of Each Variant for FcgRIIb |
|---|---|---|---|---|---|---|---|---|
| IL6R-G1d/IL6R-L | | 1.2E−10 | 9.7E−07 | 6.5E−07 | 3.9E−06 | 4.2E−07 | 1.0 | 1.0 |
| IL6R-P577/IL6R-L | E233D/G237D/P238D/V264I/S267A/H268E/P271G/Y296D/A330R/P396M | 1.1E−09 | 4.4E−08 | 1.0E−06 | 1.2E−09 | 1.2E−05 | 21.9 | 3370.7 |
| IL6R-P587/IL6R-L | E233D/P238D/V264I/S267A/H268E/P271G | 2.1E−10 | 7.1E−07 | 1.2E−05 | 1.5E−08 | 2.8E−05 | 1.4 | 255.6 |

The binding of P577 to FcgRIIaR was 21.9 times that of G1d, and its binding to FcgRIIb was 3370.7 times that of G1d. The binding of P587 to FcgRIIaR was 1.4 times that of G1d, and its binding to FcgRIIb was 255.6 times that of G1d.

By introducing alterations that lower binding to all FcgRs into the prepared two types of variants with enhanced binding to FcgRIIb, production of variants whose FcgRIIb binding is maintained at a level similar to that of a native IgG1 while binding to other FcgRs, in particular FcgRIIaR, are attenuated as much as possible was examined Alterations that greatly lower FcgRIIaR binding were found through an investigation involving comprehensive introduction of alterations to the FcgR-interacting residues. In addition to the comprehensive introduction of alterations at positions 234, 235, 236, 237, and 239 of IL6R-F652/IL6R-L according to EU numbering as shown in Example 4-1, comprehensive introduction of alterations was carried out on variants with selectively enhanced FcgRIIb binding.

Alterations that enhance FcgRIIb-binding (E233D/G237D/H268E/P271G) as reported in WO2012/115241 were introduced into IL6R-BF648 (SEQ ID NO: 2) to produce IL6R-BP267 (SEQ ID NO: 5). Variants with substitutions at positions 265, 266, 267, and 269 of IL6R-BP267, according to EU numbering, with 18 types of amino acids excluding the original amino acid and Cys were produced. IL6R-L (SEQ ID NO: 6) was utilized as a common antibody L chain, and together with the respective H chain, the antibodies were expressed and purified according to the method of Reference Example 1. These antibody variants were expressed and purified according to the method of Reference Example 1, and binding to each of the FcγRs (FcγRIa, FcγRIIa H type, FcγRIIa R type, FcgRIIb, FcγRIIIa V type) was comprehensively evaluated by the method of Reference Example 2. The relative FcgRIIaR- and FcgRIIb-binding activities of variants discovered by comprehensively introducing alterations into IL6R-F652/IL6R-L and IL6R-BP267/IL6R-L are shown in Table 13 and Table 14, respectively. These values are obtained by dividing values for the amount of each variant bound to FcgRIIaR or FcgRIIb by values for the amount of IL6R-F652/IL6R-L or IL6R-BP267/IL6R-L bound to respective FcgR, and then multiplying these values by 100.

TABLE 13

| Variant Name | Alteration introduced into IL6R-F652 | Relative FcgRIIaR-binding Activity | Relative FcgRIIb-binding Activity |
|---|---|---|---|
| IL6R-F652/IL6R-L | | 100.0 | 100.0 |
| IL6R-PD072/IL6R-L | G236Q | 20.6 | 10.4 |

TABLE 13-continued

| Variant Name | Alteration introduced into IL6R-F652 | Relative FcgRIIaR-binding Activity | Relative FcgRIIb-binding Activity |
|---|---|---|---|
| IL6R-PD085/IL6R-L | G237K | 0.5 | 11.8 |
| IL6R-PD090/IL6R-L | G237R | 7.9 | 23.7 |
| IL6R-PD026/IL6R-L | L234A | 67.2 | 37.2 |
| IL6R-PD031/IL6R-L | L234H | 41.8 | 27.6 |
| IL6R-PD033/IL6R-L | L234K | 11.2 | 6.2 |
| IL6R-PD035/IL6R-L | L234N | 44.4 | 38.3 |
| IL6R-PD038/IL6R-L | L234R | 7.8 | 5.4 |
| IL6R-PD044/IL6R-L | L235A | 37.7 | 7.9 |

TABLE 14

| Variant name | Alterations introduced into IL6R-BP267 | Relative FcgRIIaR-binding Activity | Relative FcgRIIb-binding Activity |
|---|---|---|---|
| IL6R-BP267/IL6R-L |  | 100.0 | 100.0 |
| IL6R-BP318/IL6R-L | D265K | 4.3 | 2.3 |
| IL6R-BP321/IL6R-L | D265N | 16.3 | 31.7 |
| IL6R-BP324/IL6R-L | D265R | 3.7 | 3.2 |
| IL6R-BP325/IL6R-L | D265S | 11.6 | 21.0 |
| IL6R-BP327/IL6R-L | D265V | ND | ND |
| IL6R-BP355/IL6R-L | S267K | 11.6 | 14.4 |
| IL6R-BP361/IL6R-L | S267R | 17.3 | 27.7 |
| IL6R-BP365/IL6R-L | S267Y | 9.8 | 16.7 |

From the results shown in Tables 13 and 14, the alterations were found to lower FcgRIIaR binding to at least 67% or less in comparison to before introducing the alterations, and they included some that lead to complete loss of FcgRIIaR-binding.

Next, these alterations were introduced into variants with selectively enhanced FcgRIIb-binding, and then examined. Specifically, 17 alterations shown in Tables 13 and 14 were introduced into IL6R-P577 and IL6R-P587 according to the method of Reference Example 1. It is reported that removing the N-type sugar chain attached to Asn at position 297 of the Fc region, according to EU numbering, remarkably lowers FcgR-binding by antibodies (The Journal of Biological Chemistry, 2000, 276, 6591-6604). Therefore, in this Example, in addition to the 17 alterations described above, N297A was introduced into IL6R-P577 and IL6R-P587 according to the method of Reference Example 1 to remove the N-type sugar chain attached to Asn297. IL6R-L (SEQ ID NO: 6) was utilized as a common antibody L chain, and together with the respective H chain, the antibodies were expressed and purified according to the method of Reference Example 1. Binding of the obtained variants to FcgRIa, FcgRIIaR, FcgRIIaH, FcgRIIb, and FcgRIIIaV was evaluated according to the method of Reference Example 2. Table 15 shows the relative binding activities of each variant to FcgRIIaR and FcgRIIb. These values are obtained by dividing values for the amount of each variant bound to FcgRIIaR or FcgRIIb by values for the amount of IL6R-G1d/IL6R-L bound to FcgRIIaR or FcgRIIb, and then multiplying these values by 100.

TABLE 15

| Variant Name | Alterations that are included in the introduction | Relative FcgRIIaR-binding Activity | Relative FcgRIIb-binding Activity |
|---|---|---|---|
| IL6R-G1d/IL6R-L |  | 100.0 | 100.0 |
| IL6R-F648/IL6R-L | P238D | 29.9 | 138.5 |
| IL6R-P606/IL6R-L | E233D/P238D/S239K/V264I/S267A/H268E/P271G | 4.8 | 7.7 |
| IL6R-P607/IL6R-L | E233D/G237D/P238D/S239K/V264L/S267A/H268E/P271G/Y296D/A330R/P396M | 5.1 | 21.8 |
| IL6R-P609/IL6R-L | E233D/L234A/P238D/V264I/S267A/H268E/P271G | 82.6 | 178.4 |
| IL6R-P611/IL6R-L | E233D/L234A/G237D/P238D/V264L/S267A/H258E/P271G/Y296D/A330R/P396M | 107.4 | 183.3 |
| IL6R-P613/IL6R-L | E233D/L235A/P238D/V264I/S267A/H268E/P271G | 61.2 | 120.3 |
| IL6R-P614/IL6R-L | E233D/L235A/G237D/P238D/V264I/S267A/H268E/P271G/Y296D/A330R/P396M | 69.5 | 176.0 |
| IL6R-P616/IL6R-L | E233D/L234A/L235A/P238D/V264I/S267A/H268E/P271G | 41.8 | 89.2 |
| IL6R-P617/IL6R-L | E233D/L234A/L235A/G237D/P238D/V264I/S267A/H268E/P271G/Y296D/A330R/P396M | 49.2 | 157.6 |
| IL6R-P623/IL6R-L | E233D/L234H/P238D/V264I/S267A/H268E/P271G | 44.7 | 151.8 |
| IL6R-P624/IL6R-L | E233D/L234N/P238D/V264I/S267A/H268E/P271G | 67.1 | 172.9 |
| IL6R-P625/IL6R-L | E233D/L234K/P238D/V264I/S267A/H268E/P271G | 25.8 | 141.1 |
| IL6R-P626/IL6R-L | E233D/L234R/P238D/V264I/S267A/H268E/P271G | 24.4 | 129.2 |
| IL6R-P627/IL6R-L | E233D/G238Q/P238D/V264I/S267A/H268E/P271G | 48.5 | 138.5 |
| IL6R-P628/IL6R-L | E233D/G237R/P238D/V264I/S267A/H268E/P271G | 48.1 | 176.5 |
| IL6R-P629/IL6R-L | E233D/G237K/P238D/V264I/S267A/H268E/P271G | 29.9 | 163.9 |
| IL6R-P630/IL6R-L | E233D/P238D/V264I/D265K/S267A/H268E/P271G | 4.1 | 7.1 |
| IL6R-P631/IL6R-L | E233D/P238D/V264I/D265N/S267A/H268E/P271G | 26.7 | 109.8 |
| IL6R-P632/IL6R-L | E233D/P238D/V264I/D265R/S267A/H268E/P271G | 4.1 | 8.0 |
| IL6R-P633/IL6R-L | E233D/P238D/V264I/D265S/S267A/H268E/P271G | 15.3 | 55.4 |
| IL6R-P634/IL6R-L | E233D/P238D/V264I/D265V/S267A/H268E/P271G | 2.8 | 6.5 |
| IL6R-P635/IL6R-L | E233D/P238D/V264I/S267K/H268E/P271G | 6.4 | 71.9 |
| IL6R-P636/IL6R-L | E233D/P238D/V264I/S267R/H268E/P271G | 13.8 | 119.8 |
| IL6R-P637/IL6R-L | E233D/P238D/V264I/S267Y/H268E/P271G | 9.1 | 55.5 |
| IL6R-P638/IL6R-L | E233D/L234H/G237D/P238D/V264I/S267A/H268E/P271G/Y296D/A330R/P396M | 78.3 | 170.4 |
| IL6R-P639/IL6R-L | E233D/L234N/G237D/P238D/V264I/S267A/H268E/P271G/Y296D/A330R/P396M | 108.7 | 184.2 |
| IL6R-P640/IL6R-L | E233D/L234K/G237D/P238D/V264I/S267A/H268E/P271G/Y296D/A330R/P396M | 75.1 | 178.3 |
| IL6R-P641/IL6R-L | E233D/L234R/G237D/P238D/V264I/S267A/H268E/P271G/Y296D/A330R/P396M | 61.5 | 170.1 |
| IL6R-P642/IL6R-L | E233D/G236Q/G237D/P238D/V264I/S267A/H268E/P271G/Y296D/A330R/P396M | 103.2 | 175.0 |
| IL6R-P643/IL6R-L | E233D/G237R/P238D/V264I/S267A/H268E/P271G/Y296D/A330R/P396M | 58.7 | 177.7 |
| IL6R-P644/IL6R-L | E233D/G237K/P238D/V264I/S267A/H268E/P271G/Y296D/A330R/P396M | 34.0 | 170.8 |
| IL6R-P645/IL6R-L | E233D/G237D/P238D/V264I/D265K/S267A/H268E/P271G/Y296D/A330R/P396M | 5.2 | 13.7 |
| IL6R-P646/IL6R-L | E233D/G237D/P238D/V264I/D265N/S267A/H268E/P271G/Y296D/A330R/P396M | 72.5 | 175.3 |
| IL6R-P647/IL6R-L | E233D/G237D/P238D/V264I/D265R/S267A/H268E/P271G/Y296D/A330R/P396M | 5.6 | 15.2 |
| IL6R-P648/IL6R-L | E233D/G237D/P238D/V264I/D265S/S267A/H268E/P271G/Y296D/A330R/P396M | 40.3 | 152.3 |
| IL6R-P649/IL6R-L | E233D/G237D/P238D/V264I/D265V/S267A/H268E/P271G/Y296D/A330R/P396M | 2.9 | 6.9 |
| IL6R-P650/IL6R-L | E233D/G237D/P238D/V264I/S267K/H268E/P271G/Y296D/A330R/P396M | 41.6 | 154.9 |
| IL6R-P651/IL6R-L | E233D/G237D/P238D/V264I/S267R/H268E/P271G/Y296D/A330R/P396M | 75.7 | 168.5 |
| IL6R-P652/IL6R-L | E233D/G237D/P238D/V264I/S267Y/H268E/P271G/Y296D/A330R/P396M | 27.5 | 148.8 |
| IL6R-P664/IL6R-L | E233D/P238D/V264I/S267A/H268E/P271G/N297A | 10.8 | 33.9 |
| IL6R-P665/IL6R-L | E233D/G237D/P238D/V264I/S267A/H268E/P271G/Y296D/N297A/A330R/P396M | 15.0 | 121.4 |
| IL6R-P696/IL6R-L | E233D/G237R/P238D/V264I/S267R/H268E/P271G | 6.1 | 73.7 |
| IL6R-P697/IL6R-L | E233D/G237K/P238D/V264I/S267R/H268E/P271G | 3.6 | 28.7 |

TABLE 15-continued

| Variant Name | Alterations that are included in the introduction | Relative FcgRIIaR-binding Activity | Relative FcgRIIb-binding Activity |
|---|---|---|---|
| IL6R-P700/IL6R-L | E233D/L234A/P238D/V264I/S267R/H268E/P271G | 5.8 | 38.1 |
| IL6R-P701/IL6R-L | E233D/L234N/P238D/V264I/S267R/H268E/P271G | 7.0 | 47.8 |

As shown in Table 15, variants P606 and P607 produced by introducing S239K, P630 and P645 produced by introducing D265K, P632 and P647 produced by introducing D265R, and P634 and P649 produced by introducing D265V showed hardly any binding to FcgRIIaR and FcgRIIb. This means that these alterations will remarkably reduce the FcgRIIb-binding activity even if they are introduced into variants with enhanced FcgRIIb binding. On the other hand, P636 produced by introducing S267R into P587, and P665 produced by introducing N297A into P577 showed almost the same FcgRIIb-binding as that of G1d and greatly reduced FcgRIIaR-binding.

From among the variants shown in Table 15, variants with FcgRIIb binding maintained at 80% or more of the binding activity of G1d, and FcgRIIaR binding suppressed to 30% or less of the binding activity of G1d, and their KD values for each FcgR are shown in Table 16. The relative binding activity in the table is a value obtained by dividing the KD value of IL6R-G 1 d/IL6R-L by the KD value of each variant, and represents the relative binding activity of each variant when the KD value of IL6R-G1d/IL6R-L for each FcgR is defined as 1. Among the KD values shown in the table, the values in the solid gray boxes are values calculated by utilizing Equation 2 of Reference Example 2, as the binding of FcgR to each variant is very weak and cannot be accurately analyzed by kinetic analysis.

$$KD=C\cdot R_{max}/(R_{eq}-RI)-C \quad \text{[Equation 2]}$$

Among these variants, the one showing the most reduced FcgRIIaR binding was P636 produced by introducing S267R into P587. The KD of P636 for FcgRIIaR was 0.023 times that of G1d, but the KD for FcgRIIb was maintained at 1.8 times that of G1d. Furthermore, FcgRIa binding was suppressed to 0.0007 times that of G1d, FcgRIIaH-binding was suppressed to 0.006 times, and FcgRIIIaV binding was suppressed to 0.008 times. The above-mentioned results showed that it is possible to obtain variants whose FcgRIIb binding is maintained at a level similar to that of IgG1 while binding to other FcgRs is lowered in comparison to those of IgG1 by introducing alterations that lower binding to all FcgRs into a variant with selectively enhanced FcgRIIb binding.

(4-3) Examination of a Combination of Alterations that have an Effect of Lowering FcgRIIaR Binding Production of better variants was examined by combining alterations found in 4-1 and 4-2 that maintain FcgRIIb binding at a level similar to that of G1d while lowering FcgRIIaR binding.

Results of examining the combinations are shown in Table 17. The relative binding activities shown in the table are values obtained by dividing the KD value of IL6R-G1d/IL6R-L by the KD value of each variant, and represent the relative binding activities for each variant when the KD value of IL6R-G1d/IL6R-L for each FcgR is defined as 1. Among the KD values shown in the table, the values in the solid gray boxes are values calculated by utilizing Equation

TABLE 16

| Variant name | Included Alterations | KD (M) for FcgRIa | KD (M) for FcgRIIaR | KD (M) for FcgRIIaH | KD (M) for FcgRIIb |
|---|---|---|---|---|---|
| IL6R-G1d/IL6R-L | | 3.3E−10 | 1.2E−06 | 9.6E−07 | 5.1E−06 |
| IL6R-F648/IL6R-L | P238D | 8.0E−09 | 1.9E−05 | 7.9E−05 | 1.9E−06 |
| IL6R-P625/IL6R-L | E233D/L234K/P238D/V264I/S267A/H268E/P271G | 5.0E−07 | 2.4E−05 | 1.8E−04 | 1.7E−06 |
| IL6R-P626/IL6R-L | E233D/L234R/P238D/V264I/S267A/H268E/P271G | 7.4E−07 | 3.1E−05 | 2.0E−04 | 2.7E−06 |
| IL6R-P629/IL6R-L | E233D/G237K/P238D/V264I/S267A/H268E/P271G | 3.3E−09 | 2.7E−05 | 1.0E−04 | 6.5E−07 |
| IL6R-P631/IL6R-L | E233D/P238D/V264I/D265N/S267A/H268E/P271G | 1.1E−08 | 2.6E−05 | 9.6E−05 | 4.4E−06 |
| IL6R-P636/IL6R-L | E233D/P238D/V264I/S267R/H268E/P271G | 4.6E−07 | 5.4E−05 | 1.7E−04 | 2.9E−06 |
| IL6R-P652/IL6R-L | E233D/G237D/P238D/V264I/S267Y/H268E/P271G/ Y296D/A330R/P396M | 7.2E−07 | 2.4E−05 | 1.7E−04 | 1.2E−06 |
| IL6R-P665/IL6R-L | E233D/G237D/P238D/V2641/S267A/H268E/P271G/ Y296D/N297A/A330R/P396M | 1.9E−06 | 4.9E−05 | 4.5E−04 | 3.2E−06 |

| Variant name | KD (M) for FcgRIIIaV | Relative FcgRIa-binding Activity | Relative FcgRIIaR-binding Activity | Relative FcgRIIaH-binding Activity | Relative FcgRIIb-binding Activity | Relative FcgRIIIaV-binding Activity |
|---|---|---|---|---|---|---|
| IL6R-G1d/IL6R-L | 3.4E−07 | 1.0000 | 1.000 | 1.000 | 1.000 | 1.000 |
| IL6R-F648/IL6R-L | 6.9E−05 | 0.0413 | 0.065 | 0.012 | 2.749 | 0.005 |
| IL6R-P625/IL6R-L | 6.6E−05 | 0.0007 | 0.051 | 0.005 | 3.060 | 0.005 |
| IL6R-P626/IL6R-L | 7.5E−05 | 0.0004 | 0.041 | 0.005 | 1.897 | 0.005 |
| IL6R-P629/IL6R-L | 4.7E−05 | 0.1000 | 0.047 | 0.010 | 7.969 | 0.007 |
| IL6R-P631/IL6R-L | 4.7E−05 | 0.0300 | 0.048 | 0.010 | 1.158 | 0.007 |
| IL6R-P636/IL6R-L | 4.5E−05 | 0.0007 | 0.023 | 0.006 | 1.772 | 0.008 |
| IL6R-P652/IL6R-L | 7.2E−05 | 0.0005 | 0.051 | 0.006 | 4.179 | 0.005 |
| IL6R-P665/IL6R-L | 6.7E−05 | 0.0002 | 0.025 | 0.002 | 1.601 | 0.005 |

2 of Reference Example 2, as the binding of FcgR to each variant is very weak and cannot be accurately analyzed by kinetic analysis.

$$KD = C \cdot R_{max}/(R_{eq}-RI)-C \quad \text{[Equation 2]}$$

TABLE 17

| Variant name | Included alterations | KD (M) for FcgRIa | KD (M) for FcgRIIaR | KD (M) for FcgRIIaH | KD (M) for FcgRIIb |
|---|---|---|---|---|---|
| IL6R-G1d/IL6R-L | | 3.3E−10 | 1.2E−06 | 9.6E−07 | 5.1E−06 |
| IL6R-F648/IL6R-L | P238D | 8.0E−09 | 1.9E−05 | 7.9E−05 | 1.9E−06 |
| IL6R-P694/IL6R-L | E233D/P238D/V264I/S267R/H268E/P271G/Y296E | 4.1E−07 | 0.1E−05 | 2.0E−04 | 2.8E−06 |
| IL6R-P699/IL6R-L | E233D/P238D/V264I/S267R/H268P/P271G | 6.9E−07 | 5.7E−05 | 2.5E−04 | 4.1E−06 |
| IL6R-P702/IL6R-L | E233D/P238D/F241M/V264I/S267R/H268E/P271G | 5.7E−07 | 5.4E−05 | 1.7E−04 | 4.0E−06 |
| IL6R-P712/IL6R-L | E233D/P238D/V264I/S267R/H268P/P271G/Y296E | 6.8E−07 | 7.1E−05 | 3.0E−04 | 3.4E−06 |
| IL6R-P730/IL6R-L | E233D/G237Q/P238D/V264I/S267R/H268P/P271G/Y296E | 1.5E−06 | 9.5E−05 | 3.1E−04 | 1.0E−05 |

| Variant name | KD (M) for FcgRIIIaV | Relative FcgRIa-binding Activity | Relative FcgRIIaR-binding Activity | Relative FcgRIIaH-binding Activity | Relative FcgRIIb-binding Activity | Relative FcgRIIIaV-binding Activity |
|---|---|---|---|---|---|---|
| IL6R-G1d/IL6R-L | 3.4E−07 | 1.000 | 1.000 | 1.000 | 1.000 | 1.000 |
| IL6R-F648/IL6R-L | 6.9E−05 | 0.0413 | 0.065 | 0.012 | 2.749 | 0.005 |
| IL6R-P694/IL6R-L | 4.7E−05 | 0.0008 | 0.020 | 0.005 | 1.829 | 0.007 |
| IL6R-P699/IL6R-L | 6.5E−05 | 0.0005 | 0.022 | 0.004 | 1.263 | 0.005 |
| IL6R-P702/IL6R-L | 4.4E−05 | 0.0006 | 0.023 | 0.006 | 1.275 | 0.008 |
| IL6R-P712/IL6R-L | 8.2E−05 | 0.0005 | 0.017 | 0.003 | 1.516 | 0.004 |
| IL6R-P730/IL6R-L | 7.3E−05 | 0.0002 | 0.013 | 0.003 | 0.504 | 0.005 |

Among the variants shown in Table 17, the one showing the most reduced FcgRIIaR binding was P712 produced by introducing a combination of S267R, H268P, and Y296E into P587, which is a variant with selectively enhanced FcgRIIb binding; and its FcgRIIb binding was maintained at 1.5 times that of G1d while its FcgRIIaR-binding was lowered to 0.017 times that of G1d. Furthermore, its FcgRIa binding was suppressed to 0.0005 times that of G1d, FcgRIIaH binding was suppressed to 0.003 times, and FcgRIIIaV binding was suppressed to 0.004 times.

Example 5

Production of Variants Whose FcgRIIb Binding is Maintained at a Level Similar to that of the Native Type, with Attenuated Binding to Other FcgRs as Well as Attenuated Complement-Binding Similarly to ADCC, complement-dependent cytotoxicity (CDC) is an effector function that initiates immune response. The variants produced so far all have greatly reduced binding activities for activating receptors except for FcgRIIb, and their ADCC activities are considered to be greatly attenuated. However, since the binding site between an antibody and a complement is different from the binding site between an antibody and an FcgR, it is possible that the complement-binding activity is maintained. Therefore, the complement-binding activity of each variant was evaluated, and variants with attenuated complement-binding were produced by combining alterations that lower complement-binding.

The interaction between an antibody and human C1q was analyzed using Biacore T200 (GE Healthcare). HBS-EP+ (GE Healthcare) was used as the running buffer, and the measurement temperature was set at 25° C. Chips produced by immobilizing Protein L (ACTIGEN or BioVision) onto Series S sensor Chip CM4 (GE Healthcare) by amine coupling were used.

The antibodies of interest were captured onto these sensor chips, and allowed to interact with human complement C1q (PROSPEC or Calbiochem) diluted in the running buffer. The amount of antibody binding was determined, and comparisons were made among the antibodies. However, since the amount of C1q bound depends on the amount of captured antibodies, corrected values obtained by dividing the amount of C1q bound by the amount of each antibody captured were compared. Furthermore, by reaction with 10 mM glycine-HCl, pH 1.5, the antibodies captured onto the sensor chips were washed, and the sensor chips were recycled and reused.

For the alteration to lower C1q binding, K322A described in a prior document (J. Immunol, 2003, 164, 4178-4184) was used. Furthermore, since substitution of oppositely charged Glu for Lys at position 322 according to EU numbering was also expected to lower C1q binding, K322E was also examined. Furthermore, the remarkably low CDC activity of IgG4 in comparison to IgG1 has been reported to be caused by difference in the C-terminal sequences of the CH2 domains (J. Exp. Med., 1991, 173, 1025-1028). Therefore, lowering C1q binding by substituting Gly for Ala at position 327, Ser for Ala at position 330, and Ser for Pro at position 331 of IgG1, according to EU numbering, to produce an IgG4-type sequence was also examined.

Human C1q binding was evaluated for variants with enhanced FcgRIIb binding and variants with maintained FcgRIIb binding as well as lowered binding to other FcgRs. Variants were produced by combining the above variants with alterations that lower C1q binding, and the variants were evaluated. Furthermore, binding to each FcgR was evaluated for all variants produced according to the method of Reference Example 2. Human IgG4 was used as a negative control for evaluation of C1q binding. IL6R-G4d (SEQ ID NO: 52) comprising G4d prepared by substituting Pro for Ser at position 228 according to EU numbering and removing Gly and Lys from the C terminus of human IgG4, was produced. IL6R-L (SEQ ID NO: 6) was utilized as a common antibody L chain.

Table 18 shows the results of evaluating the binding of the produced variants to human C1q. "Amount of C1q binding when that for G1d is defined as 100" in the table is a value obtained by dividing the amount of C1q bound to each variant by the amount of each variant captured, then dividing it by the value obtained by dividing the amount of C1q bound to IL6R-G1d/IL6R-L by the amount of IL6R-G1d/IL6R-L captured, and then multiplying that value by 100. More specifically, it is a value that shows the level of C1q binding in comparison to that of IL6R-G1d/IL6R-L.

TABLE 18

| Variant name | Included alterations | Amount of C1q-binding when that for G1d is Defined as 100 |
|---|---|---|
| IL6R-G1d/IL6R-L | | 100.0 |
| IL6R-G4d/IL6R-L | | 15.5 |
| IL6R-G1dK322A/IL6R-L | K3322A | 20.5 |
| IL6R-G1dK322E/IL6R-L | K322E | 2.3 |
| IL6R-G1dGSS/IL6R-L | A327G/A330S/P331S | 15.2 |
| IL6R-P648/IL6R-L | P238D | 21.5 |
| IL6R-P741/IL6R-L | P238D/K322A | 1.4 |
| IL6R-P742/IL6R-L | P238D/K322E | 14.1 |
| IL6R-P743/IL6R-L | P238D/A327G/A330S/P331S | 20.9 |
| IL6R-P600/IL6R-L | P238D/S298A | 2.4 |
| IL6R-P744/IL6R-L | P238D/S298A/K322A | 13.6 |
| IL6R-P745/IL6R-L | P238D/S298A/K322E | 20.9 |
| IL6R-P691/IL6R-L | L235F/G237Q/P238D/F241M/Y296E | 21.0 |
| IL6R-P746/IL6R-L | L235F/G237Q/P238D/F241M/Y296E/K322A | 1.4 |
| IL6R-P747/IL6R-L | L235F/G237Q/P238D/F241M/Y296E/K322E | 13.7 |
| IL6R-P727/IL6R-L | G237Q/P238D/F241M/H268P/Y296E/A330H | 35.5 |
| IL6R-P748/IL6R-L | G237Q/P238D/F241M/H268P/Y296E/K322A/A330H | 1.4 |
| IL6R-P749/IL6R-L | G237Q/P238D/F241M/H268P/Y296E/K322E/A330H | 13.8 |
| IL6R-P729/IL6R-L | L235F/G237Q/P238D/F241M/H268P/Y296E | 22.8 |
| IL6R-P750/IL6R-L | L235F/G237Q/P238D/F241M/H268P/Y296E/K322A | 1.2 |
| IL6R-P751/IL6R-L | L235F/G237Q/P238D/F241M/H268P/Y296E/K322E | 13.9 |
| IL6R-P733/IL6R-L | L235F/G237Q/P238D/F241M/H268P/Y296E/S324H | 23.0 |
| IL6R-P752/IL6R-L | L235F/G237Q/P238D/F241M/H268P/Y296E/K322A/S324H | 1.1 |
| IL6R-P753/IL6R-L | L235F/G237Q/P238D/F241M/H268P/Y296E/K322E/S324H | 14.0 |
| IL6R-P737/IL6R-L | G237Q/P238D/F241M/H268P/Y296E/S324H/A330H | 45.7 |
| IL6R-P754/IL6R-L | G237Q/P238D/F241M/H268P/Y296E/K322A/S324H/A330H | 1.8 |
| IL6R-P755/IL6R-L | G237Q/P238D/F241M/H268P/Y296E/K322E/S324H/A330H | 14.4 |
| IL6R-P587/IL6R-L | E233D/P238D/V264I/S267A/H268E/P271G | 131.7 |
| IL6R-P588/IL6R-L | P238D/V264I/S267A/H268E/P271G | 108.1 |
| IL6R-P756/IL6R-L | E233D/P238D/V264I/S267A/H268E/P271G/A327G/A330S/P331S | 15.0 |
| IL6R-P757/IL6R-L | P238D/V264I/S267A/H268E/P271G/A327G/A330S/P331S | 22.6 |
| IL6R-P758/IL6R-L | G237D/P238D/H268D/P271G/A327G/A330S/P331S | 2.0 |
| IL6R-P759/IL6R-L | E233D/G237D/P238D/H268D/P271G/A327G/A330S/P331S | 14.5 |
| IL6R-P760/IL6R-L | G237D/P238D/H268E/P271G/A327G/A330S/P331S | 21.7 |
| IL6R-P761/IL6R-L | E233D/G237D/P238D/H268E/P271G/A327G/A330S/P331S | 2.1 |
| IL6R-P762/IL6R-L | P238D/P271G/A327G/A330S/P331S | 14.6 |
| IL6R-P766/IL6R-L | P238D/S267A/H268E/P271G/A327G/A330S/P331S | 21.8 |
| IL6R-P767/IL6R-L | P238D/V264I/H268E/P271G/A327G/A330S/P331S | 1.7 |
| IL6R-P768/IL6R-L | P238D/V264I/S267A/P271G/A327G/A330S/P331S | 14.0 |
| IL6R-P769/IL6R-L | P238D/V264I/P271G | 31.3 |
| IL6R-P770/IL6R-L | P238D/V264I/P271G/A327G/A330S/P331S | 1.5 |
| IL6R-P771/IL6R-L | P238D/V264I/P271G/K322A | 14.3 |
| IL6R-P772/IL6R-L | P238D/V264I/P271G/K322E | 21.6 |
| IL6R-P773/IL6R-L | P238D/S267A/H268E/P271G/K322A | 1.7 |
| IL6R-P774/IL6R-L | P238D/S267A/H268E/P271G/K322E | 15.2 |
| IL6R-P112/IL6R-L | P238D/P271G | 24.2 |
| IL6R-P555/IL6R-L | G237D/P238D/H268D/P271G | 29.1 |
| IL6R-P556/IL6R-L | E233D/G237D/P238D/H268D/P271G | 33.5 |
| IL6R-P559/IL6R-L | G237D/P238D/H268E/P271G | 34.1 |
| IL6R-P562/IL6R-L | E233D/G237D/P238D/H268E/P271G | 29.4 |
| IL6R-P763/IL6R-L | P238D/S267A/H268E/P271G | 41.7 |
| IL6R-P764/IL6R-L | P238D/V264I/H268E/P271G | 23.1 |
| IL6R-P765/IL6R-L | P238D/V264I/S267A/P271G | 46.6 |
| IL6R-P775/IL6R-L | P238D/P271G/K322A | 21.8 |
| IL6R-P776/IL6R-L | P238D/P271G/K322E | 0.7 |
| IL6R-P777/IL6R-L | E233D/P238D/V264I/S267A/H268E/P271G/K322A | 12.4 |
| IL6R-P778/IL6R-L | E233D/P238D/V264I/S267A/H268E/P271G/K322E | 23.9 |
| IL6R-P779/IL6R-L | P238D/V264I/S267A/H268E/P271G/K322A | 0.8 |
| IL6R-P780/IL6R-L | P238D/V264I/S267A/H268E/P271G/K322E | 12.9 |
| IL6R-P781/IL6R-L | P238D/S298A/A327G/A330S/P331S | 24.0 |
| IL6R-P782/IL6R-L | E233D/P238D/A327G/A330S/P331S | 1.3 |
| IL6R-P783/IL6R-L | G237D/P238D/A327G/A330S/P331S | 13.3 |
| IL6R-P784/IL6R-L | E233D/G237D/P238D/A327G/A330S/P331S | 24.2 |
| IL6R-P785/IL6R-L | E233D/P238D/S298A/A327G/A330S/P331S | 1.3 |
| IL6R-P786/IL6R-L | G237D/P238D/S298A/A327G/A330S/P331S | 12.9 |
| IL6R-P787/IL6R-L | E233D/G237D/P238D/S298A/A327G/A330S/P331S | 24.0 |

When the value for G1d comprising the native sequence was defined as 100, the value for the negative control, G4d, was 15.5. C1q binding of G1dK322A, G1dK322E, and G1dGSS which have been produced by introducing into G1d alterations that lower C1q binding had values of 20.5, 2.3, and 15.2, respectively, which were values equivalent to or lower than that of G4d. This showed that C1q binding was greatly lowered compared to before introducing the alterations. Furthermore, F648 produced by introducing the P238D alteration which selectively enhances FcgRIIB binding was found to have C1q binding nearly equal to that of G4d even without the use of alterations that lower C1q binding. The C1q-binding ability of P741, P742, and P743 produced by further introducing alterations that lower C1q binding into these variants all had values equivalent to or less than that of G4d.

Among P600, P691, P727, P729, P733, and P737 which are variants with their FcgRIIb-binding maintained at the same level as that of the native type and attenuated ability to bind to other FcgRs, P600, P691, P729, and P733 all had a C1q-binding activity equivalent to that of G4d. On the other hand, while P727 and P737 showed largely attenuated binding abilities compared to that of G1d, they were two-fold or higher in comparison to that of G4d. The A330H alteration is commonly introduced into both variants, and this is thought to enhance C1q binding. By introducing into all variants K322A or K322E which are alterations that lower C1q binding, the C1q-binding activity was suppressed to a level lower than that of G4d.

Among P587, P588, P769, P112, P555, P556, P559, P562, P763, P764, and P765 which are variants with enhanced FcgRIIb binding, P587 and P588 have been found to have C1q binding equal to or greater than that of G1d. Furthermore, in comparison to G1d, the binding abilities of P769, P556, P559, P562, P763, and P765 were greatly attenuated; however, they were nearly twice that of G4d. On the other hand, the C1q-binding activities of P112 and P764 were nearly equal to that of G4d. Furthermore, introducing alterations that lower C1q binding suppressed the C1q-binding activities in all variants to levels equivalent to or lower than that of G4d.

Table 19 shows the relative binding activities of each variant for FcgRIIaR and FcgRIIb. These values are obtained by dividing values for the amount of each variant bound to FcgRIIaR or FcgRIIb by values for the amount of IL6R-G1d/IL6R-L bound to FcgRIIaR or FcgRIIb, and then multiplying the values by 100.

TABLE 19

| Variant name | Alterations Introduced into G1d | Relative FcgRIIaR-binding Activity | Relative FcgRIIb-binding Activity |
|---|---|---|---|
| IL6R-G1d/IL6R-L | | 100.0 | 100.0 |
| IL6R-G1dK322A/IL6R-L | K322A | 105.2 | 108.6 |
| IL6R-G1dK322E/IL6R-L | K322E | 111.7 | 129.1 |
| IL6R-G1dGSS/IL6R-L | A327G/A330S/P331S | 98.5 | 115.2 |
| IL6R-F648/IL6R-L | P238D | 30.7 | 185.3 |
| IL6R-P741/IL6R-L | P238D/K322A | 20.5 | 162.8 |
| IL6R-P742/IL6R-L | P238D/K322E | 26.6 | 171.0 |
| IL6R-P743/IL6R-L | P238D/A327G/A330S/P331S | 13.5 | 69.4 |
| IL6R-P600/IL6R-L | P238D/S298A | 15.6 | 101.6 |
| IL6R-P744/IL6R-L | P238D/S298A/K322A | 11.1 | 81.4 |
| IL6R-P745/IL6R-L | P238D/S298A/K322E | 13.7 | 95.4 |
| IL6R-P691/IL6R-L | L235F/G237Q/P238D/F241M/Y296E | 10.8 | 119.2 |
| IL6R-P746/IL6R-L | L235F/G237Q/P238D/F241M/Y296E/K322A | 7.0 | 57.5 |
| IL6R-P747/IL6R-L | L235F/G237Q/P238D/F241M/Y296E/K322E | 10.0 | 98.1 |
| IL6R-P727/IL6R-L | G237Q/P238D/F241M/H268P/Y296E/A330H | 9.7 | 93.0 |
| IL6R-P748/IL6R-L | G237Q/P238D/F241M/H268P/Y296E/K322A/A330H | 5.1 | 42.7 |
| IL6R-P749/IL6R-L | G237Q/P238D/F241M/H268P/Y296E/K322E/A330H | 6.8 | 73.9 |
| IL6R-P729/IL6R-L | L235F/G237Q/P238D/F241M/H268P/Y296E | 9.0 | 100.2 |
| IL6R-P750/IL6R-L | L235F/G237Q/P238D/F241M/H268P/Y296E/K322A | 6.1 | 48.1 |
| IL6R-P751/IL6R-L | L235F/G237Q/P238D/F241M/H268P/Y296E/K322E | 7.4 | 72.5 |
| IL6R-P733/IL6R-L | L235F/G237Q/P238D/F241M/H268P/Y296E/S324H | 8.1 | 84.8 |
| IL6R-P752/IL6R-L | L235F/G237Q/P238D/F241M/H268P/Y296E/K322A/S324H | 7.2 | 62.9 |
| IL6R-P753/IL6R-L | L235F/G237Q/P238D/F241M/H268P/Y296E/K322E/S324H | 10.4 | 103.3 |
| IL6R-P737/IL6R-L | G237Q/P238D/F241M/H268P/Y296E/S324H/A330H | 8.0 | 78.7 |
| IL6R-P754/IL6R-L | G237Q/P238D/F241M/H268P/Y296E/K322A/S324H/A330H | 5.6 | 85.8 |
| IL6R-P755/IL6R-L | G237Q/P238D/F241M/H268P/Y296E/K322E/S324H/A330H | 9.8 | 130.2 |
| IL6R-P587/IL6R-L | E233D/P238D/V264I/S267A/H268E/P271G | 106.3 | 349.5 |
| IL6R-P588/IL6R-L | P238D/V264I/S267A/H268E/P271G | 100.5 | 346.0 |
| IL6R-P756/IL6R-L | E233D/P238D/V264I/S267A/H268E/P271G/A327G/A330S/P331S | 92.4 | 323.4 |
| IL6R-P757/IL6R-L | P238D/V264I/S267A/H268E/P271G/A327G/A330S/P331S | 89.2 | 326.8 |
| IL6R-P758/IL6R-L | G237D/P238D/H268P/P271G/A327G/A330S/P331S | 90.6 | 285.1 |
| IL6R-P759/IL6R-L | E233D/G237D/P238D/H268P/P271G/A327G/A330S/P331S | 96.5 | 304.7 |
| IL6R-P760/IL6R-L | G237D/P238D/H268E/P271G/A327G/A330S/P331S | 97.1 | 304.1 |
| IL6R-P761/IL6R-L | E233D/G237D/P238D/H268E/P271G/A327G/A330S/P331S | 103.3 | 319.7 |
| IL6R-P762/IL6R-L | P238D/P271G/A327G/A330S/P331S | 75.8 | 252.2 |
| IL6R-P766/IL6R-L | P238D/S267A/H268E/P271G/A327G/A330S/P331S | 88.1 | 285.8 |
| IL6R-P767/IL6R-L | P238D/V264I/H268E/P271G/A327G/A330S/P331S | 84.2 | 317.9 |
| IL6R-P768/IL6R-L | P238D/V264I/S267A/P271G/A327G/A330S/P331S | 80.9 | 305.2 |
| IL6R-P769/IL6R-L | P238D/V264I/P271G | 86.7 | 196.2 |
| IL6R-P770/IL6R-L | P238D/V264I/P271G/A327G/A330S/P331S | 78.2 | 188.5 |
| IL6R-P771/IL6R-L | P238D/V264I/P271G/K322A | 75.8 | 195.3 |
| IL6R-P772/IL6R-L | P238D/V264I/P271G/K322E | 84.3 | 195.5 |
| IL6R-P773/IL6R-L | P238D/S267A/H268E/P271G/K322A | 87.3 | 192.3 |
| IL6R-P774/IL6R-L | P238D/S267A/H268E/P271G/K322E | 98.8 | 199.6 |

TABLE 19-continued

| Variant name | Alterations Introduced into G1d | Relative FcgRIIaR-binding Activity | Relative FcgRIIb-binding Activity |
|---|---|---|---|
| IL6R-P112/IL6R-L | P238D/P271G | 75.7 | 287.2 |
| IL6R-P555/IL6R-L | G237D/P238D/H268D/P271G | 83.8 | 305.0 |
| IL6R-P556/IL6R-L | E233D/G237D/P238D/H268D/P271G | 81.7 | 294.0 |
| IL6R-P559/IL6R-L | G237D/P238D/H268E/P271G | 89.4 | 318.7 |
| IL6R-P562/IL6R-L | E233D/G237D/P238D/H268E/P271G | 89.7 | 311.0 |
| IL6R-P763/IL6R-L | P238D/S267A/H268E/P271G | 100.7 | 331.9 |
| IL6R-P764/IL6R-L | P238D/V264I/H268E/P271G | 89.5 | 328.6 |
| IL6R-P765/IL6R-L | P238D/V264I/S267A/P271G | 93.2 | 339.8 |
| IL6R-P775/IL6R-L | P238D/P271G/K322A | 64.2 | 180.5 |
| IL6R-P776/IL6R-L | P238D/P271G/K322E | 77.4 | 189.7 |
| IL6R-P777/IL6R-L | E233D/P238D/V264I/S267A/H268E/P271G/K322A | 97.5 | 198.1 |
| IL6R-P778/IL6R-L | E233D/P238D/V264I/S267A/H268E/P271G/K322E | 105.1 | 198.4 |
| IL6R-P779/IL6R-L | P238D/V264I/S267A/H268E/P271G/K322A | 96.0 | 200.8 |
| IL6R-P780/IL6R-L | P238D/V264I/S267A/H268E/P271G/K322E | 101.4 | 199.9 |
| IL6R-P781/IL6R-L | P238D/S298A/A327G/A330S/P331S | 7.8 | 51.1 |
| IL6R-P782/IL6R-L | E233D/P238D/A327G/A330S/P331S | 14.2 | 95.1 |
| IL6R-P783/IL6R-L | G237D/P238D/A327G/A330S/P331S | 20.5 | 97.9 |
| IL6R-P784/IL6R-L | E233D/G237D/P238D/A327G/A330S/P331S | 28.6 | 118.5 |
| IL6R-P785/IL6R-L | E233D/P238D/S298A/A327G/A330S/P331S | 9.1 | 58.4 |
| IL6R-P786/IL6R-L | G237D/P238D/S298A/A327G/A330S/P331S | 11.5 | 62.4 |
| IL6R-P787/IL6R-L | E233D/G237D/P238D/S298A/A327G/A330S/P331S | 14.7 | 84.9 |

Variants containing alterations that lower complement-binding shown in Table 19 had a relative FcgRIIaR-binding activity 105% or less when compared to that of G1d, and a relative FcgRIIb-binding activity maintained at 48% or more when compared to that of G1d.

Binding of these variants to each FcgR is shown in Table 20. The relative binding activity in the table is a value obtained by dividing the KD value of IL6R-G1d/IL6R-L by the KD value of each variant, and represents the relative binding activity of each variant when the KD value of IL6R-G1d/IL6R-L for each FcgR is defined as 1. Among the KD values shown in the table, the values in the solid gray boxes are values calculated by utilizing Equation 2 of Reference Example 2, as the binding of FcgR to each variant is very weak and cannot be accurately analyzed by kinetic analysis.

$$KD = C \cdot R_{max}/(R_{eq}-RI) - C \qquad \text{[Equation 2]}$$

TABLE 20

| Variant name | Alterations introduced into IL6R-G1d | KD (M) for FcgRIa | KD (M) for FcgRIIaR | KD (M) for FcgRIIaH | KD (M) for FcgRIIb | KD (M) for FcgRIIIaV | Relative FcgRIa-binding Activity | Relative FcgRIIaR-binding Activity | Relative FcgRIIaH-binding Activity | Relative FcgRIIb-binding Activity | Relative FcgRIIIaV-binding Activity |
|---|---|---|---|---|---|---|---|---|---|---|---|
| IL6R-G1d/IL6R-L | | 3.2E−10 | 1.1E−06 | 6.2E−07 | 2.1E−06 | 3.7E−07 | 1.000 | 1.00 | 1.000 | 1.0 | 1.000 |
| IL6R-G1dK322A/IL6R-L | K322A | 2.5E−10 | 9.5E−07 | 9.0E−07 | 2.1E−06 | 5.0E−07 | 1.280 | 1.16 | 0.689 | 1.0 | 0.740 |
| IL6R-G1dK322E/IL6R-L | K322E | 1.8E−10 | 8.1E−07 | 6.8E−07 | 2.0E−06 | 4.7E−07 | 1.778 | 1.36 | 0.912 | 1.1 | 0.787 |
| IL6R-G1dGSS/IL6R-L | A327G/A330S/P331S | 3.3E−10 | 1.4E−06 | 1.2E−06 | 2.4E−06 | 1.6E−06 | 0.970 | 0.79 | 0.517 | 0.9 | 0.231 |
| IL6R-F648/IL6R-L | P238D | 6.4E−09 | 1.6E−05 | 3.7E−05 | 1.2E−06 | 5.8E−05 | 0.050 | 0.07 | 0.017 | 1.8 | 0.006 |
| IL6R-P741/IL6R-L | P238D/K322A | 1.3E−08 | 2.0E−05 | 6.4E−05 | 1.5E−06 | 9.4E−05 | 0.025 | 0.06 | 0.010 | 1.4 | 0.004 |
| IL6R-P742/IL6R-L | P238D/K322E | 8.2E−09 | 1.6E−05 | 3.6E−05 | 1.2E−06 | 5.3E−05 | 0.039 | 0.07 | 0.017 | 1.8 | 0.007 |
| IL6R-P743/IL6R-L | P238D/A327G/A330S/P331S | 1.8E−08 | 2.0E−05 | 4.6E−05 | 3.6E−06 | 5.7E−05 | 0.018 | 0.06 | 0.013 | 0.6 | 0.006 |
| IL6R-P600/IL6R-L | P238D/S298A | 3.6E−09 | 3.9E−05 | 5.2E−05 | 3.2E−06 | 5.7E−05 | 0.089 | 0.03 | 0.012 | 0.7 | 0.006 |
| IL6R-P744/IL6R-L | P238D/S298A/K322A | 1.0E−08 | 1.8E−05 | 4.8E−05 | 3.2E−06 | 5.4E−05 | 0.032 | 0.06 | 0.013 | 0.7 | 0.007 |
| IL6R-P745/IL6R-L | P238D/S298A/K322E | 5.0E−09 | 2.6E−05 | 4.4E−05 | 3.1E−06 | 5.0E−05 | 0.064 | 0.04 | 0.014 | 0.7 | 0.007 |
| IL6R-P691/IL6R-L | L235F/G237Q/P238D/F241M/Y296E | 1.3E−07 | 2.8E−05 | 6.2E−05 | 2.3E−06 | 8.8E−05 | 0.002 | 0.04 | 0.010 | 0.9 | 0.004 |
| IL6R-P746/IL6R-L | L235F/G237Q/P238D/F241M/Y296E/K322A | 7.4E−09 | 1.8E−05 | 6.0E−05 | 3.0E−06 | 7.0E−05 | 0.043 | 0.06 | 0.010 | 0.7 | 0.005 |
| IL6R-P747/IL6R-L | L235F/G237Q/P238D/F241M/Y296E/K322E | 9.0E−08 | 2.7E−05 | 5.1E−05 | 2.7E−06 | 6.2E−05 | 0.004 | 0.04 | 0.012 | 0.8 | 0.006 |
| IL6R-P727/IL6R-L | G237Q/P238D/F241M/H268P/Y296E/A330H | 7.1E−08 | 3.4E−05 | 4.2E−05 | 2.7E−06 | 5.5E−05 | 0.005 | 0.03 | 0.015 | 0.8 | 0.007 |
| IL6R-P748/IL6R-L | G237Q/P238D/F241M/H268P/Y296E/K322A/A330H | 1.0E−07 | 3.9E−05 | 6.0E−05 | 6.2E−06 | 7.7E−05 | 0.003 | 0.03 | 0.010 | 0.3 | 0.005 |
| IL6R-P749/IL6R-L | G237Q/P238D/F241M/H268P/Y296E/K322E/A330H | 5.2E−08 | 2.2E−05 | 7.0E−05 | 4.0E−06 | 8.6E−05 | 0.006 | 0.05 | 0.009 | 0.5 | 0.004 |
| IL6R-P729/IL6R-L | L235F/G237Q/P238D/F241M/H268P/Y296E | 2.2E−07 | 1.6E−05 | 4.7E−05 | 3.0E−06 | 5.7E−05 | 0.001 | 0.07 | 0.013 | 0.7 | 0.006 |
| IL6R-P750/IL6R-L | L235F/G237Q/P238D/F241M/H268P/Y296E/K322A | 2.3E−07 | 4.9E−05 | 4.8E−05 | 4.0E−06 | 5.7E−05 | 0.001 | 0.02 | 0.013 | 0.5 | 0.006 |
| IL6R-P751/IL6R-L | L235F/G237Q/P238D/F241M/H268P/Y296E/K322E | 2.4E−07 | 1.9E−05 | 4.9E−05 | 3.5E−06 | 5.6E−05 | 0.001 | 0.06 | 0.013 | 0.6 | 0.007 |
| IL6R-P733/IL6R-L | L235F/G237Q/P238D/F241M/H268P/Y296E/S324H | 2.0E−07 | 1.3E−05 | 4.4E−05 | 4.5E−06 | 5.5E−05 | 0.002 | 0.08 | 0.014 | 0.5 | 0.007 |
| IL6R-P752/IL6R-L | L235F/G237Q/P238D/F241M/H268P/Y296E/K322A/S324H | 1.5E−07 | 4.1E−05 | 4.8E−05 | 4.2E−06 | 5.9E−05 | 0.002 | 0.03 | 0.013 | 0.5 | 0.006 |
| IL6R-P753/IL6R-L | L235F/G237Q/P238D/F241M/H268P/Y296E/K322E/S324H | 1.1E−07 | 1.8E−05 | 4.3E−05 | 2.8E−06 | 5.5E−05 | 0.003 | 0.06 | 0.014 | 0.8 | 0.007 |
| IL6R-P737/IL6R-L | G237Q/P238D/F241M/H268P/Y296E/S324H/A330H | 4.6E−08 | 3.7E−05 | 4.0E−05 | 4.3E−06 | 5.6E−05 | 0.007 | 0.03 | 0.016 | 0.5 | 0.007 |
| IL6R-P754/IL6R-L | G237Q/P238D/F241M/H268P/Y296E/K322A/S324H/A330H | 1.9E−07 | 1.0E−05 | 2.2E−04 | 7.7E−06 | 1.0E−04 | 0.002 | 0.11 | 0.003 | 0.3 | 0.004 |
| IL6R-P755/IL6R-L | G237Q/P238D/F241M/H268P/Y296E/K322E/S324H/A330H | 8.5E−08 | 1.7E−05 | 1.3E−04 | 4.1E−06 | 6.9E−05 | 0.004 | 0.06 | 0.005 | 0.5 | 0.005 |
| IL6R-P587/IL6R-L | E233D/P238D/V264I/S267A/H268E/P271G | 7.1E−10 | 1.2E−06 | 1.4E−05 | 2.8E−08 | 3.2E−05 | 0.451 | 0.92 | 0.044 | 75.0 | 0.012 |
| IL6R-P588/IL6R-L | P238D/V264I/S267A/H268E/P271G | 1.4E−09 | 1.6E−06 | 1.8E−05 | 3.8E−08 | 3.3E−05 | 0.229 | 0.69 | 0.034 | 55.3 | 0.011 |
| IL6R-P756/IL6R-L | E233D/P238D/V264I/S267A/H268E/P271G/A327G/A330S/P331S | 1.1E−09 | 1.7E−06 | 2.1E−05 | 5.2E−08 | 5.3E−05 | 0.291 | 0.65 | 0.030 | 40.4 | 0.007 |
| IL6R-P757/IL6R-L | P238D/V264I/S267A/H268E/P271G/A327G/A330S/P331S | 1.7E−09 | 2.3E−06 | 2.4E−05 | 1.0E−07 | 4.7E−05 | 0.188 | 0.48 | 0.026 | 21.0 | 0.008 |
| IL6R-P758/IL6R-L | G237D/P238D/H268D/P271G/A327G/A330S/P331S | 1.1E−08 | 1.9E−06 | 3.0E−05 | 2.6E−07 | 6.2E−05 | 0.029 | 0.58 | 0.021 | 8.1 | 0.006 |
| IL6R-P759/IL6R-L | E233D/G237D/P238D/H268D/P271G/A327G/A330S/P331S | 5.5E−09 | 1.4E−06 | 2.6E−05 | 1.5E−07 | 7.6E−05 | 0.058 | 0.79 | 0.024 | 14.0 | 0.005 |
| IL6R-P760/IL6R-L | G237D/P238D/H268E/P271G/A327G/A330S/P331S | 1.5E−08 | 1.6E−06 | 2.3E−05 | 1.9E−07 | 4.7E−05 | 0.021 | 0.69 | 0.027 | 11.1 | 0.008 |
| IL6R-P761/IL6R-L | E233D/G237D/P238D/H268E/P271G/A327G/A330S/P331S | 8.0E−09 | 1.1E−06 | 1.7E−05 | 1.2E−07 | 4.8E−05 | 0.040 | 1.00 | 0.036 | 17.5 | 0.008 |
| IL6R-P762/IL6R-L | P238D/P271G/A327G/A330S/P331S | 6.1E−09 | 3.4E−06 | 3.0E−05 | 5.5E−07 | 5.5E−05 | 0.052 | 0.32 | 0.021 | 3.8 | 0.007 |
| IL6R-P766/IL6R-L | P238D/S267A/H268E/P271G/A327G/A330S/P331S | 9.7E−10 | 2.2E−06 | 2.5E−05 | 2.9E−07 | 4.4E−05 | 0.330 | 0.50 | 0.025 | 7.2 | 0.008 |
| IL6R-P767/IL6R-L | P238D/V264I/H268E/P271G/A327G/A330S/P331S | 5.4E−09 | 2.8E−06 | 3.1E−05 | 1.2E−07 | 8.2E−05 | 0.059 | 0.39 | 0.020 | 17.5 | 0.005 |
| IL6R-P768/IL6R-L | P238D/V264I/S267A/P271G/A327G/A330S/P331S | 3.3E−09 | 2.8E−06 | 2.3E−05 | 1.7E−07 | 4.8E−05 | 0.097 | 0.39 | 0.027 | 12.4 | 0.008 |
| IL6R-P769/IL6R-L | P238D/V264I/P271G | 1.2E−08 | 2.9E−06 | 9.5E−05 | 7.4E−08 | 6.3E−05 | 0.027 | 0.38 | 0.007 | 28.4 | 0.006 |
| IL6R-P770/IL6R-L | P238D/V264I/P271G/A327G/A330S/P331S | 1.5E−08 | 3.4E−06 | 1.1E−04 | 1.7E−07 | 5.2E−05 | 0.021 | 0.32 | 0.006 | 12.4 | 0.007 |
| IL6R-P771/IL6R-L | P238D/V264I/P271G/K322A | 1.4E−08 | 4.3E−06 | 8.5E−05 | 1.4E−07 | 3.7E−05 | 0.023 | 0.26 | 0.007 | 15.0 | 0.010 |
| IL6R-P772/IL6R-L | P238D/V264I/P271G/K322E | 9.1E−09 | 3.1E−06 | 9.8E−05 | 9.7E−08 | 6.4E−05 | 0.035 | 0.35 | 0.006 | 21.6 | 0.006 |
| IL6R-P773/IL6R-L | P238D/S267A/H268E/P271G/K322A | 2.1E−09 | 2.7E−06 | 9.8E−05 | 1.4E−07 | 4.2E−05 | 0.152 | 0.41 | 0.006 | 15.0 | 0.009 |
| IL6R-P774/IL6R-L | P238D/S267A/H268E/P271G/K322E | 1.1E−09 | 2.0E−06 | 7.5E−05 | 8.8E−08 | 3.0E−05 | 0.291 | 0.55 | 0.008 | 23.9 | 0.012 |
| IL6R-P112/IL6R-L | P238D/P271G | 3.5E−09 | 3.4E−06 | 3.5E−05 | 2.8E−07 | 7.6E−05 | 0.091 | 0.32 | 0.018 | 7.5 | 0.005 |
| IL6R-P555/IL6R-L | G237D/P238D/H268D/P271G | 1.1E−08 | 2.8E−06 | 2.9E−05 | 2.1E−07 | 4.0E−05 | 0.029 | 0.39 | 0.021 | 10.0 | 0.009 |

TABLE 20-continued

| Variant name | Alterations introduced into IL6R-G1d | KD (M) for FcgRIa | KD (M) for FcgRIIaR | KD (M) for FcgRIIaH | KD (M) for FcgRIIb | KD (M) for FcgRIIIaV | Relative FcgRIa-binding Activity | Relative FcgRIIaR-binding Activity | Relative FcgRIIaH-binding Activity | Relative FcgRIIb-binding Activity | Relative FcgRIIIaV-binding Activity |
|---|---|---|---|---|---|---|---|---|---|---|---|
| IL6R-P556/IL6R-L | E233D/G237D/P238D/H268D/P271G | 3.7E-09 | 2.4E-06 | 3.3E-05 | 1.8E-07 | 5.5E-05 | 0.086 | 0.46 | 0.019 | 11.7 | 0.007 |
| IL6R-P559/IL6R-L | G237D/P238D/H268E/P271G | 9.1E-09 | 2.4E-06 | 3.0E-05 | 1.4E-07 | 4.3E-05 | 0.035 | 0.46 | 0.021 | 15.0 | 0.009 |
| IL6R-P562/IL6R-L | E233D/G237D/P238D/H268E/P271G | 4.2E-09 | 2.0E-06 | 2.8E-05 | 1.3E-07 | 5.2E-05 | 0.076 | 0.55 | 0.022 | 16.2 | 0.007 |
| IL6R-P763/IL6R-L | P238D/S267A/H268E/P271G | 7.3E-10 | 1.6E-06 | 1.8E-05 | 1.0E-07 | 2.7E-05 | 0.438 | 0.69 | 0.034 | 21.0 | 0.014 |
| IL6R-P764/IL6R-L | P238D/V264I/H268E/P271G | 3.7E-09 | 2.1E-06 | 2.4E-05 | 5.0E-08 | 6.1E-05 | 0.086 | 0.52 | 0.026 | 42.0 | 0.006 |
| IL6R-P765/IL6R-L | P238D/V264I/S267A/P271G | 1.8E-09 | 2.1E-06 | 2.2E-05 | 5.3E-08 | 4.8E-05 | 0.178 | 0.52 | 0.028 | 39.6 | 0.008 |
| IL6R-P775/IL6R-L | P238D/P271G/K322A | 8.6E-09 | 5.4E-06 | 1.3E-04 | 4.0E-07 | 5.0E-05 | 0.037 | 0.20 | 0.005 | 5.3 | 0.007 |
| IL6R-P776/IL6R-L | P238D/P271G/K322E | 5.2E-09 | 4.0E-06 | 9.6E-05 | 2.8E-07 | 3.6E-05 | 0.062 | 0.28 | 0.006 | 7.5 | 0.010 |
| IL6R-P777/IL6R-L | E233D/P238D/V264I/S267A/H268E/P271G/K322A | 1.6E-09 | 1.9E-06 | 7.3E-05 | 5.2E-08 | 5.0E-05 | 0.200 | 0.58 | 0.008 | 40.4 | 0.007 |
| IL6R-P778/IL6R-L | E233D/P238D/V264I/S267A/H268E/P271G/K322E | 9.6E-10 | 1.3E-06 | 6.0E-05 | 2.5E-08 | 4.1E-05 | 0.333 | 0.85 | 0.010 | 84.0 | 0.009 |
| IL6R-P779/IL6R-L | P238D/V264I/S267A/H268E/P271G/K322A | 3.4E-09 | 2.2E-06 | 7.0E-05 | 5.0E-08 | 3.3E-05 | 0.094 | 0.50 | 0.009 | 42.0 | 0.011 |
| IL6R-P780/IL6R-L | P238D/V264I/S267A/H268E/P271G/K322E | 2.1E-09 | 1.7E-06 | 7.8E-05 | 3.4E-08 | 4.9E-05 | 0.152 | 0.65 | 0.008 | 61.8 | 0.008 |
| IL6R-P781/IL6R-L | P238D/S298A/A327G/A330S/P331S | 1.7E-08 | 1.1E-05 | 2.2E-04 | 9.0E-06 | 5.1E-05 | 0.019 | 0.10 | 0.003 | 0.2 | 0.007 |
| IL6R-P782/IL6R-L | E233D/P238D/A327G/A330S/P331S | 3.0E-08 | 3.7E-06 | 1.3E-04 | 3.6E-06 | 6.1E-05 | 0.011 | 0.03 | 0.005 | 0.6 | 0.006 |
| IL6R-P783/IL6R-L | G237D/P238D/A327G/A330S/P331S | 1.6E-07 | 3.9E-05 | 9.8E-05 | 3.8E-06 | 5.7E-05 | 0.002 | 0.03 | 0.006 | 0.6 | 0.006 |
| IL6R-P784/IL6R-L | E233D/G237D/P238D/A327G/A330S/P331S | 8.8E-08 | 2.1E-05 | 8.7E-05 | 2.2E-06 | 3.8E-05 | 0.004 | 0.05 | 0.007 | 1.0 | 0.010 |
| IL6R-P785/IL6R-L | E233D/P238D/S298A/A327G/A330S/P331S | 2.3E-08 | 8.7E-05 | 9.4E-05 | 7.9E-06 | 4.1E-05 | 0.014 | 0.01 | 0.007 | 0.3 | 0.009 |
| IL6R-P786/IL6R-L | G237D/P238D/S298A/A327G/A330S/P331S | 1.2E-07 | 6.7E-05 | 1.0E-04 | 8.5E-06 | 3.6E-05 | 0.003 | 0.02 | 0.006 | 0.2 | 0.010 |
| IL6R-P787/IL6R-L | E233D/G237D/P238D/S298A/A327G/A330S/P331S | 5.6E-08 | 5.1E-05 | 8.6E-05 | 4.6E-06 | 3.6E-05 | 0.006 | 0.02 | 0.007 | 0.5 | 0.010 |

Comparing effects of the C1q-binding-lowering alterations on the FcgRIIb-binding ability shows that the binding ability of G1dK322A produced by introducing K322A into G1d was 1.0-times that of G1d, the binding ability of G1dK322E produced by introducing K322E was 1.1-times that of G1d, the binding ability of G1dGSS produced by introducing A327G/A330S/P331S was 0.9-times that of G1d; and all alterations that lower C1q binding hardly had any effects on FcgRIIb binding. In P741 produced by introducing K322A into F648 which contains the P238D alteration that selectively enhances FcgRIIb binding, or in P742 produced by introducing K322E into F648, hFcgRIIb binding was hardly changed in comparison to that of F648 before introduction of the alteration, whereas in P743 produced by introducing A327G/A330S/P331S, the FcgRIIb-binding ability decreased slightly and became 0.6-times that of G1d. From the above-mentioned results, when combined with P238D, the K322A and K322E alterations attenuate the C1q-binding ability without lowering the ability to bind FcgRIIb, but the A327G/A330S/P331S alterations were found to slightly decrease the FcgRIIb-binding ability. The same results were obtained when the alterations were introduced into other variants carrying the P238D alteration. For example, FcgRIIb binding of P744 produced by introducing K322A into P600 was 0.7 times in comparison to that of G1d, the binding of P745 produced by introducing K322E was 0.7 times that of G1d, and the binding of P781 produced by introducing A327G/A330S/P331S was 0.2 times that of G1d, which was somewhat decreased.

On the other hand, from the view point of immunogenicity, rather than introducing the K322A or K322E alteration, introducing A327G/A330S/P331S which is of the native human IgG4 sequence, may be more preferable. Therefore, when introducing C1q-binding-lowering alterations into a variant produced by introducing alterations that enhance FcgRIIb binding, the A327G/A330S/P331S alteration may be more preferable. For example, introduction of the A327G/A330S/P331S alteration into P787, which was produced by combined introduction of E233D and G237D into P781, resulted in lowered C1q binding, and at the same time, it did not greatly enhance binding to activating FcgRs, and improved FcgRIIb binding from 0.2-fold to 0.5-fold.

Variants produced in this examination, whose FcgRIIb-binding was enhanced or maintained and complement-binding was lowered, all had FcgRIIb binding of 0.2 times or more that of G1d and FcgRIIaR binding suppressed to 1.0 times or less that of G1d. Furthermore, FcgRIa binding was suppressed to 0.85 times or less that of G1d, FcgRIIaH binding was suppressed to 0.036 times or less that of G1d, and FcgRIIIaV binding was suppressed to 0.012 times or less that of G1d. Among them, the variants produced by introducing the A327G/A330S/P331S alteration, P756, P757, P758, P759, P760, P761, P762, P766, P767, P768, P770, and P784 all had enhanced FcgRIIb binding in comparison to that of G1d, and their FcgRIIaR binding was 1.0-times or less that of G1d.

The above-mentioned results showed that it is possible to produce variants with excellent FcgRIIb-binding selectivity and attenuated C1q binding by introducing alterations that lower complement-binding into variants whose FcgRIIb binding has been enhanced or is maintained at the same level as that of the native type and whose binding to other FcgRs has been attenuated.

Example 6

Evaluation of Dendritic Cell (DC)-Activating Ability of Fc Variants (6-1) Evaluation of Dendritic Cell (DC)-Activating Ability of Fc Variants To date, dendritic cells have been reported to be activated by crosslinking of activating FcγRs, in particular FcγRIIa, expressed on the cell surface via the antibody Fc region (The Journal of Clinical Investigation, 2005, 115, 2914-2923, The Journal of Immunology, 2003, 170, 3963-3970). Whether the antibody Fc region-mediated ability to activate dendritic cells is lowered was examined for the Fc variants produced in Example 4 with selectively reduced binding to activating FcγRs.

(6-2) Preparation of Fc Variants

XolairH-G1d (SEQ ID NO: 18), XolairH-F648 in which Asp is substituted for Pro at position 238 of XolairH-G1d according to EU numbering, and XolairH-P600 in which Asp is substituted for Pro at position 238 and Ala is substituted for Ser at position 298 according to EU numbering in XolairH-G1d, were prepared according to the method of Reference Example 1. XolairL-k0 (SEQ ID NO: 7) was utilized as a common antibody L chain, and together with the respective H chain, the antibodies were expressed and purified according to the method of Reference Example 1. The Fc variants have been noted as G1d, F648, and P600, respectively.

(6-3) Isolation of Monocytes and Induction of Differentiation into Dendritic Cells Equivalent amounts of human whole blood and RPMI medium were mixed, and the leukocyte layer was separated by ficol. Monocytes were isolated from the leukocyte layer using Monocyte Isolation Kit II (Miltenyi Biotec). The monocytes were placed in the RPMI medium (10% FBS, 100 ng/mL hIL-4 (R&D systems), 250 ng/mL hGM-CSF (R&D systems)) at $5\times10^5$ cells/mL, and the cells were cultured at 37° C. for seven days for inducing differentiation into DC.

(6-4) Plate Coating and DC Stimulation

A solution containing the respective Fc variant (G1d, F648, or P600) diluted with PBS (50 μg/mL) or PBS was added to a 96-well plate (Maxisorp, Nunc) at 100 μL/well, and this was shaken at room temperature for one hour. Washing three times with PBS was followed by seeding DC at $2\times10^5$ cells/well. After incubation at 37° C. for four hours, the cells were collected, and RNA extraction was performed using the RNeasy 96 Kit (QIAGEN).

(6-5) Evaluation of IL-8 Expression

The mRNA expression levels of GAPDH and IL-8 were determined by real-time PCR (Applied Biosystems 7900HT Fast Real Time PCR System) using QuantiTect Probe RT-PCR (QIAGEN). The IL-8 expression level was corrected by the GAPDH expression level. In this evaluation system, when G1d which is the positive control was used, the IL-8 expression level increased to 8.2; and when PBS was added instead of the antibody solution, the IL-8 expression level was found to be 0.03.

In this evaluation system, when the IL-8 expression levels of DC were compared when Fc variants F648 and P600 were individually added, the results of FIG. 6 were obtained.

These results showed that P600 suppresses the IL-8 expression level in DC in comparison to F648, or more specifically, lowers the property of activating DC. In comparison to F648, P600 has reduced binding to FcγRIIa, which is an activating FcγR. Therefore, P600 was considered to show suppressed DC activation due to reduction of the IL-8 expression level in DC caused as a result of reduced FcγRIIa binding in particular.

More specifically, this showed that antigen-binding molecules comprising an Fc region of the present invention with selectively reduced binding to activating FcγRs including FcγRIIa, may be excellent molecules that have overcome the problem of immune cell activation without losing the property of native IgG1 to quickly decrease antigen concentration in plasma.

Example 7

Assessment of Platelet Aggregation Ability of Antibodies Comprising an Fc Region Subjected to Existing Alterations that Enhance FcγRIIb Binding (7-1) Background of Platelet Activation and Aggregation by IgG1 Antibodies So far, several IgG1 antibodies have been reported to present side-effects through induction of platelet activation via interaction with FcγRs. For example, risk of thromboembolism is known to increase in the group of patients who have been administered with bevacizumab, an anti-VEGF antibody (J. Natl. Cancer Inst. (2007) 99 (16), 1232-1239). Furthermore, thromboembolism was similarly observed in clinical development studies of antibodies against the CD40 ligand (CD154), and clinical trials were discontinued (Arthritis. Rheum. (2003) 48 (3), 719-727). On platelet cells, FcγRIIa which is an activating Fcγ receptor is expressed rather than FcγRIIb which is an inhibitory Fcγ receptor (J. Exp. Med. (2006) 203 (9), 2157-2164). Later studies using animal models have suggested that the administered antibodies cause aggregation of platelets through binding to FcγRIIa on platelets, and this results in thrombus formation (J. Thromb. Haemost. (2009) 7 (1), 171-181, and J. Immunol. (2010) 185 (3), 1577-1583). It has been reported that in patients with systemic lupus erythematosus which is an autoimmune disease, platelets are activated by an FcγRIIa-dependent mechanism and platelet activation correlates with severity of the disease (Sci. Transl. Med. (2010) 2 (47), 47-63). This way, even native IgG1 antibodies may activate platelets and exhibit severe side-effects.

(7-2) Evaluation of Platelet Activation Using Anti-CD154 Antibodies

Platelet activation has been reported to originate from the interaction between FcγRIIa expressed on platelets and Fc of IgG1; therefore, whether this platelet activation can be avoided was examined using antibodies produced by reducing the FcγRIIa binding of IgG1.

The method of Reference Example 2 was used to prepare 5c8-G1d (heavy chain SEQ ID NO: 8, light chain SEQ ID NO: 9), which is an IgG1 antibody against the CD40 ligand. Next, the method of Reference Example 2 was used to prepare the 5c8-F648 (light chain SEQ ID NO: 9) antibody comprising an Fc region in which Asp has been substituted for Pro at position 238 according to EU numbering in the Fc region of 5c8-G1d, which is an existing art with reduced FcγRIIa binding. In addition, the method of Reference Example 2 was used to prepare the 5c8-P600 (light chain SEQ ID NO: 9) antibody comprising an Fc region in which Glu has been substituted for Pro at position 238 and Ala has been substituted for Ser at position 298 according to EU numbering in the Fc region of 5c8-G1d, an antibody whose FcγRIIa binding has been further lowered from existing art. 5c8-G1d, 5c8-F648, and 5c8-P600 have been noted below as G1d, F648, and P600, respectively. Platelet aggregation abilities of these Fc variants were evaluated.

Platelet activation was evaluated by the method below. First, approximately 50 mL of collected whole blood derived from a donor with FcγRIIa gene polymorphism (R131/R131) was divided into aliquots and placed into a 4.5-mL vacuum blood collection tube containing 0.5 mL of 3.2% sodium citrate, this was centrifuged at 200 g for 15 minutes, and the collected supernatant was used as Platelet Rich Plasma (PRP). PRP was washed using buffer A (137 mM NaCl, 2.7 mM KCl, 12 mM NaHCO$_3$, 0.42 mM NaH$_2$PO$_4$, 2 mM MgCl$_2$, 5 mM HEPES, 5.55 mM dextrose, 1.5 U/mL apyrase, and 0.35% BSA), and then the buffer was replaced with buffer B (137 mM NaCl, 2.7 mM KCl, 12 mM NaHCO$_3$, 0.42 mM NaH$_2$PO$_4$, 2 mM MgCl$_2$, 5 mM HEPES, 5.55 mM dextrose, 2 mM CaCl$_2$, and 0.35% BSA). As a result, washed platelets with a density of approximately 300,000 cells/μL were prepared. 168 μL of the washed platelets were dispensed into a measurement cuvette equipped with a stirring rod, and this was placed into a device for measuring the platelet aggregation ability. The platelets were stirred at 1000 rpm by the stirring rod in the cuvette maintained at 37.0° C. in the device. Then, 42 μL of an immune complex solution comprising the respective antibody and antigen, which had been prepared so that the final concentrations were 120 μg/mL antibody and 111 μg/mL antigen, was added; and the platelets and the immune complex were allowed to react for five minutes. Furthermore, adenosine diphosphate (ADP, SIGMA) was added to the reaction solution at a concentration that will not cause secondary aggregation, and whether activation will be enhanced was confirmed.

Platelet activation can be determined from an increase in the expression of activation markers such as CD62p (p-selectin) or activated integrin (PAC-1), on the platelet membrane surface. 2 μL of the immune complex was added to 8 μL of the washed platelets prepared by the previously described method, and this was allowed to react at room temperature for five minutes. Then, ADP was added at a concentration that induces slight activation to bring about activation, and whether activation by ADP was enhanced by the immune complex was confirmed. A sample prepared by adding a phosphate buffer (pH 7.4) (Gibco) instead of the immune complex was used as the negative control. A PE-labeled anti-CD62 antibody (BECTON DICKINSON), a PerCP-labeled anti-CD61 antibody, and an FITC-labeled PAC-1 antibody (BD bioscience) were added to each of the reacted samples for staining. The fluorescence intensity of each staining was measured using a flow cytometer (FACS CantoII, BD bioscience). When 5c8-G1d was added as the positive control in this assay system, CD62p-expression and PAC-1-expression in platelets were confirmed to be enhanced.

Figure 7:
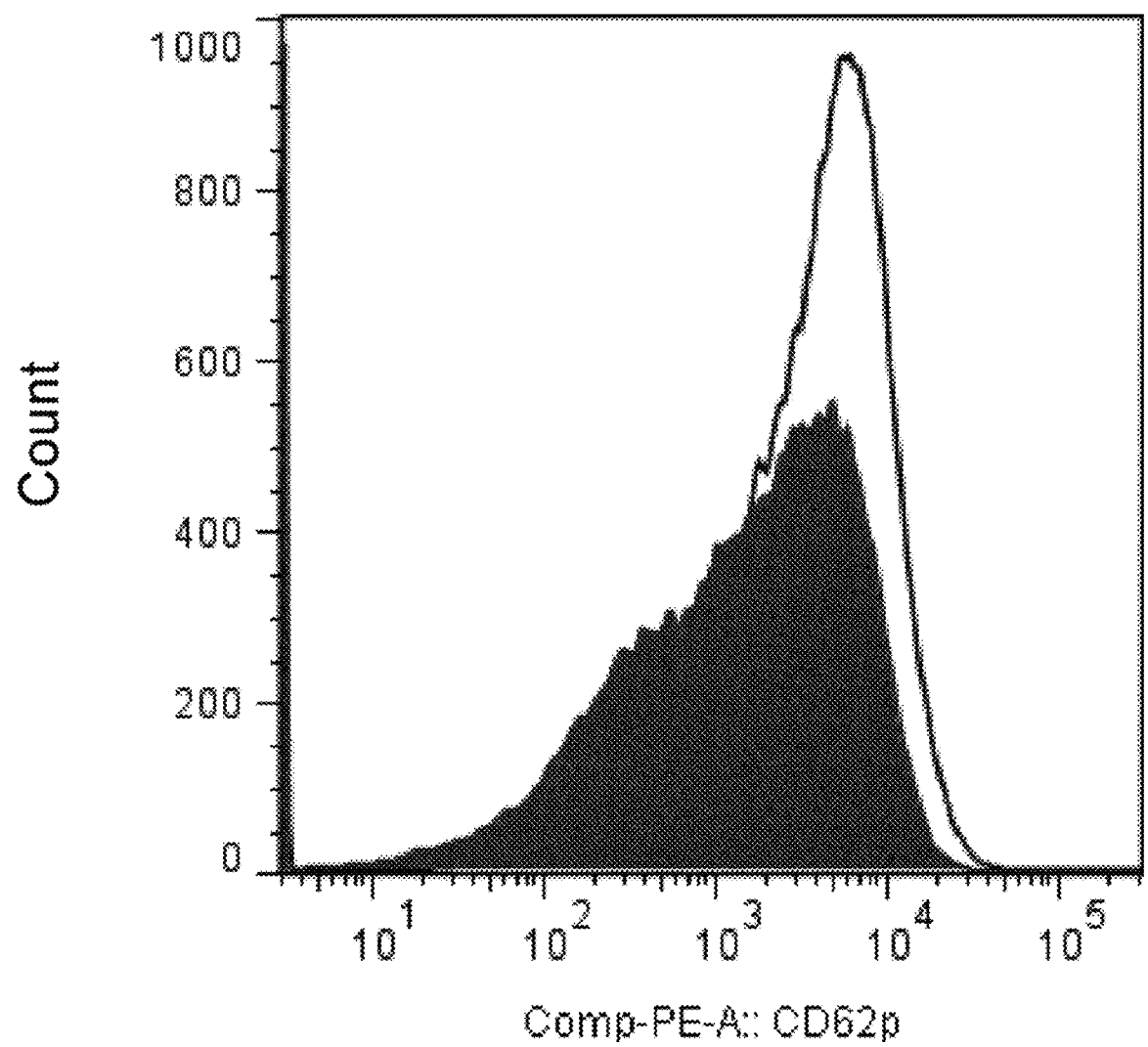
Figure 8:
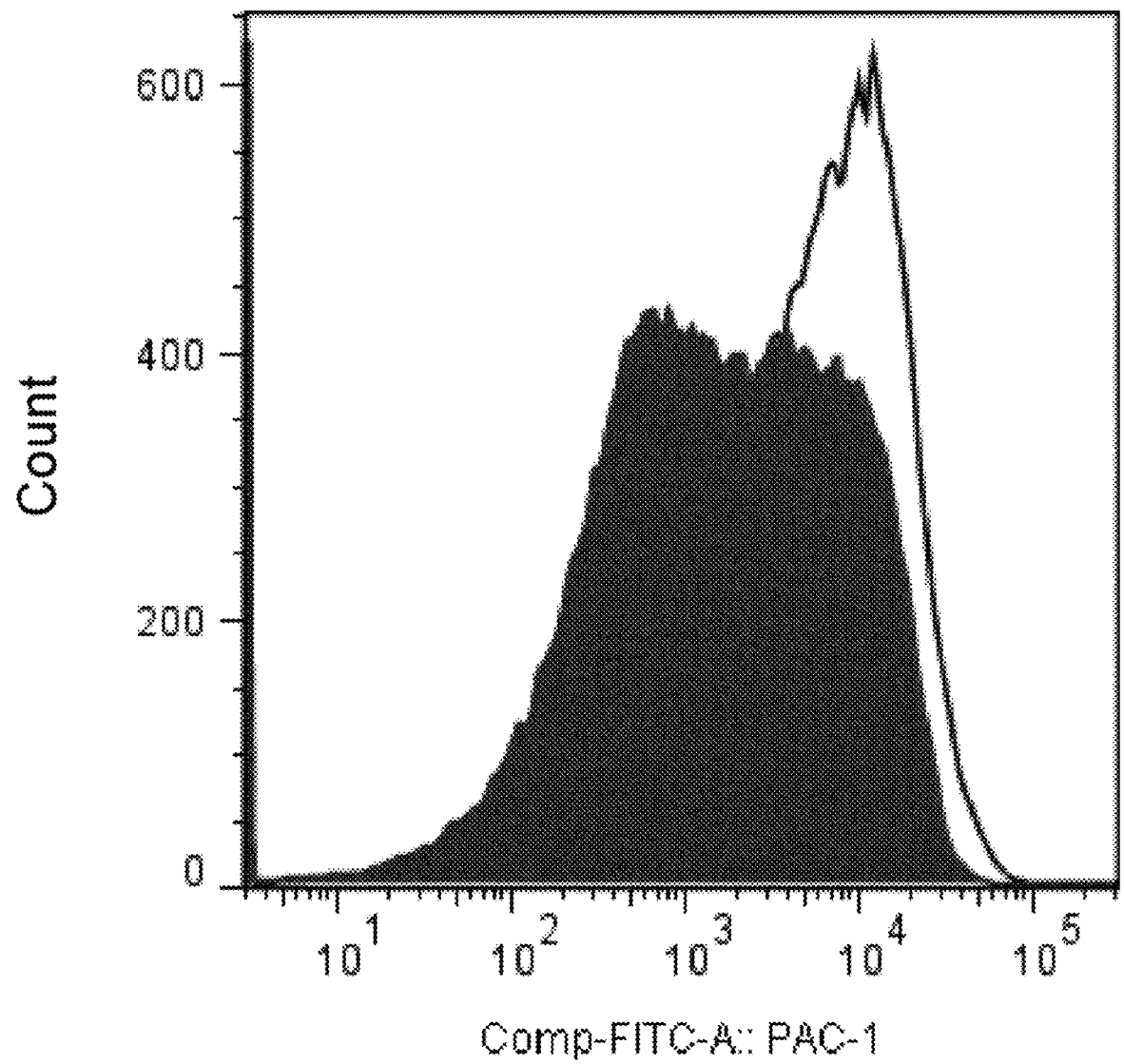

The platelet activation abilities of F648 and P600 were compared using this assay system. The results of CD62p expression and activated integrin expression when each Fc variant was added are shown in FIGS. 7 and 8, respectively. Expression of CD62p and activated integrin, whose expressions are induced on the platelet membrane surface by ADP stimulation, was enhanced when F648 was added, but not when P600 was added.

These results showed that greater suppressive effects are observed in antibodies comprising an Fc region that has been altered to have reduced human FcγRIIa binding through substitution of Asp for Pro at position 238 and Ala for Ser at position 298 according to EU numbering in the Fc region of IgG1, in comparison to Fc variants of existing art whose FcγRIIb binding has been selectively enhanced.

More specifically, it was shown that antigen-binding molecules comprising an Fc region of the present invention whose FcγRIIa binding has been selectively lowered even further, may be excellent molecules that have overcome the problem of platelet activation without losing the property of native IgG1 to rapidly lower the plasma antigen concentration.

Reference Example 1

Construction of Antibody Expression Vectors; and Expression and Purification of Antibodies Synthesis of full-length genes encoding the nucleotide sequences of the H chain and L chain of the antibody variable regions was carried out by production methods known to those skilled in the art using Assemble PCR and such. Introduction of amino acid substitutions was carried out by methods known to those skilled in the art using PCR or such. The obtained plasmid fragment was inserted into an animal cell expression vector, and the H-chain expression vector and L-chain expression vector were produced. The nucleotide sequence of the obtained expression vector was determined by methods known to those skilled in the art. The produced plasmids were introduced transiently into the HEK293H cell line derived from human embryonic kidney cancer cells (Invitrogen) or into FreeStyle293 cells (Invitrogen) for antibody expression. The obtained culture supernatant was collected, and then passed through a 0.22 μm MILLEX®-GV filter (Millipore), or through a 0.45 μm MILLEX®-GV filter (Millipore) to obtain the culture supernatant. Antibodies were purified from the obtained culture supernatant by methods known to those skilled in the art using rProtein A Sepharose Fast Flow (GE Healthcare) or Protein G Sepharose 4 Fast Flow (GE Healthcare). For the concentration of the purified antibodies, their absorbance at 280 nm was measured using a spectrophotometer. From the obtained value, the extinction coefficient calculated by the methods such as PACE was used to calculate the antibody concentration (Protein Science 1995; 4: 2411-2423).

Reference Example 2

Method for Preparing FcγRs and Method for Analyzing the Interaction Between an Altered Antibody and FcγR Extracellular domains of FcγRs were prepared by the following method. First, a gene of the extracellular domain of FcγR was synthesized by a method well known to those skilled in the art. At that time, the sequence of each FcγR was produced based on the information registered at NCBI. Specifically, FcγRI was produced based on the sequence of NCBI Accession No. NM_000566.3, FcγRIIa was produced based on the sequence of NCBI Accession No. NM_001136219.1, FcγRIIb was produced based on the sequence of NCBI Accession No. NM_004001.3, FcγRIIIa was produced based on the sequence of NCBI Accession No. NM_001127593.1, and FcγRIIIb was produced based on the sequence of NCBI Accession No. NM_000570.3, and a His tag was attached to the C terminus. Furthermore, polymorphism is known for FcγRIIa, FcγRIIIa, and FcγRIIIb, and the polymorphic sites were produced by referring to J. Exp. Med., 1990, 172: 19-25 for FcγRIIa; J. Clin. Invest., 1997, 100 (5): 1059-1070 for FcγRIIIa; and J. Clin. Invest., 1989, 84, 1688-1691 for FcγRIIIb.

The obtained gene fragments were inserted into an animal cell expression vector, and expression vectors were produced. The produced expression vectors were introduced transiently into human embryonic kidney cancer cell line-derived FreeStyle293 cells (Invitrogen) to express the proteins of interest. Regarding FcγRIIb used for crystallographic analysis, the protein of interest was expressed in the presence of Kifunesine at a final concentration of 10 μg/mL, so that the sugar chain added to FcγRIIb will be the high-mannose type. Cells were cultured, and after collection of the obtained culture supernatant, this was passed through a 0.22 μm filter to obtain the culture supernatant. In principle, the obtained culture supernatants were purified in the following four steps. The steps carried out were, cation exchange column chromatography (SP Sepharose FF) in step 1, affinity column chromatography (HisTrap HP) for His tag in step 2, gel filtration column chromatography (Superdex200) in step 3, and aseptic chromatography in step 4. However, for FcγRI, anion exchange column chromatography using Q sepharose FF was performed as step 1. The purified proteins were subjected to absorbance measurements at 280 nm using a spectrophotometer; and from the obtained values, the concentrations of the purified proteins were calculated using the absorption coefficient calculated using methods such as PACE (Protein Science 1995; 4: 2411-2423).

Analysis of interaction between each altered antibody and the Fcγ receptor prepared as mentioned above was carried out using a Biacore™ T100 surface plasmon resonance system (GE Healthcare), a Biacore™ T200 surface plasmon resonance system (GE Healthcare), a Biacore™ A100 surface plasmon resonance system, or a Biacore™ 4000 surface plasmon resonance system. HBS-EP+solution (0.01 M HEPES pH 7.4, 0.15 M NaCl, 3 mM ethylene diamine tetraacetic acid (EDTA), 0.05% polysorbate 20) (GE Healthcare) was used as the running buffer, and the measurement temperature was set to 25° C. Chips produced by immobilizing the antigen peptide, Protein A (Thermo Scientific), Protein A/G (Thermo Scientific), and Protein L (ACTIGEN or Bio Vision) by the amine coupling method to a Series S Sensor Chip CM5 (GE Healthcare) or Series S Sensor Chip CM4 (GE Healthcare), or alternatively, chips produced by allowing preliminarily biotinylated antigen peptides to interact with and immobilize onto a Series S Sensor Chip SA (certified) (GE Healthcare) were used.

After capturing of antibodies of interest onto these sensor chips, an Fcγ receptor diluted with the running buffer was allowed to interact, the amount bound to an antibody was measured, and the antibodies were compared. However, since the amount of Fcγ receptor bound depends on the amount of the captured antibodies, the amount of Fcγ receptor bound was divided by the amount of each antibody captured to obtain corrected values, and these values were compared. Furthermore, antibodies captured onto the chips were washed by reaction with 10 mM glycine-HCl, pH 1.5, and the chips were regenerated and used repeatedly.

Kinetic analyses for calculating the KD values of each altered antibody for FcγR were performed according to the following method. First, antibodies of interest were captured onto the above-mentioned sensor chips, and an Fcγ receptor diluted with the running buffer was allowed to interact. The Biacore Evaluation Software was used to globally fit the measured results to the obtained sensorgram using the 1:1 Langmuir binding model, and the association rate constant ka (L/mol/s) and the dissociation rate constant kd (1/s) were calculated; and from those values the dissociation constants KD (mol/L) were calculated.

When the interaction between each of the altered antibodies and FcγR was weak, and correct analysis was determined to be impossible by the above-mentioned kinetic analysis, the KD for such interactions were calculated using the following 1:1 binding model equation described in the Biacore T100 Software Handbook BR1006-48 Edition AE.

The behavior of interacting molecules according to the 1:1 binding model on Biacore can be described by Equation 1 shown below.

$$R_{eq}=C \cdot R_{max}/(KD+C)+RI \quad \text{[Equation 1]}$$

$R_{eq}$: a plot of steady-state binding levels against analyte concentration
C: concentration
RI: bulk refractive index contribution in the sample
$R_{max}$: analyte binding capacity of the surface When this equation is rearranged, KD can be expressed as Equation 2 shown below.

$$KD=C \cdot R_{max}/(R_{eq}-RI)-C \quad \text{[Equation 2]}$$

KD can be calculated by substituting the values of $R_{max}$, RI, and C into this equation. The values of RI and C can be determined from the sensorgram of the measurement results and measurement conditions. $R_{max}$ was calculated according to the following method. As a target of comparison, for antibodies that had sufficiently strong interactions as evaluated simultaneously in the same round of measurement, the $R_{max}$ value was obtained through global fitting using the 1:1 Langmuir binding model, and then it was divided by the amount of the comparison antibody captured onto the sensor chip, and multiplied by the captured amount of an altered antibody to be evaluated.

Reference Example 3

Preparation of Antibodies that Bind to Human IgA in a Calcium-Dependent Manner (3-1) Preparation of Human IgA (hIgA)

Human IgA (hereinafter also referred to as hIgA), which is an antigen, was prepared using recombination techniques such as below. hIgA expressed by culturing host cells carrying a recombinant vector comprising H (WT)-IgA1 (SEQ ID NO: 19) and L (WT) (SEQ ID NO: 20), was purified using ion-exchange chromatography and gel filtration chromatography by a method known to those skilled in the art.

(3-2) Antibodies with Calcium-Dependent Binding

H54/L28-IgG1 disclosed in WO2009/125825 is a humanized anti-IL-6 receptor antibody, and Fv4-IgG1 is a humanized anti-IL-6 receptor antibody produced by conferring H54/L28-IgG1 with the property of binding to a soluble human IL-6 receptor in a pH-dependent manner (binds under a neutral condition and dissociates under an acidic condition). In the in vivo mouse test disclosed in WO2009/125825, elimination of the soluble human IL-6 receptor was shown to be greatly accelerated in the group administered with a mixture of Fv4-IgG1 and the soluble human IL-6 receptor (antigen), in comparison to the group administered with a mixture of H54/L28-IgG1 and the soluble human IL-6 receptor (antigen).

Soluble human IL-6 receptor bound to a typical antibody that binds to the soluble human IL-6 receptor is recycled into plasma via FcRn along with the antibody. On the other hand, an antibody that binds to the soluble human IL-6 receptor in a pH-dependent manner dissociates a soluble human IL-6 receptor bound to the antibody under acidic conditions in the endosome. Since the dissociated soluble human IL-6 receptor is degraded in lysosomes, elimination of the soluble human IL-6 receptor from plasma can be accelerated greatly, and antibodies that bind to the soluble human IL-6 receptor in a pH-dependent manner are recycled into the plasma by FcRn after dissociating the soluble human IL-6 receptor, and the recycled antibodies can bind again to a soluble human IL-6 receptor. By repetition of the above-mentioned cycle (uptake of antigen-bound antibodies into cells>dissociation of the antigen from the antibody>degradation of the antigen and recycling of the antibody to plasma), a single antibody molecule can repeatedly bind to the soluble human IL-6 receptor several times (FIG. 9).

Furthermore, as disclosed in WO2011/122011, H54/L28-IgG1 is a humanized anti-IL-6 receptor antibody, Fv4-IgG1 is a humanized anti-IL-6 receptor antibody produced by conferring H54/L28-IgG1 with the property of binding to a soluble human IL-6 receptor in a pH-dependent manner (binds under a neutral condition and dissociates under an acidic condition), and Fv4-IgG1-v2 is a humanized anti-IL-6 receptor antibody produced by conferring Fv4-IgG1 with enhanced FcRn binding under neutral pH conditions. In the in vivo mouse test disclosed in WO2011/122011, elimination of the soluble human IL-6 receptor was greatly accelerated in a group administered with a mixture of Fv4-IgG1-v2 and the soluble human IL-6 receptor (antigen) in comparison to a group administered with a mixture of Fv4-IgG1 and the soluble human IL-6 receptor (antigen). More specifically, it has been reported that enhancement of the FcRn binding of an antibody that binds to an antigen in a pH-dependent manner under a neutral pH condition (pH 7.4) further improves the effect of the enhanced altered antibody to bind repeatedly to antigens and the effect of promoting elimination of antigens from plasma, and that administration of this antibody enables antigen elimination from plasma (FIG. 10).

Figure 10:
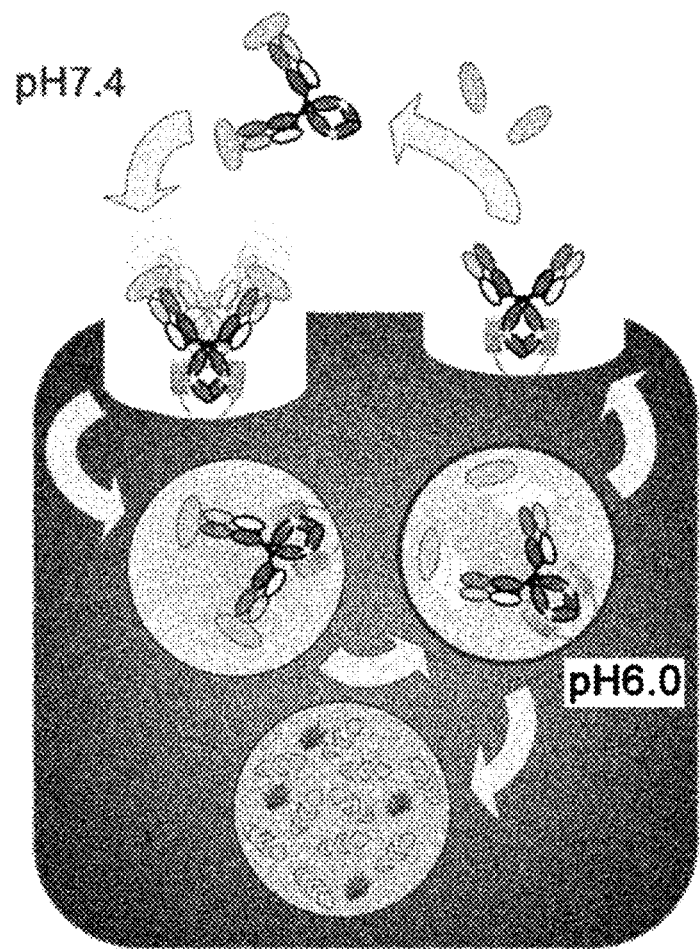

In the actions of antibodies that bind to an antigen in a pH-dependent manner, as shown in FIGS. 9 and 10, difference in the plasma and endosomal environments, i.e., difference in pH (plasma: pH 7.4; endosomes: pH 6.0) was used to utilize the property of the antibodies to strongly bind to antigens in plasma and release the antigens in the endosomes. To utilize such differences to the antigen-binding ability of antibodies that bind to antigen in a pH-dependent manner in plasma and in endosomes, the properties of the environmental factors in the plasma and endosomes as well as the degree of difference in those properties are important. pH difference is namely a difference in the hydrogen ion concentration. More specifically, as the hydrogen ion concentration in plasma (at pH 7.4) is approximately 40 nM and the hydrogen ion concentration in the endosome (at pH 6.0) is approximately 1000 nM, the difference in hydrogen ion concentrations between the plasma and the endosomes, which may be one of the environmental factors, is approximately 25 fold.

Furthermore, to achieve the effects shown in FIGS. 9 and 10 in a different embodiment, or to simultaneously achieve these embodiments, one may use antibodies that show antigen binding in a manner that depends on an environmental factor other than the hydrogen ion concentration that greatly differs in the plasma and in endosome. As a result of searching for an environmental factor that greatly differs between the plasma concentration and the endosome concentration, calcium was found. The calcium ion concentration in plasma is about 1.1-1.3 mM while the calcium ion concentration in the endosome is about 3 µM; therefore, difference in the calcium ion concentration, which is considered to be one of the environmental factors in plasma and in endosome, is approximately 400 times and was found to be larger than the hydrogen ion concentration difference (25 fold). More specifically, use of an antibody that binds to an antigen in an ionized calcium concentration-dependent manner, which binds to the antigen under high-calcium concentration conditions (1.1-1.3 mM) and dissociates the antigen under a low-calcium concentration condition (3 µM), may enable dissociation of antigens from the antibody in endosomes at a degree equivalent to or greater than that of antibodies with pH-dependent antigen binding.

(3-3) Expression and Purification of hIgA-Binding Antibodies

GA1-IgG1 (heavy chain SEQ ID NO: 21 and light chain SEQ ID NO: 22) and GA2-IgG1 (heavy chain SEQ ID NO: 23 and light chain SEQ ID NO: 24) are antibodies that bind to hIgA. DNA sequences encoding GA1-IgG1 (heavy chain SEQ ID NO: 21 and light chain SEQ ID NO: 22) and GA2-IgG1 (heavy chain SEQ ID NO: 23 and light chain SEQ ID NO: 24) were inserted into plasmids for animal cell expression by a method known to those skilled in the art. Antibodies were expressed using the following method. Cells of the human fetal kidney cell-derived FreeStyle 293-F line (Invitrogen) were suspended in FreeStyle 293 Expression Medium (Invitrogen). The cell suspension was plated at a cell density of $1.33 \times 10^6$ cells/ml in 3 ml to each well of a 6-well plate. Then, the prepared plasmid was introduced into cells by the lipofection method. The cells were cultured in a $CO_2$ incubator (37° C., 8% $CO_2$, 90 rpm) for 4 days. From the isolated culture supernatant, the antibody was purified by a method known to those skilled in the art using rProtein A Sepharose™ Fast Flow (Amersham Biosciences). The absorbance (wavelength: 280 nm) of the solution of the purified antibody was measured using a spectrophotometer. The antibody concentration was determined using the extinction coefficient calculated from the measured value by the PACE method (Protein Science (1995) 4, 2411-2423).

(3-4) Assessment of the Calcium-Dependent hIgA-Binding Ability of the Obtained Antibodies The hIgA-binding activities (dissociation constant $K_D$ (M)) of the antibodies isolated in (1-3) were assessed using Biacore T200 (GE Healthcare). Measurements were performed using a 0.05% tween20, 20 mmol/L ACES, 150 mmol/L NaCl (pH 7.4 or pH 5.8) solution containing 3 µM or 1.2 mM $CaCl_2$, or a 0.05% tween20, 20 mmol/L ACES, 150 mmol/L NaCl (pH 8.0) solution containing 0.1 µM or 10 mM $CaCl_2$ as a running buffer.

Figure 11:
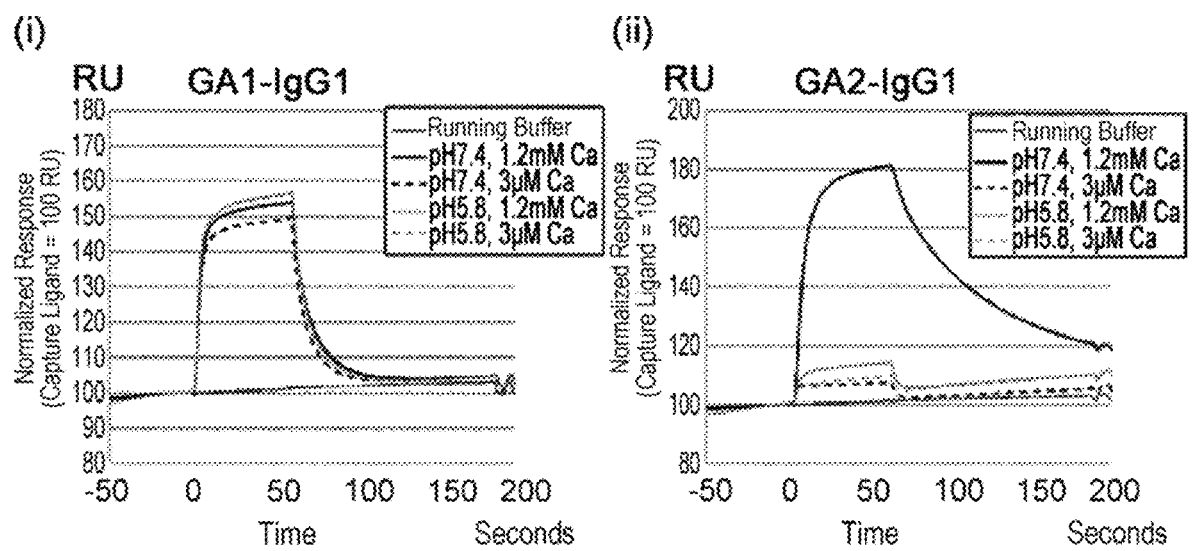
FIG. 11 shows sensorgrams obtained using Biacore, demonstrating the interaction of anti-human IgA antibodies with human IgA at pH 7.4 or pH 5.8, and 1.2 mM $Ca^{2+}$ or 3 μM $Ca^{2+}$.

An appropriate amount of recombinant Protein A/G (Thermo Scientific) was immobilized onto a Sensor chip CM5 (GE Healthcare) by an amino coupling method, and the antibody was allowed to bind thereto. Then, an appropriate concentration of hIgA (described in (1-1)) was injected as an analyte and allowed to interact with the antibody on the sensor chip. The measurement was carried out at 37° C. After measurement, 10 mmol/L glycine-HCl (pH 1.5) was injected to regenerate the sensor chip. From the measurement result, the dissociation constant KD (M) was calculated by curve fitting analysis and equilibrium analysis using Biacore T200 Evaluation Software (GE Healthcare). The result is shown in Table 21. Obtained sensorgram is shown in FIG. 11. GA2-IgG1 strongly bound to hIgA at a $Ca^{2+}$ concentration of 1.2 mM, and weakly bound to hIgA at a $Ca^{2+}$ concentration of 3 µM. Meanwhile, at a $Ca^{2+}$ concentration of 1.2 mM, GA2-IgG1 strongly bound to human IgA at pH 7.4, and weakly bound to human IgA at pH 5.8. In summary, GA2-IgG1 was demonstrated to bind to human IgA in a pH- and calcium-dependent manner.

TABLE 21

| Antibody Name | Condition | Fit | ka | kd | KD [M] |
|---|---|---|---|---|---|
| GA1-IgG1 | pH 8.0, 10 mM Ca | 1:1 binding model | 1.2E+06 | 1.2E−01 | 1.0E−07 |
|  | pH 8.0, 0.1 µM Ca | 1:1 binding model | 1.1E+06 | 2.4E−01 | 2.2E−07 |
|  | pH 7.4, 1.2 mM Ca | 1:1 binding model | 5.7E+05 | 8.4E−02 | 1.5E−07 |
|  | pH 7.4, 3 µM Ca | 1:1 binding model | 6.4E+05 | 1.2E−01 | 1.9E−07 |
|  | pH 5.8, 1.2 mM Ca | 1:1 binding model | 6.8E+05 | 9.9E−02 | 1.4E−07 |
|  | pH 5.8, 3 µM Ca | 1:1 binding model | 7.1E+05 | 1.1E−01 | 1.5E−07 |
| GA2-IgG1 | pH 7.4, 1.2 mM Ca | 1:1 binding model | 4.0E+05 | 1.6E−02 | 3.9E−08 |
|  | pH 7.4, 3 µM Ca | Steady State Affinity | — | — | 6.7E−06 |
|  | pH 5.8, 1.2 mM Ca | Steady State Affinity | — | — | 4.0E−06 |
|  | pH 5.8, 3 µM Ca | Steady State Affinity | — | — | 5.0E−06 |

Reference Example 4

Preparation of Variants of an Antibody that Binds to hIgA in a Calcium-Dependent Manner To further enhance elimination of antigens (hIgA) from plasma, GA2-N434W (light chain SEQ ID NO: 24) was prepared, in which the N434W amino acid substitution for enhancing mouse FcRn binding at pH 7.4 was introduced into GA2-IgG1 which binds to hIgA in a calcium-dependent manner. Furthermore, to remove the FcγR-binding properties of GA2-IgG1, GA2-FcγR(−) (light chain SEQ ID NO: 24) was prepared by introducing the L235R and S239K amino acid substitutions into GA2-IgG1. Using plasmids for expression in animals which had been introduced with DNA sequences encoding GA2-N434W (light chain SEQ ID NO: 24) and GA2-FcγR(−) (light chain SEQ ID NO: 24) by methods known to those skilled in the art, antibody variants were expressed by the above-described method and the concentrations of these antibody variants were determined after purification. Assessment of the binding of GA2-FcγR (−) to each of mouse FcγRs (mFcγRI, mFcγRII, mFcγRIII, and mFcγRIV) showed that binding could not be observed for any of the receptors.

Reference Example 5

Preparation of Antibody Variants that Bind to hIgA in a Calcium-Dependent Manner Next, to further accelerate antigen (hIgA) elimination from plasma, GA2-F1087 was produced by substituting Tyr for Leu at position 328 (EU numbering) in GA2-IgG1 for enhancing the mouse FcγR binding of GA2-IgG1 that binds to hIgA in a calcium-dependent manner. A DNA sequence encoding GA2-F1087 (light chain SEQ ID NO: 24) was inserted into an animal expression plasmid by a method known to those skilled in the art. Antibody variants were expressed by the above-described method using the plasmid. The concentrations of the variants were measured after purification. Antibodies comprising the above modification exhibited significantly enhanced mouse FcγR binding, as shown in Reference Example 5.

Reference Example 6

Assessment of the Effect on the Plasma Antigen Retention in Normal Mice Administered with Ca-Dependent hIgA-Binding Antibodies (6-1) In Vivo Tests Using Normal Mice hIgA (human IgA, prepared as described in Reference Example (3-1)) was administered alone or in combination with an anti-hIgA antibody to normal mice (C57BL/6J mouse, Charles River Japan). After administration, the in vivo dynamics of hIgA and anti-hIgA antibodies was assessed. An hIgA solution (80 μg/ml) or a mixed solution of hIgA and an anti-hIgA antibody was administered once at a dose of 10 ml/kg into the caudal vein. The anti-hIgA antibodies used were GA2-IgG1 and GA2-F1087 described above.

In all of the mixed solutions, the concentration of hIgA was 80 μg/ml, and the concentration of anti-hIgA antibody was 2.69 mg/ml. In this experiment, the anti-hIgA antibodies were present significantly in excess over hIgA, and thus most of hIgA was thought to bind to the antibodies. In the group administered with GA-IgG1, from the mice, the blood was collected five minutes, seven hours, one day, two days, three days, and seven days after administration. Meanwhile, in the group administered with GA-F1087, from the mice, the blood was collected five minutes, 30 minutes, one hour, two hours, one day, three days, and seven days after administration. The collected blood was immediately centrifuged at 12,000 rpm and 4° C. for 15 minutes to isolate the plasma. The isolated plasma was stored in a freezer at −20° C. or below until use.

Figure 12:
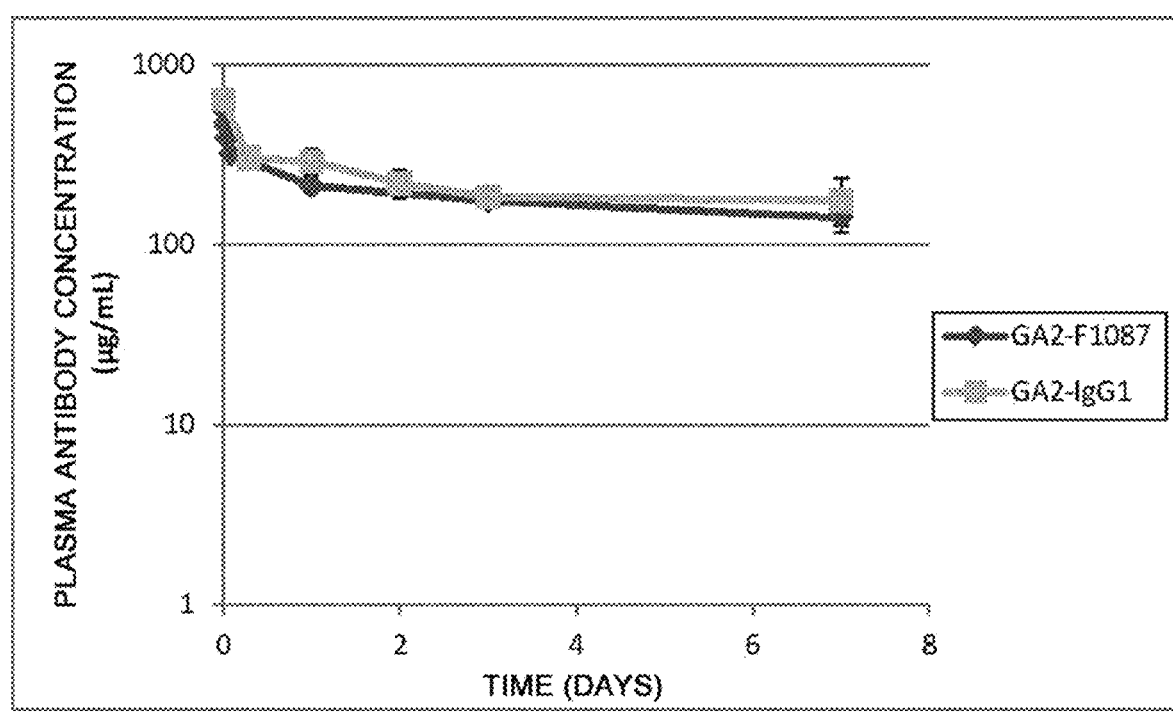
FIG. 12 shows changes in the plasma concentrations of the GA2-IgG1 and GA2-F1087 antibodies in normal mice.

(6-2) Determination of the Plasma Anti-hIgA Antibody Concentration in Normal Mice by the ELISA Method Anti-hIgA antibody concentrations in mouse plasma were measured by the ELISA method. First, to prepare an anti-human IgG-immobilized plate, Anti-Human IgG (γ-chain specific) F(ab')$_2$ Fragment of Antibody (SIGMA) was aliquoted to each well of a Nunc-Immuno Plate, MaxiSorp (Nalge nunc International), and the plate was allowed to stand at 4° C. overnight. Calibration curve samples of anti-hIgA antibody prepared as standard solutions for the plasma concentration (0.5, 0.25, 0.125, 0.0625, 0.03125, 0.01563, and 0.007813 μg/ml) and assay samples of mouse plasma diluted 100 times or more, were aliquoted to the above-mentioned anti-human IgG-immobilized plate. After one hour of incubation of the plate at 25° C., Goat Anti-Human IgG (γ chain specific) Biotin (BIOT) Conjugate (Southern Biotechnology Associates Inc.) was aliquoted to each well of the plate. Then, the plate was incubated at 25° C. for one hour. Next, Streptavidin-PolyHRP80 (Stereospecific Detection Technologies) was aliquoted to each well of the plate. Then, the plate was incubated at 25° C. for one hour. Chromogenic reaction was performed using as a substrate TMB One Component HRP Microwell Substrate (BioFX Laboratories). After terminating the reaction with 1N sulfuric acid (Showa Chemical), the absorbance of the reaction solution in each well was measured at 450 nm with a microplate reader. Anti-hIgA antibody concentrations in mouse plasma were determined based on the absorbance of the standard curve using the analysis software SOFTmax PRO (Molecular Devices). A time course of the antibody concentrations of GA2-IgG1 and GA2-F1087 in the plasma of normal mice after intravenous administration, which were measured by the method described above, is shown in FIG. 12. The results demonstrate that, with respect to the clone GA2-IgG1 that has pH- and Ca-dependent, strong hIgA-binding activity, the plasma concentration of the antibody is not significantly reduced even if the FcγR binding is enhanced.

Figure 13:
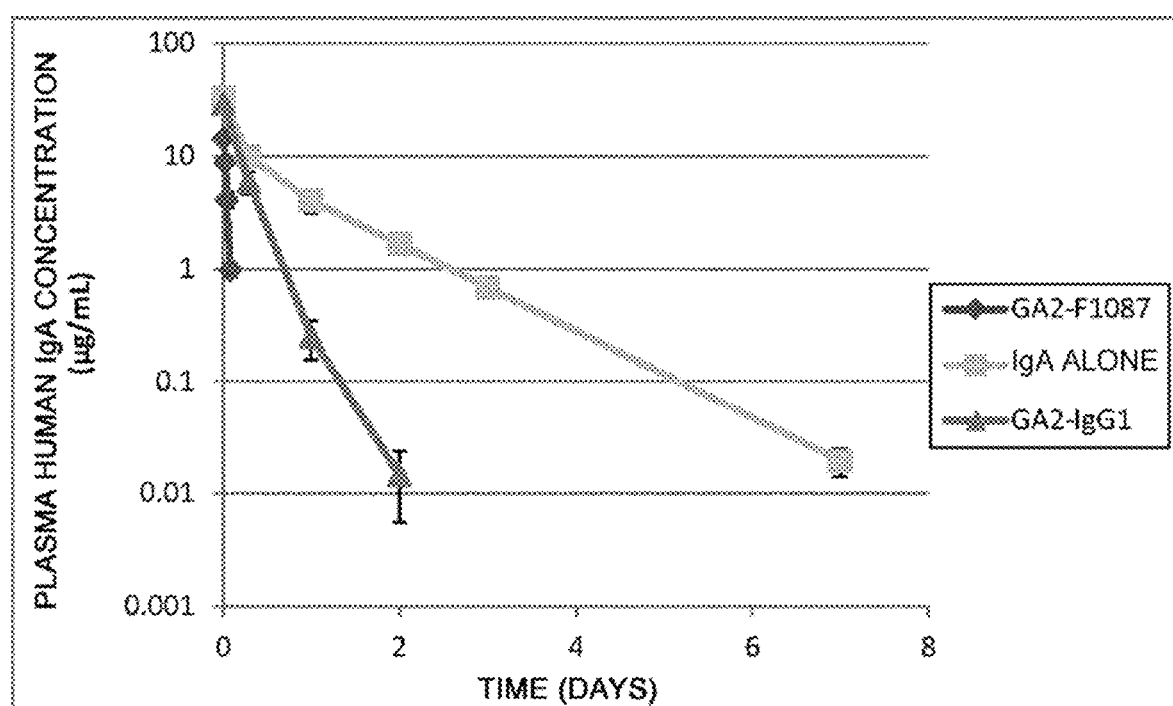
FIG. 13 shows changes in plasma hIgA concentration in normal mice administered with hIgA alone, GA2-IgG1 or GA2-F1087.

(6-3) Determination of the Plasma hIgA Concentration by the ELISA Method hIgA concentrations in mouse plasma were measured by the ELISA method. First, to prepare an anti-human IgA-immobilized plate, Goat anti-Human IgA Antibody (BETHYL) was aliquoted to each well of a Nunc-Immuno Plate, MaxiSoup (Nalge nunc International), and the plate was allowed to stand at 4° C. overnight. Calibration curve samples of hIgA were prepared as standard solutions for the plasma concentration (0.4, 0.2, 0.1, 0.05, 0.025, 0.0125, and 0.00625 μg/ml), and used. 100 μl each of the calibration curve samples and assay samples of mouse plasma diluted 100 times or more, was combined with 200 μl of 500 ng/ml hsIL6R. This was mixed and incubated at room temperature for one hour. Then, 100 μl of the mixtures was aliquoted to the anti-human IgA-immobilized plate. The plate was allowed to stand at room temperature for one hour. Next, Biotinylated Anti-human IL-6 R Antibody (R&D) was aliquoted to each well of the plate. After one hour of incubation at room temperature, Streptavidin-PolyHRP80 (Stereospecific Detection Technologies) was aliquoted to each well of the plate. The plate was incubated at room temperature for one hour. Chromogenic reaction was performed using as a substrate TMB One Component HRP Microwell Substrate (BioFX Laboratories). After terminating the reaction with 1N sulfuric acid (Showa Chemical), the absorbance of the reaction solution in each well was measured at 450 nm with a microplate reader. The concentrations in mouse plasma were determined based on the absorbance of the standard curve using the analysis software SOFTmax PRO (Molecular Devices). A time course of the hIgA concentration in the plasma of normal mice after intravenous administration, which was measured by the above method, is shown in FIG. 13.

The result showed that, in mice administered with hIgA in combination with GA2-IgG1 having a Ca-dependent hIgA-binding activity of 100 times or more greater, hIgA elimination was accelerated compared to the administration of hIgA alone. Meanwhile, in the plasma of mice administered with GA2-F1087 with enhanced binding to hIgA and FcγR, the concentration of hIgA was reduced below the measurable range (0.006 μg/ml or more) one day after administration, and thus the hIgA elimination was significantly accelerated compared to the plasma of mice administered with GA-IgG1. The above shows that in mice administered with hIgA and an anti-hIgA antibody that form immune complexes, the effect of eliminating the antigen (hIgA) from plasma by the antibody with enhanced FcγR binding was enhanced in comparison to the effect of eliminating the antigen (hIgA) by the antibody from which the antibody with enhanced FcγR binding is derived.

Reference Example 7

Effects of Antigen Elimination from Plasma of Antigen-Binding Molecules Whose FcγR-Binding Activity is Higher than the Binding Activity of the Native Mouse IgG Fc Region (7-1) Antigen-Eliminating Effect of Mouse Antibodies with Enhanced FcγR-Binding Activity Whether an antigen-binding molecule comprising a mouse antibody Fc region and having the property of binding to a human IL-6 receptor in a pH-dependent manner has the effect of accelerating elimination of a soluble human IL-6 receptor in the plasma of normal mice carrying mouse FcRn was examined by the method below.

(7-2) Production of Mouse Antibodies with Enhanced FcγR-Binding Activity

VH3-mIgG1 (SEQ ID NO: 25) and VL3-mk1 (SEQ ID NO: 26) were produced as a heavy chain and a light chain, respectively, of the mouse IgG1 antibody having the property of binding to the human IL-6 receptor in a pH-dependent manner, using the method of Reference Example 1. Furthermore, to enhance the binding activity of VH3-mIgG1 to mouse FcγR, VH3-mIgG1-mF44 was produced by substituting Asp for Ala at position 327 according to EU numbering. Similarly, VH3-mIgG1-mF46 was produced by substituting Asp for Ser at position 239 and Asp for Ala at position 327 according to EU numbering in VH3-mIgG1. Fv4-mIgG1, Fv4-mIgG1-mF44, or Fv4-mIgG1-mF46 which comprises VH3-mIgG1, VH3-mIgG1-mF44, or VH3-mIgG1-mF46, respectively, as a heavy chain and VL3-mk1 as a light chain was produced using the method of Reference Example 1.

(7-3) Confirmation of the Mouse FcγR-Binding Activity

VH3/L (WT)-mIgG1, VH3/L (WT)-mIgG1-mF44, or VH3/L (WT)-mIgG1-mF46 comprising VH3-mIgG1, VH3-mIgG1-mF44, or VH3-mIgG1-mF46, respectively, as a heavy chain and L (WT)-CK (SEQ ID NO: 27) as a light chain was produced by the method of Reference Example 1. The binding activities of these antibodies to the mouse FcγRs were evaluated by the method of Reference Example 2. The results are shown in Table 22. Furthermore, Table 23 shows how much increase was observed for the binding activities of each variant to the mouse FcγRs in comparison to those of mIgG1 before introducing the alteration. In the table, VH3/L (WT)-mIgG1, VH3/L (WT)-mIgG1-mF44, and VH3/L (WT)-mIgG1-mF46 are shown as mIgG1, mF44, and mF46, respectively.

TABLE 22

| VARIANT | KD (M) | | | |
|---|---|---|---|---|
| NAME | mFcγRI | mFcγRIIb | mFcγRIII | mFcγRIV |
| mIgG1 | NOT DETECTED | 1.1E-07 | 2.1E-07 | NOT DETECTED |
| mF44 | NOT DETECTED | 8.9E-09 | 6.7E-09 | NOT DETECTED |
| mF46 | NOT DETECTED | 1.2E-09 | 3.6E-09 | NOT DETECTED |

TABLE 23

| VARIANT | BINDING RATIO TO mIgG1 | | | |
|---|---|---|---|---|
| NAME | mFcγRI | mFcγRIIb | mFcγRIII | mFcγRIV |
| mIgG1 | NOT DETECTED | 1.0 | 1.0 | NOT DETECTED |
| mF44 | NOT DETECTED | 11.9 | 31.0 | NOT DETECTED |
| mF46 | NOT DETECTED | 91.4 | 57.5 | NOT DETECTED |

The assessment result of Example 4 showing that VH3/L (WT)-mIgG1 having the Fc region of native mouse IgG1 antibody only binds to mouse FcγRIIb and mouse FcγRIII but not to mouse FcγRI and mouse FcγRIV, suggests that mouse FcγRs important for the reduction of antigen concentration are mouse FcγRII and/or mouse FcγRIII. VH3/L (WT)-mIgG-mF44 and VH3/L (WT)-mIgG1-mF46 introduced with an alteration that is thought to increase the FcγR-binding activity of VH3/L (WT)-mIgG1 was demonstrated to have increased binding activity to both of mouse FcγRIIb and mouse FcγRIII.

(7-4) Assessment of the Effect to Reduce the Soluble IL-6 Receptor Concentration in the Plasma of Normal Mice The effect to eliminate soluble IL-6 receptor from the plasma of normal mice administered with the anti-human IL-6 receptor antibody Fv4-mIgG1, Fv4-mIgG1-mF44, or Fv4-mIgG1mF46 was assessed as follows.

Animal models in which the concentration of soluble human IL-6 receptor in plasma was maintained at a steady state were produced by implanting an infusion pump (MINI-OSMOTIC PUMP MODEL2004, alzet) loaded with soluble human IL-6 receptor, subcutaneously at the back of normal mice (C57BL/6J mouse, Charles River Japan). Anti-human IL-6 receptor antibodies were administered to the animal models, and then pharmacokinetics of the soluble human IL-6 receptor was evaluated. To suppress the production of antibodies against the soluble human IL-6 receptor, monoclonal anti-mouse CD4 antibodies were administered once to the tail vein at a dose of 20 mg/kg. Then, an infusion pump containing 92.8 μg/ml soluble human IL-6 receptor was subcutaneously implanted on the back of the mice. Three days after implantation of the infusion pump, an anti-human IL-6 receptor antibody was administered once at 1 mg/kg into the caudal vein. The blood was collected from the mice 15 minutes, seven hours, one day, two days, four days, seven days, 14 days (or 15 days), and 21 days (or 22 days) after administration of the anti-human IL-6 receptor antibody. Immediately, the collected blood was centrifuged at 15,000 rpm and 4° C. for 15 minutes to prepare plasma. The isolated plasma was stored in a freezer set at −20° C. or below until use.

Figure 14:
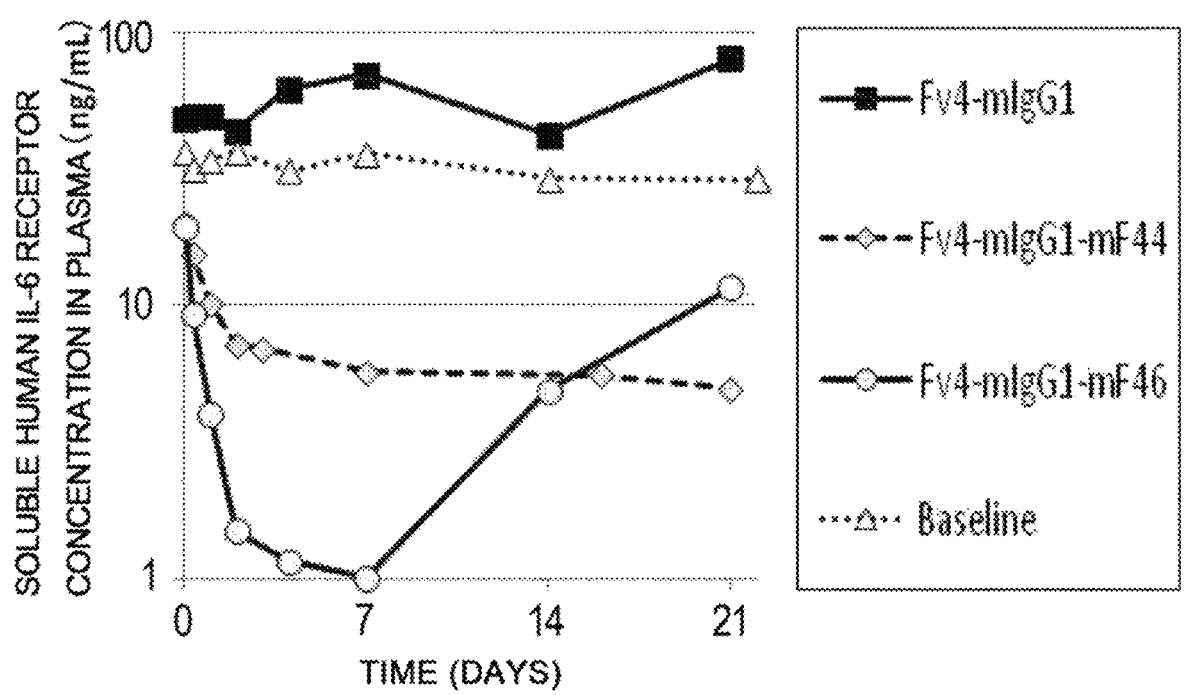
FIG. 14 shows changes in the human IL-6 receptor concentration in mouse plasma when Fv4-mIgG1, Fv4-mIgG1-mF44 which is an Fv4-mIgG1 variant with enhanced binding to mouse FcγRIIb and mouse FcγRIII, and Fv4-mIgG1-mF46 which is an Fv4-mIgG1 variant with further enhanced binding to mouse FcγRIIb and mouse FcγRIII were administered to normal mice.

The soluble human IL-6 receptor concentration in plasma, the hsIL-6R soluble human IL-6 receptor concentrations in mouse plasma were determined by an electrochemiluminescent method. hsIL-6R soluble human IL-6 receptor standard curve samples prepared at 2000, 1000, 500, 250, 125, 62.5, and 31.25 pg/ml and assay samples of mouse plasma diluted 50 times or more were mixed with Monoclonal Anti-human IL-6R Antibody (R&D), Biotinylated Anti-human IL-6 R Antibody (R&D), Tocilizumab, which had been ruthenated with SULFO-TAG NHS Ester (Meso Scale Discovery). The mixtures were incubated at 37° C. overnight. Tocilizumab was prepared at a final concentration of 333 μg/ml. Then, the reaction mixtures were aliquoted in an MA400 PR Streptavidin Plate (Meso Scale Discovery). The solution reacted at room temperature for one hour was washed out, and then Read Buffer T (×4) (Meso Scale Discovery) was aliquoted Immediately thereafter, the measurement was carried out using SECTOR PR 400 Reader (Meso Scale Discovery). The concentration of hsIL-6R soluble human IL-6 receptor was determined based on the response of the standard curve using analysis software SOFTmax PRO (Molecular Devices). The results are shown in FIG. 14.

Surprisingly, it was demonstrated that, in mice administered with mF44 and mF46 introduced with an alteration to increase the binding activity of mIgG1 (native mouse IgG1) to mouse FcγRIIb and mouse FcγRIII, the plasma IL-6 receptor concentration was markedly reduced as compared to mice administered with mIgG1. In particular, even on day 21 after administration of mF44, the plasma IL-6 receptor concentration in the mF44-administered group was reduced by about 6 times as compared to the plasma IL-6 receptor concentration in the group without antibody administration, and about 10 times as compared to the mIgG1-administered group. On the other hand, on day seven after administration of mF46, the plasma IL-6 receptor concentration in the mF46-administered group was markedly reduced by about 30 times as compared to the plasma IL-6 receptor concentration in the group without antibody administration, and about 50 times as compared to the mIgG1-administered group.

The above findings demonstrate that the elimination of soluble IL-6 receptor from plasma was also accelerated in mice administered with antibodies in which the mouse FcγR-binding activity of an antigen-binding molecule having the Fc regions of mouse IgG1 antibody is increased, as with antibodies in which the mouse FcγR-binding activity of an antigen-binding molecule having the Fc region of human IgG1 antibody is increased. Without being bound by a particular theory, the phenomenon observed as described above can be explained as follows.

When administered to mice, antibodies that bind to a soluble antigen in a pH-dependent manner and have increased FcγR-binding activity are actively incorporated mainly into cells expressing FcγR on the cell membrane. The incorporated antibodies dissociate the soluble antigen under an acidic pH condition in the endosome, and then recycled to plasma via FcRn. Thus, a factor that achieves the effect of eliminating the plasma soluble antigen of such an antibody is the FcγR-binding activity level of the antibody. Specifically, as the FcγR-binding activity is greater, the incorporation into FcγR-expressing cells occurs more actively, and this makes the elimination of soluble antigens from plasma more rapid. Furthermore, as long as the FcγR-binding activity has been increased, the effect can be assessed in the same manner regardless of whether the Fc region contained in an antibody originates from human or mouse IgG1. Specifically, the assessment can be achieved for an Fc region of any animal species, such as any of human IgG1, human IgG2, human IgG3, human IgG4, mouse IgG1, mouse IgG2a, mouse IgG2b, mouse IgG3, rat IgG, monkey IgG, and rabbit IgG, as long as the binding activity to the FcγR of the animal species to be administered has been increased.

Reference Example 8

The Antigen Elimination Effect by Antibodies with the Binding Activity Increased in an FcγRIIb-Selective Manner (8-1) The Antigen Elimination Effect of Antibodies in which the FcγRIIb-Binding Activity has been Selectively Increased FcγRIII-deficient mice (B6.129P2-FcgrR3tm1Sjv/J mouse, Jackson Laboratories) express mouse FcγRI, mouse FcγRIIb, and mouse FcγRIV, but not mouse FcγRIII. Meanwhile, Fc receptor γ chain-deficient mice (Fcer1g mouse, Taconic, Cell (1994) 76, 519-529) express mouse FcγRIIb alone, but not mouse FcγRI, mouse FcγRIII, and mouse FcγRIV.

As described in Reference Example 7, it was demonstrated that mF44 and mF46 with increased FcγR-binding activity of native mouse IgG1 show selectively enhanced binding to mouse FcγRIIb and mouse FcγRIII. It was conceived that, using the selectively increased binding activity of the antibodies, the condition under which an antibody with selectively enhanced mouse FcγRIIb binding is administered can be mimicked by administering mF44 and mF46 to mouse FcγRIII-deficient mice or Fc receptor γ chain-deficient mice which do not express mouse FcγRIII.

Figure 15:
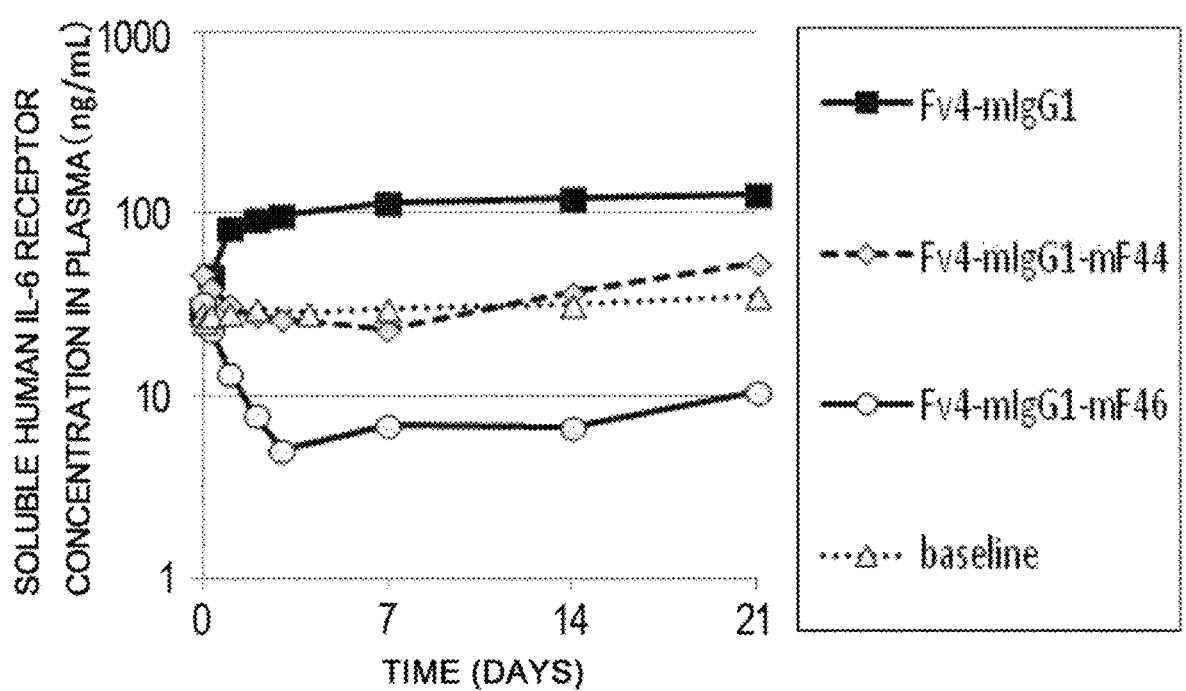
FIG. 15 shows changes in the human IL-6 receptor concentration in mouse plasma when Fv4-mIgG1, Fv4-mIgG1-mF44 which is an Fv4-mIgG1 variant with enhanced binding to mouse FcγRIIb and mouse FcγRIII, and Fv4-mIgG1-mF46 which is an Fv4-mIgG1 variant with further enhanced binding to mouse FcγRIIb and mouse FcγRIII were administered to FcγRIII-deficient mice.

(8-2) Assessment of the Antigen Elimination Effect by Selective Enhancement of Binding to Mouse FcγRIIb Using FcγRIII-Deficient Mice The effect to eliminate soluble IL-6 receptor from plasma in FcγRIII-deficient mice administered with the anti-human IL-6 receptor antibody Fv4-mIgG1, Fv4-mIgG1-mF44, or Fv4-mIgG1-mF46 was assessed by the same method described in Example 5. The soluble human IL-6 receptor concentrations in the plasma of the mice were determined by the method described above in Reference Example (7-4). The result is shown in FIG. 15.

Surprisingly, it was demonstrated that, the plasma IL-6 receptor concentrations in FcγRIII-deficient mice administered with mF44 and mF46, which mimic the condition under which the mouse FcγRIIb-binding activity of mIgG1 (native mouse IgG1) is selectively increased, were markedly reduced as compared to the plasma IL-6 receptor concentration in mice administered with mIgG1. In particular, the plasma IL-6 receptor concentration of the mF44-administered group was reduced by about three times as compared to that of the mIgG1-administered group and the accumulation of antibody concentration due to antibody administration was suppressed. Meanwhile, on day three after administration, the plasma IL-6 receptor concentration of the mF46-administered group was markedly reduced by about six times as compared to the plasma IL-6 receptor concentration of the group without antibody administration, and about 25 times as compared to the plasma IL-6 receptor concentration of the mIgG1-administered group. This result shows that, as the mouse FcγRIIb-binding activity of an anti-human IL-6 receptor antibody that binds to the antigen in a pH-dependent manner is greater, the IL-6 receptor concentration can be reduced more in the plasma of mice administered with the antibody.

Figure 16:
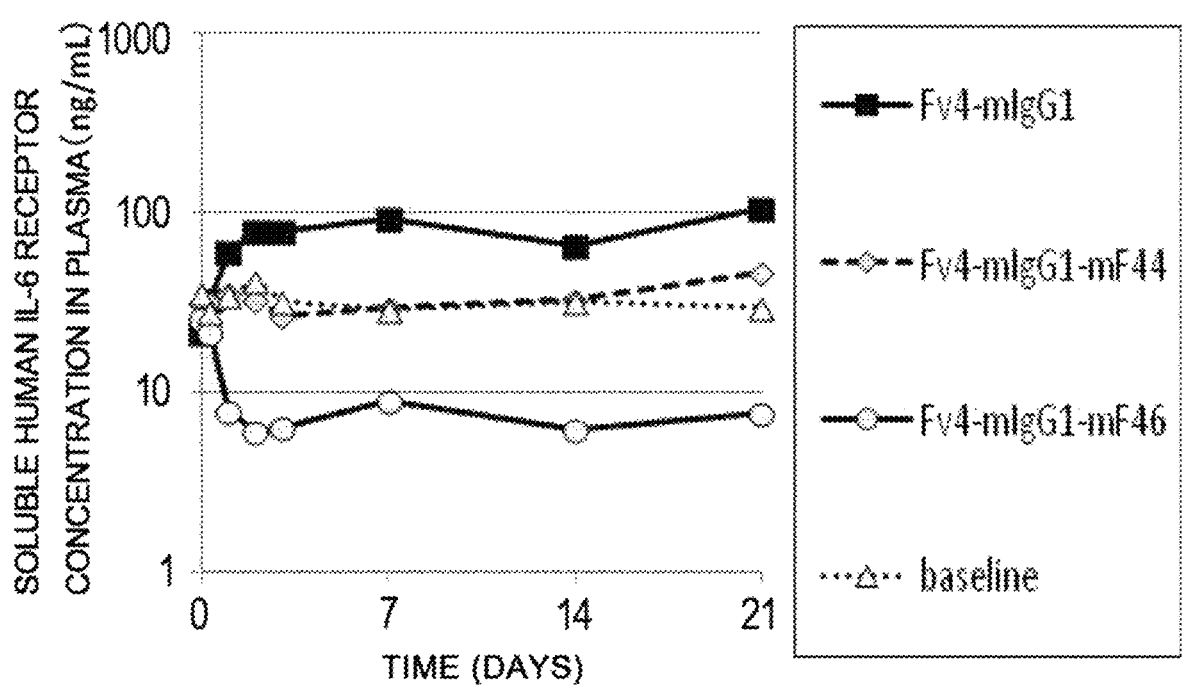
FIG. 16 shows changes in the human IL-6 receptor concentration in mouse plasma when Fv4-mIgG1, Fv4-mIgG1-mF44 which is an Fv4-mIgG1 variant with enhanced binding to mouse FcγRIIb and mouse FcγRIII, and Fv4-mIgG1-mF46 which is an Fv4-mIgG1 variant with further enhanced binding to mouse FcγRIIb and mouse FcγRIII were administered to Fc receptor γ-chain-deficient mice.

(8-3) Assessment of the Antigen Elimination Effect by Selective Enhancement of Mouse FcγRIIb Binding Using Fc Receptor γ Chain-Deficient Mice The effect to eliminate soluble IL-6 receptor from the plasma of Fc receptor γ chain-deficient mice administered with the anti-human IL-6 receptor antibody Fv4-mIgG1, Fv4-mIgG1-mF44, or Fv4-mIgG1mF46, was assessed by the same method as described in Example 6. The soluble human IL-6 receptor concentrations in the plasma of the mice were determined by the method described above in Reference Example (7-4). The result is shown in FIG. 16.

As with the case where mF44 and mF46 were administered to FcγRIII-deficient mice, the plasma IL-6 receptor concentration in Fc receptor γ chain-deficient mice administered with mF44 and mF46, which mimic the condition resulting from the selective increase in the mouse FcγRIIb-binding activity of mIgG1 (native mouse IgG1), was demonstrated to be markedly reduced as compared to the plasma IL-6 receptor concentration in Fc receptor γ chain-deficient mice administered with mIgG1. In particular, the plasma IL-6 receptor concentration in the mF44-administered group was reduced to about three times that in the mIgG1-administered group, and the accumulation of antigen concentration due to antibody administration was suppressed. Meanwhile, on day three after administration, the plasma IL-6 receptor concentration in the mF46-administered group was markedly reduced by about five times as compared to that in the group without antibody administration, and about 15 times as compared to that in the mIgG1-administered group.

The results described in Reference Examples (8-2) and (8-3) show that the soluble antigen concentration in the plasma is markedly reduced in the group administered with an antibody that binds to a soluble antigen in a pH-dependent manner and has selectively increased mouse FcγRIIb-binding activity.

Reference Example 9

The Antigen Elimination Effect of Antibodies with Selective Enhancement of the Binding to FcγRIII (9-1) The Antigen Elimination Effect of Antibodies with Selectively Enhanced FcγRIII Binding FcγRIIb-deficient mice (Fcgr2b (FcγRII) mouse, Taconic) (Nature (1996) 379 (6563), 346-349) express mouse FcγRI, mouse FcγRIII, and mouse FcγRIV, but not mouse FcγRIIb. As described in Example 5, it was demonstrated that mF44 and mF46 resulting from increasing the FcγR-binding activity of native mouse IgG1 show selectively enhanced binding to mouse FcγRIIb and mouse FcγRIII. It was conceived that, based on the use of the selectively increased binding activity of the antibodies, the condition of administration of an antibody with selectively enhanced binding to mouse FcγRIII can be mimicked by administering mF44 or mF46 to mouse FcγRIIb-deficient mice which do not express mouse FcγRIIb.

As described in Reference Example 8, the soluble antigen concentration was reduced in the plasma of FcγRIII-deficient mice, which mimic the condition of administration of an antibody with selectively increased mouse FcγRIIb-binding activity. Meanwhile, whether the soluble antigen concentration is reduced in the plasma of FcγRIIb-deficient mice, which mimic the condition of administration of an antibody with selectively increased mouse FcγRIII-binding activity, was assessed by the test described below.

Figure 17:
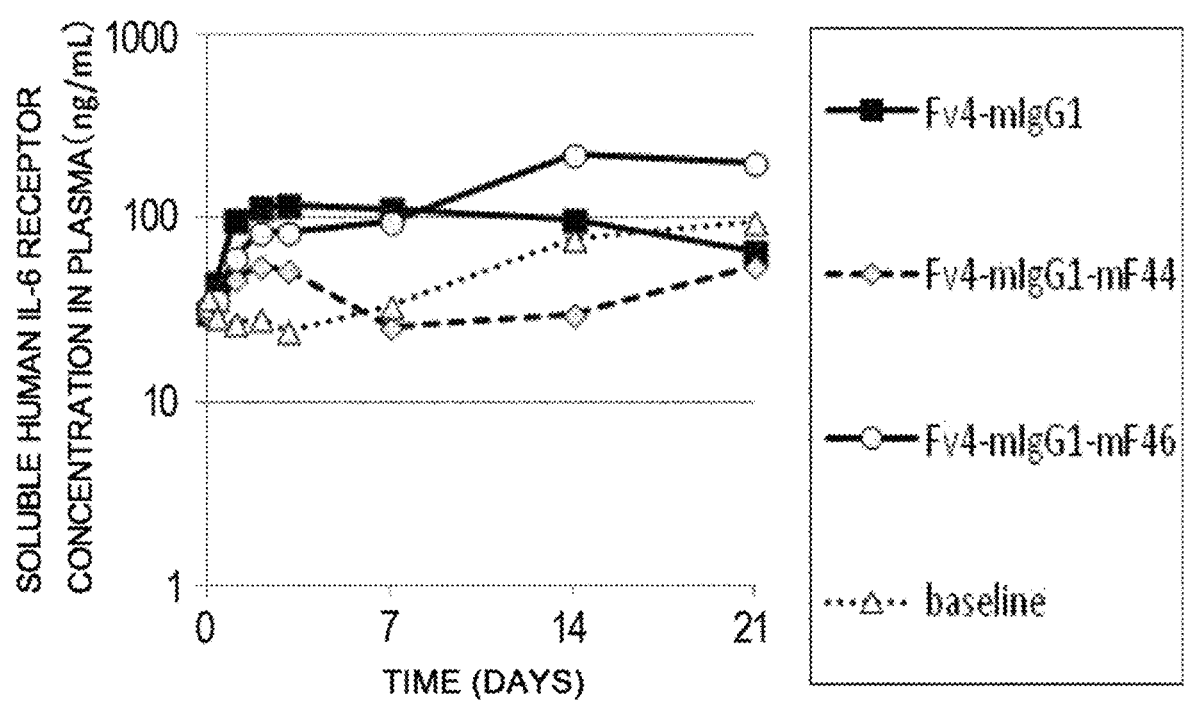
FIG. 17 shows changes in the human IL-6 receptor concentration in mouse plasma when Fv4-mIgG1, Fv4-mIgG1-mF44 which is an Fv4-mIgG1 variant with enhanced binding to mouse FcγRIIb and mouse FcγRIII, and Fv4-mIgG1-mF46 which is an Fv4-mIgG1 variant with further enhanced binding to mouse FcγRIIb and mouse FcγRIII were administered to FcγRIIb-deficient mice.

(9-2) Assessment of the Antigen Elimination Effect by Selective Enhancement of Mouse FcγRIII Binding Using FcγRIIb-Deficient Mice The effect to eliminate soluble IL-6 receptor from the plasma of FcγRIIb-deficient mice administered with the anti-human IL-6 receptor antibody Fv4-mIgG1, Fv4-mIgG1-mF44, or Fv4-mIgG1mF46, was assessed by the same method as described in Example 5. The soluble human IL-6 receptor concentrations in plasma were determined by the method described above in Reference Example (7-4). The result is shown in FIG. 17.

Surprisingly, in the groups administered with mF44 and mF46, which mimic selective increase of the mouse FcγRIII-binding activity of mIgG1 (native mouse IgG1), the plasma IL-6 receptor concentration was reduced, but the remarkable reduction was not confirmed compared to that shown in Reference Example 8.

Without being bound by a particular theory, based on the results described in Reference Examples 7, 8, and 9, the following discussion is possible. The elimination of soluble IL-6 receptor from plasma was found to be markedly accelerated in normal mice expressing both mouse FcγRIIb and mouse FcγRIII that were administered with mF44 and mF46 with selectively increased binding activity of mIgG1 (native mouse IgG1) to mouse FcγRIIb and mouse FcγRIII. Furthermore, it was revealed that, when mF44 and mF46 were administered to mice that express mouse FcγRIIb but not mouse FcγRIII (i.e., FcγRIII-deficient mice and Fc receptor γ chain-deficient mice), the elimination of soluble IL-6 receptor from plasma was also accelerated markedly in the mice. Meanwhile, when mF44 and mF46 were administered to mice that express mouse FcγRIII but not mouse FcγRIIb (i.e., FcγRII-deficient mice), the elimination of soluble IL-6 receptor from plasma was not remarkably accelerated in the mice.

From the above findings, it is thought that, the antibodies mF44 and mF46 in which the binding activity of mIgG1 (native mouse IgG1) to mouse FcγRIIb and mouse FcγRIII is increased, are incorporated into FcγR-expressing cells mainly by mouse FcγRIIb, and thus the soluble antigen in the plasma that binds to the antibodies is eliminated. Meanwhile, the FcγRIII-mediated incorporation of antibody/antigen complexes into FcγR-expressing cells is thought not to significantly contribute to the elimination of the soluble antigen from plasma.

Furthermore, the plasma concentration of soluble IL-6 receptor was markedly reduced in mice administered with Fv4-IgG1-F1087 (heavy chain SEQ ID NO: 28; light chain SEQ ID NO: 29) having increased binding activity to mouse FcγRIIb and mouse FcγRIII. Meanwhile, the effect to eliminate soluble IL-6 receptor from the plasma of mice administered with Fv4-IgG1-F1182 with increased binding activity to mouse FcγRI and mouse FcγRIV was confirmed to be smaller than that of Fv4-IgG1-F1087.

Fv4-IgG1-Fuc (produced by expressing Fv4-IgG1 (heavy chain SEQ ID NO: 30; light chain SEQ ID NO: 29) using CHO cells lacking the fucose transporter gene (WO2006/067913) as host cells) has greatly enhanced binding activity to mouse FcγRIV, since it has a low-fucose-type sugar chain (Science (2005) 310 (5753) 1510-1512). While the concentration of the soluble IL-6 receptor in plasma of Fv4-IgG1-Fuc-administered mice was decreased in comparison to that of Fv4-IgG1-administered mice, that decreasing effect was approximately two-fold, and was confirmed to be small. Therefore, uptake of antibodies into FcγR-expressing cells via mouse FcγRIV may not be contributing greatly to elimination of soluble antigens in plasma.

In view of the above, it was demonstrate that, of several mouse FcγRs, mouse FcγRIIb plays a major role in antibody incorporation into FcγR-expressing cells in mice. Thus, it would be thought that mutations to be introduced into the mouse FcγR-binding domain particularly preferably include, but are not particularly limited to, mutations that enhance the binding to mouse FcγRIIb.

The present examinations showed that administration of an antigen-binding molecule that binds to a soluble antigen in a pH-dependent manner and has enhanced FcγR-binding activity can accelerate elimination of the soluble antigen in the plasma of the antibody-administered organism. This elimination of soluble antigens in plasma via FcγRs was shown to take place mainly via FcγRIIb among the FcγRs in mice. More specifically, to accelerate the elimination of soluble antigens in plasma using the interaction between FcγR and the antibody-antigen complex, FcγRIIb is particularly important among the FcγRs, and as long as FcγRIIb binding is maintained, the elimination effect is maintained. Accordingly, it is revealed that when an antigen-binding molecule that binds to soluble antigens in a pH-dependent manner and has enhanced FcγRIIb-binding activity was administered in vivo, it can accelerate elimination of soluble antigens in plasma to effectively reduce the concentration of soluble antigens in plasma, and clearly shows very effective actions.

INDUSTRIAL APPLICABILITY

The present invention provides Fc region variants with decreased binding activities to all activating FcγRs, in particular FcγRIIa (R type), while maintaining their FcγRIIb-binding activity in comparison to those of a polypeptide containing a native IgG Fc region; and polypeptides comprising such Fc region variants. By using the polypeptides, it is possible to transduce inhibitory signals of inflammatory immune response mediated by phosphorylation of ITIM in FcγRIIb. Furthermore, by conferring an antibody Fc with the property of selective FcγRIIb binding, immunosuppressive actions via FcγRIIb may enable suppression of anti-antibody production.

The invention claimed is:

1. An Fc region variant comprising a human IgG Fc region comprising Gln at position 237 (EU numbering), Asp at position 238 (EU numbering), and one of the following combinations (i) to (x) (all positions by EU numbering):
   (i) Met at position 241, Glu at position 296, His at position 330, and His at position 324; or
   (ii) Met at position 241, Pro at position 268, Glu at position 296, and His at position 330; or
   (iii) Phe at position 235, Met at position 241, Glu at position 296, and His at position 324; or
   (iv) Phe at position 235, Met at position 241, Pro at position 268, and Glu at position 296; or
   (v) Met at position 241, Pro at position 268, Glu at position 296, and His at position 324; or
   (vi) Phe at position 235, Met at position 241, Pro at position 268, Glu at position 296, and His at position 324; or
   (vii) Phe at position 235, Met at position 241, Glu at position 296, His at position 330, and His at position 324; or
   (viii) Phe at position 235, Met at position 241, Pro at position 268, Glu at position 296, and His at position 330; or
   (ix) Met at position 241, Pro at position 268, Glu at position 296, His at position 330, and His position 324; or
   (x) Asp at position 233, Ile at position 264, Arg at position 267, Pro at position 268, Gly at position 271, and Glu at position 296.

2. An Fc region variant comprising a human IgG Fc region comprising Gln at position 237 (EU numbering), Asp at position 238 (EU numbering), and one of the following combinations (i) to (iv) (all positions by EU numbering):
   (i) Met at position 241 and Glu at position 296; or
   (ii) Met at position 241, Glu at position 296, and His at position 330; or
   (iii) Phe at position 235, Met at position 241, and Glu at position 296; or
   (iv) Phe at position 235, Met at position 241, Glu at position 296, and His at position 330.

3. An Fc region variant comprising a human IgG Fc region comprising one of the following combinations (i) to (x) (all positions by EU numbering):
   (i) Gln at position 237, Asp at position 238, Met at position 241, Glu at position 296, His at position 324, and His at position 330; or
   (ii) Gln at position 237, Asp at position 238, Met at position 241, Pro at position 268, Glu at position 296, and His at position 330; or
   (iii) Phe at position 235, Gln at position 237, Asp at position 238, Met at position 241, Glu at position 296, and His at position 324; or
   (iv) Phe at position 235, Gln at position 237, Asp at position 238, Met at position 241, Pro at position 268, Glu at position 296; or
   (v) Gln at position 237, Asp at position 238, Met at position 241, Pro at position 268, Glu at position 296, and His at position 324; or
   (vi) Phe at position 235, Asp at position 238, Pro at position 268, Glu at position 296, and His at position 324; or
   (vii) Phe at position 235, Gln at position 237, Asp at position 238, Met at position 241, Pro at position 268, Glu at position 296, and His at position 324; or
   (viii) Phe at position 235, Gln at position 237, Asp at position 238, Met at position 241, Glu at position 296, His at position 324, and His at position 330; or (ix) Phe at position 235, Gln at position 237, Asp at position 238, Met at position 241, Pro at position 268, Glu at position 296, and His at position 330; or
(x) Gln at position 237, Asp at position 238, Met at position 241, Pro at position 268, Glu at position 296, His at position 324, and His at position 330.

* * * * *